(12) United States Patent
DiMaio et al.

(10) Patent No.: US 9,962,090 B2
(45) Date of Patent: **\*May 8, 2018**

(54) REFLECTIVE MODE MULTI-SPECTRAL TIME-RESOLVED OPTICAL IMAGING METHODS AND APPARATUSES FOR TISSUE CLASSIFICATION

(71) Applicant: SPECTRAL MD, INC., Dallas, TX (US)

(72) Inventors: John Michael DiMaio, Dallas, TX (US); Wensheng Fan, Dallas, TX (US); Jeffrey E. Thatcher, Dallas, TX (US); Weizhi Li, Dallas, TX (US); Weirong Mo, Dallas, TX (US)

(73) Assignee: Spectral MD, Inc., Dallas, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/646,683

(22) Filed: Jul. 11, 2017

(65) Prior Publication Data

US 2017/0319073 A1 Nov. 9, 2017

Related U.S. Application Data

(63) Continuation of application No. 15/367,087, filed on Dec. 1, 2016, now Pat. No. 9,717,417, which is a (Continued)

(51) Int. Cl.
*A61B 5/00* (2006.01)
*A61B 5/026* (2006.01)
*A61B 5/0295* (2006.01)

(52) U.S. Cl.
CPC .......... *A61B 5/0075* (2013.01); *A61B 5/0064* (2013.01); *A61B 5/0261* (2013.01); *A61B 5/0295* (2013.01); *A61B 5/445* (2013.01)

(58) Field of Classification Search
CPC ..... A61B 5/0075; A61B 5/0261; A61B 5/445; A61B 5/0064; A61B 5/0295
See application file for complete search history.

(56) References Cited

U.S. PATENT DOCUMENTS 5,074,306 A 12/1991 Green et al.
5,701,902 A 12/1997 Vari et al.
(Continued)

FOREIGN PATENT DOCUMENTS

WO WO 2016/069788 A1 5/2016

OTHER PUBLICATIONS

2011 National Burn Repository: Report of Data from 2001-2010. American Burn Association (2011) pp. 134.
(Continued)

*Primary Examiner* — Long V Le
*Assistant Examiner* — Angela M Hoffa
(74) *Attorney, Agent, or Firm* — Knobbe, Martens, Olson & Bear LLP

(57) ABSTRACT

Certain aspects relate to apparatuses and techniques for non-invasive optical imaging that acquires a plurality of images corresponding to both different times and different frequencies. Additionally, alternatives described herein are used with a variety of tissue classification applications, including assessing the presence and severity of tissue conditions, such as burns and other wounds.

19 Claims, 92 Drawing Sheets

Related U.S. Application Data continuation-in-part of application No. PCT/US2016/029864, filed on Apr. 28, 2016, and a continuation-in-part of application No. PCT/US2015/057882, filed on Oct. 28, 2015.

(60) Provisional application No. 62/297,565, filed on Feb. 19, 2016, provisional application No. 62/214,885, filed on Sep. 4, 2015, provisional application No. 62/136,398, filed on Mar. 20, 2015, provisional application No. 62/115,536, filed on Feb. 12, 2015, provisional application No. 62/114,027, filed on Feb. 9, 2015, provisional application No. 62/112,348, filed on Feb. 5, 2015, provisional application No. 62/072,177, filed on Oct. 29, 2014.

(56) References Cited

U.S. PATENT DOCUMENTS

| | | | |
|---|---|---|---|
| 6,008,889 | A | 12/1999 | Zeng et al. |
| 6,058,352 | A | 5/2000 | Lu et al. |
| 6,081,612 | A | 6/2000 | Gutkowicz-Krusin et al. |
| 6,352,517 | B1 | 3/2002 | Flock et al. |
| 6,353,753 | B1 | 3/2002 | Flock et al. |
| 6,381,488 | B1 | 4/2002 | Dickey et al. |
| 6,411,907 | B1 | 6/2002 | Lu et al. |
| 7,729,750 | B2 | 6/2010 | Tromberg et al. |
| 7,733,389 | B2 | 6/2010 | Kurosawa et al. |
| 7,860,554 | B2 | 12/2010 | Leonardi et al. |
| 8,488,024 | B2 | 7/2013 | Yano et al. |
| 8,509,879 | B2 | 8/2013 | Durkin et al. |
| 8,583,216 | B2 | 11/2013 | Pershing et al. |
| 8,605,172 | B2 | 12/2013 | Nikkanen et al. |
| 8,704,917 | B2 | 4/2014 | Rodrigues et al. |
| 8,812,083 | B2 | 8/2014 | Papazoglou et al. |
| 8,838,211 | B2 | 9/2014 | Melendez et al. |
| 8,892,192 | B2 | 11/2014 | Cuccia et al. |
| 9,295,402 | B1 | 3/2016 | Arbab et al. |
| 9,717,417 | B2 * | 8/2017 | DiMaio ............... A61B 5/0075 |
| 2002/0016533 | A1 | 2/2002 | Marchitto et al. |
| 2006/0155193 | A1 | 7/2006 | Leonardi et al. |
| 2006/0184043 | A1 | 8/2006 | Tromberg et al. |
| 2008/0278602 | A1 | 11/2008 | Otsu |
| 2009/0072142 | A1 | 3/2009 | Blitzer |
| 2009/0118600 | A1 | 5/2009 | Ortiz et al. |
| 2009/0118622 | A1 | 5/2009 | Durkin et al. |
| 2009/0275808 | A1 | 11/2009 | DiMaio et al. |
| 2009/0275841 | A1 | 11/2009 | Melendez et al. |
| 2010/0210931 | A1 | 8/2010 | Cuccia |
| 2011/0124987 | A1 | 5/2011 | Papazoglou et al. |
| 2011/0124988 | A1 | 5/2011 | Cuccia |
| 2012/0078088 | A1 | 3/2012 | Whitestone et al. |
| 2012/0172243 | A1 | 7/2012 | Davicioni et al. |
| 2012/0200700 | A1 | 8/2012 | Bennett et al. |
| 2012/0245473 | A1 | 9/2012 | Mycek et al. |
| 2012/0288230 | A1 | 11/2012 | Pologe et al. |
| 2012/0321759 | A1 | 12/2012 | Marinkovich et al. |
| 2013/0064441 | A1 | 3/2013 | Kask |
| 2013/0274612 | A1 | 10/2013 | Cuccia et al. |
| 2014/0012225 | A1 | 1/2014 | Yoo et al. |
| 2014/0092288 | A1 | 4/2014 | Hattery et al. |
| 2014/0128744 | A1 | 5/2014 | Cuccia et al. |
| 2014/0155757 | A1 | 6/2014 | Yang et al. |
| 2014/0155818 | A1 | 6/2014 | Salinas et al. |
| 2014/0213910 | A1 | 7/2014 | Durkin et al. |
| 2015/0011892 | A1 | 1/2015 | Sostek |
| 2015/0044098 | A1 | 1/2015 | Smart et al. |
| 2015/0080742 | A1 | 3/2015 | Andre et al. |
| 2015/0141839 | A1 | 5/2015 | Cuccia et al. |
| 2015/0285685 | A1 | 10/2015 | Wax et al. |
| 2015/0374309 | A1 | 12/2015 | Farkas et al. |

OTHER PUBLICATIONS

Afromowitz et al., "Clinical Evaluation of Burn Injuries Using an Optical Reflectance Technique," IEEE Transactions on Biomedical Engineering, 1987; 34(2):114-27.

Afromowitz et al., "Multispectral imaging of burn wounds: a new clinical instrument for evaluating burn depth". IEEE transactions on bio-medical engineering, 1988; 35(10):842-850.

Aldrich, John "R. A. Fisher and the Making of Maximum likelihood 1912-1922", Statistical Science, 1997; 12(3):162-176.

Alian et al., "Photoplethysmography," Best Pract. Res. Clin. Anaesthesiol., 2014; 28(4):395-406; ePub Sep. 9, 2014.

Allen, John "Photoplethysmography and its application in clinical physiological measurement.," Physiol. Meas., 2007; 28:R1-R39.

Anselmo et al., "Multispectral Photographic Analysis—A New Quantitative Tool to Assist in the Early Diagnosis of Thermal Burn Depth." Annals of Biomed Engin. 1977; 5:179-193.

Antonutto et al., "Noninvasive assessment of cardiac output from arterial pressure profiles during exercise," Eur J Appl Physiol. 1995; 72:18-24.

Arsenault et al., "The Use of Transcutaneous Oximetry to Predict Healing Complications of Lower Limb Amputations: A Systematic Review and Meta-Analysis," Eur J Vasc Endovasc Surg. 2012; 43:329-336.

Bajwa et al., "Assessment of Tissue Perfusion in the Lower Limb: Current Methods and Techniques Under Development," Circ Cardiovasc Imag. Sep. 2014; 7:836-843.

Bak et al., "Hemodynamic Changes During Resuscitation After Burns Using the Parkland Formula". J Trauma-Injury Infect Crit Care, 2009; 66(2):329-336.

Benitez et al., "Contemporary assessment of foot perfusion in patients with critical limb ischemia," Semin Vasc Surg. Mar. 2014; 27:3-15.

Branski et al., "A procine model of full-thickness burn, excision, and skin autografting," Burns 2008; 34(8):1119-1127.

Burgess et al., "Segmental Transcutaneous Measurements of PO2 in Patients Requiring Below-The-Knee Amputation for Peripheral Vascular Insufficiency," J Bone Jt Surg Am 1982; 64:378-82.

CDC, Diabetes Public Health Resource, "Number (in Thousands) of Hospital Discharges for Non-Traumatic Lower Extremity Amputation with Diabetes as a Listed Diagnosis, United States, 1988-2006," Centers for Disease Control and Prevention, Oct. 20, 2016, Available at: http://www.cdc.gov/diabetes/statistics/lea/fig1.htm; 3 pages.

Cheong et al., "A Review of the Optical Properties of Biological Tissues", IEEE J Quantum Electronics; 1990; 26(12): 2166-2185.

Cortes et al., "Support-Vectors Networks," Machine Learning 1995; 20:273-297.

Cousineau et al., "Outliers detection and treatment: a review," Inter J Psycholog Res. 2010; 3(1):58-67.

Cover et al., "Nearest Neighbor Pattern Classification", IEEE Transactions on Information Theory; 1967; 13(1):21-27.

Cross et al., "Near infrared point and imaging spectroscopy for burn depth assessment", Int'l Congress Series (2005) 1281: 137-142.

Cross et al., "Clinical Utilization of Near-infrared Spectroscopy Devices for burn depth assessment", Wound Rep Reg. (2007) 15: 332-340.

Cuccia et al., "Quantitation and mapping of tissue optical properties using modulated imaging," J Biomed Opt., 2009; 14(2): 1-31.

Desai et al., "Early Burn Wound Excision Significantly Reduces Blood Loss," Ann. Surg. 1990; 211(6):753-762.

Dillingham et al., "Reamputation, Mortality, and Health Care Costs Among Persons with Dysvascular Lower-Limb Amputations," Arch Phys Med Rehabil. 2005; 86:480-486.

Eisenbeiss et al., "Reflection-optical multispectral imaging method for objective determination of burn depth," Burns. 1999; 25:697-704.

(56) References Cited

OTHER PUBLICATIONS

Eneroth, M., "Factors affecting wound healing after major amputation for vascular disease: a review," Prosth Ortho Internat. 1999; 23:195-208.
Engrav et al., "Early Excision and Grafting vs. Nonoperative Treatment of Burns of Indeterminant Depth: A Randomized Prospective Study," J of Trauma, 1983; 23(11):1001-1004.
Fischer et al., "Multispectral and Hyperspectral imaging technologies in conservation: current research and potential applications," Stud Conserv. 2006; 7: 3-16.
Franklin et al., "Cost of lower-limb amputation in US veterans with diabetes using health services data in fiscal years 2004 and 2010," J Rehabil Res Dev (JRRD) 2014; 51(8):1325-1330.
Graham et al., "Wound Healing of Cutaneous Sulfur Mustard Injuries: Strategies for the Development of Improved Therapies," J Burns and Wounds. 2005; 4:1-45.
Grubbs, Frank E., "Procedures for detection outlying observations in samples", Ballistic Research Laboratories, Aberdeen Proving Ground, 1974; BRL Report No. 1713; 53 pages.
Guo et al., "Factors Affecting Wound Healing," J Dent Res. 2010; 89(3):219-229.
Gurfinkel et al., "Development of a Novel Animal Burn Model Using Radiant Heat in Rats and Swine," Acad Emerg Med. 2010; 17(5):514-520.
Gurfinkel et al., "Histological assessment of tangentially excised burn eschars," Can J Plast Surg. 2010; 18(3):e33-e36.
HCUP Nationwide Inpatient Sample (NIS)—2009, Healthcare Cost and Utilization Project—HCUP, A Federal-State-Industry Partnership in Health Data Issued May 2011, Updated Nov. 2015, 89 pages, Retrievable at http://www.hcup-us.ahrq.gov; 89 pages.
Heimbach et al., *Surgical management of the burn wound*, Cover and Table of Contents, New York: Raven Press, 1984; TOC only.
Heimbach, David M., "Early Burn Excision and Grafting," Surgical Clinics of North America [Burns], 1987; 67(1):93-107.
Heredia-Juesas et al., "Non-Invasive Optical Imaging Techniques for Burn-Injured Tissue Detection for Debridement Surgery," Conf Proc IEEE/EMBS, Aug. 2016; 2893-2896.
Hu et al., "Development of Effective Photoplethysmographic Measurement Techniques: From Contact to Non-Contact and from Point to Imaging." 31st Annual International Conference of the IEEE/EMBS. 2009; 6550-6553.
Jackson D. "The diagnosis of the depth of burning." Br J Surg. 1953; 40:588-596.
Jacques et al., "Absorption spectra for biological tissues," ECE532 Biomedical Optics, 1998, Available from: http://omlc.org/education/ece532/class3/muaspectra.html; 1 page.
Jacques, Steven L., "Optical properties of biological tissues: A review", Phys Med. Biol., 2013, 58(12), R37-61 and Corrigendum 2013 58:5007-5008.
Kaiser et al., "Noninvasive assessment of burn wound severity using optical technology: A review of current and future modalities." Burns. 2011; 37(3): 377-386.
Kearns et al., "Disaster planning: The past, present, and future concepts and principles of managing a surge of burn injured patients for those involved in hospital facility planning and preparedness," J Burn Care Res. Jan./Feb. 2014; 35(1):e33-e42.
King, Paul Book Reviews; "*Design of Pulse Oximeters,*" IEEE Eng. Med. Biol. Mag., 1998; p. 117.
King et al., "Surgical wound debridement sequentially characterized in a porcine burn model with multispectral imaging," Burns, 2015; 41:1478-1487.
Kono et al., "Identifying the incidence of and risk factors for reamputation among patients who underwent foot amputation," Ann Vasc Surg 2012; 26:1120-1126.
Lee et al., "Operative wound management," Chapter 13, © 2012 Elsevier Ltd, Inc, BV, DOI: 10.1016/B978-1-4377-2786-9I00013-8, pp. 157-172e2.
Li et al., "Review of spectral imaging technology in biomedical engineering: achievements and challenges," J Biomed Optics. 2013; 18(10):100901; 29 pages.
Li et al., "Burn injury diagnostic imaging device's accuracy improved by outlier detection and removal," Proc. of SPIE, vol. 9472, 2015 SPIE, pp. 947206-1 to 947206-11.
Li et al., "Outlier detection and removal improves accuracy of machine learning approach to multispectral burn diagnostic imaging," J. Bio. Optics. Dec. 2015; 20(12):121305-1 to 121305-9.
Liu et al., "Toward integrating feature selection algorithms for classification and clustering." IEEE Transactions on Knowledge and Data Engineering. 2005. 17(4): 491-502; 35 pages.
Lu et al., "Medical hyperspectral imaging: A review," J Biomed Optics Jan. 2014; 19(1):0101901, 24 pages.
Macri et al., "Immediate burn excision fails to reduce injury progression," J Burn Care Res. 2013; 34(3):153-160.
Marimont et al., "Nearest Neighbor searches and the curse of Dimensionality," J Inst Math Applics 1979; 24 (1): 59-70.
Mertens et al., "Outpatient Burn Management," Nursing Clinics of North America, Burn Mgmt. 1997; 32(2):343-364.
Middelkoop et al., "Porcine wound models for skin substitution and burn treatment," Biomaterials. 2004; 25:1559-1567.
Mo et al., "The importance of illumination in a non-contact photoplethysmography imaging system for burn wound assessment", Proc. SPIE 9303 Photonic Therapeutics and Diagnostics XI, 93030M, Feb. 2015; 10 pages.
Mook et al., "Instruments and techniques: Spectrophotometric determination of oxygen saturation of blood independent of the presence of indocyanine green," Cardiovascular Research, 1979; 13:233-237.
Moza et al., "Deep-Tissue Dynamic Monitoring of Decubitus Ulcers: Wound Care and Assessment," IEEE Eng Med Biol Mag. 2010; 29(2):71-77.
National Limb Loss Information Center, "Fact Sheet: Amputation Statistics by Cause: Limb Loss in the United States," National Limb Loss Information Center, Fact Sheet. Revised 2008, 3 pages.
Nehler et al., "Functional outcome in a contemporary series of major lower extremity amputations," J Vasc Surg. 2003; 38:7-14.
Nguyen et al., "Spatial frequency domain imaging of burn wounds in a preclinical model of graded burn severity." J Biomed Optics. 2013; 18(6): 066010; 8 pages.
Nilsson, Lena M. "Respiration Signal from Photoplethysmography.," Anesth Analg. 2013; 117(4):859-65.
Norgren et al., Inter-Society Consensus for the Management of Peripheral Arterial Disease (TASC II), J Vasc Surg. 2007; 45(Supp 1):S5A-S67A.
Orgill, D., "Excision and skin grafting of thermal burns," New Eng J Med. 2011; 360:893-901.
Ortiz-Pujols et al., "Burn care: Are there sufficient providers and facilities?" Chapel Hill, North Carolina. American College of Surgeons Health Policy Research Institute, Nov. 2011; 9:4 pages.
Pape et al., "An audit of the use of laser Doppler imaging (LDI) in the assessment of burns of intermediate depth," Burns 2001; 27:233-239.
Peng et al., "Feature Selection Based on Mutual Information: Criteria of Max-Dependency, Max-Relevance, and Min-Redundancy," IEEE Trans. on Pattern Analysis and Machine Intelligence, 2005; 27(8):1226-1238.
Resch et al., "Estimation of burn depth at burn centers in the United States: a survey." J Burn Care Res. Nov./Dec. 2014; 35: 491-497.
Resurge International, "Burns: The Neglected but Solvable Health Crisis" from Reconstructive Surgery for the World's Poor since 1969; accessed <http://www.resurge.org/transforming_lives/story_burns.cfm> Accessed Feb. 9, 2015; 3 pages.
Rogers et al., "The right to bear legs—An amendment to healthcare: how preventing amputations can save billions for the US health-care system," J Am Podiatr Med Assoc 2008; 98:166-168.
Rousseeuw, Peter J. "Least Median of Squares Regression", J Am Stat Assoc. 1984; 79(388):871-880.
Severinghaus et al., "History of Blood Gas Analysis. VII. Pulse Oximetry." J Clin Monitor. 1987; 3(2):135-138.
Singer et al., "A porcine burn model," Meth Mol Med. 2003; 78:107-119.
Sokolova et al., "A systematic analysis of performance measures for classification tasks." Info Proc Manag. 2009; 45: 427-437.

(56) References Cited

OTHER PUBLICATIONS

Sowa et al., "Near infrared spectroscopic assessment of hemodynamic changes in the early post-burn period", Burns (2001) 27: 241-249.
Sowa et al., "Classification of burn injuries using near-infrared spectroscopy", J Biomed Optics. (Sep. 2006) 11(5): 6 pages.
Squiers et al., "Multispectral imaging burn wound tissue classification system: a comparison of test accuracies between several common machine learning algorithms," Proc. of SPIE, 2016; 9785:97853L-1 to 97853L-10.
Thatcher et al., "Dynamic tissue phantoms and their use in assessment of a noninvasive optical plethysmography imaging device," SPIE Sensing Technology + Applications, May 2014; 910718, 18 pages.
Thatcher et al., "Imaging Techniques for Clinical Burn Assessment with a Focus on Multispectral Imaging," Advan Wound Care, Mar. 2016; 5(8):360-378.
Thatcher et al., "Multispectral and Photophlethysmography Optical Imaging Techniques Identify Important Tissue Characteristics in an Animal Model of Tangential Burn Excision," J Burn Care & Res., Jan./Feb. 2016, 37(1):38-52.
Tuchin, Valery V., "Light-Tissue Interactions", Biomedical Photonics Handbook, CRC Press, Boca Raton, Florida 2003; Chapter 3; pp. 123-167.
Usman et al., "Second Derivative of Photoplethysmogram in Estimating Vascular Aging Among Diabetic Patients," in Internat Conf for Technical Postgraduates 2009, TECHPOS 2009, 3 pages.
Vemulapalli et al., "Peripheral aterial testing before lower extremity amputation among Medicare beneficiaries, 2000 to 2010," Circ Cardiovasc Qual Outcomes, Jan. 2014, 7:142-150.
Waters et al., "Energy cost of walking of amputees: the influence of level of amputation," J Bone Joint Surg. 1975; 58(1):42-46.
Watts et al., "Burn depth and its histological measurement," Burns 27 (2001) 154-160.
Webb, Steve [Ed.], *The physics of medical imaging*, © 1988, IOP Publishing Ltd., TOC only.
Webster, J.G. [Ed.], *Design of Pulse Oximeters*, Medical Science Series, © IOP Publishing Ltd. 1997; TOC only.
Worsley et al., "Back to basics: biophysical methods in tissue viability research," (Draft); J Wound Care, 2013; 22(8):434-439.
Wütschert et al., "Determination of Amputation Level in Ischemic Limbs—Reappraisal of the measurement of TcPo$_2$", Diabetes Care, 1997; 20(8):1315-1318.
Ziegler-Graham et al., "Estimating the Prevalence of Limb Loss in the United States: 2005 to 2050," Arch Phys Med Rehabil. 2008; 89:422-429.
International Search Report in PCT Application No. PCT/US15/57882 dated Feb. 26, 2016 in 24 pages.
International Search Report in PCT Application No. PCT/US16/29864 dated Aug. 5, 2016 in 15 pages.
Invitation to Pay Additional Fees in PCT/US15/57882 dated Dec. 28, 2015 in 3 pages.
Cancio et al., "Burn Support for Operation Iraqi Freedom and related operations, 2003 to 2004", J Burn Care Rehabil. (2005) 26(2): 151-161.
Guyon et al., "An Introduction to Variables and Feature Selection", J Machine Learn Res. 2003; 3:1157-1182.
Jaskille et al., "Critical Review of burn depth assessment techniques: Part II. Review of Laser Doppler Technology", J Burn Care Res. (2010) 31(1): 151-157.
Kauvar et al., "Comparison of Combat and Non-Combat Burns From Ongoing U.S. Military Operations", J Surg Res. (2006) 132(1): 195-200.
Moor Instruments, "Early and Accurate Burn Assessment with Laser Doppler Imaging", Product Brochure; Dec. 2014; 16 pages.
Petricoin et al., "SELDI-TOF-based serum proteomic pattern diagnostics for early detection of cancer", Curr Opin Biotechnol. (2004) 15(1): 24-30.
Reisner et al., "Utility of the Photoplethysmogram in Circulatory Monitoring", Anesthesiol. 2008; 108:950-958.
Spectral MD, Inc., "DeepView Digital Video Physiological Portable Imaging System", FDA Traditional 510(k) Application as filed Dec. 28, 2012; 528 pages.
Zonios et al., "Skin melanin, hemoglobin, and light scattering properties can be quantitatively assessed in vivo using diffuse reflectance spectroscopy", J Invest Dermatol. (2001) 117(6): 1452-1457.

\* cited by examiner

Analysis of All U.S. Records

TABLE 9 DEPICTS THE CASE FATALITY FOR EACH DECILE OF TOTAL BURN SIZE IN EACH OF SEVERAL AGE CATEGORIES. AS AGE AND/OR BURN SIZE INCREASED, SO DID CASE FATALITY. THE NUMBERS OF CASES USED TO DETERMINE THESE VALUES (PROPORTION OF CASES IN EACH GROUP THAT DIED) ARE LISTED IN THE ROW BENEATH THE CASE FATALITY VALUES FOR EACH AGE GROUP. THE SIZE OF SOME OF THE GROUPS IS SMALL, SO THAT THE CALCULATED CASE FATALITY VALUE WOULD HAVE A HIGH VARIANCE AND STANDARD ERROR.

TABLE 9: MORTALITY RATE BY AGE GROUP AND BURN SIZE (EXPRESSED AS THE NUMBER OF DEATHS OVER THE TOTAL NUMBER OF PATIENTS IN THAT GROUP)

| AGE GROUP | 0.1-9.9 | 10-19.9 | 20-29.9 | 30-39.9 | 40-49.9 | 50-59.9 | 60-69.9 | 70-79.9 | 80-89.9 | >90 | TOTAL |
|---|---|---|---|---|---|---|---|---|---|---|---|
| BIRTH-.9 | 0.3 | 1.8 | 6.9 | 9.4 | 24.7 | 28.8 | 44.9 | 50.0 | 70.4 | 91.7 | 2.9 |
| DIED/TOTAL | 15/5558 | 26/1456 | 30/435 | 21/224 | 24/97 | 21/73 | 22/49 | 21/42 | 19/27 | 33/36 | 232/7997 |
| 1-1.9 | 0.0 | 0.4 | 0.6 | 2.7 | 8.5 | 16.7 | 28.6 | 20.0 | 25.0 | 75.0 | 0.2 |
| DIED/TOTAL | 0/10136 | 7/1998 | 2/338 | 3/112 | 4/47 | 3/18 | 6/21 | 2/10 | 1/4 | 3/4 | 31/12688 |
| 2-4.9 | 0.1 | 0.2 | 0.8 | 5.3 | 7.9 | 19.7 | 9.3 | 25.0 | 60.0 | 45.5 | 0.8 |
| DIED/TOTAL | 9/7687 | 3/1575 | 3/379 | 10/190 | 8/101 | 13/66 | 4/43 | 7/28 | 18/30 | 10/22 | 85/10121 |
| 5-15.9 | 0.1 | 0.3 | 1.1 | 2.3 | 4.3 | 5.1 | 11.6 | 13.8 | 49.0 | 60.0 | 0.7 |
| DIED/TOTAL | 8/10524 | 6/2134 | 7/640 | 7/301 | 8/186 | 6/117 | 10/86 | 8/58 | 24/49 | 21/35 | 105/14130 |
| 16-19.9 | 0.1 | 0.4 | 1.1 | 3.3 | 5.2 | 9.4 | 14.3 | 18.5 | 58.3 | 66.7 | 1.1 |
| DIED/TOTAL | 7/5404 | 5/1190 | 4/370 | 5/152 | 6/115 | 6/64 | 6/42 | 5/27 | 14/24 | 22/33 | 80/7421 |
| 20-29.9 | 0.2 | 0.6 | 1.6 | 6.2 | 12.4 | 19.5 | 25.2 | 43.5 | 60.0 | 77.0 | 1.6 |
| DIED/TOTAL | 23/14854 | 19/3368 | 18/1103 | 31/503 | 31/249 | 30/154 | 32/127 | 30/69 | 48/80 | 67/87 | 329/20594 |
| 30-39.9 | 0.3 | 0.9 | 2.9 | 6.7 | 11.0 | 25.3 | 34.7 | 51.1 | 68.9 | 94.3 | 2.3 |
| DIED/TOTAL | 35/12629 | 27/3057 | 29/993 | 32/479 | 29/264 | 40/158 | 41/118 | 46/90 | 51/74 | 82/87 | 412/17949 |
| 40-49.9 | 0.4 | 1.5 | 4.8 | 10.9 | 23.1 | 42.3 | 37.6 | 62.9 | 74.7 | 91.0 | 3.2 |
| DIED/TOTAL | 50/14033 | 51/3414 | 57/1179 | 65/596 | 74/321 | 85/201 | 53/141 | 44/70 | 65/87 | 101/111 | 645/20153 |
| 50-59.9 | 0.8 | 3.7 | 10.1 | 21.2 | 39.7 | 53.0 | 67.8 | 81.6 | 87.8 | 89.6 | 5.4 |
| DIED/TOTAL | 82/10463 | 96/2602 | 93/922 | 83/392 | 96/242 | 79/149 | 78/115 | 62/76 | 65/74 | 86/96 | 820/15131 |
| 60-69.9 | 2.0 | 6.5 | 19.1 | 42.9 | 52.5 | 67.0 | 85.7 | 90.2 | 100.0 | 89.6 | 8.3 |
| DIED/TOTAL | 115/5714 | 99/1533 | 96/502 | 100/233 | 63/120 | 61/91 | 42/49 | 46/51 | 30/30 | 43/48 | 695/8371 |
| 70-79.9 | 4.0 | 15.4 | 34.0 | 59.2 | 74.5 | 84.4 | 88.0 | 92.9 | 90.0 | 90.6 | 14.9 |
| DIED/TOTAL | 132/3268 | 138/898 | 119/350 | 109/184 | 73/98 | 54/64 | 44/50 | 26/28 | 18/20 | 29/32 | 742/4992 |
| 80 OR GREATER | 6.9 | 28.7 | 63.9 | 77.2 | 89.0 | 96.7 | 86.7 | 93.5 | 97.1 | 100.0 | 24.9 |
| DIED/TOTAL | 154/2225 | 210/731 | 179/280 | 105/136 | 73/82 | 58/60 | 39/45 | 29/31 | 34/35 | 27/27 | 908/3652 |
| TOTAL | 0.6 | 2.9 | 8.5 | 16.3 | 25.4 | 37.5 | 42.6 | 56.2 | 72.5 | 84.8 | 3.6 |
| DIED/TOTAL | 630/102495 | 687/23956 | 637/7491 | 571/3502 | 489/1922 | 456/1215 | 377/886 | 326/580 | 387/534 | 524/618 | 5084/143199 |

TOTAL N=143,199 (EXCLUDING 39,837 UNKNOWN/MISSING)
©AMERIACAN BURN ASSOCIATION, NATIONAL BURN REPOSITORY® 2012. VERSION 8.0. ALL RIGHTS RESERVED WORLDWIDE.

Sidebar sections:
1. ANALYSIS OF
2. ANALYSIS OF ALL U.S. RECORDS
3. ANALYSIS BY AGE GROUP
4. ANALYSIS BY AGE ETIOLOGY
5. HOSPITAL COMPARISONS
6. ANALYSIS OF CANADIAN AND INTL RECORDS

FIG. 6

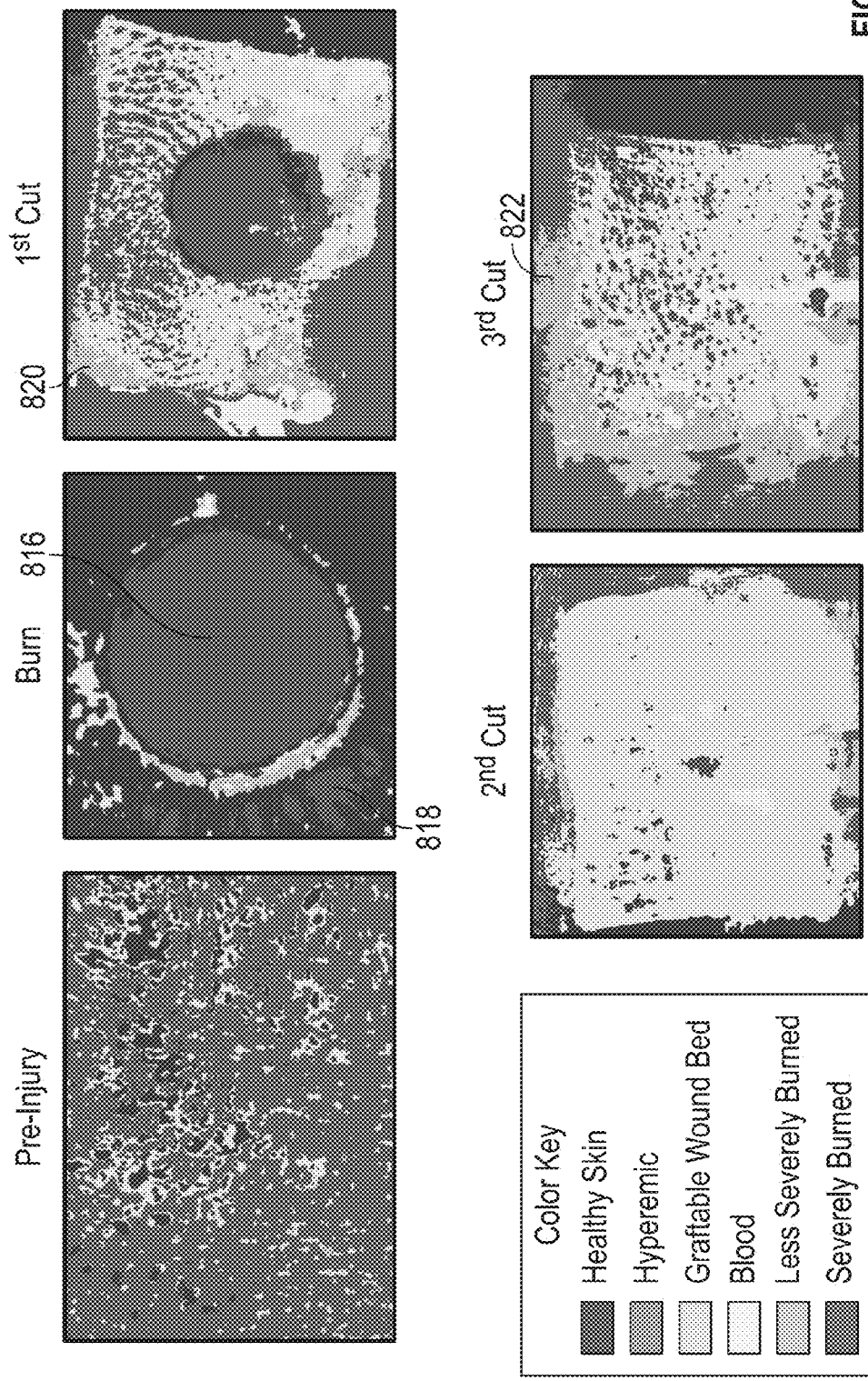

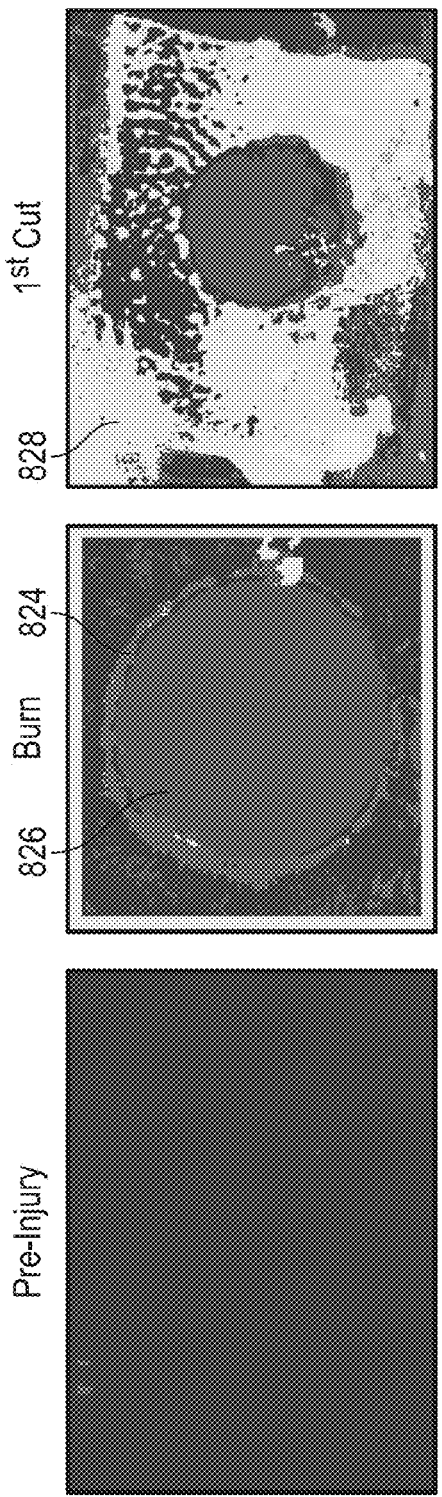
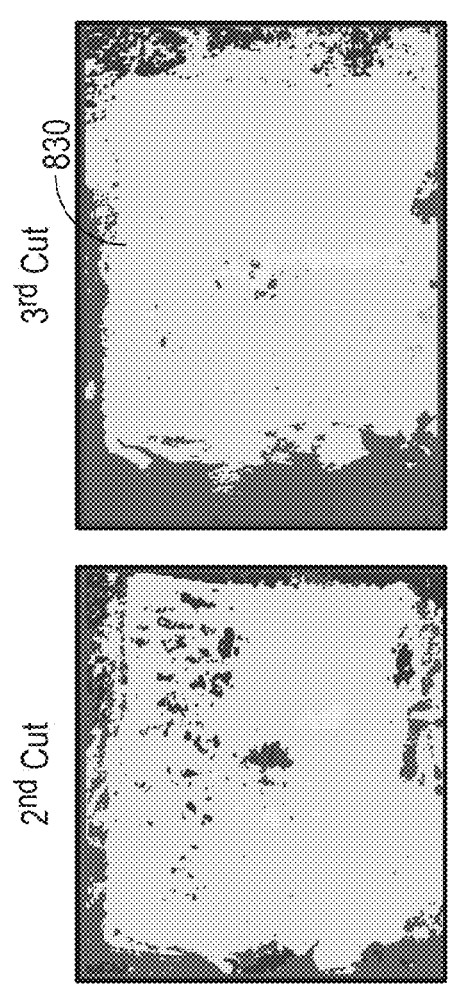
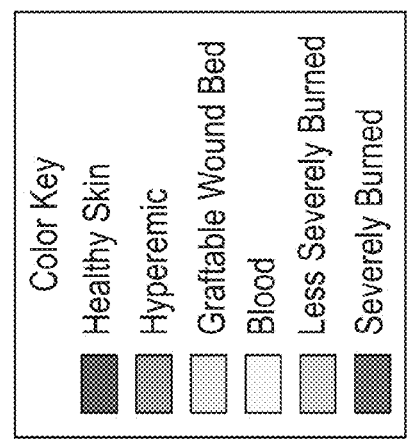
FIG. 9D

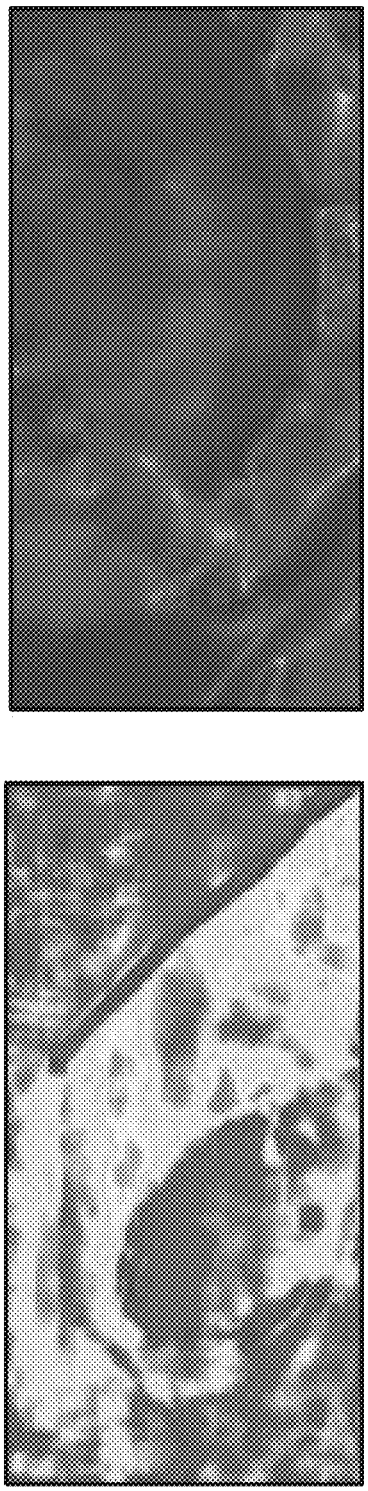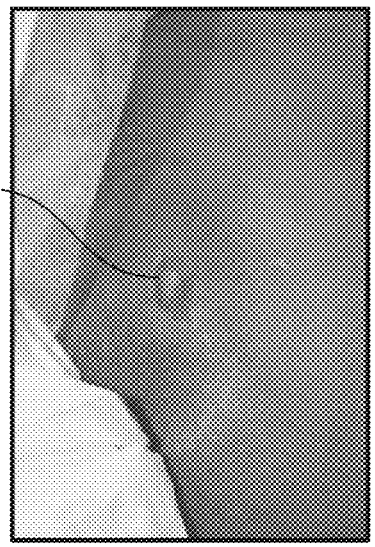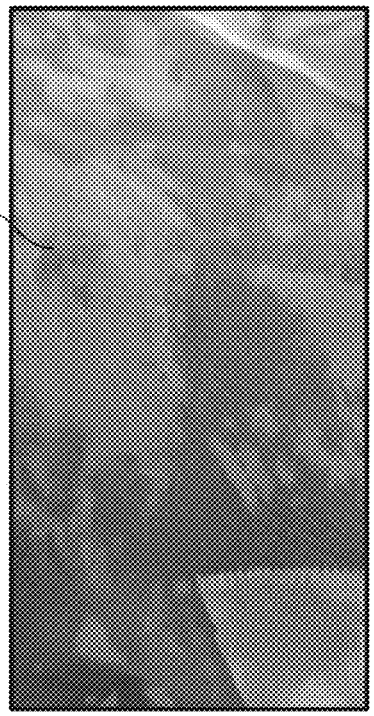
FIG. 11
FIG. 12

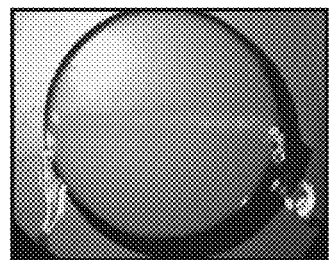 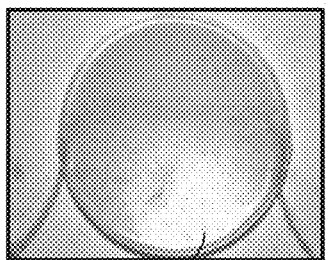 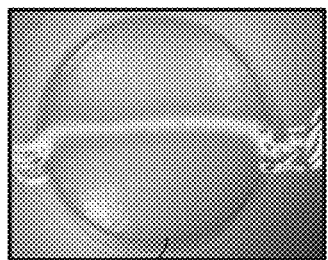
2000   2001   2002
FIG. 20A   FIG. 20B   FIG. 20C
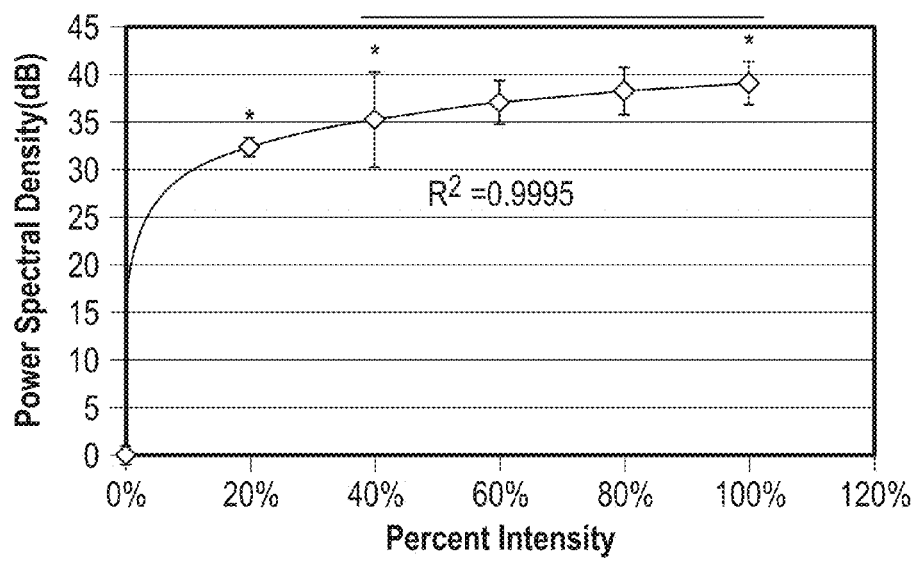
FIG. 21

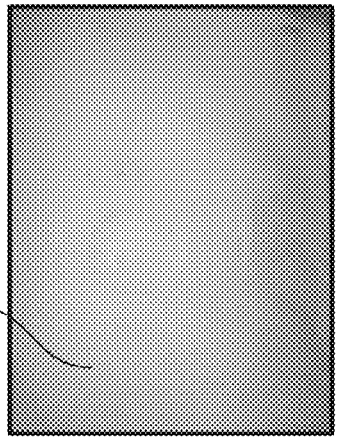
FIG. 23C
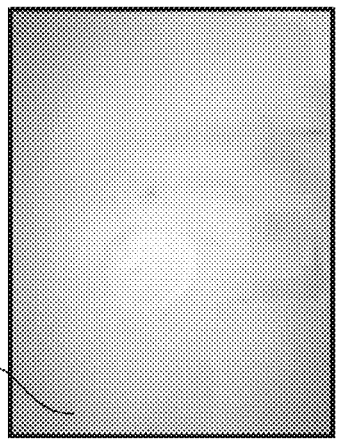
FIG. 23B
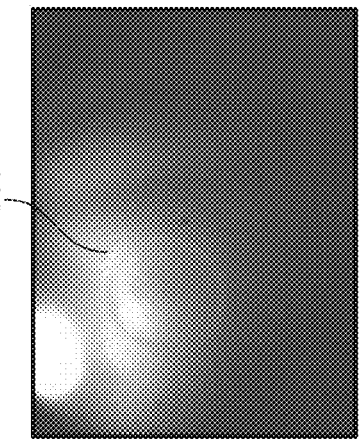
FIG. 23A
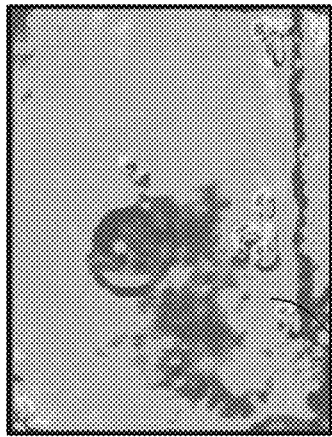
FIG. 23F
FIG. 23E
FIG. 23D

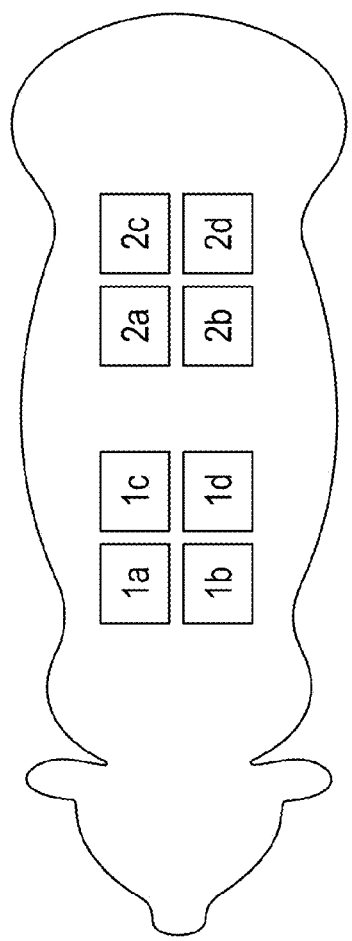
FIG. 24
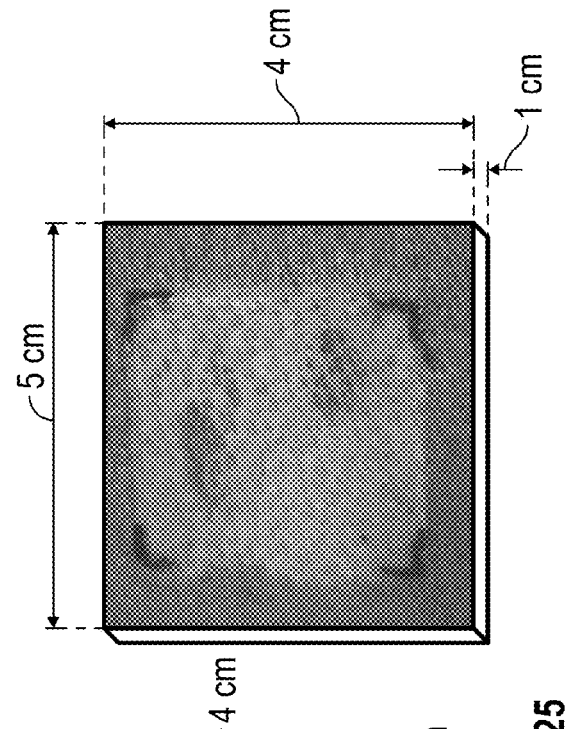
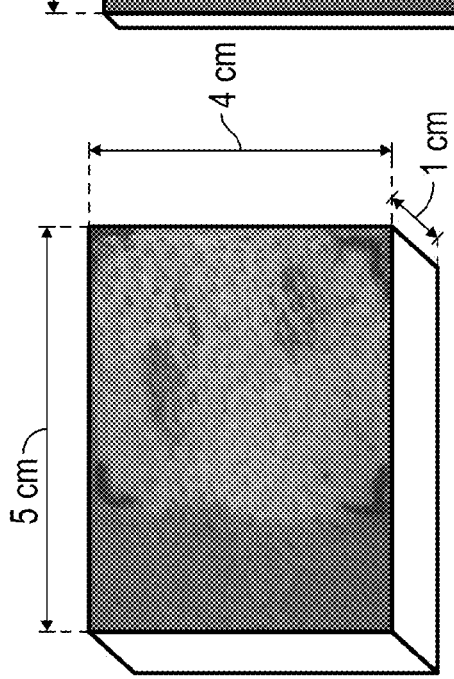
FIG. 25

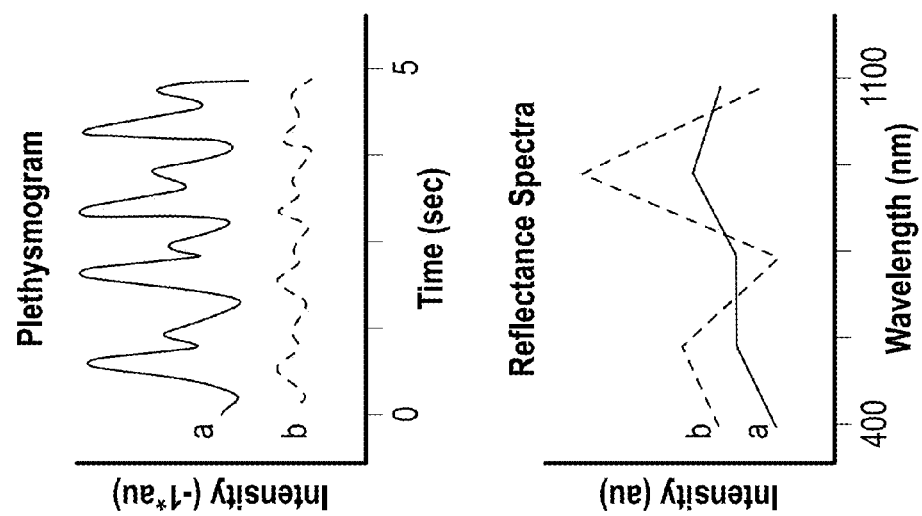
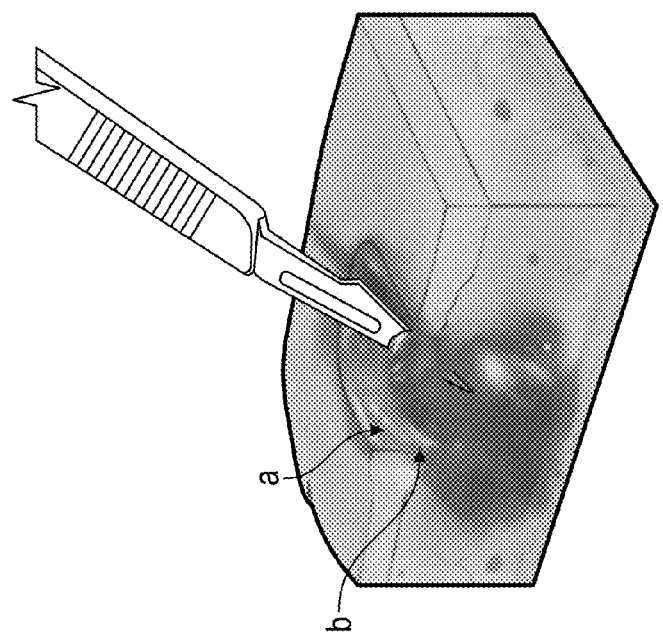
FIG. 33

Table 1: MSI confusion matrix and classification accuracy

| | | Actual State of Tissue Under Test | | | | | | |
|---|---|---|---|---|---|---|---|---|
| | | Healthy Skin | Wound Bed | Less Severe Burn | Severe Burn | Blood | Hyperemia | Accuracy | Average Effectiveness |
| Classification result | Healthy Skin | 1216 | 291 | 34 | 948 | 31 | 101 | 82% | 86% |
| | Wound Bed | 211 | 1264 | 314 | 226 | 0 | 14 | 87% | |
| | Less Severe Burn | 48 | 132 | 1175 | 21 | 5 | 250 | 89% | |
| | Severe Burn | 485 | 294 | 103 | 761 | 0 | 199 | 81% | |
| | Blood | 9 | 7 | 46 | 2 | 1061 | 13 | 92% | |
| | Hyperemia | 31 | 12 | 328 | 42 | 903 | 1423 | 84% | |

FIG. 42

Table 1 A summary of the classification and outlier detection algorithm.

Input: Dataset

1. Random selected N samples in whole dataset.
2. Sort the samples in each wavelength
3. Find the median index of these samples.
4. Set the "first window:"

The left bound is:

left = median index - ($\alpha_1$ × N)

if left < 0 left = 0

The right bound is:

right = median index + ($\alpha_2$ × N)

if right > N:

right = N

5. Calculate the means [$\mu_1, \mu_2, \mu_3 ... \mu_n$] and standard derivations [$\sigma_1, \sigma_2, \sigma_3 ... \sigma_n$] from "first window" data.
6. Assign feature importances $w_1, w_2, w_3 ... w_n$ according to desired method
7. Calculate the weight $W_i$ from the probability and feature importance of each wavelength in each sample For each sample in dataset:

$W_i = P_1 \times W_1 + P_2 \times W_2 + ... + P_{n-1} \times W_{n-1} + P_n \times W_n$
 $= \Sigma_{i=1}^{n} P_i \times W_i$ 8. Set threshold value to detect outlier if $W_i > W_{threshold}$ Will be considered to build the model Else:

Will be considered as outlier and removed from the training set.

FIG. 45

FIG. 47A
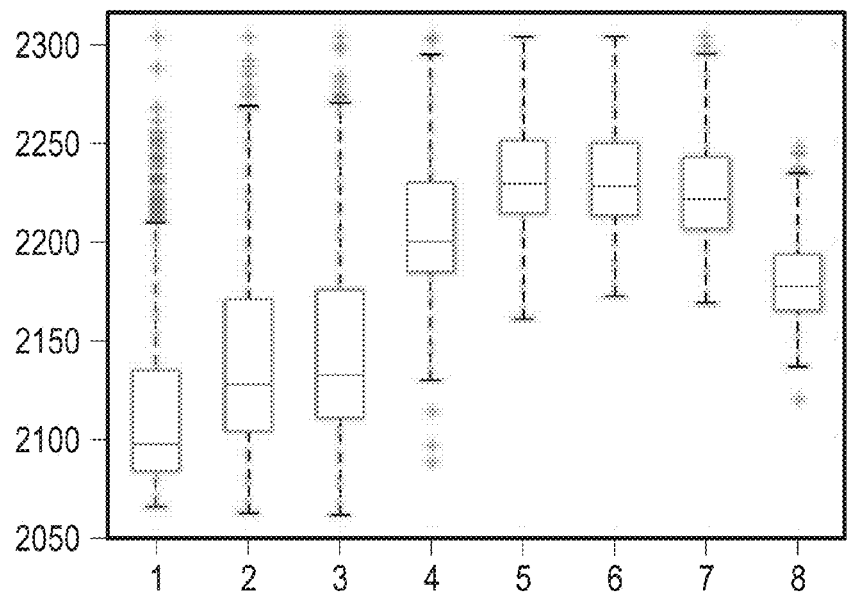
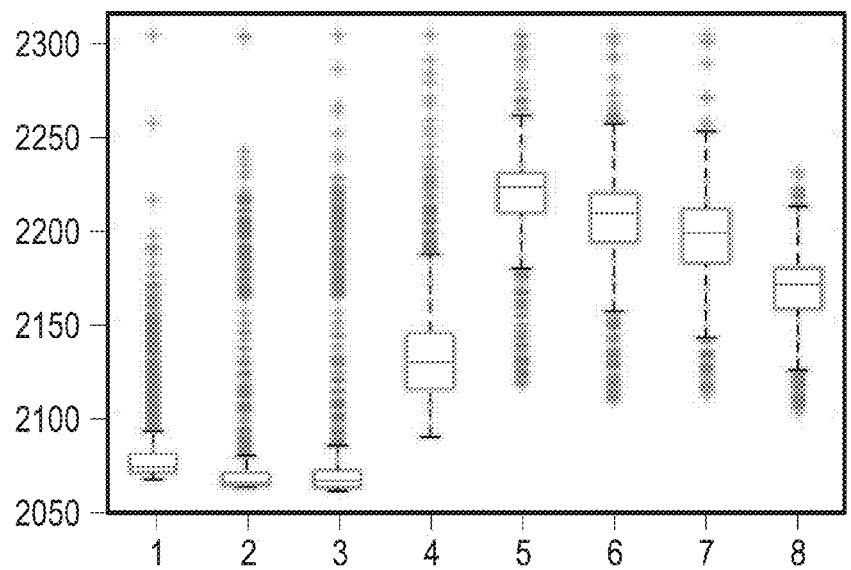

FIG. 47A Continued
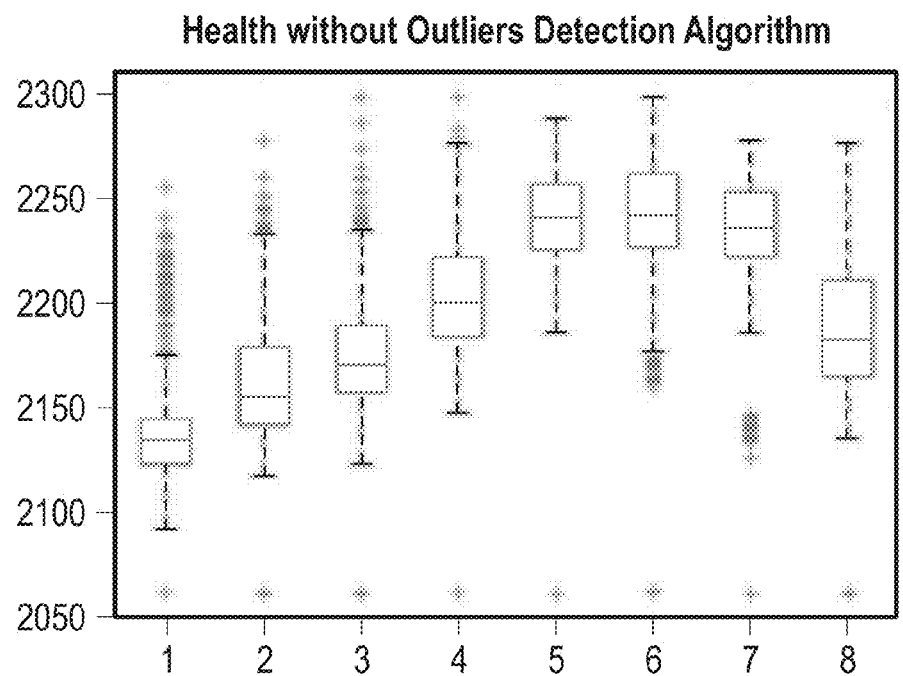
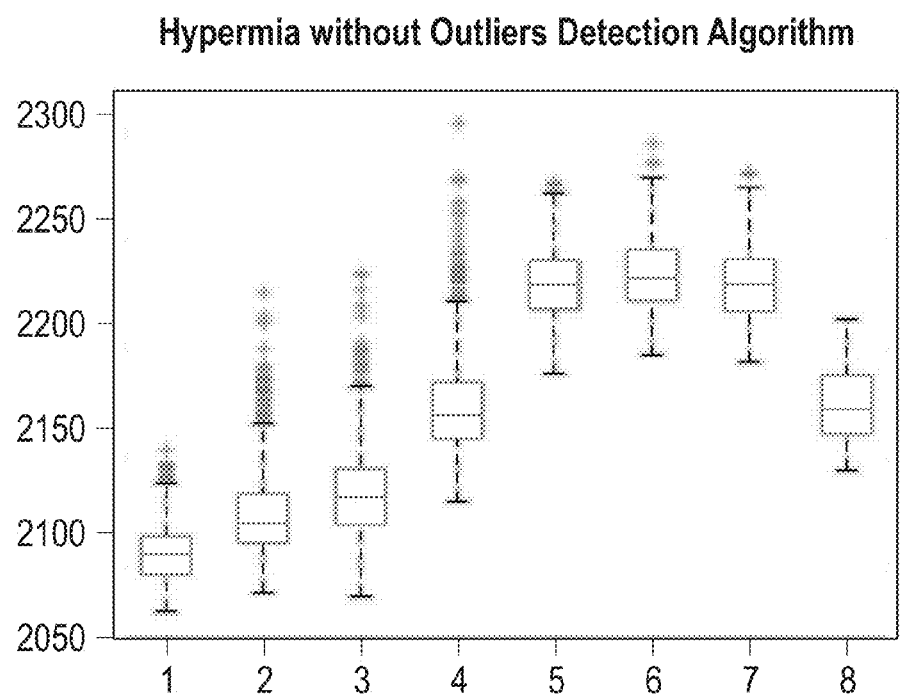

FIG. 47A Continued
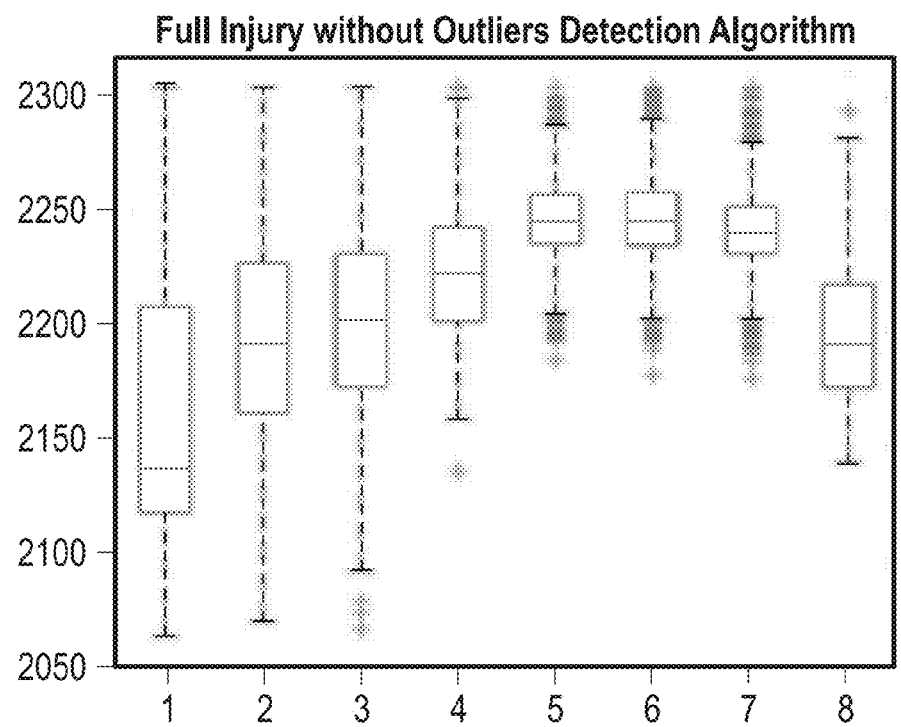
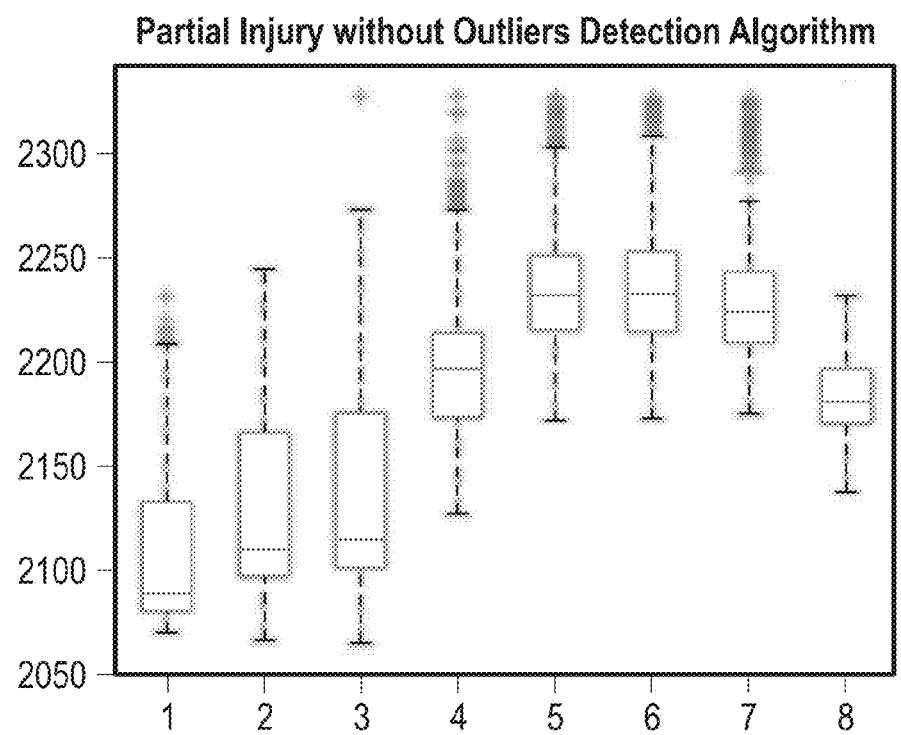

FIG. 47B
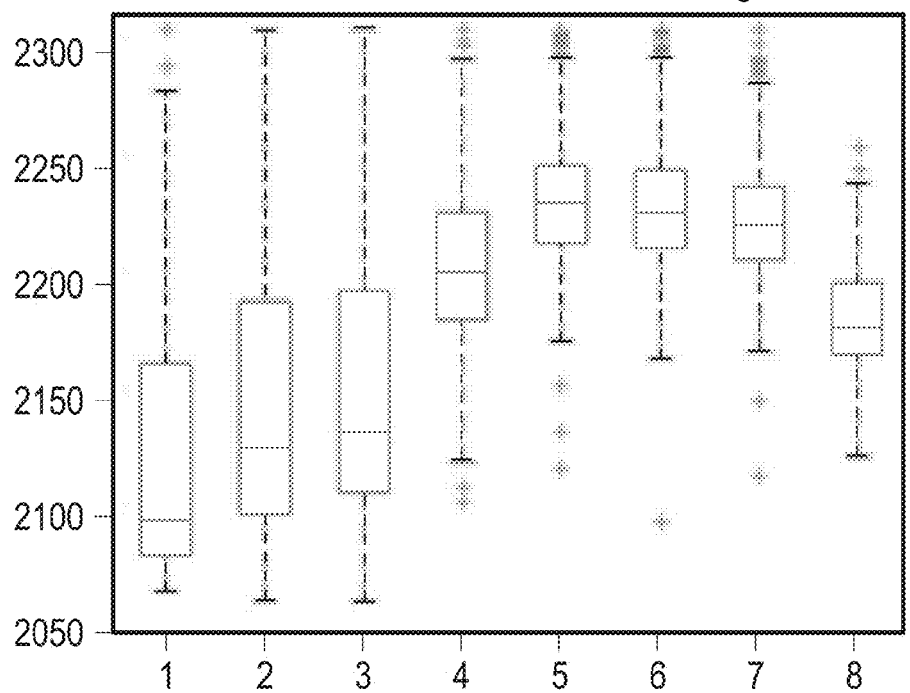
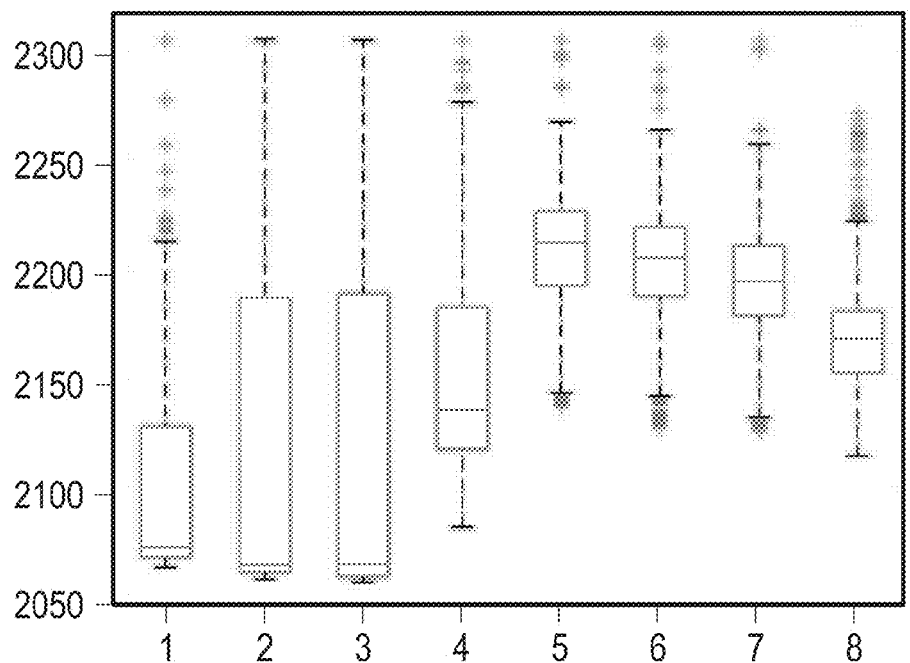

FIG. 47B Continued
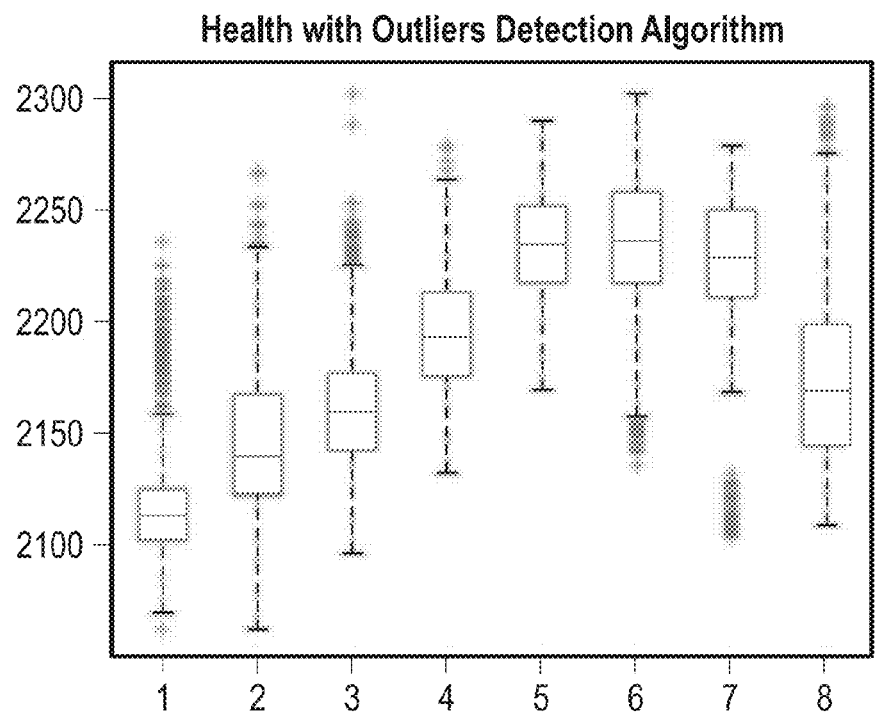
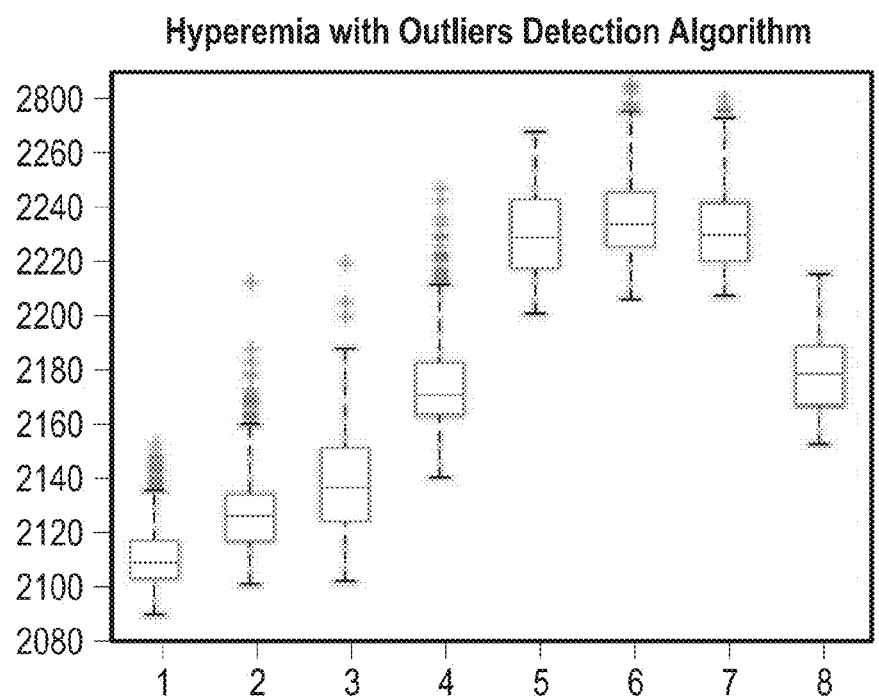

FIG. 47B Continued
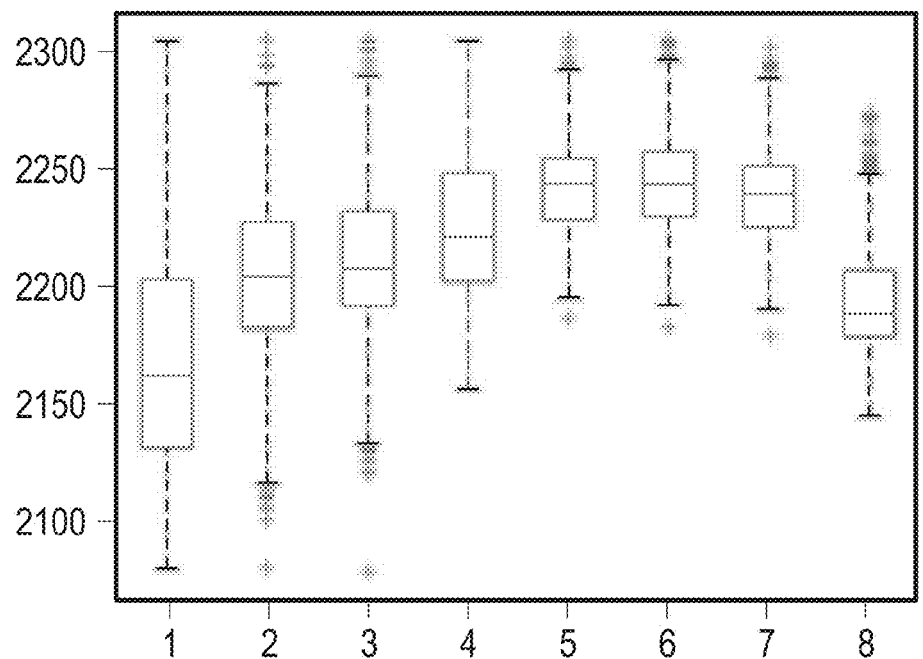
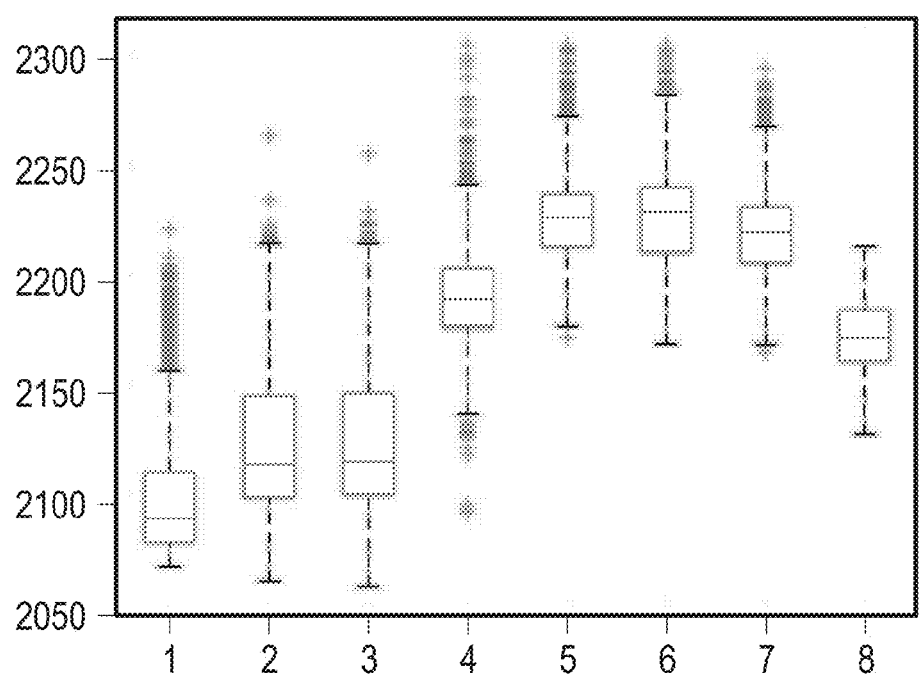

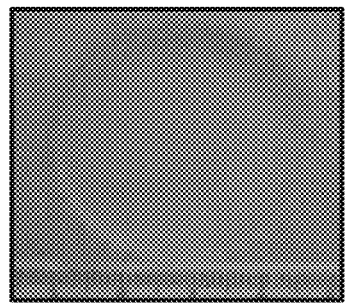
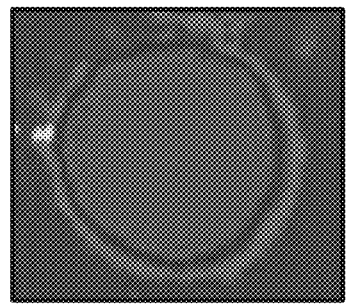
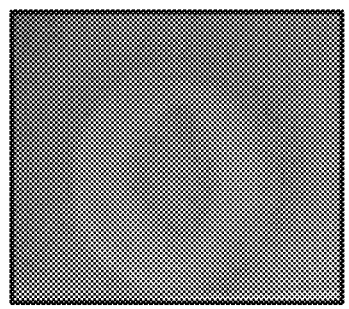
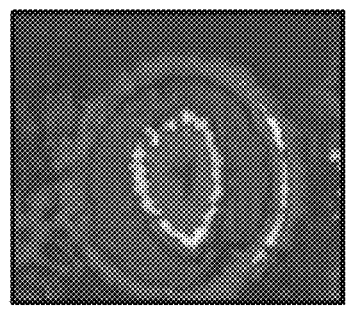
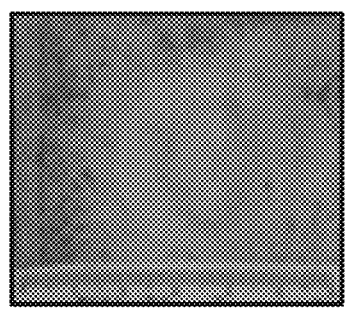
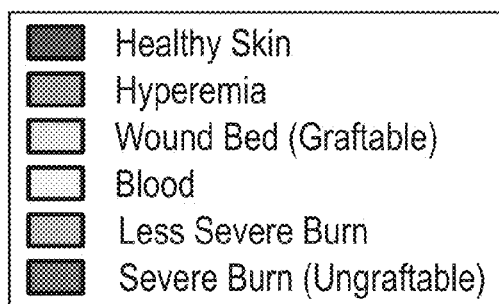
FIG. 54

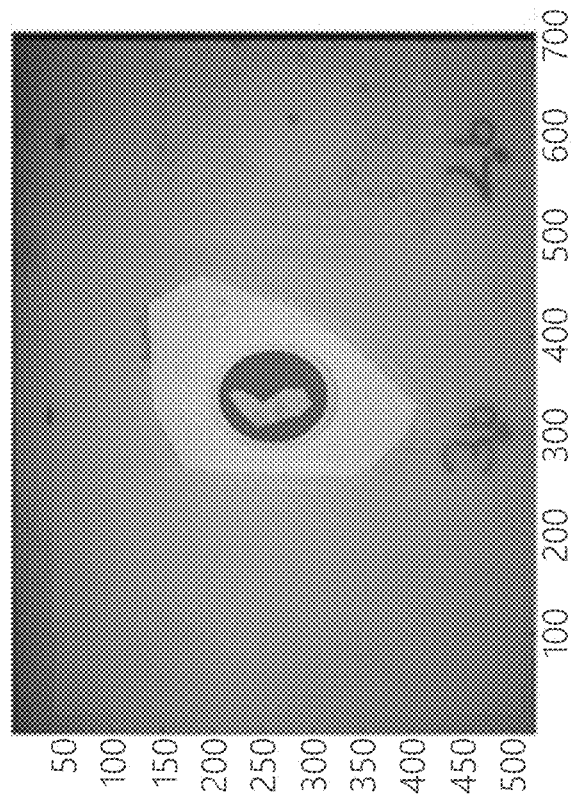
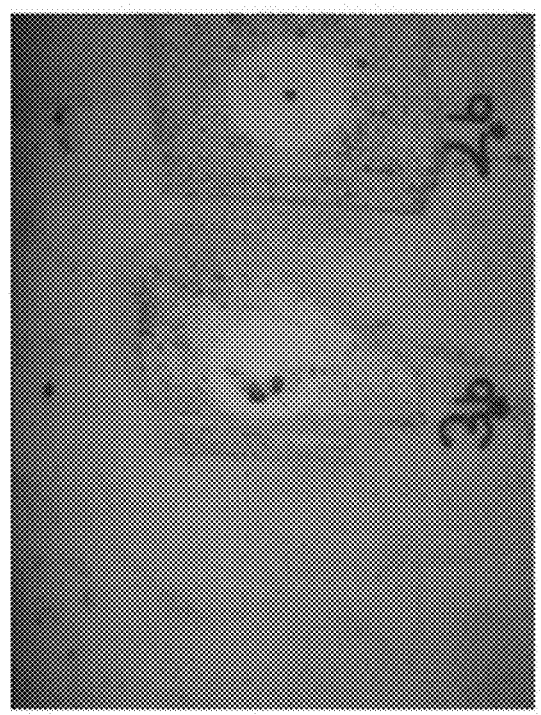
FIG. 67A
FIG. 67B

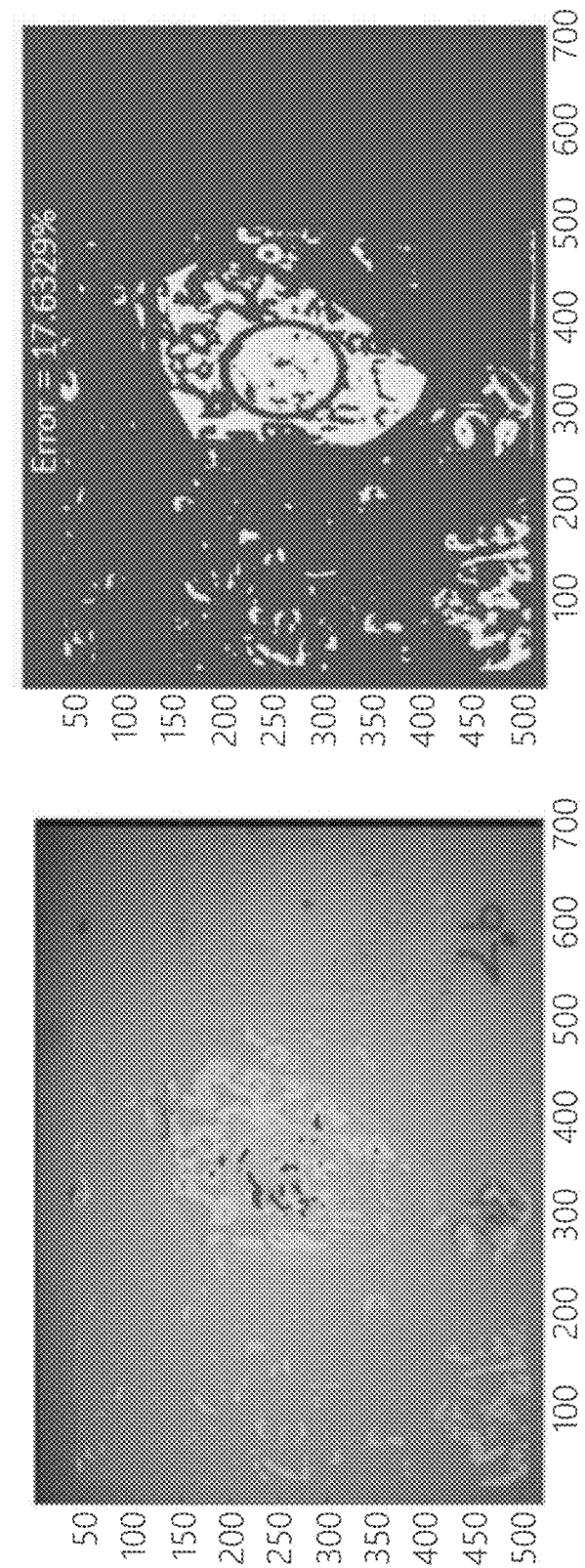

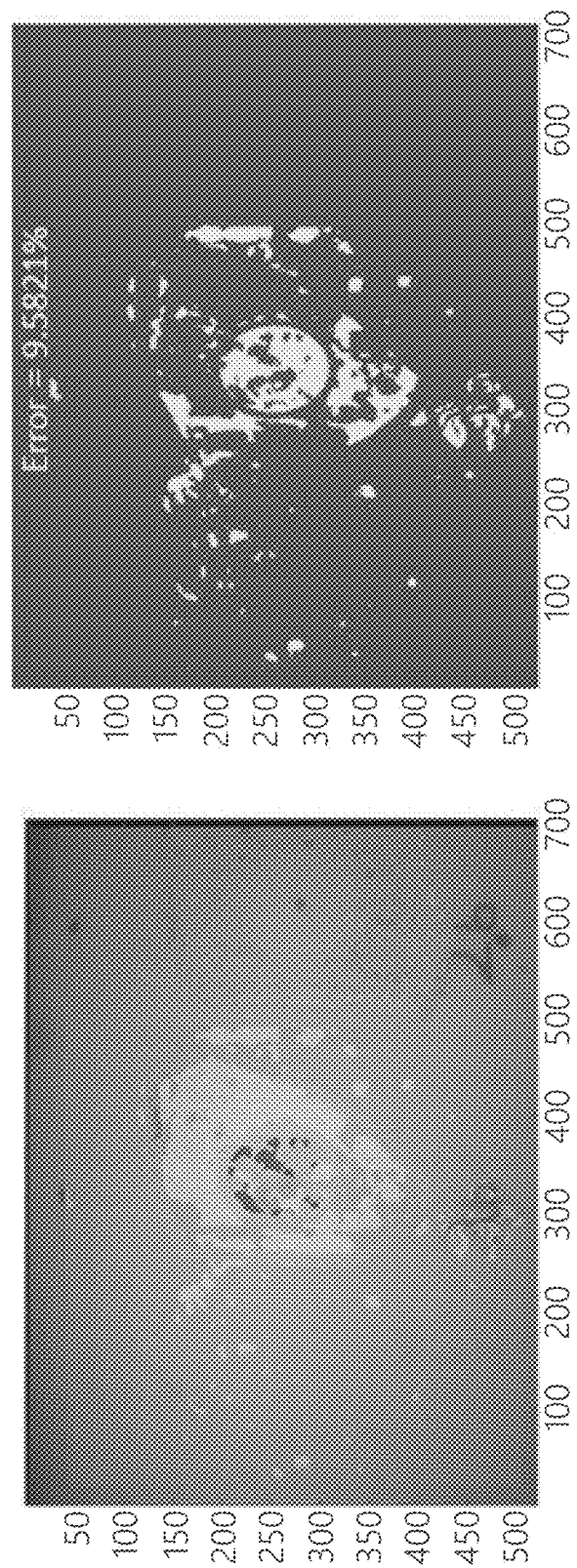

|  | | GT | | | |
|---|---|---|---|---|---|
|  | | Healthy | Excised | Shallow Burn | Burned |
| Decided | Healthy | R=0.9874<br>r=0.9945<br>C=0.8381<br>e=-0.0070 | R=0.0329<br>r=0.0053<br>C=0.0045<br>e=0.0275 | R=0.0142<br>r=0.0000<br>C=0.0000<br>e=0.0142 | R=0.0102<br>r=0.0001<br>C=0.0001<br>e=0.0100 |
| | Excised | R=0.0123<br>r=0.0734<br>C=0.0104<br>e=-0.0611 | R=0.9494<br>r=0.9139<br>C=0.1301<br>e=0.0355 | R=0.2987<br>r=0.0056<br>C=0.0008<br>e=0.2931 | R=0.0875<br>r=0.0071<br>C=0.0010<br>e=0.0804 |
| | Shallow Burn | R=0.0000<br>r=0.0016<br>C=0.0000<br>e=-0.0016 | R=0.0143<br>r=0.5628<br>C=0.0020<br>e=-0.5485 | R=0.4753<br>r=0.3661<br>C=0.0013<br>e=0.1092 | R=0.0211<br>r=0.0696<br>C=0.0002<br>e=-0.0485 |
| | Burned | R=0.0003<br>r=0.0194<br>C=0.0002<br>e=-0.0191 | R=0.0034<br>r=0.0409<br>C=0.0005<br>e=-0.0375 | R=0.2118<br>r=0.0499<br>C=0.0006<br>e=0.1619 | R=0.8812<br>r=0.8898<br>C=0.0101<br>e=-0.0086 |

FIG. 68

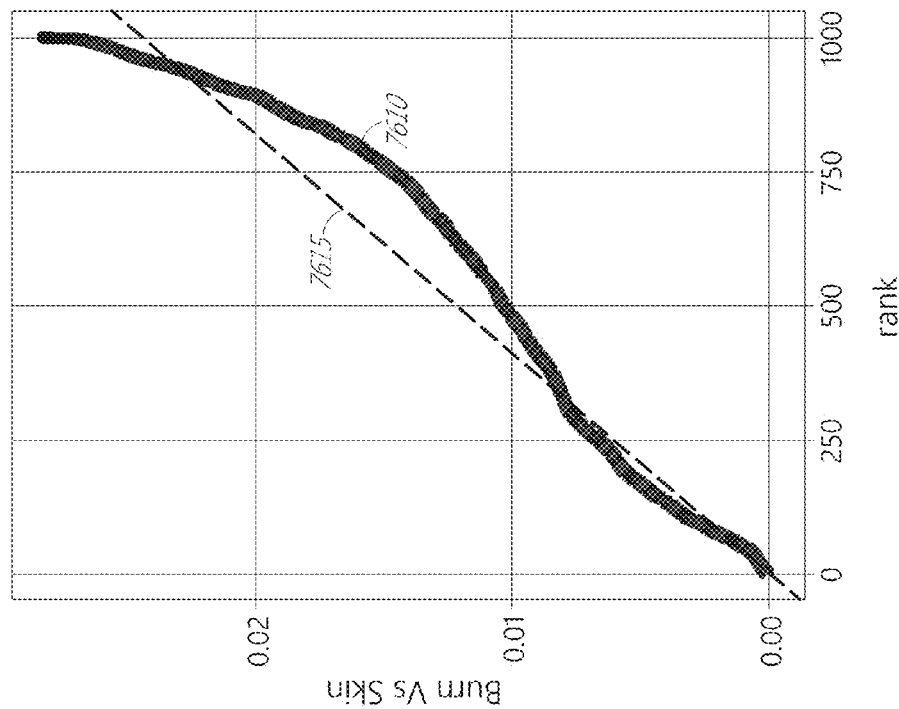
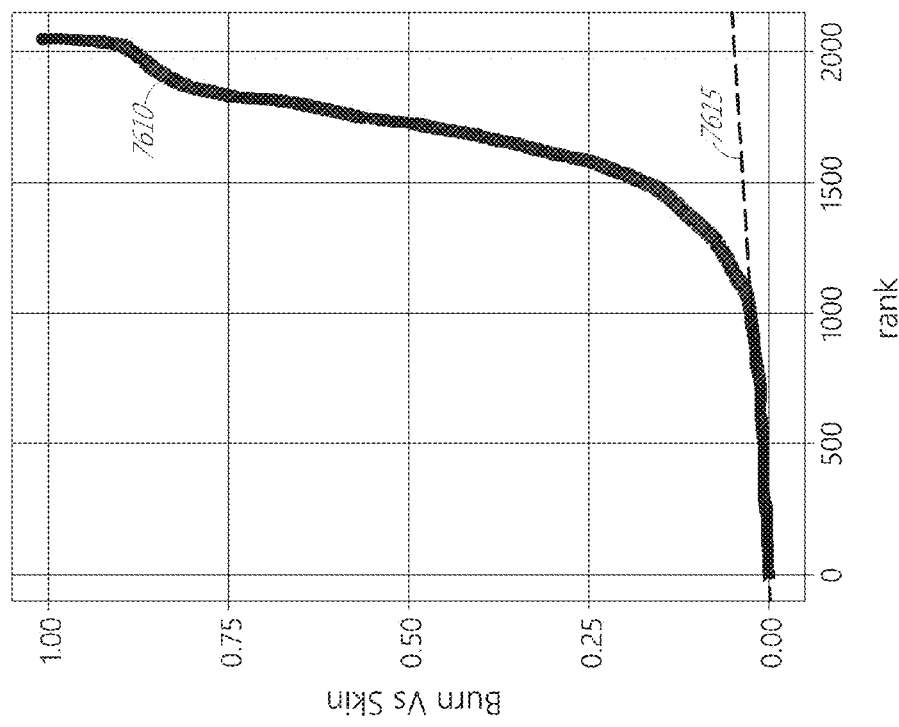

US 9,962,090 B2

REFLECTIVE MODE MULTI-SPECTRAL TIME-RESOLVED OPTICAL IMAGING METHODS AND APPARATUSES FOR TISSUE CLASSIFICATION

CROSS-REFERENCE TO RELATED APPLICATIONS

This application is a continuation of U.S. application Ser. No. 15/367,087, filed Dec. 1, 2016, which is a continuation of International Application No. PCT/US2016/029864, filed on Apr. 28, 2016, designating the United States of America and published in the English language, which claims the benefit of priority to U.S. Provisional Application No. 62/297,565, filed on Feb. 19, 2016. International Application No. PCT/US2016/029864 is a continuation-in-part of and claims the benefit of priority to International Application No. PCT/US2015/057882, filed on Oct. 28, 2015, designating the United States of America and published in the English language, which claims the benefit of priority to U.S. Provisional Application No. 62/214,885, filed on Sep. 4, 2015, U.S. Provisional Application No. 62/136,398, filed on Mar. 20, 2015, U.S. Provisional Application No. 62/115,536, filed on Feb. 12, 2015, U.S. Provisional Application No. 62/114,027, filed on Feb. 9, 2015, U.S. Provisional Application No. 62/112,348, filed on Feb. 5, 2015, and U.S. Provisional Application No. 62/072,177, filed on Oct. 29, 2014. The disclosures of the aforementioned applications are hereby expressly incorporated by reference in their entireties.

STATEMENT REGARDING FEDERALLY SPONSORED R&D

Some of the work described in this disclosure was made with United States Government support under Contract No. HHSO100201300022C, awarded by the Biomedical Advanced Research and Development Authority (BARDA), within the Office of the Assistant Secretary for Preparedness and Response in the U.S. Department of Health and Human Services. The United States Government may have certain rights in this invention.

TECHNICAL FIELD

The systems and methods disclosed herein are directed to non-invasive clinical imaging, and, more particularly, to noninvasive imaging of subdermal bloodflow, diffuse reflectance spectroscopy, and computer-aided diagnosis.

BACKGROUND

Optical imaging is an emerging technology with potential for improving disease prevention, diagnosis, and treatment in the medical office, at the bedside, or in the operating room. Optical imaging technologies can noninvasively differentiate among soft tissues, and between native soft tissues and tissue labeled with either endogenous or exogenous contrast media, using their different photon absorption or scattering profiles at different wavelengths. Such photon absorption and scattering differences offers potential for providing specific tissue contrasts, and enables studying functional and molecular level activities that are the basis for health and disease.

SUMMARY

Tissue Classification for Burn Assessment

Aspects of the invention described herein relate to devices and methods that can be used to classify a tissue using optical imaging. There has been a long felt need for non-invasive imaging techniques that can classify injured tissue, especially technology that can facilitate the rapid triage and assessment of the severity of wounds, and to monitor the progress of the healing process before, during and/or after a treatment process is initiated. One example of such a need is the desire for better imaging technology, which can be used to triage and assess the severity of burns, for example in routine burn care and/or mass-casualty burn care.

To illustrate the need for better imaging technology with respect to the example of mass-casualty burn care, consider the following. There are currently only 250 burn specialists in the United States and 1800 burn beds across the United States. These burn facilities are presently operating at 95% capacity. Any sudden increase in the number of burn patients will require immediate identification and prioritization of patients that need the attention of a burn specialist. Additionally, physicians that are not burn specialists will need to address patient needs should a catastrophic event take place. For instance, there may be sudden and rapid increases in the number of patients requiring burn treatment when there is a nuclear emergency, forest fire, or large scale pyrotechnic accident. Because of the difficulty in assessing burns even for burn specialists and the subjective nature of such assessments, which is the current state of the art, the need is manifest for devices that allow burn specialists and physicians who are not burn specialists to quickly identify or classify patients that need immediate emergency procedures and/or the care of a burn specialist. In an event of a mass casualty scenario, as many as 10,000 patients could require thermal burn care. With the limited number of specialist surgeons and burn centers in the U.S., there is a public health need for a burn wound therapy that can be quickly and broadly applied by non-specialist medical personnel following such an event in addition to burns, there are many other needs in the field for methods and devices that can rapidly classify and distinguish damaged and non-damaged tissues.

The standard of care for burn wounds begins with the use of visual and tactile cues to estimate burn depth. After the burn is classified according to its depth, an effective treatment plan can be designed. Typically, the classification of superficial and full thickness burns can be made upon presentation, but the classification of partial thickness burns as "superficial" or "deep" is often delayed. This prolongation occurs because of an inability to visualize the full extent of dermal damage until the partial burn has had time to progress.

It is important to classify partial burn depths quickly and accurately for several reasons. First, treatment protocols vary significantly between superficial versus deep partial thickness burns. Superficial partial burns require only topical salves and heal spontaneously over 7-21 days, while deep partial thickness burns must be surgically excised and auto-grafted from a donor skin site. Second, it is important to assess whether a burn requires surgical intervention as early as possible to minimize scarring and bacterial colonization of the wounds. The delayed intervention associated with classifying partial thickness burns has been shown to increase the risk of infection, metabolic distortions, and organ-failure. Moreover, it has been recently demonstrated that burn progression does not increase with delayed excision time. Finally, multi-region burns are common and will typically contain an amalgamation of burn depths. Excision and grafting of complicated burns require expert planning and careful differential excision to ensure optimal therapy of the entire burn area.

With only 250 burn specialists and 1,800 designated burn beds (operating at 95% capacity) in United States hospitals, burn care resources are scarce. Thus, the first line of care for burn patients is often non-specialists whose lack of experience in burn therapy leads to delayed and non-optimal treatment, increasing the rate of complications. Currently, the accuracy of clinical burn depth diagnosis by experts is estimated to be 70-80%, but non-specialists are just 60% accurate.

The most salient potential solutions to improve burn depth estimation include fluorescent dyes, high frequency ultrasound, nuclear imaging (MRI), photography, thermography, and Laser Doppler Imaging (LDI). Laser Doppler imaging is the only technology with a US FDA clearance that includes the diagnosis of burn wound beds. It is non-invasive, shown to be effective in wound assessment, and currently available to burn specialists. Despite its availability, it is used sparingly and mainly in major burn centers. The most cited disadvantages (requirements for a completely bare wound, motionless patient, and a 48-hour delay after the injury) result in low usability in the clinical setting. Acquisition times are also quite slow. Thermography, like LDI, is non-invasive and non-contact, but requires the patient to undergo 15-minute temperature equilibrium in a thermostatic room, and is currently not appropriate for classifying burn depth. Color photography use in burn assessment is often difficult because they offer nothing more than what the human eye can already perceive and would require a burn surgeon to interpret images. Intravascular dyes such as indocyanin green (ICG) provide information about blood flow in tissues. This technique has been explored in burns and can be used to identify regions of high or low blood perfusion in a burn. This technology is invasive, requires injection of dye for each image acquisition attempt, and some surgeries require multiple injections depending on the number of images desired, which can be expensive and time-consuming.

Notably, another potential solution, Multispectral Imaging (MSI), measures the reflectance of select wavelengths of visible and near-infrared light from the surface of a burn. Various tissue types consist of a unique combination of tissue components that interact with light differently. These light-tissue interactions produce unique reflectance signatures captured by MSI that can be used to classify burn severity. MSI is also able to assess tissue through topical wound ointments and wrappings as well as tolerate minor patient movement. These characteristics make MSI an attractive solution.

MSI has been previously tested in clinical environments, with the earliest results obtained by Anselmo et al in 1977 and Afromitz et al in 1988. These experiments were successful in classifying different burn depths, but the time necessary to complete each acquisition was on the order of days to weeks. With improvements in imaging technology and computer processing capability over the last several decades, we are better positioned to perform MSI techniques routinely as part of a patient exam or surgery.

The accuracy of MSI technology depends on the identification of valuable wavelengths to employ in clinical devices. Here, we employ a porcine burn model to test the ability of MSI, with various wavelengths, to investigate partial thickness burns at the initial injury site and during surgical debridement (also known as burn excision) procedures. The selected wavelengths account for the absorption peaks of the major components of dermal tissue (blood, melanin, water, fat, and extracellular matrix ("ECM")) and have been suggested to be capable of classifying burns by previous clinical studies, as discussed in the Theory section of the present disclosure. The clinical usefulness of a wavelength was verified by histopathological assessment of the same specimens.

Optical imaging technology provides a non-contact and quick method for assessment at or near the surface of a tissue. The study of tissue blood perfusion can be achieved using optical methods, because hemoglobin in the blood is a significant source of optical absorption in the tissue. These blood born chromophores present in the subcutaneous and superficial tissue have optical parameters (mainly absorptive), which contrast to the surrounding tissue. A time-varying signal related to blood tissue perfusion, the photoplethysmography (PPG) signal, arises from a special characteristic of blood flow in the tissue. The blood, which contains the cells that carry hemoglobin, flowing in the tissue through vessels demonstrate periodic changes in volume with every cardiac cycle. The consequent dynamic changes of the blood volume are utilized to assess tissue health including relative blood perfusion, cardiac function, and peripheral vascular health. This spectral optical imaging technique, PPG imaging, provides the ability to monitor blood perfusion through the superficial surfaces of the tissue.

Non-contact, reflectance mode PPG imaging is achieved by analysis of the backscattered light from a perfused tissue. When light incident on the tissue, a portion of that light scatters within the tissue, then interacts with the chromophores in the blood, and eventually is scattered back through the tissue surface. When observed over time, this light-tissue interaction superimposes a weak AC modulation that is approximately 1-2% compared to the total amount of light reflected from the tissue. The small AC signal of this back-scattered light can be analyzed to obtain information regarding the position, relative blood volume, and relative blood concentration of the arterial circulation. Images generated from this information provide a method to assess pathologies involving changes to tissue blood flow and pulse rate including: tissue perfusion; cardiovascular health; wounds such as ulcers; peripheral arterial disease, and respiratory health.

Optical imaging techniques that provide a reliable, low-cost, and portable measurement of tissue blood perfusion would be of high value to the medical community. PPG imaging is one such technology that has application in burn and chronic wound care. We are particularly interested in burns, because this technology is expected to provide burn patient assessment without the need for disposable or sterile body-contacting devices.

Non-contact PPG imaging normally uses near-infrared (NIR) wavelengths as illumination source to take advantage of the increased photon penetration into the tissue at this wavelength. A common setup includes positioning the light source near the target tissue to be imaged. Owing to the banana-shaped pathway of light through the tissue, PPG signals can be collected in the dark area of the image. This usually requires high dynamic range and low-light sensitive sensors (usually scientific CMOS or CCD camera) to detect the PPG signal emitted from the non-illuminated regions of the image. In this disclosure, we explore the variables of illumination pattern and intensity on the received PPG signal and hypothesized that the PPG signal strength can be enhanced by higher and more even illumination of the imager's entire field-of-view (FOV).

For example, in experiments described in this disclosure, we developed an optical PPG prototype system, which utilizes a spatially even and DC-modulated illumination light source. We describe the rationale of even illumination, assess the PPG imaging performance, and compare the performance with other types of light sources. We calibrated an evaluation imaging system through a bench-top tissue phantom with tissue-like optical properties, and conducted animal models experiment. We demonstrated that the utilization of even illumination for PPG imaging improves performance in imaging superficial blood vessels in an animal burn model.

In some alternatives described in this disclosure, we present non-contact, reflective photoplethysmogram (PPG) imaging methods and systems that may be used for identifying the presence of dermal burn wounds during a burn debridement surgery. These methods and systems may provide assistance to clinicians and surgeons in the process of dermal wound management, such as burn excision, and wound triage decisions. In some experiments, we examined the system variables of illumination uniformity and intensity and present our findings. An LED array, a tungsten light source, and eventually high-power LED emitters were studied as illumination methods for our PPG imaging device. These three different illumination sources were tested in a controlled tissue phantom model and an animal burn model. We found that the low heat and even illumination pattern using high power LED emitters provided a substantial improvement to the collected PPG signal in our animal burn model. These improvements allowed the PPG signal from different pixels to be comparable in both time-domain and frequency-domain, simplify the illumination subsystem complexity, and diminished the desirability of using high dynamic range cameras. Through the burn model output comparison, such as the blood volume in animal burn data and controlled tissue phantom model, our optical improvements have led to more clinically applicable images to aid in burn assessment.

Alternatives described herein can be used to identify and/or classify the severity of decubitus ulcers, hyperaemia, limb deterioration, Raynaud's Phenomenon, chronic wounds, abrasions, lacerations, hemorrhaging, rupture injuries, punctures, penetrating wounds, cancer, or any type of tissue change, wherein the nature and quality of the tissue differs from a normal state. The devices described herein may also be used to monitor healthy tissue, facilitate and improve wound treatment procedures, for example allowing for a faster and more refined approach for determining the margin for debridement, and evaluate the progress of recovery from a wound or disease, especially after a treatment has been applied. In some alternatives described herein, devices are provided that allow for the identification of healthy tissue adjacent to wounded tissue, the determination of an excision margin, the monitoring of the recovery process after implantation of a prosthetic, such as a left ventricular assist device, the evaluation of the viability of a tissue graft or regenerative cell implant, or the monitoring of surgical recovery, especially after reconstructive procedures. Moreover, alternatives described herein may be used to evaluate the change in a wound or the generation of healthy tissue after a wound, in particular, after introduction of a therapeutic agent, such as a steroid, hepatocyte growth factor, fibroblast growth factor, an antibiotic, or regenerative cells, such as an isolated or concentrated cell population that comprises stem cells, endothelial cells and/or endothelial precursor cells.

Alternatives in this disclosure present two optical imaging techniques that can be achieved with the same system hardware: PPG Imaging and MSI. These two modalities complement each other in the type of tissue properties they assess. For example, PPG imaging measures the intensity of arterial blood flow just below the surface of the skin to differentiate between viable and non-viable tissues. MSI analyzes the various wavelengths of light absorbed and reflected by tissues to classify tissue by comparing its investigated reflectance spectra to an established library of known reflectance spectra.

PPG imaging may use similar technology as that used in pulse oximetry to capture vital signs including: heart rate, respiratory rate, and $SpO_2$. The PPG signal may be generated by measuring light's interaction with dynamic changes in the vascularized tissues. Vascularized tissue expands and contracts in volume by approximately 1-2% with each incoming systolic blood pressure wave at the frequency of the cardiac cycle. This influx of blood not only increases the volume of the tissue, but it also brings additional hemoglobin proteins that strongly absorb light. Therefore, the absorbance of light within the tissue oscillates with each heartbeat. Changes in tissue blood flow can thereby be identified by analyzing the plethysmogram generated by recording how light is absorbed as it travels through tissue. This information is then translated into the vital signs reported by pulse oximeters.

In some cases, in order to generate images from the plethysmogram, we take advantage of the light's pathway through the tissues. A small portion of light incident on the tissue surface scatters into the tissue. A fraction of this scattered light exits the tissue from the same surface it initially entered. Using a sensitive digital camera, this backscattered light is collected across an area of tissue so that each pixel in the imager contains a unique PPG waveform determined by changes in intensity of the scattered light. To generate a 2-D map of relative tissue blood flow, the amplitude of each unique waveform is measured. To improve accuracy, we can measure the average amplitude over many heart beat samples.

MSI may measure the reflectance of select wavelengths of visible and near-infrared light from a surface. MSI is applicable to burns because various tissue types, including both viable and necrotic tissue, may consist of a unique combination of tissue components that interact with light differently. These varied light-tissue interactions produce unique reflectance signatures that are captured by MSI. Spectral signatures can be collected from a patient's burn and compared to a database of known spectral signatures to characterize the patient's burn. While MSI may in some cases have lower number of unique wavelengths to describe the tissue compared to newer hyperspectral imagers, the use of MSI may have advantages in spatial resolution, spectral range, image acquisition speed, and cost are considered. Spectral identification of burn severity has been proposed as a means to supplement clinical observation during initial patient assessment as early as the 1970's. The feasibility of identifying burn severity by studying unique optical reflectance properties of burns of differing depth was demonstrated in 1977 using a NASA developed camera equipped with interchangeable filters. Other groups also achieved some success in applying this technology to characterize burn tissues. They showed MSI was capable of improved determination of burn depth as compared to clinical judgment, but also reported MSI was limited in clinical applications by technical difficulties such as the need to filter increasingly bright spectral reflection from the moisture on the skin's surface. Most importantly, MSI required data acquisition times on the order of days when this technology was initially developed because of severe limitation in data processing that engineers no longer face today given modern computing technology.

Tissue Classification for Amputation

Approximately 185,000 lower extremity amputations occur every year in the US, and over 2 million American adults are amputees. The most significant risk factor for amputation is peripheral artery disease (PAD), with or without diabetes mellitus (DM), which accounts for well over half of all amputations, termed dysvascular amputations. Patients with DM have a 10-fold increased risk for lower extremity amputation over the general population, with over 60,000 amputations occurring annually for diabetic lower-extremity ulcers. Approximately 30 people per 100,000 individuals per year require amputation secondary to dysvascular disease, and due to the aging population of the US, this incidence is expected to increase by 50% over the next decade.

The costs, fiscal and otherwise, of limb amputation on the US healthcare system annually are immense. In one study of the Veterans Affairs (VA) system alone, the cost burden associated with diabetes-related limb loss was over $200 million ($60,647/patient) in a single year (FY2010). The hospital-associated costs for all lower extremity limb amputation in the US cost totaled $8.3 billion in FY2009, with the lifetime cost of a major amputation, including rehabilitation and prosthetics costs, approximately $500,000/patient. In addition to the heavy fiscal burden of limb amputations, patients experience significant morbidities and reduction in quality of life as a result of their amputations. Most importantly, the functional status of these patients is challenged, with only 25% of major lower extremity dysvascular amputees able to ambulate with a prosthetic outside of their home. With progressively proximal levels of amputation, likelihood of successful rehabilitation to ambulatory status decreases due to the increased energy cost associated with increasing tissue loss.

Despite the obvious preference to salvage as much limb tissue as possible during amputation, surgeons must balance against the likelihood of primary wound healing at a given level of amputation (LOA), which decreases with more distal amputations. Selection of appropriate LOA is determined primarily by clinical judgment of the surgeon (using patient history and physical exam, including color, temperature, peripheral pulses, and wound bleeding during procedure with knowledge of clinical factors such as diabetes, smoking, nutrition, etc.), possibly in conjunction with a variety of non-invasive tests designed to quantitate tissue blood flow and/or oxygenation (ankle-brachial index [ABI], transcutaneous oxygen measurement [TCOM], or skin perfusion pressure [SPP]). However, only half of patients undergoing lower extremity amputations are evaluated with the most commonly used test (ABI) despite recommendations for this practice by the current guidelines. Moreover, one study demonstrated that up to 50% of patients with a palpable pulse at the dorsalis pedis and 30% of patients with normal ABIs required reamputation after primary forefoot amputation anyway. In the same study, nearly 50% of patients who received concurrent revascularization required reamputation as well, despite the extra effort to revascularize the distal extremity. Although TCOM initially showed promise in identifying likelihood of primary wound healing after amputation, controversy still remains regarding its utility because no sufficiently large, powered studies have been completed to define TCOM's role in clinical practice. Moreover, TCOM measurements are affected by physiologic conditions such as temperature, and TCOM electrodes are only able to analyze a small area of skin. Thus, TCOM has not been adopted into routine clinical practice even though this technology been available for decades.

Given the challenging balance between maximizing tissue preservation and minimizing risk for non-healing primary wounds as well as a primary reliance on clinical judgment to determine the appropriate LOA, reported rates of re-amputation are in no way optimal. Re-amputation rates vary depending on initial level of amputation, from approximately 10% of above-the-knee (AKA) amputations to 35% of amputations at the foot requiring eventual revision to a more proximal level. Limited data capturing the direct costs of re-amputation are currently available, but clearly a significant portion of the billions of dollars spent annually on care associated with dysvascular amputation is accounted for by costs associated with amputation revision, hospital readmission, and essentially wasted wound care efforts between the index procedure and revision. Delayed and failed primary healing expose patients to increased risks, including infection, for morbidity and mortality. Moreover, delayed and failed primary wound healing after the index amputation procedure severely impacts patient quality of life. Patients requiring amputation revision are delayed to physical rehabilitation and in acquiring prosthetics to allow for a return to ambulatory status. These patients also have increased contact with the healthcare system and often undergo additional wound care therapy prior to revision, efforts that could have been avoided with proper initial selection of LOA. Finally, although rates of re-amputation are abundantly reported, no investigations have been published regarding how often physician awareness of the risk for re-amputation leads to overly aggressive selection of LOA to more proximal levels. Indeed, it is feasible that certain patients may receive amputations at a level more proximal to that which is necessary because their surgeon could not confidently predict a high likelihood of healing at the more distal level. A test to guide decision-making regarding LOA therefore has the potential to reduce rates of re-amputation as well as to spare tissue for patients facing major amputations.

However, there are currently no gold-standard tests to determine the healing capacity of the primary wound after amputation in patients with dysvascular disease. Many have attempted to find such a gold-standard by local evaluation of the tissue microcirculation alone. Several instruments that are known to accurately determine the perfusion and oxygenation of the skin tissue have been tested in this setting, including TCOM, SPP, and laser Doppler. Yet, microcirculation assessment alone has not resulted in a sufficiently accurate assessment of tissue healing capacity to replace clinical judgment when selecting LOA. Therefore, characterizing the local perfusion and oxygenation of the skin is clearly not enough information to quantify the healing potential of the tissue. What these technologies have all failed to include in their prognostics are the systemic effects of comorbidities that also impact wound healing potential. In fact, nearly two decades ago, one author concluded, regarding selection of appropriate level of amputation in a review of factors affecting wound healing after major dysvascular amputation that, "there will be no 'golden standard test' to predict the likelihood of healing after a major amputation, since it is not only the tissue blood flow that is related to wound healing. All other factors mentioned in this review [smoking, nutrition, diabetes mellitus, and infection] may also be of importance. The combination of clinical judgment and various tests therefore will be the commonest approach." Despite this author's prediction, Spectral MD has developed an imaging device with the capability to integrate information gleaned from objective tests characterizing the physiology of tissue blood flow with important patient health metrics. The aforementioned problems, among others, are addressed in some embodiments by the Machine Learning Algorithm of the present disclosure that combines optical microcirculatory assessment with overall patient health metrics to generate prognostic information. Using this method, our device can provide a quantitative assessment of wound healing potential whereas the current clinical practice standards are only capable of qualitative assessment.

Accordingly, one aspect relates to an imaging system, comprising one or more light sources configured to illuminate a first tissue region; one or more image acquisition devices configured to receive light reflected from a second tissue region; one or more controllers configured to control the one or more light sources and the one or more image acquisition devices to acquire a plurality of images corresponding to both different times and different frequency bands; and a processor configured to analyze areas of the second tissue region according to one or more clinical states based at least in part on the plurality of images.

Another aspect relates to a method, comprising illuminating a first tissue region with one or more light sources; receiving light reflected from a second tissue region with one or more image acquisition devices; acquiring a plurality of images of the second tissue region corresponding to different times and different frequency bands; and classifying areas of the second tissue region based at least in part on the plurality of images.

Another aspect relates to an imaging system, comprising one or more light sources configured to illuminate a first tissue region; one or more image acquisition devices configured to receive light reflected from a second tissue region; a means for acquiring a plurality of images of the second tissue region corresponding to different times and different frequency bands; and a means for classifying areas of the second tissue region based on the plurality of images.

Another aspect relates to a method of inducing the healing of a wound or ameliorating wound repair comprising (a) acquiring a plurality of images of a first and a second tissue region corresponding to different times and different frequency bands, such as by utilizing any system disclosed herein, wherein the second tissue region comprises at least a portion of a wound and the first tissue region comprises healthy tissue; (b) classifying areas of the second tissue region based on the plurality of images acquired in (a); and (c) providing one or both of a therapeutic agent and therapeutic technique to at least a portion of the wound so as to induce the healing of the wound.

Another aspect relates to a method of monitoring the healing of a wound or wound repair comprising (a) acquiring a plurality of images of a first and a second tissue region corresponding to different times and different frequency bands, such as by utilizing the system of any system disclosed herein, wherein the second tissue region comprises at least a portion of a wound and the first tissue region comprises healthy tissue; (b) classifying areas of the second tissue region based on the plurality of images acquired in (a); (c) providing a therapeutic agent to at least a portion of the wound so as to induce the healing of the wound; and (d) repeating at least (a) and (b) after performing (c).

Another aspect relates to a method of classifying a wound comprising (a) acquiring a plurality of images of a first and a second tissue region corresponding to different times and different frequency bands, such as by utilizing any system disclosed herein, wherein the second tissue region comprises at least a portion of a wound and the first tissue region comprises healthy tissue; and (b) classifying areas of the second tissue region based on the plurality of images acquired in (a).

Another aspect relates to a method of debriding a wound comprising (a) acquiring a plurality of images of a first and a second tissue region corresponding to different times and different frequency bands, such as by utilizing the system of any system disclosed herein, wherein the second tissue region comprises at least a portion of a wound and the first tissue region comprises healthy tissue; (b) determining a margin for debridement, such as a region proximal to the interface of healthy tissue and necrotic tissue of the wound based on the plurality of images acquired in (a); and (c) debriding the wound within the margin for debridement.

Another aspect relates to a method of identifying a chronic wound, comprising (a) acquiring a plurality of images of a first and a second tissue region corresponding to different times and different frequency bands, such as by utilizing the system of any system disclosed herein, wherein the second tissue region comprises at least a portion of a wound and the first tissue region comprises healthy tissue; and (b) classifying areas of the second tissue region based on the plurality of images acquired in (a) as areas representative of a chronic wound.

Another aspect relates to a method of assessing burn severity comprising positioning a subject approximate to a light source and an image acquisition device; illuminating a first tissue region of the subject using the light source; acquiring a plurality of images of a second tissue region using the image acquisition device; classifying a burn status of areas of the second tissue region based at least in part on the plurality of images acquired with the image acquisition device; and calculating an estimate of a percentage of total burned body surface area of the subject based at least in part on the classifying.

Another aspect relates to an apparatus for assessing burn severity of a subject comprising one or more light sources configured to illuminate a first tissue region; one or more image acquisition devices configured to receive light reflected from a second tissue region; one or more controllers configured to control the one or more light sources and the one or more image acquisition devices to acquire a plurality of images of a second tissue region; and a processor configured to classify a burn status of areas of the second tissue region based on the plurality of images and calculate an estimate of a percentage of total burned body surface area of the subject based on a classification of the burn status.

Another aspect relates to a method for storing and updating data, the method comprising under control of a Program Execution Service (PES) that includes a number of data centers, each data center including one or more physical computing systems configurable to execute one or more virtual desktop instances, each virtual desktop instance associated with a computing environment that includes an operating system configurable to execute one or more applications, each virtual desktop instance accessible by a computing device of a user of the PES via a network: forming a bi-directional connection between the PES and a first computing device of a user; receiving from the first computing device a request to synchronize a dynamic library containing data on a tissue condition on the PES; accessing file metadata, the metadata indicating whether the dynamic library is to be synchronized with one or more computing devices; determining based at least in part on the file metadata, whether the dynamic library is to be synchronized with the first computing device; and in response to determining that the dynamic library is to be synchronized with the first computing device, synchronizing the dynamic library with the first computing device using the bi-directional connection, wherein the synchronized dynamic library is stored locally on the first computing device and is accessible without the bi-directional connection between the PES and the first computing device.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements. The patent or application file contains at least one drawing executed in color. Copies of this patent or patent application publication with color drawing(s) will be provided by the Office upon request and payment of the necessary fee.

FIG. 6 is an example chart showing the mortality rate by age group and burn size produced by the American Burn Association.

FIGS. 9A, 9B, 9C, and 9D are example images taken of tissue samples from adult mini-pigs, wherein the performance of MSI, PPG, and alternatives of this disclosure were compared.

FIG. 11 shows example images taken by some alternatives described herein showing a successful and unsuccessful tissue graft.

FIG. 12 shows example images taken of a decubitus ulcer, wherein an alternative described herein was used to image the decubitus ulcer in its early stages, and a normal camera was used to image the decubitus ulcer after it was visible on the skin's surface.

FIGS. 20A-20C illustrates imaging results of tissue phantom and pulsatile phantom vessel underneath using a LED spot light (FIG. 20A), a tungsten light (FIG. 20B), and a LED emitter (FIB. 20C).

FIG. 21 illustrates a relationship between the PPG signal's power spectral density in the pulsatile region of the tissue-like phantom and the percent of the maximum intensity of light from the LED emitter module below the imager's saturation point (irradiance 0.004 $W/m^2$).

FIGS. 23A-23F illustrate various images of illumination patterns and pig skin burn wound images taken under the illumination patterns.

FIG. 24 illustrates the location of burn injuries on dorsum of the pig.

FIG. 25 illustrates the dimensions of tissue in Block I (Left) and Block II (Right).

FIG. 33 shows a wound debridement procedure. During wound debridement procedures, the viable wound bed for grafting (a) may be exposed by removing necrotic tissue (b). The PPG imaging device detects the difference in relative blood flow between these two tissues to distinguish one from the other. Meanwhile, MSI technology can differentiate the tissues using the reflectance spectra determined by the molecular and structural difference between the wound bed (a) and necrotic burn tissue (b).

FIG. 42 illustrates a test set that was classified by a previously trained quadratic discriminant analysis algorithm and compared to their actual class labels to generate a confusion matrix. This matrix shows the number of correct classifications across the diagonal in the center of the matrix. Incorrect classifications are in the off-diagonal elements.

FIG. 45 illustrates example steps for revising a data-set used for training a tissue classification algorithm.

FIGS. 47A-47B illustrates example Boxplots: Six classes in different bands before outlier removal (FIG. 47A), and six classes in different bands after outlier removal (FIG. 47B).

FIG. 54 illustrates six example physiological classes implemented in the disclosed MSI assessment.

FIGS. 67A-67L illustrate example ground truth images, real images, and classification results five different classification techniques.

FIG. 68 illustrates a confusion matrix of an example cross-validation experiment.

FIGS. 76A and 76B illustrate P-values from a first dataset arranged in ascending order with an indication of a modified level of significance of the P-values.

DETAILED DESCRIPTION

Introduction

Figure 1A:
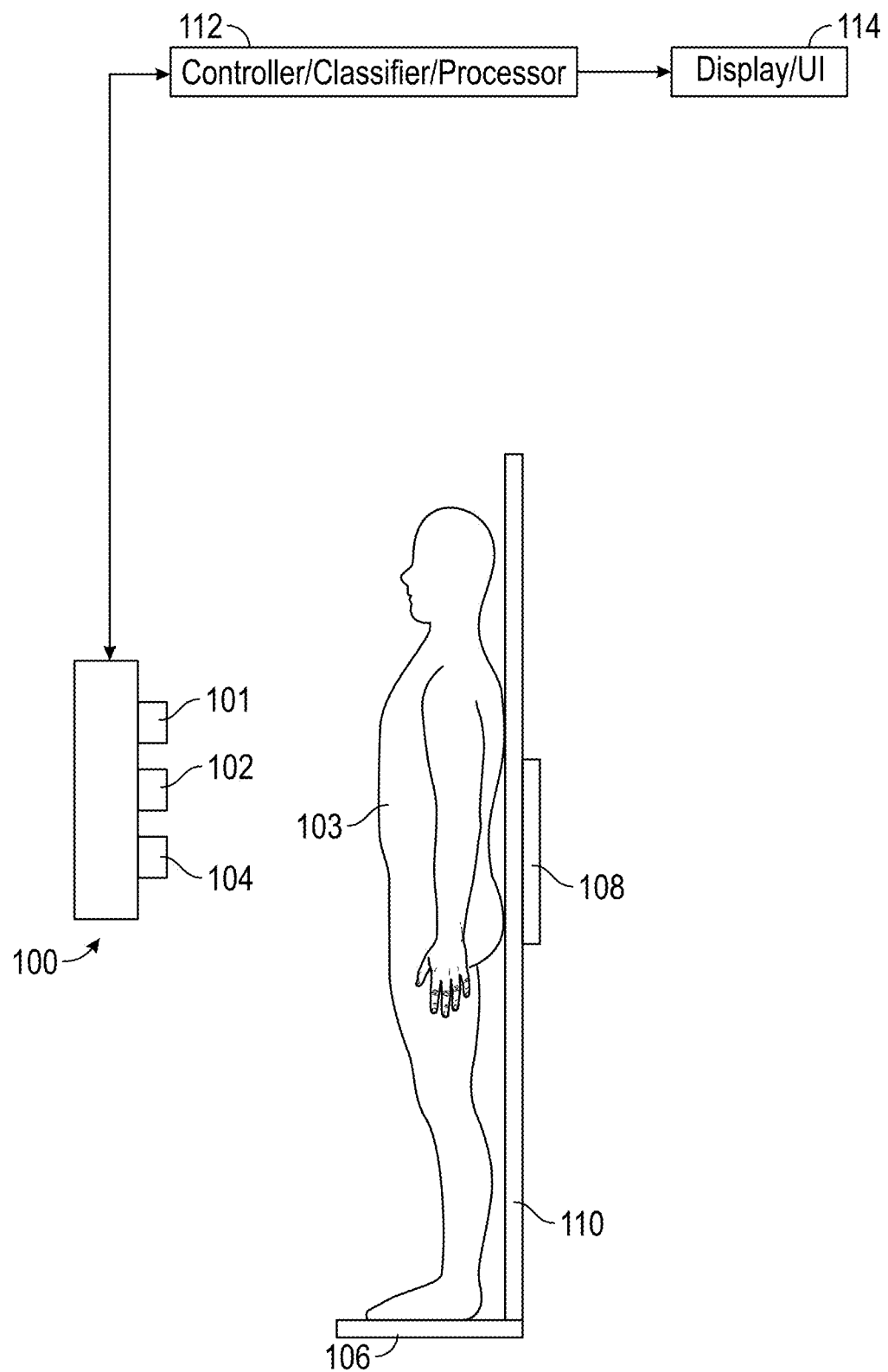
FIG. 1A illustrates example components of an imager that is imaging a subject.

Alternatives of the disclosure relate to systems and techniques for identifying, evaluating, and/or classifying a subject's tissue. Some alternatives relate to apparatuses and methods for classifying a tissue, wherein such devices include optical imaging components. Some of the alternatives described herein comprise reflective mode multi-spectral time-resolved optical imaging software and hardware, which when implemented allow for several of the methods of tissue classification provided herein.

There has been a long felt need for non-invasive medical imaging technology that can classify tissue. Classifications may include wounds and tissue conditions, such as decubitus ulcers, chronic wounds, burns, healthy tissue, tissue grafts, tissue flaps, vascular pathophysiology, and hyperemia. In particular, there is a need for technology that can assess the severity of wounds or tissue conditions and also estimate the percentage of total body surface area (% TBSA) that is afflicted. A % TBSA afflicted is defined as the surface area of a tissue region that is afflicted divided by the total body surface area, expressed as either a percent (e.g., 40%), a decimal value less than one (e.g., 0.4), or also possibly as a fraction (e.g., ⅖). Each of these forms of expression is a "% TBSA" as that term is used herein, as are numerical equivalents or near equivalents such as scaled versions thereof, separate outputs of a numerator and denominator, or the like.

Alternatives described herein allow one to assess and classify in a an automated or semi-automated manner wounded subjects that need immediate emergency procedures as opposed to those with less urgent needs, and may also provide treatment recommendations. Although superficial and shallow partial thickness burns (e.g., first and second degree burns) often heal with non-surgical procedures, deep partial and full thickness burns (e.g., third and fourth degree burns) require surgical excision to prevent loss of functionality and excessively degraded cosmetic appearance. Indeed, early excision is associated with a decrease in mortality as well as length of hospital stay. Some of the alternatives described herein are particularly suited for burn management because they allow doctors to quickly evaluate the severity of the burn so that a triage decision, such as a conclusion that surgery is urgently needed, can be made quickly and accurately even by a non-burn specialist. Some alternatives may also assist a surgeon in carefully and in a more refined manner execute the sequence of excisions (e.g., identifying an appropriate margin for the incision and/or debridement procedure). Still other alternatives described herein are particularly suited to allow doctors to make treatment decisions such as the amount of fluid to administer for resuscitation.

Moreover, in the field of burns, it is often difficult to evaluate the full extent of tissue injury until several days after the wound was received. The delayed nature of these types of wounds further complicates the treatment process as surgeons that are experienced in burn-medicine often have difficulty in reliably determining the margin where necrotic or soon-to-be necrotic tissue interfaces with healthy tissue, which will heal without surgical intervention or debridement. Burn assessment is conventionally up to the practitioner's subjective inspection of the skin, taking into account additional variability of the skin's sensibility, consistency, and tone. Yet, determining the need for surgery requires an accurate assessment of the burn, particularly the burn depth. In addition to determining the need for surgery, early detection and appropriate treatment of burns avoiding infection and sepsis, and therefore inaccurate burn classification and assessment can complicate a subject's recovery. Furthermore, it is desired that surgical intervention is kept to a minimum so as to facilitate the healing process and limit the trauma to the subject.

Nevertheless, even when surgery is desirable, one of the greatest challenges faced by the surgeon is delineating the vital, healthy tissue from the non-vital, necrotic or soon-to-be necrotic tissue. Even for experienced surgeons, the typical endpoint for the dissection depth is the presence of punctate bleeding. However, significant drawbacks exist in using this metric, including the unnecessary removal of viable tissue during surgery. Furthermore, the control of bleeding during burn excision is difficult and requires a great deal of clinical judgment, precision, and experience.

In burn surgery, under or over excision of the tissue may have life threatening consequences. Under excised burns can result in placement of grafts on devitalized tissue and ultimately poor graft uptake. Under excised burns further lead to increased risks of infection and/or longer healing times. On the other hand, over excision may lead to excessive blood loss, or bleeding of the excised surface, which also may compromise graft uptake.

There is a large unmet need for methods and apparatuses to rapidly and quantitatively evaluate burn severity over a larger tissue surface. The methods and apparatuses described herein are useful to provide a rapid and precise burn assessment, which will allow burn specialists to focus on severe burns and non-burn specialists to address the needs of patients with less severe burns. There is a similar unmet need for methods and apparatuses to rapidly and quantitatively evaluate other wounds and tissue conditions and the devices and methods described herein are useful to provide a rapid and precise evaluation of decubitus ulcers, chronic wounds, subacute and dehisced wounds, traumatic wounds, lacerations, abrasions, contusions, diabetic ulcers, pressure ulcers, surgical wounds, trauma and venous ulcers or the like, as well as to provide a rapid and precise evaluation of where healthy tissue meets necrotic or soon to be necrotic tissue, the precise site for applying a tissue graft or tissue flap, vascular pathophysiology, and hyperemia.

Throughout this specification reference is made to a wound or wounds. It is to be understood that the term "wound" is to be broadly construed and encompasses open and closed wounds in which skin is torn, cut, punctured, or diseased, or wherein trauma causes a contusion, a superficial lesion, or a condition or imperfection on the skin of a subject, for example a human or animal, in particular a mammal. A "wound" is also intended to encompass any damaged region of tissue, wherein fluid may or may not be produced as a result of an injury or disease. Examples of such wounds include, but are not limited to, acute wounds, chronic wounds, surgical incisions and other incisions, sub-acute and dehisced wounds, traumatic wounds, flaps and skin grafts, lacerations, abrasions, contusions, burns, diabetic ulcers, pressure ulcers, stoma, surgical wounds, trauma and venous ulcers or the like.

Various alternatives will be described below in conjunction with the drawings for purposes of illustration. It should be appreciated that many other implementations of the disclosed concepts are possible, and various advantages can be achieved with the disclosed implementations. All possible combinations and subcombinations are intended to fall within the scope of this disclosure. Many of the alternatives described herein include similar components, and as such, these similar components can be interchanged in different aspects of the invention.

Headings are included herein for reference and to aid in locating various sections. These headings are not intended to limit the scope of the concepts described with respect thereto. Such concepts may have applicability throughout the entire specification.

Overview of Example Alternatives Relating to Burn Assessment

Figure 1B:
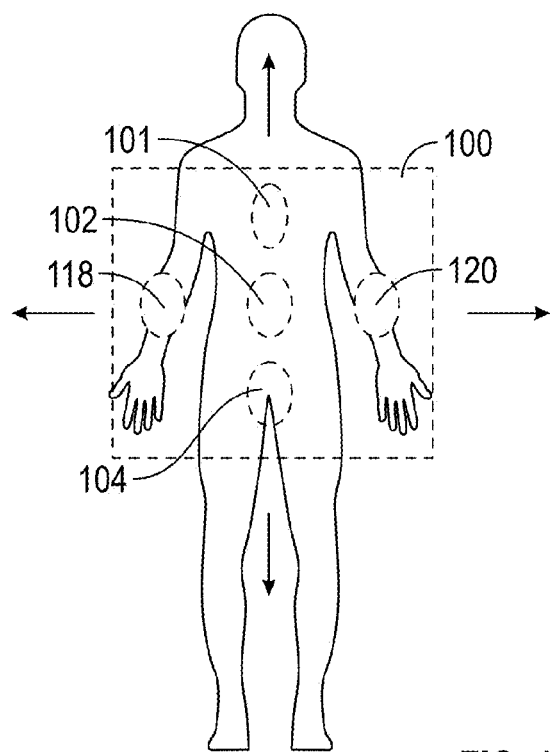
FIG. 1B is an illustration of example movements of an example imaging probe.

FIGS. 1A and 1B illustrate an example of one alternative of the present invention. The apparatus shown in these figures is especially suited for whole body assessment of burned subjects. This apparatus is especially useful for burn triage functions, where clinical decisions related to near term treatment requirements are being made. In this example, probe 100 comprises one or more light sources, in this case four light sources 101, 104, 118 and 120, and image acquisition device 102. Light sources 101, 104, 118, and 120 illuminate the tissue region, in this case, tissue 103, which advantageously includes the entire body surface of the subject facing the probe 100. In some alternatives, the one or more light sources may be light-emitting diodes (LEDs), halogen lamps, tungsten lamps, or any other illumination technology. The one or more light sources may emit white light or light that falls in one or more spectral bands that can be selected as desired by a user.

Many LEDs produce light in narrow bandwidths (e.g., full-width at half-maximum of 50 nm or less), wherein the specific LEDs can be chosen to illuminate at specific bandwidths. In general, the one or more spectral bands may be chosen in view of the light measurements most relevant to the kind of data sought and/or the clinical application. The one or more light sources may also be coupled to one or more drivers to power the light sources and control them. These drivers may be part of the light sources themselves, or separate. Multiple narrowband light sources or broadband light sources with selectable filters (e.g. filter wheels) may be used to serially or simultaneously illuminate the tissue 103 with light in multiple spectral bands. The center wavelength of the chosen spectral bands typically reside in the visible and near-infrared wavelengths, such as between about 400 nm to about 1100 nm (such as less than, at least, or equal to 400, 500, 600, 700, 800, 900, 1000, or 1100 nm or a range defined by any wavelength between any two of the aforementioned wavelengths).

In some alternatives, the light sources illuminate the tissue region with substantially uniform intensity. For example, substantially uniform intensity can be achieved by using light diffusers provided as part of the light sources 101, 104, 118 and 120 that create an approximately uniform distribution of the light intensity applied to the tissue 103. Light diffusers also have the additional benefit of reducing undesirable specular light reflection. In some instances, significant improvements to signal-to-noise ratios of the signals obtained by the image acquisition device 102 can be achieved by utilizing broad spectral spatially even illumination patterns with high powered LEDs. In some cases, patterned light systems, such as checkerboard patterned illumination may be used as well. In certain such alternatives, the field of view of the image acquisition device is directed to tissue regions that have not been directly illuminated by the light sources, but are adjacent to the illuminated areas. For example, where light of substantially uniform intensity is used, an image acquisition device, such as image acquisition device 102, may read light from outside the illuminated region. Similarly, where checkerboard-patterned illumination is used, for example, the acquisition device 102 may read light from the non-illuminated portions of the checkerboard.

Moreover, even though light of substantially uniform intensity was effective in some alternatives described herein, other alternatives may also use non-uniform light, wherein the one or more lights are positioned so as to minimize differences in light intensity across the surface. In some cases, these differences may also be accounted for during data acquisition or by backend software or hardware logic. For example, top-hat transformations or other image processing techniques may be used to compensate for non-uniform background illumination.

In certain alternatives, the light may be desirably polarized. In some cases, the light is polarized using reflection, selective absorption, refraction, scattering and/or any method of polarizing light known in the art. For example, the polarization may utilize prisms (such as a Nicol prism), mirrors and/or reflective surfaces, filters (such as a Polaroid filter), lens, and/or crystals. The light may also be cross-polarized or co-polarized. In some alternatives, the light from the one or more light sources is polarized before the light illuminates the subject. For example, polarizing filters may be provided as part of the light sources 101, 104, 118, and 120. In some alternatives, reflected light from the tissue is polarized after it has been reflected from the tissue. For example, polarized filters may be provided as part of acquisition device 102. In other alternatives the light is polarized both before it illuminates the subject and after it is reflected. For example, polarizing filters may be provided as part of light sources 101, 104, 118, and 120, as well as part of data acquisition device 102.

The type of polarization technique used may depend on factors such as the angle of illumination, the angle of reception, the kind of illumination source used, the kind of data desired (e.g., measurements of light scattered, absorbed, reflected, transmitted, and/or fluoresced), and the depth of tissue imaged. For example, when tissue is illuminated, some light may be reflected off the top layer of skin directly as surface glare and reflectance. This reflected light often has a different polarity than the light that diffuses into dermal tissue, where the light may be scattered (e.g., reflected) and change direction and polarity. Cross-polarization techniques may be used in order to minimize the amount of glare and reflectance read by an acquisition device while maximizing the amount of backscattered light read. For example, polarization filters may be provided as part of light sources 101, 104, 118, and 120, as well as part of data acquisition device 102. In such a setup, the light is first polarized before it illuminates the target 103. After the light is reflected from target 103, the reflected light may then be polarized in a direction orthogonal to the first polarization in order to measure the backscattered light while minimizing the amount of incident light reflected off the surface of the target 103 that is read.

In some circumstances, it may also be desirable to image tissue at certain depths. For example, imaging tissue at particular depths can be used in evaluating particular wounds at particular depths, locating and/or identifying the presence or absence of a cancerous tumor or determining the stage of a tumor or progression of cancer, or any of the other therapeutic applications mentioned in this disclosure. Certain polarization techniques known in the art may be used to selectively image tissue at certain depths based on optical properties and/or mean free path lengths.

In certain alternatives, other techniques for controlling imaging depth may be used. For example, the optical scattering properties of tissue change with temperature while the light penetration depth in skin increases with cooling. As such, the depth of imaging may be controlled by controlling the temperature of the imaged tissue region. Also, for example, the depth of imaging may be controlled by pulsing (or flashing) light sources at various frequencies. Pulsing light penetrates deeper into the skin than non-pulsing light: the longer the pulse widths, the deeper the light penetration. As another example, the imaged depth may also be changed by adjusting the intensity of light, where the penetration of more intense light is greater than less intense light.

As further illustrated in FIG. 1A, image acquisition device 102 is configured to receive reflected light from the tissue 103. The image acquisition device 102 can detect light from the illuminated region, a sub-region of the illuminated region, or a non-illuminated region. As illustrated further below, the field of view of the image acquisition device 102 may include the entire body surface of the subject facing the probe 100. When the entire subject facing the probe is illuminated and the entire subject facing the probe is in the field of view of the image acquisition device, the speed and ease of classification is enhanced. The image acquisition device 102 may be a two dimensional charge-coupled device (CCD) or complementary metal-oxide semiconductor (CMOS) image acquisition device with appropriate optics for imaging all or part of the illuminated tissue 103.

Module 112 is a controller, classifier, and processor that may be coupled with probe 100 in some alternatives. Module 112 controls the probe, which may include setting such parameters as its physical location, light intensity, resolution, filter color, or any parameter of the camera and/or light sources described in this disclosure. Module 112 also receives and processes data obtained by the probe, as will be described later in this disclosure.

Module 112 may be further coupled with a module 114 in some alternatives, where module 114 is a display and user interface ("UI"). The display and UI shows information and/or data to the user, which in certain alternatives includes the presence of a tissue condition, the severity of the tissue condition, and/or additional information about the subject, including any of the information mentioned in this specification. Module 114 receives user inputs, which in certain alternatives includes information about the patient such as age, weight, height, gender, race, skin tone or complexion, and/or blood pressure. Module 114 may also receive user inputs with calibration information, user selections of locations to scan, user selections of tissue conditions, and/or additional information for diagnoses, including any of the information mentioned in this disclosure. In certain alternatives, some or any of the aforementioned user inputs may be sent automatically to module 112 without the user entering information using module 114.

As illustrated in FIG. 1B, the probe 100 may in some alternatives be moved in any direction or combination of directions, such as up, down, left, right, diagonally up-right, diagonally up-left, diagonally down-right, diagonally down-left, or any combination of these directions. In some alternatives, the probe may also be moved in a direction normal to the subject, where the probe gets closer or farther away from the subject. The probe may, for example, be coupled to rails or an articulating arm with position controlled manually or automatically by the controller 112 or a combination of both. In some alternatives, either the light sources or the image acquisition device may be fixed, and in other alternatives, either may be movable independently. Certain alternatives couple the image acquisition device with a motor to automate the movement of the image acquisition device so as to allow the camera to image each section of the subject. The camera can also be coupled to rails, tracks, guides, and/or actuatable arms. The light source(s) may illuminate the entire tissue area 103 while the image acquisition device moves, or the light source(s) may be controlled during a scanning process to only illuminate a desired tissue portion that the camera is imaging.

In the alternative shown in FIG. 1A, the subject stands in an upright position against a backdrop 110 as images of the subject or a portion thereof (e.g., the entire body of the subject or a desired tissue location) are acquired. In some alternatives, the backdrop 110 is a support structure that the subject lies on or against in a horizontal or angled position as the images are acquired. Scales 106 and 108 may be provided to weigh the subject as the images are acquired. In addition or alternatively to scales, other biometric readers for measuring heart rate, temperature, body composition, body mass index, body shape, blood pressure and other physiological data may be provided.

Figure 2:
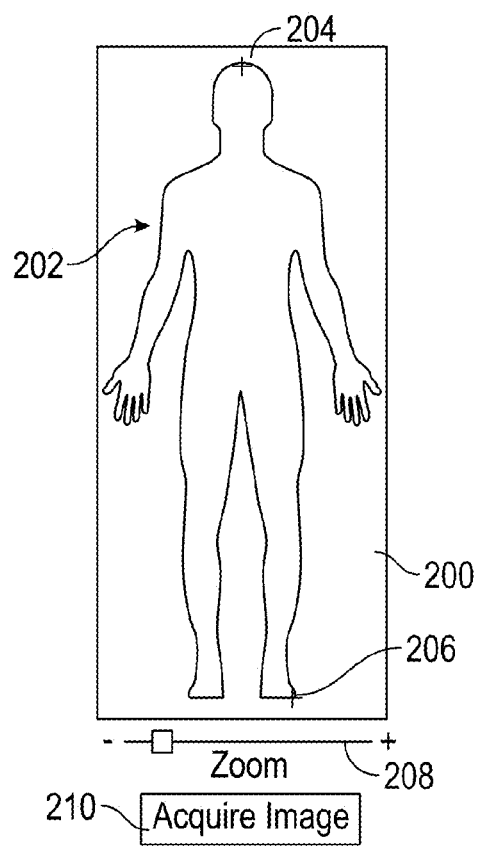
FIG. 2 is an illustration of an example user interface for acquiring an image.

FIG. 2 shows an example UI 200 presented on display/UI 114 for acquiring an image with the apparatus. In this alternative, the user interface displays the field of view of the image acquisition device when the tissue 103 is being illuminated by the light sources. In certain alternatives, the user may position the field of view of the image acquisition device 102 so as to include the entire subject 202. The user may use zoom component 208 to adjust the image acquisition device 102 so that the subject nearly fills the field of view. In some alternatives, the user may use the user interface to obtain other information about the subject 202. For example, the user may select position 204 and position 206 in order to measure the height of the subject. In some cases, the user instructs the image acquisition device to acquire images of the subject using the user interface, such as by pushing an acquire image button 210.

When acquiring images of the subject to perform tissue classification using those images, the light sources (with associated filters if provided) and image acquisition device are controlled to acquire multiple images of the subject, with the separate images being associated with different spectral bands of reflected light and/or separated in time. Images acquired at different spectral bands may be processed according to MSI techniques to classify tissue regions, and images separate in time may be processed according to PPG techniques to classify tissue. In some alternatives, both types of image sets are acquired, and the results are merged to perform a more accurate classification, as described further below.

For burn patients, image acquisition may be performed with the subject in multiple orientations, such as front facing, rear facing, left side facing, and right side facing. The patient may stand in these various orientations against the backdrop 110, or if the backdrop 110 is a support structure in a horizontal orientation, the patient may lay in different orientations on the backdrop 110. The data from the acquired images is then used to classify different areas of the skin of the subject as burned or not, and may classify burn degree for those burned areas as well.

Following image acquisition in different orientations, the controller/classifier/processor 112 may process the image data for each subject orientation. When the backdrop 110 is a characteristic color different from skin tissue, the controller/classifier/processor may separate the subject from the background, assigning each pixel in each acquired image as either background or subject. As another alternative, the UI can be used to trace the outline of the subject (with a stylus on a touchscreen or a mouse and cursor for example) in the initial image (e.g., such as shown in FIG. 2) to distinguish the background from the subject. When the pixels of the image associated with the subject are identified, these may be analyzed using MSI and/or PPG techniques to classify areas of the skin of the subject according to burn status.

Figure 3:
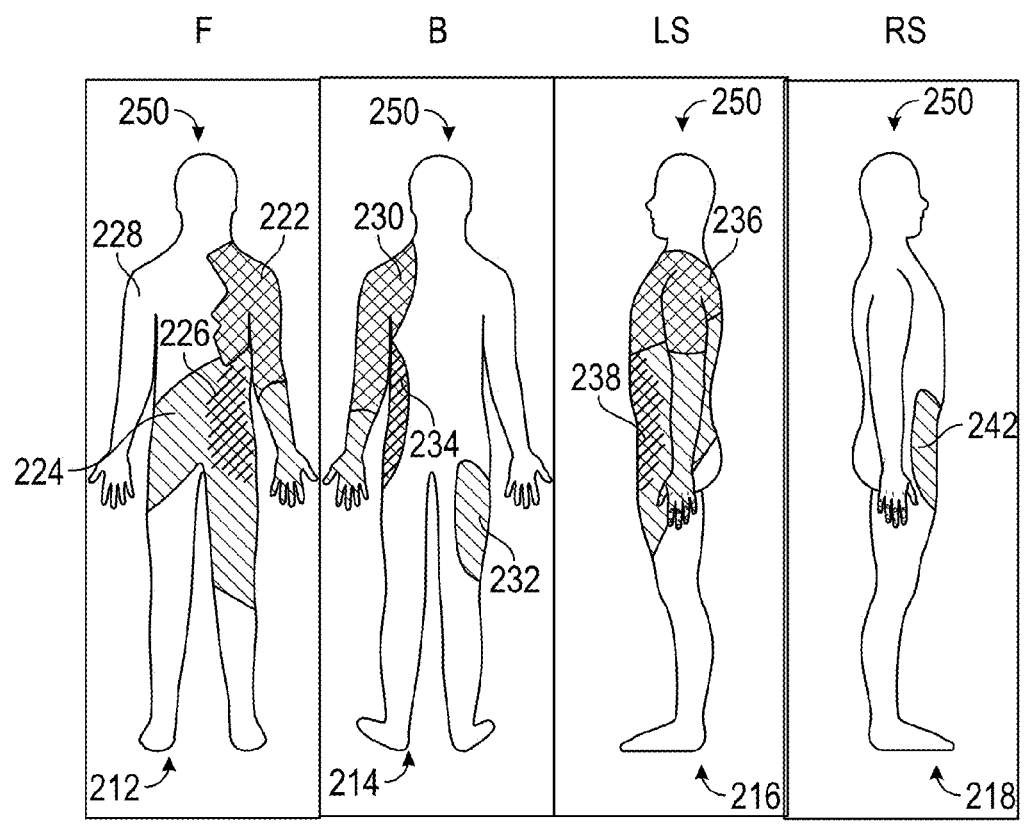
FIG. 3 is an example illustration showing images of multiple surfaces of a subject.

An example output to the display/UI 114 following this process is illustrated in FIG. 3. In this alternative, output image 212 shows a front view of a subject 250, wherein the multiple acquired images of the front of the patient have been used to classify different portions of the skin of the front of the patient. The output image 212 may show the different classifications with different colors in the output image for example. For example, the controller/classifier/processor may identify region 222 as a third degree burn, region 224 as a first degree burn, and region 226 as a second degree burn. The processor might also identify healthy tissue, for example, region 228. Image 214 is an illustrative example of a back view of the subject 250 showing region 230 classified as a third degree burn, region 232 as a first degree burn, and region 234 as a second degree burn. It may also identify other tissue regions as healthy tissue. Image 216 and Image 218 show left side and right side views, respectively, of subject 250, where region 236 is classified as a third degree burn, region 238 as a second degree burn, and region 242 as a first degree burn. It may also identify other tissue regions as healthy tissue.

From this classification data shown in images 212, 214, 216, and 218, certain alternatives may calculate a % TBSA burned, and output that result to the user on the UI as shown in the box 220 of FIG. 3. When classifications according to degree of burns are made, the apparatus may further output % TBSA for one or more classifications of burns as also shown in box 220 of FIG. 3. Although optical imaging methods have been used to assess burned tissue, no apparatus that generates an estimate of % TBSA burned has previously been developed.

Producing a % TBSA burned using image data of all or part of the patient involves complications that have not previously been resolved. In one alternative, it has been found that a simple calculation using the four images 212, 214, 216, and 218 of FIG. 3 can produce a sufficiently accurate estimate for triage purposes. In this alternative, the % TBSA burned may be estimated by generating a first count that is the sum of all the pixels classified as burned in all the images, generating a second count that is the sum of all the pixels of the subject in all the images, and dividing the first count by the second count. For example, to calculate the % TBSA that is third degree burned, the system may count the pixels of regions 222, 230, and 236, and divide that total by the total number of pixels of all surfaces of the subject 250 by counting and adding the total pixels of the subject 250 found in each of images 212, 214, 216, and 218.

In certain alternatives, an adjusted addition of areas may be used to refine the % TBSA burned estimate. For example, instead of simply adding together regions, a processor, such as module 112, may analyze the images to identify those areas that appear in more than one image. In this way, areas captured by multiple images would not be counted more than once. For example both region 222 of image 212 and region 236 of image 216 capture a portion of subject 250's chest area. If the area of region 236 and 222 were added tougher, it would count part of the chest more than once. In certain alternatives, a processor would analyze region 222 and 236 (or images 212 and 216 as wholes) and only count the chest region once. In some alternatives, the overlap and/or similarities of regions could be computed using image processing techniques (such as edge detection and segmentation), reference markers, and/or predictive analysis and computer learning to estimate overlap due to standardized body shapes.

In certain alternatives, a three dimensional body model may be constructed for the subject. The body model may be based on a standardized body model and/or a constructed body model produced by parameters such as height, weight, body composition (e.g., percent body fat), body mass index, specific measurements taken of the body in whole or in part, or any metric of body size or shape. These parameters may be entered by the user using a UI, such as module 114, and/or parameters measured or calculated by probe 100, biometric readers 106 and/or 108, or any metric received or calculated by the processor/classifier, such as module 112. Once the three-dimensional body model is created, the classified tissue regions can be projected onto areas of the three-dimensional body model. In the case of overlap, the processor resolves the differences such that regions of overlap are not counted multiple times. The % TBSA burned can be estimated by using the summation of areas falling into one or more classifications (e.g., first degree burn, second degree burn, third degree burn, or healthy tissue) divided by the total body surface area.

In some alternatives, a processor, such as module 112, may reconstruct a three-dimensional model from multiple two-dimensional images (e.g., images 212, 214, 216, and 218). In some alternatives, such a reconstruction may be performed using projections, such as Euclidean reconstruction, linear stratification, or any other known method of converting multiple two-dimensional images into a three-dimensional reconstruction. In certain alternatives, the conversion from two-dimensional images into a three-dimensional reconstruction may take into account known parameters, such as the angle of the camera, the distance between the camera and the subject, measurements taken from the subject, and/or any reference measurements or objects. Once the three-dimensional model is created using the two-dimensional images, the % TBSA burned can be estimated by using the summation of areas falling into one or more classifications (e.g., first degree burn, second degree burn, third degree burn, or healthy tissue).

Once the % TBSA burned is calculated by the processor, the results may be output to the user. For example, output 220 shows an example where the % TBSA of burns is calculated to be 40%, and the % TBSA of third degree burns is calculated to be 12%. This information may be displayed to the user using a display, such as module 114. The display, such as module 114, may also display other information such as a mortality estimate or other pertinent information to the treatment of the subject. In the example of a mortality estimate, data such as the data in the chart of FIG. 6, may be stored in the processor 112 and used to estimate the mortality rate based on % TBSA and/or the age of the subject that may be known or estimated by a user and inputted into the system.

Figure 4:
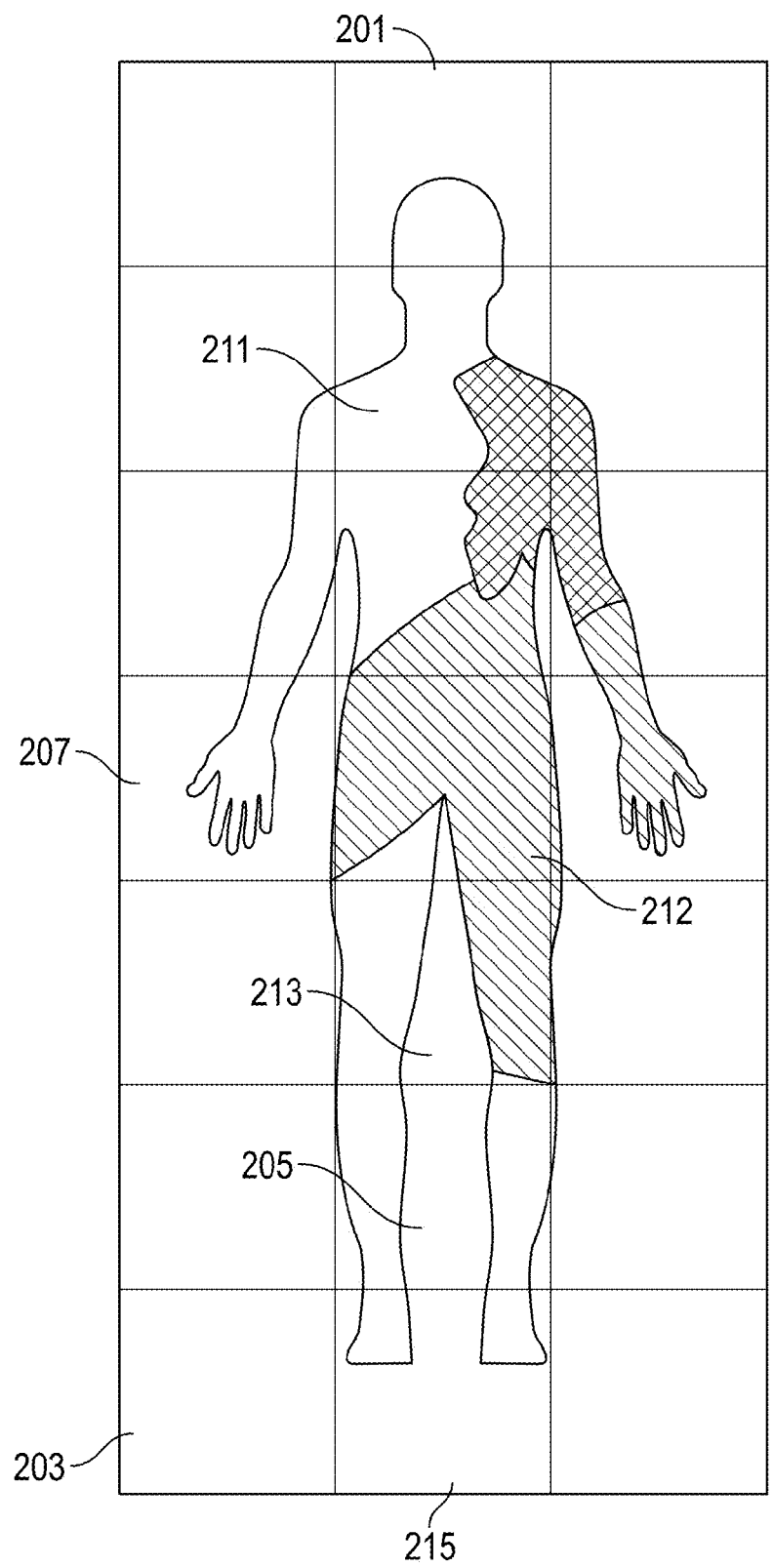
FIG. 4 is an example diagram showing the mosaic technique for triage, which is used with certain alternatives described herein.

FIG. 4 illustrates another example of how some devices described herein can calculate % TBSA burned. This figure shows a mosaic technique, wherein several pictures are added together to calculate a % TBSA burned. In some instances, the mosaic may be created using an automated program where the probe, such as probe 100, is automatically positioned for each image. The automation may utilize an actuatable arm, motor, rails, or any other method or apparatus for moving the probe. The end result, in some instances, is that the probe might take images in a specific pattern, such as the grid pattern shown in FIG. 4. Alternatively, the mosaic may be created by the user positioning a probe, such as probe 100. The user can then take any number of pictures at any number of locations of a subject.

In any case, using some alternatives of the mosaic technique, mosaic portion 201 may be one image of the surface of the head. Mosaic portion 207, may be a separate image that is an image of the hand, and might also capture a piece of the torso. There may be any number of additional images taken of the subject or a portion thereof (including images of different surfaces) forming other mosaic portions. Some of these images may be duplicative, and others may be distinct. By duplicating the images, and/or generating a plurality of images of the same feature, site, location, or tissue position (e.g., from different perspectives) and employing overlaying or masking techniques, greater resolution and/or a three-dimensional rendering of the desired tissue can be obtained.

These various images can be pieced together or stitched to calculate or estimate the entire body surface area as well. In some cases, before piecing the images together, the background is removed using image processing techniques, leaving only the subject's body. An edge detection technique may also be used to obtain the contours of the body sections in order to facilitate the piecing together of images. In cases of images that overlap in their capturing of a section of the body, a cross-correlation of the tissue can be performed to determine how the sections should be correctly joined, stitched, and pieced together.

In some cases, the entire surface area of a tissue classification may be pieced together from various images. For example, mosaic portions 211 and 212 may be some of the images used to estimate the surface area afflicted with tissue condition such as a burn. Again, some of the images that are assembled may be distinct or duplicative or are taken from different perspectives of the same tissue site or location. The process of piecing the images together takes the plurality of images of the tissue classified as the tissue condition and combines them to estimate the surface area of the classified region.

In some alternatives, areas may need to be estimated using interpolation techniques to account for regions not imaged. For example, in some instances, parts of the subject may have been accidentally omitted from imaging or omitted because they are clearly not burned or otherwise afflicted with the condition being assessed. In some other instances, certain areas of the subject may have been difficult to image owing to their location (e.g., under the subject's arms) or physical limitations of the subject (e.g., the subject is too injured to move). Such interpolation may use body symmetry to estimate the region not imaged or may involve projecting straight lines between one region and another. For example, if calf image 205 were missing, straight lines could be projected from the leg boundary shown in upper leg image 213 to the boundary of the ankle and foot in lower leg images 203 and/or 215. This projection can give an approximate leg shape, which would allow the un-imaged leg surface(s) to be estimated.

Figure 5:
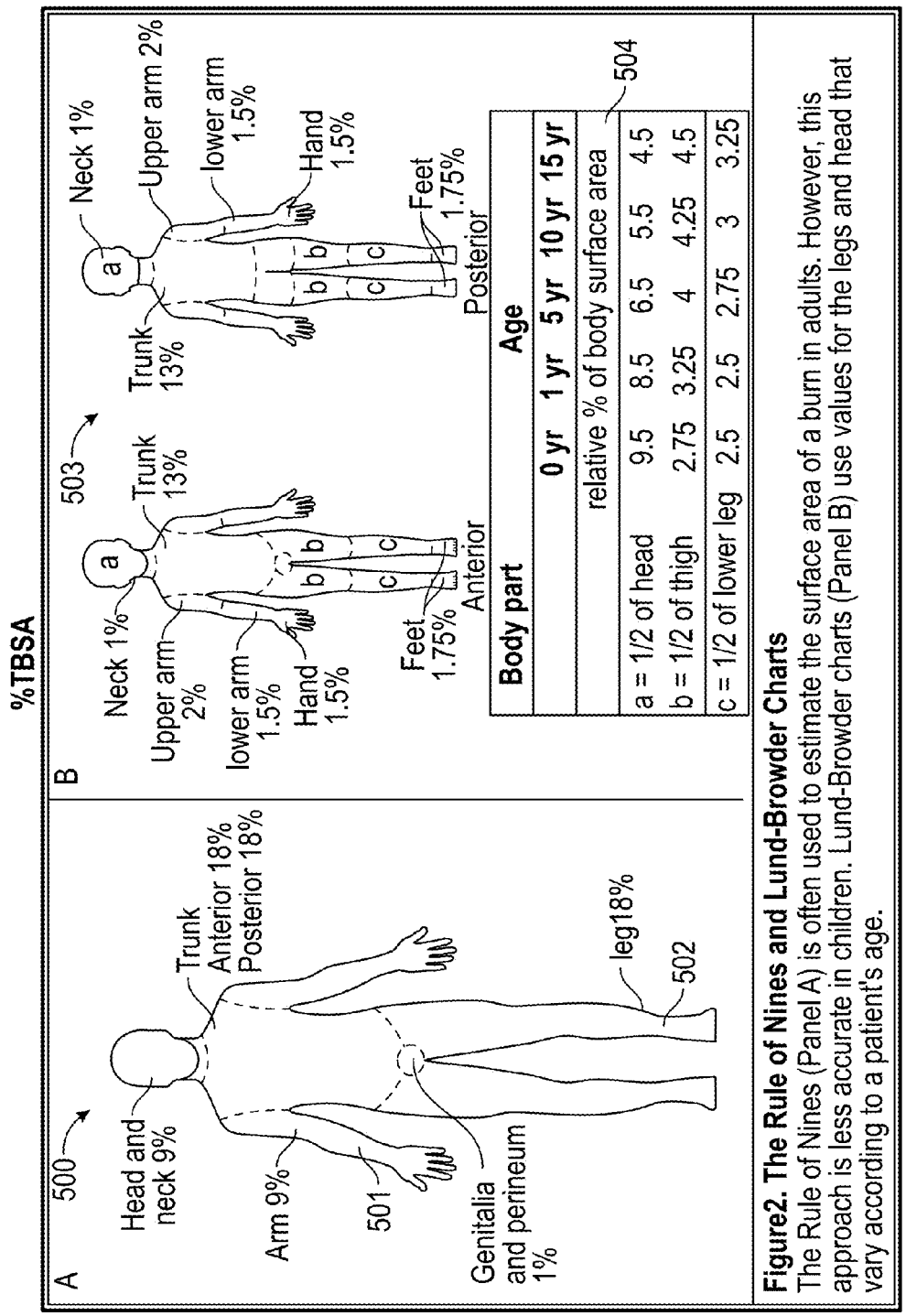
FIG. 5 is an example illustration describing the Rule of Nines and Land-Bowler Charts used to calculate the percentage of total body surface area in some alternatives described herein.

There are other formulas that can be used to estimate the surface area of the various parts of a subject. For example FIG. 5 shows the Rule of Nines and Lund-Browder Charts. For example, illustration 500 shows the Rule of Nines, wherein the head and neck, and arm are each estimated to be 9% of total body surface area. For example, the total surface area of arm 501 can be estimated to be 9% of the total body surface area of the illustrated person under the Rule of Nines. Under the Rule of Nines, each leg and each of the anterior and posterior surfaces of the trunk are estimated to be 18% of the total body surface area. For example, the total surface area of leg 502 can be estimated to be 18% of the total body surface area of the illustrated person under the Rule of Nines.

Illustration 503 is an example that shows that there are other formulas for estimating the surface area of various body parts. Lund-Browder Chart 504 shows one way of estimating surface area according to the patient's age. The chart shows various estimates for the relative percentage of body surface area of ½ of head, ½ of thigh, and ½ of lower leg for children 0, 1, 5, 10, and 15 years of age.

Both the Rule of Nines and the Lund-Browder Chart are just example estimations that can be used for calculating total body surface area (TBSA). These estimations can also be used to supplement the aforementioned techniques, wherein parts of the body are not imaged. For example, the surface area of an un-imaged leg can be accounted for by assuming that it would take up 18% of the TBSA.

In some patients, Rule of Nines, Lund-Browder, and other ways of estimation, will not apply. For example, overweight patients or patients with excess body tissue in certain regions of their body may have body parts with different relative surface areas. Accordingly, the imaging techniques described herein can provide a more accurate % TBSA burned calculation than relying only on these charts as is conventionally done. Furthermore, any data inputted into module 114, or any data automatically sent to module 112, may be used in any of the % TBSA calculations described herein. For example, the age of the subject may be effectively used in an estimation of relative percentage of body surface area using a Lund-Browder Chart. In alternative examples, other data, including gender, weight, height, body type, body shape, skin tone, race, orientation of an imaged body, and/or any relevant data mentioned in this disclosure may also be inputted or acquired for calculating % TBSA.

Finding the % TBSA of a tissue classification can be important for proper treatment decisions. For example, in burns, fatality rates increase with increasing % TBSA burned. FIG. 6 is a compilation put together by the American Burn Association. It shows the mortality rate by age group and burn size (as a % TBSA). Noticeably, the mortality rate increases on average as the patients' % TBSA burned increases. Thus, it can be important to identify those patients with higher % TBSA burned as quickly as possible to perform emergency treatment procedures. Moreover, the slope of mortality rates increase with larger % TBSA burned. As such, having enhanced accuracy over conventional methods at higher % TBSA burned is important in distinguishing those subjects having much greater risk of death from others. The ability to make such a distinction may become especially significant in emergencies such as mass casualty situations, where resources are limited. Thus, present alternatives' abilities to calculate % TBSA burned addresses this long felt need.

One treatment decision that is desired, for example, is the determination of the amount of fluid for resuscitation. The loss of fluid is often one of the greatest problems facing those with major burn injuries. Accordingly, proper management of the amount of fluid administered to a burn patient can be an important aspect to recovery. In many cases, too little fluid can lead to burn edema, burn shock, dehydration, death and/or other complications. Too much fluid is also associated with increased risk of complications such as infection, edema, acute respiratory distress syndrome, abdominal compartment syndrome, overhydration, and/or death. The amount of fluid required for resuscitation is correlated with the % TBSA burned. For example, minor burn injuries can generally be resuscitated with oral hydration. However, as the % TBSA burned approaches 15-20% (e.g., 15, 16, 17, 18, 19, or 20 percent or any percentage defined by a range that is in between any two of the aforementioned percentages) there may be larger fluid shifts in the subject, making fluid management even more important to avoid burn edema and burn shock. Current recommendations initiate formal intravascular fluid resuscitation when % TBSA is greater than approximately 20% (e.g., 20, 30, 40, 50, 60, 70, 80, 90, or 100 percent or any percentage defined by a range that is in between any two of the aforementioned percentages).

In certain alternatives, the % TBSA burned that is calculated may be used by a processor, such as processor 112, to determine the amount of fluid that should be given to the patient. For example, the Parkland formula may be used to estimate resuscitation volumes during the first twenty-four (24) hours of treatment based on the % TBSA. The Parkland formula is expressed as $V=4*m*(A*100)$, where V is the resuscitation volume in milliliters, m is the mass of the subject in kilograms, and A is the % TBSA expressed as a fraction (e.g. 0.5 for a subject with 50% of their body surface burned). The first half of the calculated volume is given in the first eight (8) hours, and the remaining half is given over the next sixteen (16) hours. A fluid administration schedule may be output to a user of the system on the UI such as part of output 220 illustrated in FIG. 3. For example, for a 100 kg subject with 50% burned surface area, the system may output a 24 hour fluid resuscitation schedule according to the above Parkland formula as 1250 ml/hr for the next 8 hours, 625 ml/hr for the following 16 hours.

The Parkland formula may also be adjusted to fit the needs of a particular patient. For example, the amount of fluid administered to an elderly patient may need to be decreased due to higher susceptibilities to edema and other complications due to overhydration. On the other hand, younger patients, such as infants, present lower risks of complications due to too much fluid. Other factors may also be used to adjust the amount of fluid administered, such as condition (e.g., severity of burns), pulse, blood pressure, respiratory rate, and other physiological parameters. In certain alternatives, a processor, such as processor 112, uses these factors to adjust the amount of fluid administered. These factors may be entered through a user interface (such as display/UI 114), measured by probe 100 or biometric readers 106 and/or 108, and/or otherwise entered, calculated, estimated, or obtained by the processor 112. These factors may also include other data from the patient's medical history, or data from other patients. The processor may also obtain information from a dynamic library, as will be later discussed in this application, in order to obtain other data to factor into the calculation, such as additional patient data, calibration information, and data from other patients.

In some alternatives, another factor that may be considered is the overall blood volume and/or changes in overall blood volume of the patient. Lower blood volumes indicate that a patient needs more fluid for resuscitation. There are various ways the blood volume may be measured and/or estimated. For example, when a patient has a greater blood volume, more light is absorbed by the patient's tissue. Such an effect can be more easily measured in the red or near infrared light range (e.g., near or around 840-880 nm, including 840, 850, 860, 870, or 880 nm wavelengths or a range defined by any wavelength that is between any two of those wavelengths) because those wavelengths of light pass more easily through the tissue. Alternatives described in this disclosure can be used to measure the changes in the amount of red or near infrared light reflected over time in order to estimate overall blood volume and/or changes in overall blood volume. For example, the amount of red or near infrared light reflected over time in some alternatives can be used to measure phase shifts in the systolic and diastolic activities of the heartbeat waveform. These shifts can be used to find systolic and diastolic pressures, which in some circumstances can be used to estimate the pulse pressures for the right and left ventricle. An external cuff may also be used to measure systolic and diastolic pressure as an addition or an alternative. The pulse pressures may then be used to estimate the stroke volume (the volume of blood pumped from a ventricle of the heart with each beat) for the left and right ventricles. With the stroke volume, the cardiac output for the ventricles may be calculated by multiplying the heart rate (which can also be measured by alternatives of this disclosure) and the stroke volume. This cardiac output may be used to estimate the blood volume and/or changes of blood volume.

Other alternatives known in the art may also be used to measure or estimate blood volume and/or changes in blood volume, such as, for example, PPG, catheters, plethysmographs, other imaging techniques, and/or other measurements of the distensibility of veins. For example, a patient may wear a pulse oximeter in order to measure oxygen saturation and pulse. However, the pulse oximeter may also act as a PPG device as well, measuring blood volume or changes in blood volume in a vascular bed (such as a finger, ear or forehead).

In some alternatives, the overall blood volume and/or overall change in blood volume data is inputted by the user, such as by using UI 114, or otherwise inputted into the processor along data paths (e.g., plugged in using a wire or wirelessly transmitted). The overall blood volume and/or overall changes in blood volume may be used, by themselves or in combination with % TBSA or any other factor mentioned in this disclosure, to calculate the amount of fluid to be administered to a patient. These additional factors and modifications can be automatically incorporated into a displayed fluid resuscitation schedule.

Additionally, other alternatives use other ways of calculating the amount of fluid to be administered to a burn patient based on % TBSA. These include the Brooke formula, modified Brooke formula, modified Parkland formula, and any other correlation known in the art. Alternatives may not use a standard formula at all. For example, the amount of fluid to be administered can be calculated through machine learning or otherwise projected from historical data, which may include a patient's medical records or medical records of other patients.

Turning now to specific apparatus and methods that may be used for illuminating tissue, acquiring images, and analyzing the image data, it will be appreciated that numerous attempts have been made to develop apparatuses and methods to assess burns and other wounds. Some methods include thermographics, nuclear magnetic resonance, spectroscopy, laser Doppler flowmetry, and ultrasound. Additionally, photoplethysmography (PPG) has been used to detect blood volume changes in microvascular beds of tissue. In some instances, PPG alone does not fully classify tissue because it only makes volumetric measurements. Also, multispectral imaging (MSI) has been used to discern differences in skin tissue but this technique does not fully classify tissue. With current MSI technology, it can often be challenging to account for variations due to skin types, differences of skin in different body areas, and possible pre-treatment of wounds. MSI alone may also not give an overall assessment of a skin condition because it only measures skin appearance or the constituents of the skin, and not dynamic variables important to skin classification, such as the availability of nutrients and oxygen to the tissue.

Some alternatives described herein combine MSI and PPG to improve the speed, reliability, and accuracy of skin classification. The alternatives described herein can use, for example, image data to measure the contributions of blood, water, collagen, melanin, and other markers to develop a more refined view of the skin's structure and ability to properly function, as in a normal state, as opposed to skin that has suffered trauma. In addition, alternatives described herein also detect variations in light reflected from the skin over time, which allows one to gain significant physiological information allowing a clinician to rapidly assess tissue viability and features such as blood perfusion and oxygenation at a tissue site.

Figure 7:
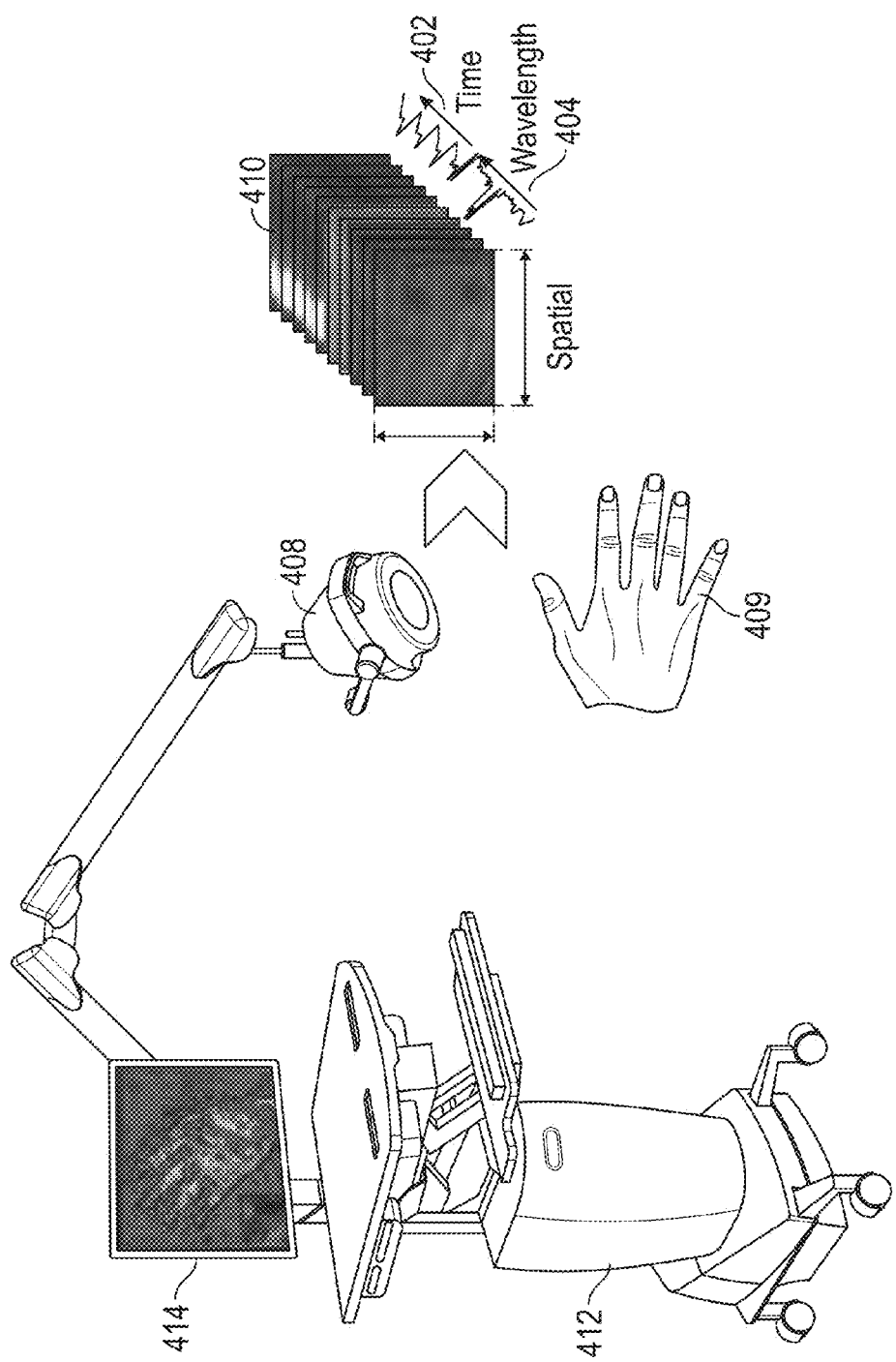
FIG. 7 is an example illustration of the high resolution multi-spectral video camera used in some alternatives described herein, and the data that can be obtained.

FIG. 7 illustrates a system that can be (but is not necessarily) used as the probe 100, controller/classifier/processor 112 and display/UI 114 in some alternatives. The system of FIG. 7 described below, with its combination of MSI and PPG technologies, can also be used to analyze and classify tissue regions of smaller areas as well with higher accuracy than previously available, and need not be used only in association with the whole body analysis systems and methods described above.

In the system of FIG. 7, probe 408 includes one or more light sources and one or more high resolution multi-spectral cameras that record a target tissue region 409 with a plurality of images while maintaining temporal, spectral, and spatial resolutions to perform highly accurate tissue classifications. Probe 408 can comprise multiple cameras and imagers, prisms, beam-splitters, photodetectors, and filters, as well as light sources of multiple spectral bands. The camera(s) can measure scattering, absorption, reflection, transmission, and/or florescence of different wavelengths of light over time from the tissue region. The system also comprises a display/UI 414, and a controller/classifier/processor 412 that controls the operation of the probe 408, receives inputs from the user, controls the display outputs, and performs the analysis and classification of image pixels.

Data set 410 is an example output of probe 408, which contains data regarding reflected light of different wavelengths and at different times for imaged spatial locations. An example of data regarding light of different wavelengths for imaged spatial locations is shown in data subset 404. Data subset 404 may include multiple images of the tissue region, each measuring light reflected from the tissue region in a different selected frequency band. The multiple images of data subset 404 may be acquired simultaneously or essentially simultaneously, where essentially simultaneously means within one second of each other. An example of data regarding reflected light from the tissue region at different times for imaged spatial locations is shown in data subset 402. Data subset 402 includes multiple images taken at different times over a period longer than one second, usually longer than two seconds. The multiple images of data subset 402 may be acquired at a single selected frequency band. In some cases, the multiple images of data subset 404 may be acquired over a time period longer than one second, and the multiple images of data subset 402 may be taken at multiple frequency bands. However, the combined data set including subset 404 and subset 402 includes images taken that correspond to both different times and different frequency bands.

To collect the images of data subset 404, in some alternatives, the one or more cameras are coupled to a filter wheel with a plurality of filters with different passbands. As the one or more cameras acquire images of the tissue region of the subject, the wheel of filters rotates, allowing the one or more cameras to record the subject in different spectral bands by acquiring images synchronized with filter positions of the filter wheel as it rotates. In this way, the camera receives the light reflected at each pixel of the tissue region in different frequency bands. Indeed, in many cases, the filters allow the devices described herein to analyze light in spectrums that would not be distinguishable by the human eye. In many cases, the amount of light reflected and/or absorbed in these various spectrums can give clues about the chemical and physical composition of the subject's tissue or a specific region of the tissue. In some cases, the data obtained using the filters forms three-dimensional data arrays, wherein the data arrays have one spectral and two spatial dimensions. Each pixel in the two spatial dimensions can be characterized by a spectral signature defined by reflected light intensity in each acquired spectral band. The intensity of light at the various wavelengths gives information about the composition of the target because different compositions scatter, absorb, reflect, transmit, and/or fluoresce different frequencies of light differently. By measuring light in these various wavelengths, probe 408 captures this composition information at each spatial location corresponding to each image pixel.

In certain alternatives for acquiring the images at multiple spectral bands for the data set 404, the one or more cameras comprise a hyperspectral line-scan imager. A hyperspectral line-scanner has continuous spectral bands instead of the discrete bands of each filter in a filter wheel. The filters of the hyperspectral line-scanner can be integrated with a CMOS image sensor. In some instances, the filters are monolithically integrated optical interference filters, wherein the plurality of filters is organized in stepwise lines. In some cases, the filters form a wedge and/or a staircase shape. In some instances there may be dozens to hundreds of spectral bands corresponding to wavelengths between 400 to 1100 nm, such as at 400, 500, 600, 700, 800, 900, 1000, or 1100 nm or a range defined by any wavelength that is between any two of the aforementioned wavelengths. The imager scans the tissue using each filter line and senses the light reflected from the tissue through each of those filters.

In still other alternatives, there are other filter systems that can be implemented to filter light in different spectral bands. For example, a Fabry-Perot filter is used in some alternatives, as well as, other filter organization approaches, for example by putting the filters in a tile structure or by depositing the filter directly onto the imaging sensor (CMOS, CCD, etc.) in a pattern such as a Bayer-array or multi-sensor array.

In any case, the passbands of the filters are selected based on the type of information sought. For example, burn sites might be imaged with wavelengths between 400-1100 nm (such as at 400, 500, 600, 700, 800, 900, 1000, or 1100 nm or a range defined by any wavelength that is between any two of the aforementioned wavelengths) at each stage of debridement in order to capture the contributions of blood, water, collagen, and melanin from the burn site and surrounding tissue. In certain experiments using porcine burn models to study partial thickness burns of varying severity, absorbance spectra of approximately 515 nm, 750 nm, and 972 nm wavelengths were desired for guiding the debridement process, while the absorbance spectra of approximately 542 nm, 669 nm, and 960 nm wavelengths were desired for distinguishing between deep-intermediate partial thickness and deep-partial thickness burns.

In another experiment, images were taken of adult minipigs with partial thickness burns. Samples of healthy skin, burn injuries, and excisions of the burn injuries were used to classify tissue as healthy skin, hyperemia, graftable, blood, less severely burned, and severely burned. In the experiment, healthy skin included areas of skin that did not have an injury associated with a burn. Hyperemia corresponded to areas of high perfusion, typically first degree burns that were expected to heal without treatment. The graftable categorization corresponded to skin that was typically light pink with punctate bleeding. This tissue was typically desirable for skin grafts. The blood categorization corresponded to larger regions of accumulated blood that should be removed and re-imaged since the blood was covering the tissue to be categorized. The "less severely burned" category corresponded to the zone of stasis with decreased perfusion, but potentially salvageable tissue. The severely burned categorization corresponded to regions of protein coagulation that produced irreversible tissue loss where excision was desirable.

Alternatives of this disclosure were used to measure light reflected from the tissue samples at various wavelengths in the range 400 nm to 1100 nm (such as at 400, 500, 600, 700, 800, 900, 1000, or 1100 nm or a range defined by any wavelength between any two of the aforementioned wavelengths) in order to determine which sets of wavelengths provided higher amounts of variability between the light reflected from tissues of different tissue types. This variability could be used to effectively separate tissue classes by at least the categories of healthy skin, hyperemia, graftable, blood, less severely burned, and severely burned. The optimal sets were sometimes identified as the wavelength sets that contained the maximally relevant wavelengths with the minimum amount of redundancy. In this context, maximum relevance was sometimes found when wavelengths could effectively separate one particular tissue class from the other classes. Minimum redundancy was sometimes found by including only one of a plurality of wavelengths that measured the same information. After sets of wavelengths were used to classify the tissue samples, the classifications were compared to accurate assessments of the tissue samples by practitioners.

Data splits across different experiments were used to test classification accuracy. In a first set of experiments, the wavelengths 475, 515, 532, 560, 578, 860, 601, and 940 nm were measured. In a second set of experiments, the wavelengths 420, 542, 581, 726, 800, 860, 972, and 1064 nm were measured. In a third set of experiments, the wavelengths 420, 542, 581, 601, 726, 800, 972, and 860 nm were measured. And in a fourth set of experiments, the wavelengths 620, 669, 680, 780, 820, 839, 900, and 860 nm were measured.

The wavelengths that provided the best variability for tissue classification from the first and second experiment sets were used in order to categorize tissue with 83% accuracy. These wavelengths were (in order of relative weight) 726, 420, 515, 560, 800, 1064, 972, and 581 nm. Similarly, the wavelengths that provided the best variability for tissue classification from the third and fourth experiments were used in order to categorize tissue with 74% accuracy. These wavelengths were (in order of relative weight) 581, 420, 620, 860, 601, 680, 669, and 972 nm. The accuracy of both of these sets were higher than the current standard of care for clinical judgment, which is 67-71% accuracy in determining burn depth. Also, noticeably, the wavelength of 860 nm was particularly effective for both MSI and PPG algorithms, and thus, for the combination device. These experimental sets show that wavelengths in the range 400 nm to 1100 nm (such as at 400, 500, 600, 700, 800, 900, 1000, or 1100 nm or a range defined by any wavelength that is between any two of the aforementioned wavelengths) can be used for effective tissue classification. As previously noted, other sets of wavelengths may be effective as well. For example, the effective wavelength sets in the experiment minimized redundancy. As such, other wavelengths may be used to classify some aspects of the tissue effectively. Also, using the experiment described above, other wavelengths for effectively classifying burns and/or any other tissue condition described in this disclosure may be found.

Overall, the experiment described above found that wavelengths in the range 400 nm to 900 nm (including 400, 500, 600, 700, 800, or 900 nm or a range defined by any wavelength that is between any two of the aforementioned wavelengths) were particularly effective in imaging burns. More particularly, of that range, a set of wavelengths could be constructed to image burns where: at least one (1) wavelength was less than 500 nm; at least two (2) wavelengths were between 500-650 nm; and at least three (3) were between 700-900 nm. This set was effective at imaging burns and separating imaged burn tissue into categories.

Also based on the experiment, the below ranking lists each tested wavelength in order of their apparent significance in classification:

TABLE 1

| Rank | Wavelength |
| --- | --- |
| 1 | 420 |
| 2 | 560 |
| 3 | 860 |
| 4 | 620 |
| 5 | 726 |
| 6 | 800 |
| 7 | 581 |
| 8 | 542 |
| 9 | 578 |
| 10 | 601 |
| 11 | 972 |
| 12 | 532 |
| 13 | 475 |
| 14 | 515 |
| 15 | 940 |
| 16 | 680 |
| 17 | 900 |
| 18 | 1064 |
| 19 | 669 |
| 20 | 780 |
| 21 | 839 |
| 22 | 820 |

To collect the images of data subset 402, the one or more cameras are also configured to acquire a selected number of images having temporal spacing between each image short enough to measure temporal variations in reflected light intensity due to motions of the tissue region that correspond to physiological events or conditions in the patient. In some cases, the data obtained from the multiple time separated images forms three-dimensional data arrays, wherein the data arrays have one time and two spatial dimensions. Each pixel in the three dimensional array can be characterized by a time domain variation in reflected light intensity. This time domain signal has different energies at different frequency components related to blood pressure, heart rate, vascular resistance, nervous stimuli, cardiovascular health, respiration, temperature, and/or blood volume. In certain alternatives, a filter may be used to filter out noise. For example, an 860 nm bandpass filter may be used to filter out light wavelengths that correspond to the predominant wavelength spectrum of the ambient lighting in the room, so that the acquired images correspond to reflected light that originates with the light sources in the probe 408. This can reduce and/or prevent aliasing of ambient light fluctuations, such as the 60 Hz fluctuations present in ambient lighting due to the AC power line frequency.

Figure 8:
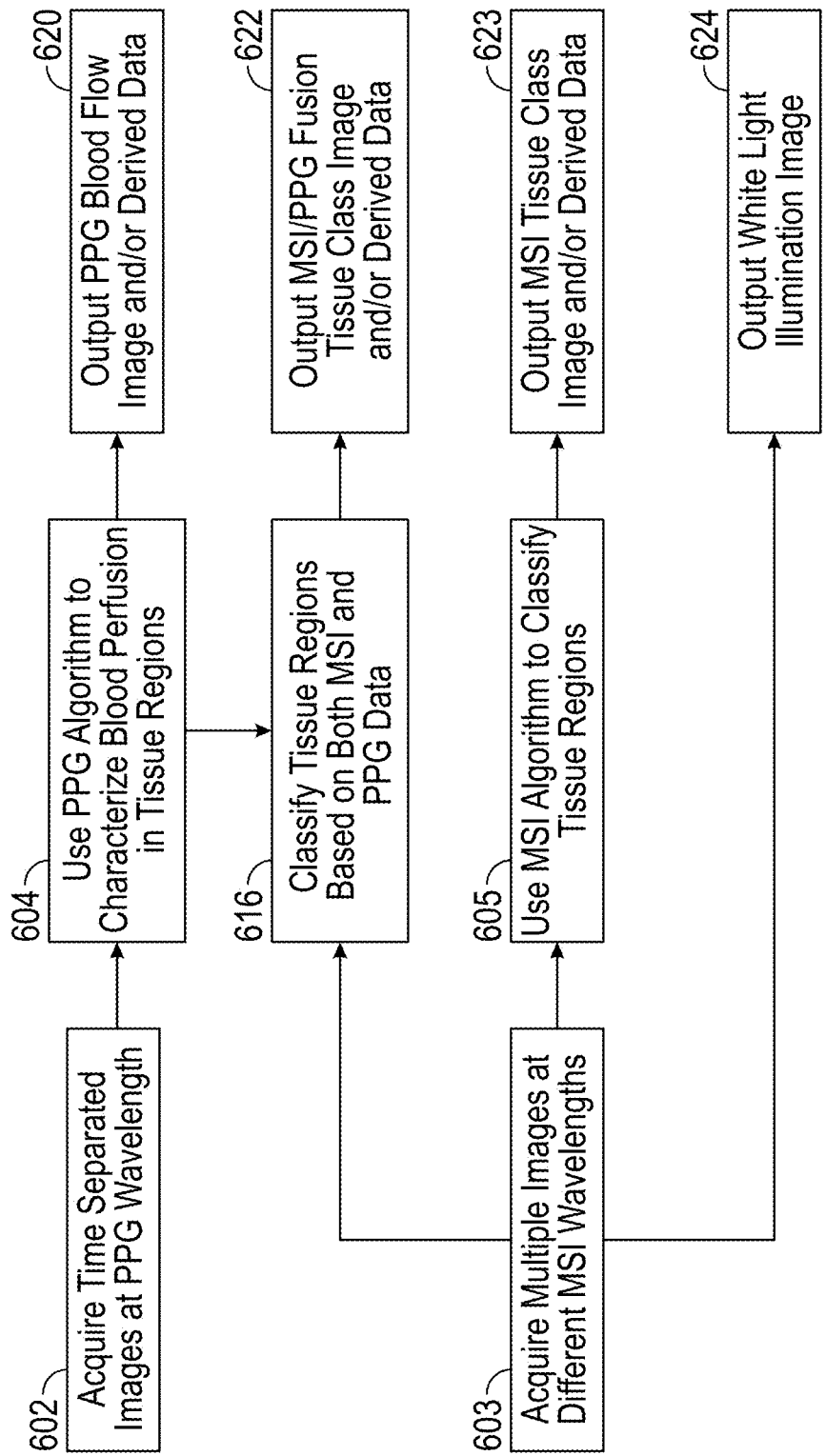
FIG. 8 is an example flow chart showing the steps used for tissue classification in certain alternatives described herein.

Additional detail regarding advantageous image acquisition and signal processing procedures are described with reference to FIG. 8, which illustrates processes that may be performed by the apparatus of FIG. 7. FIG. 8 shows an example flow diagram 600 of the processes used by some alternatives to classify tissue. Blocks 602 and 603 show that some alternatives take multi-spectral images and multiple time separated images (e.g. videos) using, for example, the probe 408. For the time separated images, for example data subset 402, in order to obtain a signal with less overall noise and higher signal-to-noise ratios, it was found that a relatively long exposure time was desirable. In certain cases, a capture time of twenty-seven (27) seconds was used, which is longer than the seven (7) second capture time of conventional PPG imaging processes. Accordingly, capture times of at least, greater than, or any number in between 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds, or a range defined by a capture time that is between any two of the aforementioned numbers is desired in some alternatives. During these capture times, the number of frames per second captured by the imager may be set. In some circumstances, thirty (30) frames per second (fps) or sixty (60) fps may be effective at imaging tissue. At 30 fps over 27 seconds, the imager takes about 810 images. At 60 fps over 27 seconds, the imager takes about 1620 images. In some alternatives, the number of images taken may vary depending on the resolution of data needed (e.g., to capture the human heart beat). For example, for CMOS cameras, twenty (20) to one hundred twenty (120) fps may be used. This includes sample rates of 20, 30, 40, 50, 60, 70, 80, 90, 100, 110, or 120 fps or a range of rates defined by a sample rate that is between any two of the aforementioned rates.

Also, in certain alternatives, light source placement was important due to illumination spots, which were locations of light high intensity that saturated the signal and masked pulse waveforms. In some alternatives, this issue was resolved by using diffusers and other front-end hardware techniques. However, in cases where the illumination spots could not be eliminated by front-end techniques, signal processing was used in some alternatives to eliminate the illumination spots. Indeed, to create reliable images of tissue pathologies, the signal is desirably preserved and displayed while the noise is discarded. This process involves removing the noise associated with illumination spots and other irrelevant signals.

At block 604 the time-resolved image sequence (data subset 402 for example) is sent to the controller/classifier/processor 412 for processing, which then uses a PPG algorithm to calculate the blood flow perfusion in the tissue area. This process can involve amplification, linearization, signal averaging, correlation, and/or one or more filters (e.g., bandpass, highpass, or lowpass) to eliminate noise, isolate the portions of signal of interest, and boost signal-to-noise ratios. The choice of filters is important because too much filtering can cut out essential data while too little filtering can make the signal harder to analyze. Cross-correlation and auto-correlation can also be used to eliminate noise. In some alternatives, sample signals can also be used to eliminate noise, as will be described below. The signal is then transformed into the frequency domain. For example, in some alternatives, a fast Fourier transform (FFT) is used. After performing the FFT, the signal is then analyzable by frequency. The time domain variation of reflected light intensity at each pixel over the course of the multiple time separated images has signal energy at various frequencies. These frequencies, and the physiological events to which they correspond, give an indication of the impact of the occurrence and intensity of those physiological events at the tissue location imaged with the pixel. For example, the signal intensity at a pixel in a band around 1.0 Hz, which is approximately the frequency of a resting human heart beat, can be used to assess the blood flow to and around the tissue at the location of the pixel in the image.

In some alternatives, relevant signals can be identified by looking at local maxima. For example, heart rates were found by looking at the signal energy in the band around the frequency at the highest peak and assuming that the peak was part of due to heartbeat induced blood pressure changes. However, this method may not identify noise that has a peak higher than the signal from the actual heart rate. In such a case, other alternatives utilize signal processing that employs computer learning and training based on examples or on a database of references of noisy signals, white noise signals, and other example signals. The computer analyzes examples of relevant signals and noise to learn to identify the signals over the noise. For example, in the case of identifying signals related to blood flow, signals that have the same frequency content as the heart beat may be relevant. The computer learning utilizes example heart rate signals or refers to a database of heart rate signals as a reference so as to identify the heart rate from the noise. The computer learning process can also analyze white noise, false heart rate signals, and noise signals with peaks higher than a heart rate signal utilizing such reference points and databases. The computer learning can identify the signals based on characteristics such as frequency, amplitude, signal-to-noise ratio, zero crossings, typical shape, or any other characteristic of a signal.

In some circumstances, additional comparisons are utilized to identify signals. For example, in some alternatives, compilations of hand-picked clinical stage signals are created. The hand-picked clinical stage signals are then compared to the measured signals to classify the measured signal as a signal of interest or noise. Another technical advancement that was implemented was the removal of edge effects. In some alternatives, images showed grainy noise around the edge, and in some instances, regions of interest were also less pronounced than desired. When the edge effects were removed, regions of interest showed higher signal strength. In some alternatives, edge removal was accomplished by using image processing, including averaging, dilation and erosion, and edge detection and enhancement.

Another technical advancement was the automatic removal of motion artifacts. Motion artifacts include motion associated with a patient's breathing, a patient's movements, or any general vibrations around the camera or patient that may skew an image. To remove these motion artifacts, the signal was processed with "windowing", which identifies regions of the time domain that are much larger and noisier than surrounding portions and identifies those regions as "motion." These segments are then clipped out of the time domain, allowing a modified signal without the motion artifact. Other filters and selection methods may also be used to remove noise and otherwise unwanted signal portions. After this processing, the computed signal energy at the desired frequency (e.g. generally about 1 Hz) can be classified for tissue region (e.g. for each two dimensional pixel position) into categories defining blood perfusion at that pixel position.

At substantially the same time as the performance of blocks 602 and 604, some alternatives also perform blocks 603 and 605. Block 603 acquires the images forming the multi-spectral data cube (data subset 404 of FIG. 7 for example). The data cube comprises 2D images at every MSI spectral band. At block 605, these alternatives then apply MSI algorithms to analyze the data, and at block 614, the system assigns a category of tissue composition to each tissue region (e.g. for each two dimensional pixel position).

Block 616 then combines the blood perfusion and MSI data from blocks 603 and 604 to create tissue classifications based on both MSI and PPG data.

For example, for illustrative purposes, eight bandpass filters may be used to produce eight reflectivity values for each pixel imaged, each one corresponding to a selected spectral band. Also, 810 images may be acquired over 27 seconds at 30 frames per second taken using a filter with center wavelength at an infrared or near infrared wavelength (e.g., near or around 840-880 nm, including 840, 850, 860, 870, or 880 nm wavelengths or a range defined by any wavelength that is between any two of those wavelengths). These 810 images could be analyzed in the frequency domain as described above to produce PPG data characterizing blood perfusion at each spatial location imaged, producing a perfusion value for each pixel imaged. Thus, each pixel of an imaged tissue region would have measurements corresponding to measurements taken with each of the eight bandpass filters and a value corresponding to local blood flow. This is a total of nine (9) measurements at each pixel. Using these 9 measurements, the pixels can be segmented (e.g., categorized) into different categories. As will be appreciated by someone having ordinary skill in the art, any number of measurements (e.g., 2, 10, 20, or a range defined by any number of measurements that is between any two of those measurements or greater than any one of those measurements), may be taken for each pixel, and the pixels may be segmented by those measurements.

Various segmentation/classification methods could be used. Generally, classifiers are trained using a "training" data set where the measured parameters are known as well as the appropriate classification. The trained classifier is then tested on a "test" data set where also the measured parameters are known as well as the appropriate classification, but which was not used to train the classifier. The classifier quality can be assessed by how well the classifier successfully classifies the test data set. In some alternatives, a predetermined number of categories could be used, and the pixels sorted into those predetermined categories. For example, for categorizing burns in a triage environment, categories of healthy skin, hyperemia, less severely burned, and severely burned may be used.

In other alternatives, the number of categories is unknown, and the processor, such as processor 112, creates categories based on groupings of pixels and their characteristics relative to each other. For example, the processor could identify a tissue region with much poorer blood flow and much lower normalized pixel intensities at certain wavelengths as being associated with a severe burn by virtue of these measurements relative to surrounding measurements.

In some alternatives, the pixels are distributed based on preset ranges of values for each of the categories. For example, certain ranges of values for light reflectance may be associated with healthy skin. When data falls within those ranges, the tissue is identified as healthy skin. These preset ranges may be stored in memory on the system 412, entered by a user, or otherwise determined automatically by system learning or adaptive algorithms. In some alternatives, categories are defined by information transferred to the system by an external source, such as by a data uplink, cloud (as will be discussed later in this disclosure), or any data source. In other alternatives, present ranges of values for each category are unknown and the processor adapts categories based on comparing measurements at each pixel to each other.

In some alternatives, an adaptive algorithm may be used to categorize pixels into groups with common characteristics, and identify those groups. For example, graph theory may be used to divide the pixels into categories by finding graph cuts, such as minimum cuts. Other segmentation methods could also be used, such as thresholding, clustering (e.g., k-means, hierarchical clustering, and fuzzy clustering), watershed algorithms, edge detection, region growing, statistical grouping, shape recognition, morphological image processing, computer training/computer vision, histogram-based methods, and any segmentation method known in the art of categorizing data into groups.

In some alternatives, historical data may be used to further inform the segmentation. The historical data may include data previously obtained by the patient and/or data from other patients. In certain alternatives, other data, such as skin tone, race, age, weight, gender, and other physiological factors, are considered in the segmentation process. In any case, data may be uploaded, obtained from a cloud, or otherwise inputted in the system, including using UI 114. In certain alternatives, a dynamic library of patient data is analyzed. Statistical methods, including t-tests, f-tests, z-tests, or any other statistical method for comparison, may be used to compare previously identified images to acquired images. Such comparisons, for example, might take into account measured pixel intensities, relative measurements of pixels to other pixels in an image, and pixel distributions.

In certain alternatives, the dynamic library may be updated with exemplary images of tissue conditions, such as burns, to aid in the classification of tissue. In other alternatives, the images may be designated and identified by what tissue conditions they show, and how well they show them. Desirably, a full range of images at different angles should be in the dynamic library in order to account for the variations in the angles, quality, and conditions of the skin conditions imaged.

Turning back to FIG. 8, a variety of data outputs may be presented to the user. These include a PPG perfusion image 620 based on the PPG data, an MSI classification image based on the MSI data, a white light illumination image based on normal RGB data, and a MSI/PPG fusion image 622 which illustrates classification based on the combined MSI and PPG data. For example, in the triage device described above with reference to FIGS. 1-6, the display outputs 212, 214, 216, and 218 of FIG. 3 could be combined MSI/PPG fusion classification images 622. In such images, each tissue region (e.g. pixel) of the subject is classified into a burn classification such as healthy, hyperemia, severely burned, and less severely burned as described above. Additionally or alternatively, data outputs as shown in FIG. 3 such as % TBSA in each category could be presented to the user.

Figure 9A:
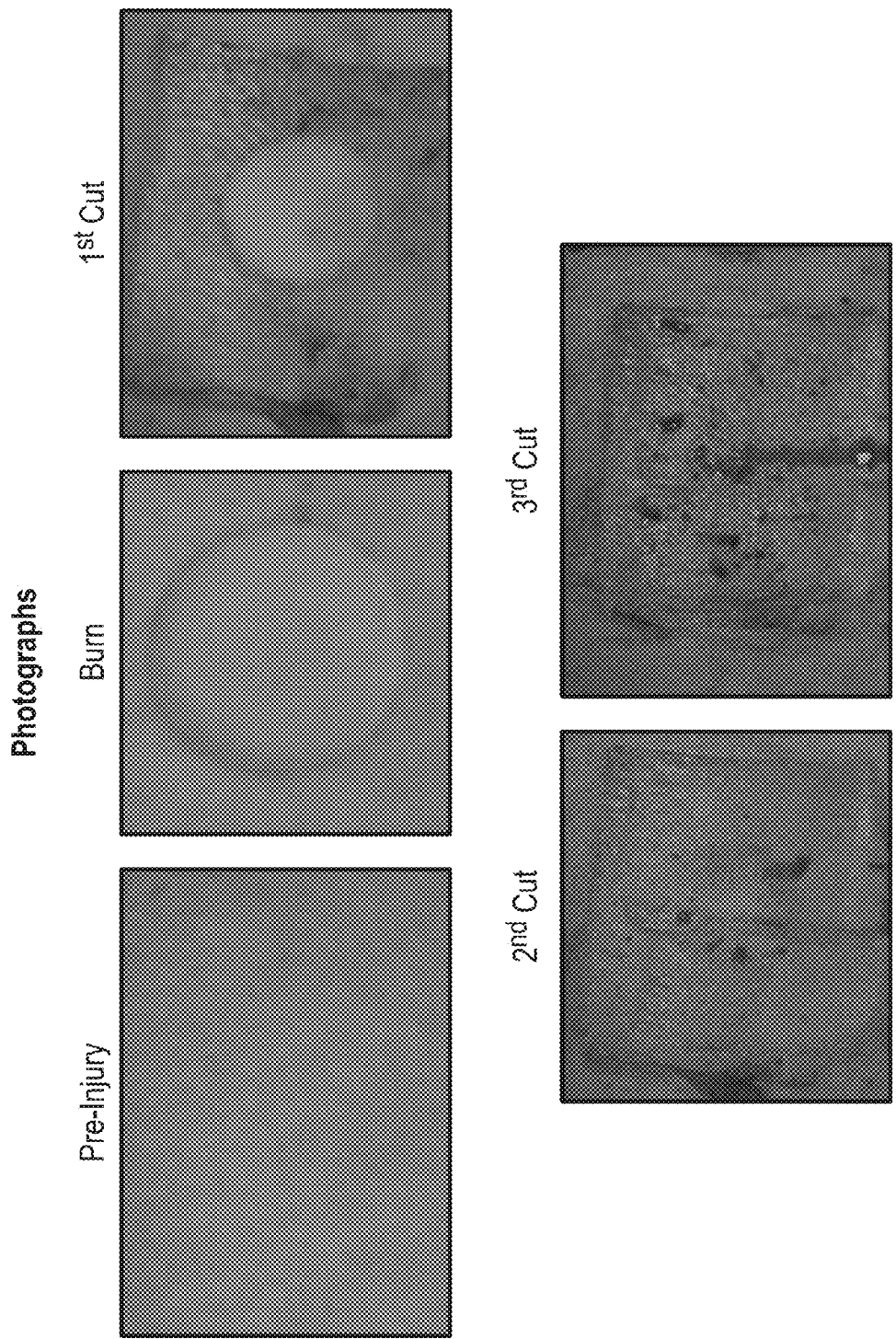

The use of both the composition and viability data in classifying tissue is a significant advancement over the prior art. FIGS. 9A, 9B, 9C, and 9D illustrate some of these advantages for burn classification. In an experiment, images were taken of adult mini-pigs with partial thickness burns. FIG. 9A shows an example five tissue samples that were used in the experiment. FIG. 9A was taken using a normal, photographic camera. The images were taken of a tissue surface pre-injury (e.g., pre-burning), of the surface after a burn, and then of three excisions ($1^{st}$ cut, $2^{nd}$ cut, and $3^{rd}$ cut) tangential to the burn. These same five tissue samples were used to compare the results of PPG, MSI, and a new system according to certain alternatives of this disclosure, where tissue is classified based on both PPG and MSI algorithms. Because the images in the experiment were taken of tissue that could be independently analyzed by a practitioner, the effectiveness of the different imaging techniques could be assessed by comparing the results of the imagers to how a tissue should be classified.

Figure 9B:
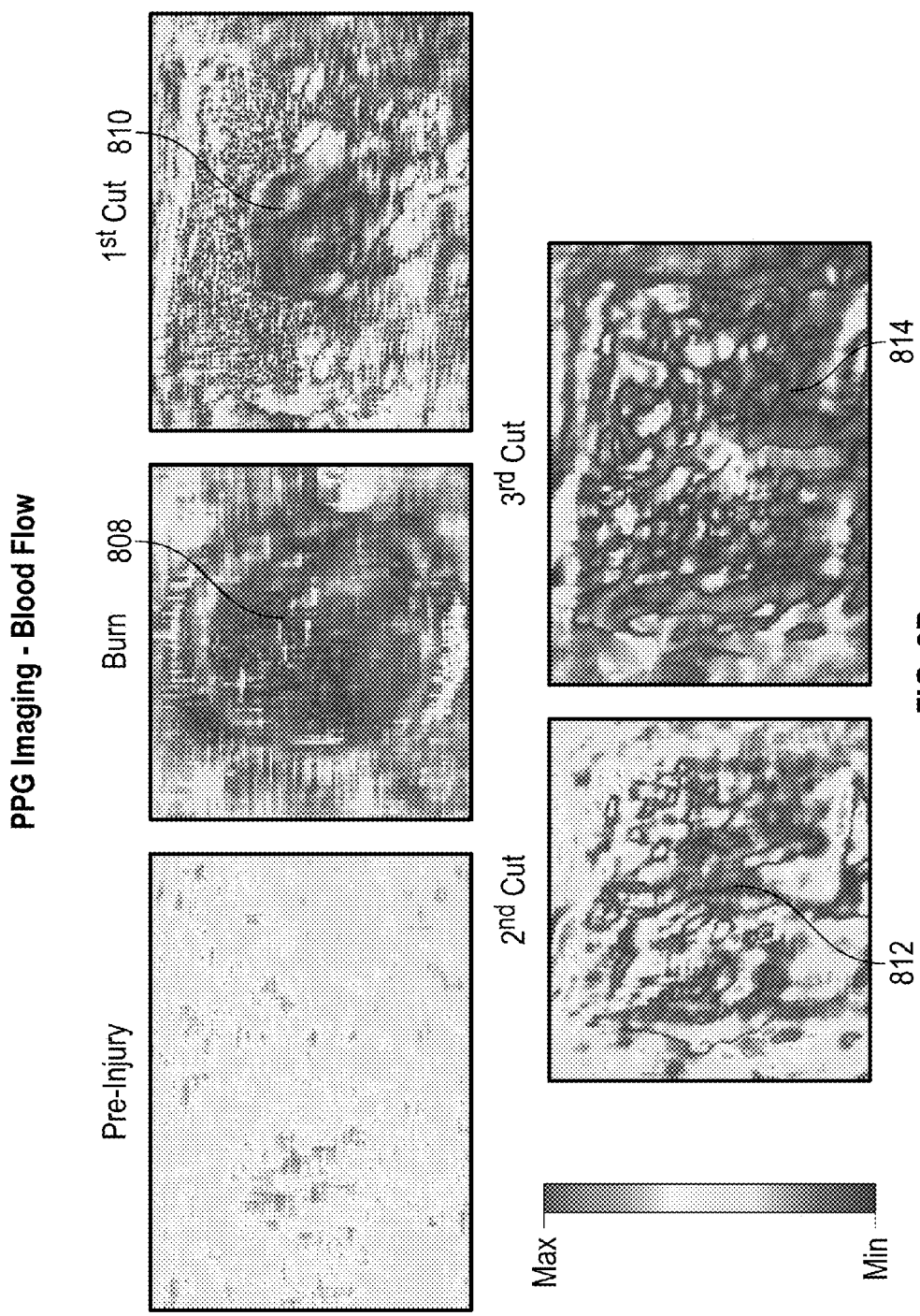

FIG. 9B is an example of these five images showing PPG imaging data alone at each pixel of the image. The images show that there are limitations to correctly classifying tissue solely based on PPG data. Only the most severely burned tissue that had minimal blood flow could be readily identified from this example data. Tissue regions 808, 810, 812, and 814 are examples of such tissue regions with minimal blood flow, which have been scaled to appear much darker in color than other regions. The other regions fall somewhere in the spectrum between minimum and maximum blood flow readings, and are difficult to categorize and classify.

FIG. 9C is an example of these five images showing MSI imaging data alone at each pixel of the image. The image shows that there are also limitations to correctly classifying tissue solely based on this MSI data. In the pre-injury image, much of the tissue is classified as "hyperemic" when it should actually be "healthy skin". In the burn image, region 816 is correctly identified as severely burned. However, certain regions, such as region 818, are incorrectly classified as "severely burned" instead of "healthy skin". In the $1^{st}$ cut, regions, such as region 820, are incorrectly identified as "less severely burned" when they should be classified as "graftable wound bed." Similarly, tissue region 820 of the $3^{rd}$ cut was also incorrectly identified as "less severely burned" when it should have been classified as "graftable wound bed."

FIG. 9D is an example of the same five images showing data from the new system according to certain alternatives of this disclosure, which utilize at least both MSI and PPG algorithms. The new system correctly identifies the pre-injury image as "healthy skin." In the burn image, the new system correctly identifies region 824 as a ring of "hyperemic" tissue surrounding the "severely burned" tissue of region 826. This ring was not correctly identified by PPG or MSI. In the burn image, the new system also reduced errors of identifying "severely burned" tissue where there was actually healthy tissue. Similarly, in the $1^{st}$ cut and $3^{rd}$ cut images, the new system correctly identified graftable wound beds where the MSI and PPG images did not. Namely, the MSI imager had incorrectly classified regions 820 and 822 as "less severely burned" when they should have been "graftable wound bed". The new system correctly identifies these same regions, shown as regions 828 and 830, as "graftable wound bed".

As can be seen by the results of this experiment, the new system that classified tissue based on both composition and viability better classified burn injuries at the different stages of debridement than the prior art, including PPG alone and MSI alone. As such, the new system presents a sizeable, and unexpected, advancement over other systems and methods in the prior art.

Figure 10:
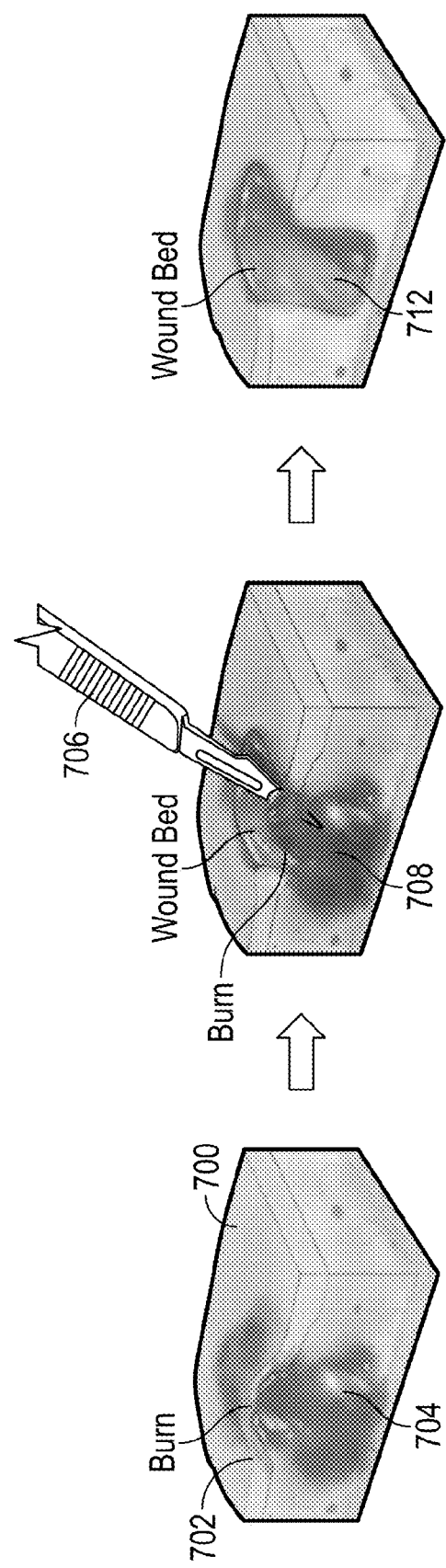
FIG. 10 is an example illustration of a burn and a debridement procedure.

One clinical application of some alternatives described herein is the classification of burns. FIG. 10 shows a high-level flow diagram of a burn treatment. Tissue 700 shows a burn on tissue. Skin layer 702 shows a burn at the surface of the skin. Often burns can lead to discolored skin or a loss of epidermis. Below skin layer 702 is tissue layer 704, which is denatured skin without blood supply. Sometimes this is called the zone of coagulation, zone of coagulative necrosis, or eschar. It is dead tissue. Near or around tissue layer 704 can be other tissue with modified blood flow, depending on the degree of the burn. This is sometimes called the zone of stasis, which is an area surrounding the zone of coagulation where the cellular damage is less severe. Farther from the zone of coagulation, and outside the zone of stasis, is the zone of hyperaemia, where the tissue will likely recover. Burns are classified in degrees first through fourth, where a first degree burn is the least severe and closest to the surface, and fourth is the most severe extending into the muscle and bone.

The subtle difference between burns of varying severity can be difficult to distinguish with the naked eye, if they can be distinguished at all. Indeed, at their early stages, the full effect of burns may be buried deep within the skin surface, making a determination of the degree of burn and even the presence of burn tissue nearly impossible without surgical intervention. Nevertheless, despite these differences, time is of the essence for treating burns. Indeed, early treatment can make all the difference for burn recovery.

Some alternatives are effective at identifying and assessing the severity of burns. Indeed, the devices described herein can physically locate and identify burns, including their burn severity (e.g., the degree of the burn and whether it is superficial, shallow partial thickness burns, deep partial, or full thickness), and also find % TBSA of burns in general or for each burn severity. As described above, the nature and quality of skin tissue changes after a burn. As a result, the way the various layers of tissue absorb and reflect light differs from other sorts of tissue and depending on the degree of the burn. In these cases, the high resolution multi-spectral camera of some alternatives described herein can pick up these differences and use them to assess the composition of the skin to identify burns and the severity of burns. However, just this information alone can sometimes provide an incomplete evaluation of the severity of the burn. As mentioned before, the severity of the burn is not only related to how the skin is presently damaged, but also to the presence or absence of a blood flow to the tissue. Accordingly, the high resolution multi-spectral camera utilized in some alternatives can also desirably measure the blood flow to a tissue region, wherein the combined information of the composition of the skin and the blood flow gives a refined and precise determination of the presence of a burn and the severity of the burn.

Scalpel 706 is an example way that a burn may be treated. Through debridement, the dead, damaged, infected, necrotic or soon to be necrotic tissue is excised in order to improve and facilitate the healing of the remaining healthy tissue. Indeed, as described earlier, over- and under-excision of the tissue may have life threatening consequences. Under excised burns result in placement of grafts on devitalized tissue and poor graft uptake. Under excised burns further lead to increased risks of infection and/or longer healing times. On the other hand, over excision may lead to excessive blood loss, or bleeding of the excised surface, which can compromise graft uptake. The devices described herein provide a quantitative way of identifying the boundaries between healthy tissue and the tissue needed to be excised. This is an advancement over the current state of the art, which relies on a specialist's subjective opinion of the tissue.

In this example, burn 708 is excised to leave the wound bed 710. After the dead tissue is removed, the clean wound bed 712 is ready for a graft, which would transplant healthy tissue to the excised region and aid in the tissue recovery. Indeed, a benefit of the devices and methodologies described herein is that a non-burn specialist can rapidly evaluate the severity of a burn with a non-invasive tool prior to surgical intervention and grafting.

FIG. 11 shows the application of some of the devices described herein, wherein these devices are used to assess graft viability. A graft, as used in some alternatives, is a transplant of tissue or regenerative cells, which can comprise stem cells, endothelial cells, endothelial precursor cells and/or a mixture of these cells in an isolated, enriched, or concentrated form or a prosthetic, support, or medical device. The graft, as used in some alternatives, may comprise a tissue and/or the aforementioned cells with a scaffold, prosthetic, or medical device. In cases where no blood supply is transplanted with the tissue, a successful graft will have a new blood supply formed by surrounding tissue to support it. Some applications comprise the introduction of regenerative cells, which can comprise stem cells, endothelial cells, endothelial precursor cells and/or a mixture of these cells in an isolated, enriched, or concentrated form and this graft can provide a blood supply by virtue of the ability of said cells to generate or cause to generate a new blood supply by, for example angiogenesis or arteriogenesis. Some applications, comprise utilization of a graft and/or regenerative cells, which can comprise stem cells, endothelial cells, endothelial precursor cells and/or a mixture of these cells in an isolated, enriched, or concentrated form alone or in combination with a scaffold, support, prosthetic, or medical device are supplemented with one or more growth factors, such as FGF, HGF, or VEGF. The devices described herein can classify a graft according to whether there has been a successful uptake of the graft or whether the graft will be rejected and become necrotic tissue. Image 900 shows an image produced by an alternative described herein, wherein the tissue region is imaged corresponding to both different times and different frequency bands. The colors on the image indicate that there is healthy tissue that is being supplied with blood. Image 902, in contrast, shows unhealthy tissue with no blood supply, which indicates a graft failure.

Another clinical application of the devices described herein is to classify decubitus ulcers, also known as pressure ulcers or bed sores. These wounds develop because of pressure applied to tissue resulting in the obstruction of blood flow to that tissue. As a result of the obstruction, tissue necrosis and tissue loss occurs. In many cases, in later stages, this leads to visible alterations in the color of the tissue. Decubitus ulcers may be categorized in stages one through four, which relate to the amount of tissue loss that has occurred.

Part of the difficulty of identifying decubitus ulcers is that early obstruction can cause changes in the tissue that are not readily observable on the tissue's surface. Devices described herein are effective in identifying decubitus ulcers at early stages of development, which facilitates early and preventative treatment. FIG. 12 shows an application of the devices described herein to identify the presence or induction of decubitus ulcers and the classification of different stages of decubitus ulcers. Image 800 shows an illustration of a skin tissue that has been overlaid with tissue classification data. The colors indicate the presence of a decubitus ulcer below the surface. A device manufactured as described herein made the classifications by reading light reflectance in both different times and in different frequency bands, which allowed the detection of a difference in the composition of the tissue and a difference in blood flow to the tissue. Image 806 is a picture of the tissue surface thirteen days later, where the patient had a stage II decubitus ulcer.

In contrast to decubitus ulcers where blood to tissue is obstructed, tissue may also suffer from too much blood. In hyperaemia, which can manifest as erythema, there is an increase in blood flow to tissue. This can lead to swelling, discoloration, and necrosis. It may also be accompanied by engorged capillaries and veins, excessive hemosiderin in the tissue, and fibrosis. Alternatives of the present invention may be effective in identifying and assessing tissue suffering from hyperaemia at its early stages. Again, the combination of being able to detect the changes in the nature and quality of the tissue, along with the blood flow to the tissue, allows these alternatives to readily identify and assess the severity of tissue suffering from hyperaemia.

Alternative devices described herein have numerous other applications in the medical field where tissue needs to be classified and assessed. Like burns, decubitus ulcers, and hyperaemia, there are other types of wounds that these alternatives can classify and assess, including: abrasions; lacerations; hemorrhaging; rupture injuries; punctures; penetrating wounds; chronic wounds; or, any type of wound where the nature and quality of the tissue changes along with a change in blood flow to the tissue. The alternatives presented herein provide physiological information relating to tissue viability in a simple image format to medical practitioners. Information such as blood perfusion and oxygenation at the wound site are important indicators of wound healing. By imaging these hemodynamic characteristics hidden beneath the skin, physicians can be better informed about the progress of wound healing and make better educated and timely patient-care decisions. At the same time, some devices described herein can give information about the composition of the skin, which is indicative of the skin's condition.

Moreover, the use of some of the devices described herein are not limited to applications where there has been damaged tissue. Indeed, some alternatives may also detect healthy tissue and differentiate the healthy tissue form necrotic tissue or tissue that is soon to be necrotic.

One natural place healthy tissue may be classified and assessed is in comparison to a wound or skin condition. For example, along with a burn, there may be regions of healthy tissue associated with or juxtaposed to the burn. It would helpful to both burn diagnosis and treatment to be able to identify where the margin of healthy tissue exists with respect to necrotic tissue or tissue that has a predestination to become necrotic tissue. The healthy tissue may be identified by imaging the skin in both different times and different frequency bands to assess the composition of the skin, as well as, blood perfusion and oxygenation at the tissue site.

Alternatives described herein may also classify tissue based on its likely success as a graft tissue or a regenerative cell implant. This classification would take into account the quality and nature of the recipient tissue, as well as, the recipient tissue's ability to accept a new blood supply. Alternatives may also classify the receiving tissue based on how likely the tissue will be able to form a new blood supply for the graft or regenerative cell implant, and how healthy the skin is generally. In both classifying the graft tissue or the receiving tissue, some devices described herein can analyze a plurality of images corresponding to different times and different frequency bands.

In addition to merely classifying the health of tissue, alternatives as described herein may also measure various aspects of the tissue, such as, the thickness of a region of skin and skin granulation tissue may also be assessed. In another example, the health of tissue around a suture, and the healing of a suture can be monitored and assessed with the devices described herein.

Another application of some of the devices described herein is to monitor tissue healing. The devices described herein can also obtain several images at numerous points in time to monitor how a wound changes, or how healthy tissue forms. In some cases, a therapeutic agent, such as a steroid, hepatocyte growth factor (HGF), fibroblast growth factor (FGF), an antibiotic, an isolated or concentrated cell population that comprises stem cells and/or endothelia cells, or a tissue graft may be used to treat a wound or other ailment and such treatments can be monitored using a device as described herein. Some alternatives can monitor the effectiveness of therapeutic agents by evaluating the healing of tissue before, during, or after application of a particular treatment. Some alternatives do so by taking a plurality of images at both different times and different frequency bands. According to these images, the light reflected from the skin can be used to assess the nature and quality of the tissue, as well as the blood flow to the tissue. As a result, the devices as described herein can give valuable information about how a tissue is healing, and the effectiveness and speed at which a therapeutic agent facilitates the healing process.

Some alternatives may be used to monitor the introduction of a left ventricular assist device (LVAD) and the healing process after such an implant. As LVAD flow increases, the diastolic pressure rises, the systolic pressure remains constant, and the pulse pressure decreases. The pulse pressure, which is the difference in systolic and diastolic pressures, is influenced by the contractility of the left ventricle, intravascular volume, pre-load and after-load pressure, and pump speed. Therefore, assessment of the arterial blood pressure values and waveforms gives valuable information about the physiologic interaction between the LVAD and the cardiovascular system. For instance, poor left ventricle function is related to arterial waveforms that do not show pulsatility. Alternatives described herein can be used to monitor the return of pulsatile flow in patients after LVAD implantation and provide a powerful tool in monitoring and aiding patients' recovery.

Certain alternatives may also be used in providing intra-operative management of plastic surgery tissue transfer and reconstructive procedures. For example, in the case of breast cancer patients, treatment may involve a total mastectomy followed by breast reconstruction. Complications for breast reconstruction have been reported to be as high as 50%. The devices described herein can facilitate evaluation of both tissue that is ready to receive the graft, and the graft tissue itself. The evaluation in these alternatives looks at the health and quality of the tissue and the blood perfusion and oxygenation using the methodologies discussed above.

Certain alternatives may also be used to facilitate the analysis of the treatment of chronic wounds. Chronic wound patients often receive expensive advanced treatment modalities with no measure of their efficacy. Alternatives described herein can image the chronic wound and give quantitative data to its status, including the size of the wound, the depth of the wound, the presence of wounded tissue, and the presence of healthy tissue using the aforementioned imaging techniques.

Certain alternatives described herein may also be used in identifying limb deterioration. In these applications, the images identify the peripheral perfusion in limbs. This can be used to monitor the health of normal limbs, as well as, to detect peripheral blood flow insufficiency in limbs (e.g., regions of limb ischemia or peripheral vascular disease) that may require specialized treatments, such as the introduction of growth factors (FGF, HGF, or VEGF) and/or regenerative cells including, but not limited to, stem cells, endothelial precursor cells, endothelial progenitor cells, or concentrated or isolated populations of cells comprising these cell types. In some cases, this allows for early treatment that could save a limb from amputation. In other, more severe cases, it may give medical professionals the data needed to make informed decisions of whether a limb needs to be amputated.

Another application of the devices described herein concerns the treatment of Raynaud's Phenomenon, which occurs when a patient experiences brief episodes of vasospasm (i.e., the narrowing of blood vessels). The vasospasm typically occurs in the digital arteries that supply blood to the fingers, but has also been seen to occur in the feet, nose, ears, and lips. Some alternative devices can accurately and precisely identify when a patient is suffering from Raynaud's Phenomenon, which can aid in its diagnosis at any stage.

Some alternative devices may also be used to identify, classify, or evaluate the presence of cancer cells, cancer cell proliferation, metastasis, tumor burden, or cancer stage, and after treatment, a reduction in the presence of cancer cells, cancer cell proliferation, metastasis, tumor burden, or a cancer stage. These alternatives measure the light reflected off tissue to determine the composition of the skin, which can reflect an abnormal composition associated with cancer cells. Alternatives also can measure the blood flow to the cancer cells by evaluating images at different times. The blood flow can indicate abnormal blood flow to tissue associated with the presence of cancer cells, cancer cell proliferation, metastasis, tumor burden, or a cancer stage. After the removal of cancer cells, alternatives of the present invention may also be used to monitor the recovery, including the growth of healthy tissue and any return of cancer cells.

Aspects of the aforementioned alternatives have been successfully tested in a laboratory setting, as well as, in the clinic. For example, in an experiment using optical tissue phantoms that mechanically mimicked the dynamic changes in tissue owing to pulsatile blood flow, the devices described herein had greater optical penetration than laser Doppler imaging, and also correctly detected the pulsing fluid flow under the tissue phantom material. The experiment tested pulsatile flows in the range of 40 to 200 bpm (0.67 Hz to 3.33 Hz) to test a full range of human heart rates from rest to high rates during exercise or exertion.

Also, on experiments on porcine burn models, which were imaged with burns of varying severity, it was found that the images produced by alternatives described herein, as well as the use of a reference library and computer training, accurately identified regions corresponding to healthy skin, hyperemia, burns greater than 1.0 mm, burns less than 1.0 mm, blood, and a healthy wound bed. These were the tissue types that a surgeon would encounter when conducting a debridement process.

Moreover, a clinical study was conducted using the devices described herein for some of the aforementioned conditions. Participants in the study were imaged following a cardiothoracic procedure. The inclusion criteria was as follows: 18+ years of age; currently admitted or will be admitted in hospital following cardiothoracic procedure; and a presence of wounds with no wound size excluded, or a presence of potential risks that may lead to wound development. Risk factors included poor circulation, mechanical stress of tissue, temperature, moisture, infection, medications, nutrition, disease, age, and body type. Wounds that satisfied the inclusion criteria included wounds from skin flaps, wounds from burns, nosocomial wounding or decubitus ulcers, as well as, diabetic ulcers of the feet and cases of peripheral vascular insufficiency. Subjects were imaged during regular 30 minute sessions for a period of up to three months. Some patients were imaged up to three times a week to monitor the rate of change of tissue. The following summarizes some of the observations made during the study.

TABLE 2

| Pathology | Number of Patients | Number of Scans | Observations |
|---|---|---|---|
| Decubitus Ulcers | 8 | 18 | There is the potential to scan for ulcer risk |
| LVAD recovery | 6 | 26 | Can see return in pulsatility |
| Skin graft viability | 2 | 2 | Successful vs. non-successful graft uptake visible |
| Limb deterioration | 1 | 7 | No pulsatility in limbs to be amputated |
| Raynaud's | 1 | 2 | "cold hands" visible |
| Piriformis Syndrome | 1 | 1 | Too deep to image |
| Suture | 2 | 3 | Pulsatility around suture |

Another aspect of some alternatives described herein is that the devices may be coupled with a dynamic library containing one or more reference points of tissue conditions. In some cases, the dynamic library may contain base point images that contain information about healthy skin tissue. The dynamic library may also contain various images of wounds or skin conditions as points of comparison to see the evolution and/or healing of the wound or skin condition. The dynamic library may also contain sample signals of relevant signals, such as samples of normal heart rates, abnormal heart rates, noise signals, signals corresponding to healthy tissue, and signals corresponding to unhealthy tissue.

In some alternatives the images in the dynamic library are other images or data taken by the devices described herein. In some alternatives, the dynamic library contains images and/or data taken by apparatuses that are not aspects of the present invention. These images can be used to assess or otherwise treat a subject.

Figure 13:
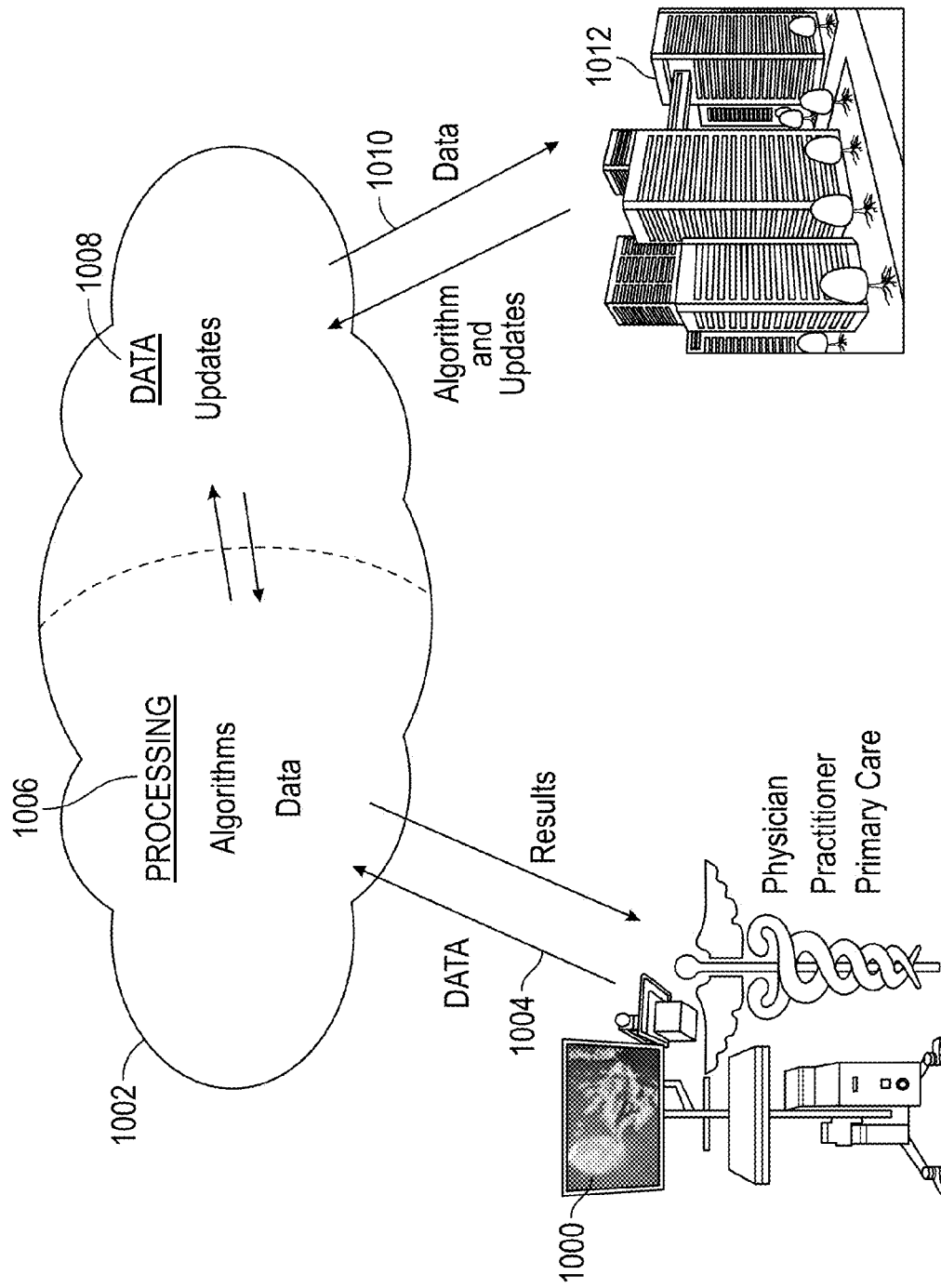
FIG. 13 is an example diagram showing how certain alternatives described herein interact with a data cloud.

FIG. 13 shows one example of the dynamic library. In the figure, example imaging device 1000 is connected to example cloud 1002. The example imaging device 1000 may be a device as described herein, or it may be any other computer or user device also connected to the dynamic library. In some cases, the cloud 1002 may comprise of a program execution service (PES) that includes a number of data centers, each data center including one or more physical computing systems configurable to execute one or more virtual desktop instances, each virtual desktop instance associated with a computing environment that includes an operating system configurable to execute one or more applications, each virtual desktop instance accessible by a computing device of a user of the PES via a network. The cloud may also comprise other approaches to synchronize computing and storage.

Data paths 1004 illustrate bi-directional connections between imaging device 1000 and cloud 1002. Cloud 1002 itself has processing components 1006, which is where cloud 1002 receives signals, processes data, performs sorting algorithms, and generates metadata, which indicates whether the dynamic library is to be synchronized with one or more computing devices.

In some alternatives, data analysis and classification is performed in the cloud. Such analysis can involve collecting data on sample signals for comparison to obtained signals. Such sampling may be used in classifying tissue regions in obtained signals. In other alternatives, processing components may be located onboard imaging device 1000 to perform processing locally at data collection sites.

In addition to collecting and analyzing data in a dynamic library, the processing component may also contain general error data and calculations. Errors can be calculated at local sites and aggregated in the cloud and/or be calculated in the cloud. In some circumstances error thresholds for particular classification models can be established. The threshold values consider the consequences for type I and type II errors (i.e., false positives and false negatives), and the standards for clinical reliability.

The processing components 1006 may also perform analysis on the data. Cloud 1002 also has data components 1008, which includes the information in the dynamic library itself, and also receives updates. Data components 1008 and processing components 1006 are coupled to each other.

There may be other sources and repositories also connected to the cloud. In this example, entity 1012 is also connected to cloud 1002. Entity 1012 is an entity that might provide updates and algorithms to improve system functionality for any device or system, such as system 1000, that is connected to cloud 1002. Through learning and experience, the methods at each stage may be updated to reduce total error. Entity 1012 may quickly assess changes on multiple classification algorithms simultaneously and provide systemic improvements. It may also upload new data sets and models for new clinical applications. In addition, entity 1012 may update system 1000, or any device or system connected to cloud 1002, to acquire data and analyze that data for new therapeutic uses, such as, for example, analyzing frost bite. This expands functionality and allows the system to adapt due to improvements in scientific knowledge.

Additionally, various aspects of alternatives described in this disclosure have been the subject of experiments demonstrating their efficacy in tissue phantoms and animal models. These experiments demonstrated that alternatives of this disclosure may be effective at treating at least burns. The following non-limiting examples are presented for illustrative purposes. The examples provide further details on the experiments performed.

1. EXPERIMENTS

1.1 Example 1: Experiment Using Spot Light Illumination and Planar Illumination on Tissue Phantoms and Animal Models

1.1.1 Materials and Methods

Figure 14A:
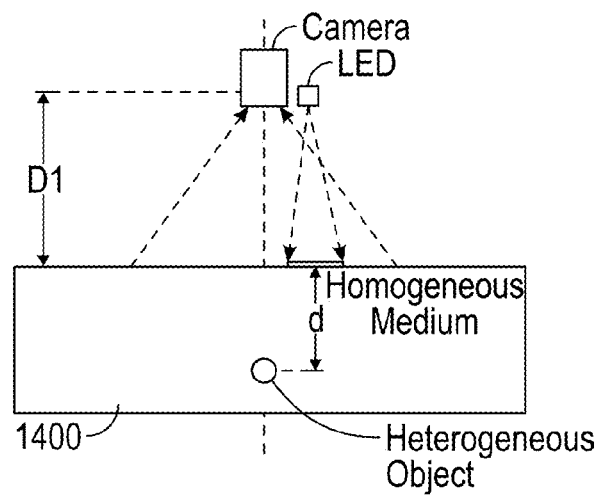
FIGS. 14A-14C illustrate a bench top system working in a reflective mode.
Figure 14B:
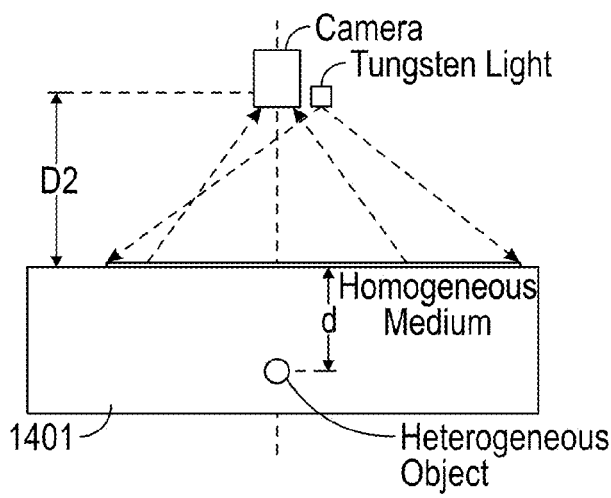
Figure 14C:
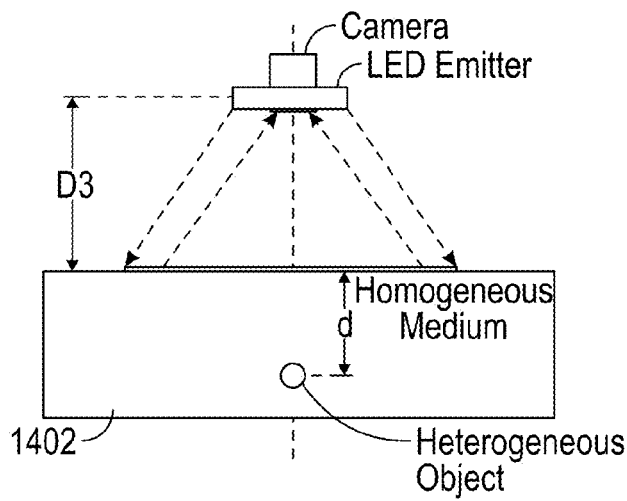

The PPG systems in this research consist of three functional modules: illumination; sensor (a CMOS camera); and the imaging target. The illumination and the sensing modules are placed on the same side relative to the target (i.e., in a reflective mode; FIGS. 24A-14C). The optical beam incident on the object scatters into the target, then the back-scattered optical signals are captured by the camera. The imaging target buried in the opaque medium varies over time (i.e., a blood vessel changing in volume owing to pulsatile blood flow), causing the back-scattered light to have a modulation in intensity.

1.1.1.a. Illumination Modules

Three different illumination modules are compared: 1) spot light illumination using a single wavelength LED diode; 2) planar illumination using a broad spectral tungsten light bulb; and 3) planar illumination using high power single wavelength LED emitters. Three illumination modules are powered by a highly stable DC supply, with temporal intensity vibration less than 1%.

FIGS. 34A-14C illustrate a bench top system working in a reflective mode. Diagram 1400 of FIG. 14A illustrates a single wavelength LED spotlight, diagram 1401 of FIG. 14B illustrates a tungsten light bulb, and diagram 1402 of FIG. 14C illustrates a high-power LED emitters. The object under illumination is an optically opaque medium, with a more opaque object buried underneath at depth=d.

1.1.1.a.i. Single LED

A single LED diode at 850 nm (e.g., KCL-5230H, Kodenshi AUK) was fixed side-by-side to a CMOS camera (e.g., Nocturn XL, Photonis USA) at distance D1=18 cm to the object surface (see, e.g., diagram 1400). The LED's full radiation angle of 12 degrees generates a spot circle in the sensor's field of view, off-centered, and with a diameter of approximately 3.8 cm. The center of the circular illumination spot is within the FOV, but slightly displaced from the center of the target.

1.1.1.a.ii. Tungsten Light Bulb

A tungsten-halogen light bulb (e.g., ViP Pro-light, Lowel Inc.) was mounted adjacent to a camera (e.g., BM-141GE, JAI Inc) at a distance D2=60 cm to the object (see, e.g., diagram B 1401). Two pieces of frosted glass diffuser (e.g., model: iP-50, Lowel Inc.) were mounted in front of the bulb to reduce the light bulb's projection directivity and more evenly illuminate the target. The illumination area appeared broader than the FOV of the camera, and the spatial evenness of the illumination appeared better than the spot LED.

1.1.1.a.iii. High Power LED Emitters

Four high power monolithic LED emitters (e.g., SFH 4740, OSRAM) were positioned in a 2×2 array mounted in the same plane as the sensor (e.g., Nocturn XL, Photonis USA) in a co-axial mode. The LED emitter arrays were placed with camera at D3=30 cm to the target surface (see, e.g., diagram 1402). The spatial intensity variation reduced to less than 15%. The FOV of the camera was controlled by the optical lens and slightly narrower than the illumination area.

1.1.1.b. System Setup

For the systems using LED spot lights or LED emitters, a monochromatic CMOS camera (e.g., Nocturn XL, Photonis USA) was used as a detector, which provides low dark noise and high dynamic range. The 10-bit ADC resolution offers a signal-to-noise ratio of 60 dB. For the tungsten light illumination system, the camera (e.g., BM-141GE, JAI Inc.) provides comparable dynamic range (58 dB) and the same 10-bit ADC resolution as the Nocturn XL camera. The images captured by these two cameras were cropped down to 1280×1040 (aspect ratio 5:4). The tungsten illumination system utilized a telescopic lens (e.g., Distagon T*2.8/25 ZF-IR, Zeiss Inc.) to control the FOV, because the imaging distance in tungsten light is longer than other two setups due to the heat generated by the tungsten light bulb.

For these three system setup, cameras were mounted vertically and facing down to the object surface. A common FOV of 20×16 cm were controlled for inter-system comparison. The exposure times of the cameras in each system setup were calibrated with a reflectance reference standard (e.g., 95% reflective rate standard panel; Spectralon SG3151, LabSphere Inc.). The exposure time were timed to utilize the full range of each camera's dynamic range.

1.1.1.c. Phantom

Figure 15:
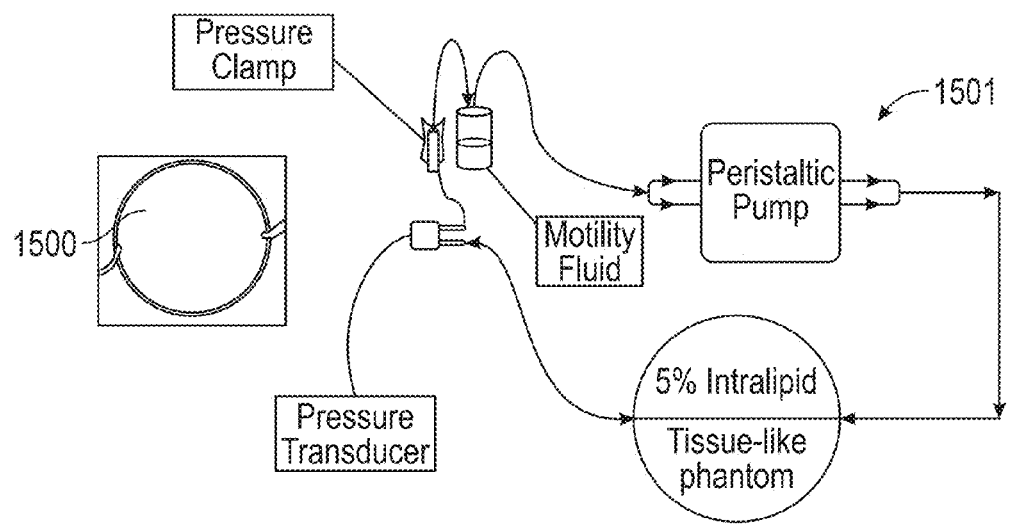
FIG. 15 illustrates a tissue phantom in a petri dish and a phantom apparatus to simulate human pulsatile blood flow.

FIG. 15 illustrates a tissue phantom in a petri dish and a phantom apparatus to simulate human pulsatile blood flow. Tissue phantom 1500 is in a petri dish with an elastic tube beneath the homogeneous phantom, which mimics blood flow under the skin. Phantom apparatus 1501 is designed to simulate human pulsatile blood flow in a laboratory setting. The peristaltic pump drives the motility fluid through an elastic phantom vessel pulsing below 8.0 mm of the gelatin-Intralipid tissue-like phantom matrix. Owing to the elasticity of the tubing an approximately 2% volume expansion in the phantom vessel, similar to that of human arteries, occurs with each cycle of the peristaltic pump.

The tissue-like phantom model was designed to mimic the blood flowing beneath the skin surface. The tissue phantom matrix was made according to Thatcher et al. (FIG. 15). Briefly, the gelatin (e.g., Type B, JT Baker) in Tris-buffered saline (e.g., pH 7.4, Alfa Aesar) 10% (w/v) is mixed with a sterile Intralipid fat emulsion (e.g., 20% w/v, Baxter). The final Intralipid concentration was controlled at 20%. In addition, 0.2% of the motility standard (e.g., polystyrene bead and India ink mixture) was added to the gelatin matrix to mimic the absorption property of tissue. The mixture was poured into a petri dish (e.g., Novatech, diameter 150 mm) to form the homogeneous background medium. A Silastic tube (e.g., Dow-Corning) with inner diameter 1.58 mm mimicking blood vessel was placed at d=8 mm beneath the surface. During each pump cycle, the inner diameter expands about 2%, which mimics the diameter change of peripheral arteries during the cardiac cycle.

To mimic the pulsatile cardiac cycle, the absorptive blood-like fluid inside the tube was pumped by a two roller peristaltic pump (e.g., Watson Marlow, Model # sciQ32) at a frequency at 40 Hz, which mimics the normal human heart rate at 80 bpm (FIG. 15). This pulsatile flow through the phantom vessel causes a PPG signal that is the subject of measurement by the PPG imaging apparatus.

1.1.1.d. Animal Model

Figure 16:
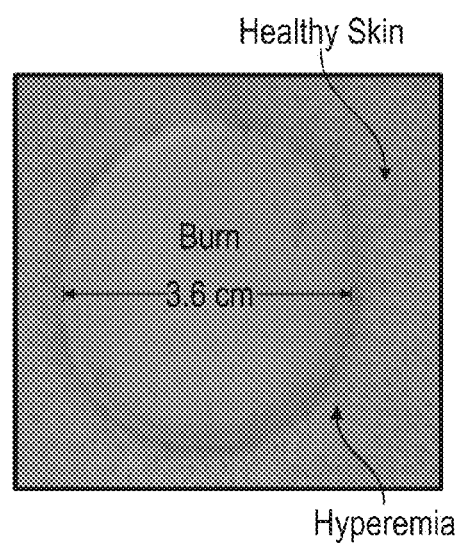
FIG. 16 illustrates an in-vivo thermal burn wound on an animal skin in a circular shape and the debridement model.

FIG. 16 illustrates an in-vivo thermal burn wound on an animal skin in a circular shape and the debridement model. Hanford swine were selected as the animal model, because of their skin's anatomic similarity to humans. The thickness of the pig's epidermis is 30-40 µm, which approximates the human epidermis 50-120 µm. In addition the vascular structure and the extracellular matrix composition resemble that of the human skin. The animal was cared for as outlined in the Public Health Services (PHS) Policy on Humane Care and Use of Laboratory Animals. The procedure was performed in a fully equipped large animal surgical suite. The burn model and study protocol were approved by the Institutional Animal Care and Use Committee (IACUC).

Thermal burn models were prepared by using a brass rod with controlled temperature and pressure. The rod was heated to 100 degrees Celsius in an oven, and then pressed to the skin on pig's dorsum at a pressure of 0.2 kg/cm$^2$ for 60 seconds. This method created a deep partial-thickness burn. Wound sites contained one 3.6 cm diameter deep partial thickness burn (FIG. 16). Images of burns were collected from each imaging system in order to compare illumination uniformity and PPG signal strength.

1.1.1.e. Comparison by Pixel

Figure 17:
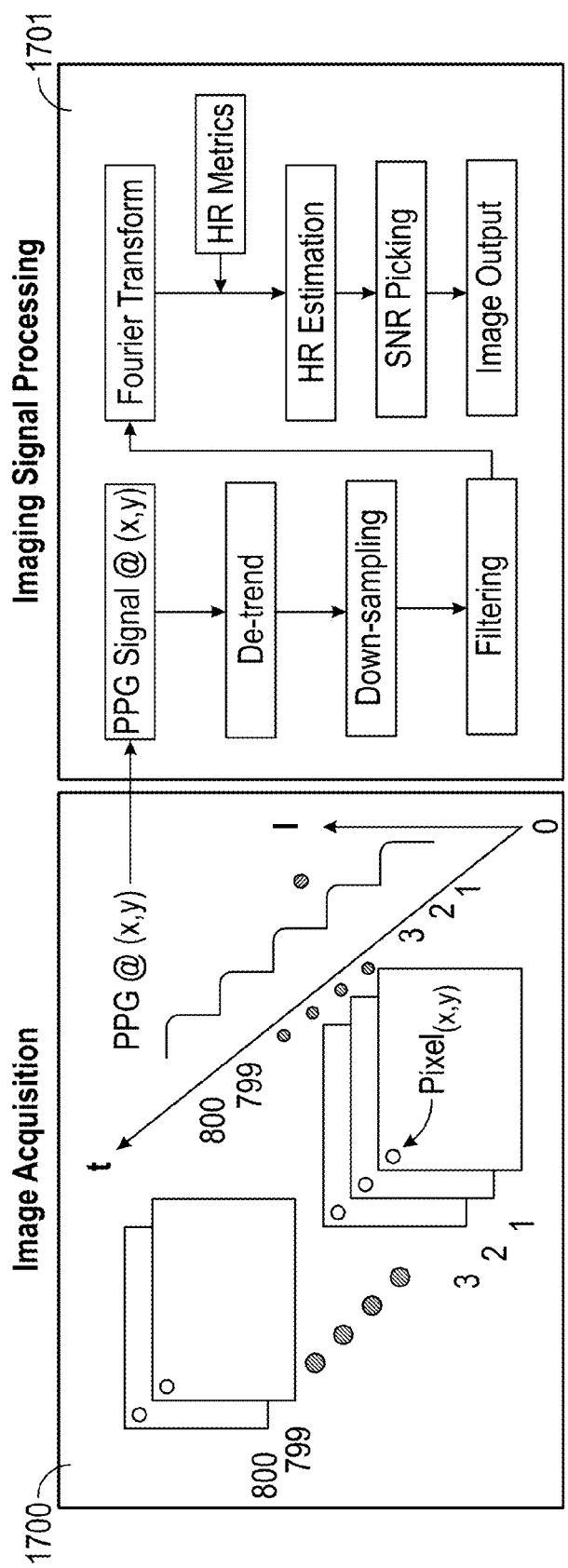
FIG. 17 illustrates a time-resolved PPG signal extraction.

FIG. 17 illustrates a time-resolved PPG signal extraction. Diagram 1700 shows intensity at image pixel (x,y) extracted sequentially from 800 contingent frames. Diagram 1701 shows a processing method for quantifying PPG signals.

A sequence of 800 images at a frame rate of 30 frames-per-second were acquired and stored as uncompressed TIFF files. The PPG signal intensity was calculated on a pixel-by-pixel basis. The key steps for PPG signal and image processing are as follows (FIG. 17): (1) de-trending, which removes the DC wandering; (2) down-sampling in time-domain to reduce the data volume; (3) filtering of the signal; (4) fast Fourier transformation (FFT) converting time-resolved signal to frequency-domain; (5) The spectral power, particularly at the frequency equivalent to the heart rate, was then extracted; (6) the ratio of the summation of intensity in heart rate band to the summation of the intensity in higher frequency band (regarded as noise) was calculated as the signal-to-noise ratio (SNR); (7) PPG image outputs use a color map to represent each pixel's PPG SNR. The colors are mapped linearly from lowest signal present to highest signal preset within a single image.

Signal processing was conducted with MATLAB (Version 2014a, MathWorks, Inc., USA).

1.1.2. Results 1.1.2.a. Illumination Pattern Assessment

In order to characterize the light pattern of the three illumination modules, we placed a diffuse reflective panel (SPECTRALON®, LabSphere Inc.) under the camera and light source. The panel surface was perpendicular to the camera.

Figure 18A:
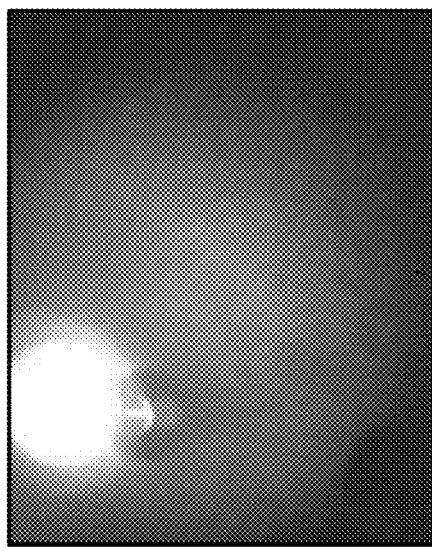
FIGS. 18A-18C illustrates a comparison of spatial illumination intensity between LED spot light (FIG. 18A), tungsten light (FIG. 18B), and LED emitter (improved (FIG. 18C) using an even reflective panel as an imaging target.
Figure 18B:
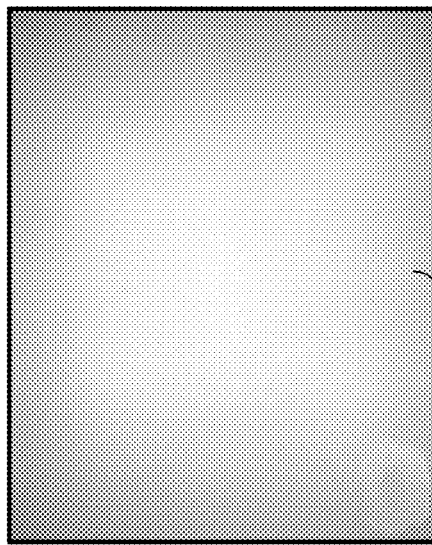
Figure 18C:
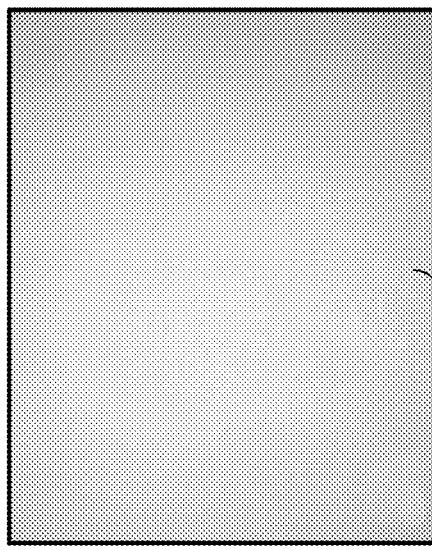

FIGS. 18A-18C illustrates a comparison of spatial illumination intensity between LED spot light (uneven illumination) (image 1800 of FIG. 18A), tungsten light (even illumination) (image 1801 of FIG. 18B), and LED emitter (improved even illumination) (image 1802 of FIG. 18C) using even reflective panel as imaging target.

The illumination pattern image varied between the three illumination modules (FIG. 18). In the LED spot light reflection pattern (image 1800), there is a highly bright spot within the FOV, which shows a high-intensity area surrounded by regions that become darker with distance from the source. The use of a single LED introduces an additional shadow on the target, which is due to the presence of the LED enclosure structure. The presence of the shadow further reduces the evenness of the illumination. With the Tungsten light (image 1801), the illumination pattern is more even than the spot illumination, and the shadow effect was removed within the FOV. From the LED emitters (image 1802), the least amount of variation in illumination intensity was observed. The spatial variation was controlled to be less than 15% and the temporal stability is well controlled to be less than 1%.

Figure 19:
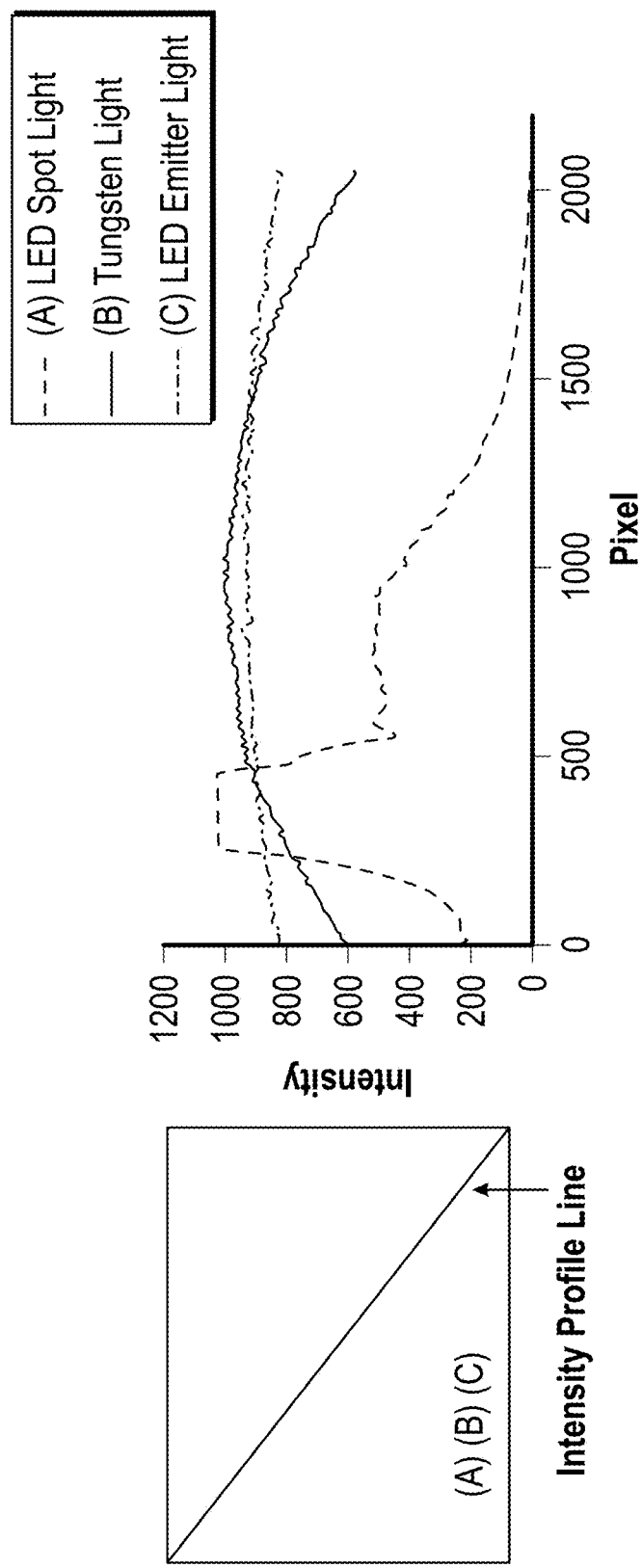
FIG. 19 illustrates a comparison of intensity profile line between three illumination patterns.

FIG. 19 illustrates a comparison of intensity profile line between three illumination patterns. The diagonal intensity profile lines in spot light (see image 1800), Tungsten light (see image 1801), and LED emitter light (see image 1802) from a SPECTRALON® panel.

The diagonal intensity profile line crossing these three illumination patterns highlights the intensity variation (FIG. 19). Clearly the FOV of the spot light have to request a full dynamic range of the camera (e.g., 10 bit, intensity values from 0-1024) to contain the saturation the spot area (flat top), the surrounding dimmed rim (shoulder) for actually working area, and the less useful rolling off area. The tungsten light and LED emitter light both improve the spatial evenness and reduce the necessity of using a high dynamic range camera.

1.1.2.b. Phantom Results

FIGS. 20A-20C illustrates imaging results of tissue phantom and pulsatile phantom vessel underneath using a LED spot light (image 2000 of FIG. 20A), a tungsten light (image 2001 of FIG. 20B), and a LED emitter (image 2002 of FIG. 20C), respectively. The imaging results are overlaid with the image of the phantom.

The tissue-like phantom imaging target was placed under these three illumination modules in order to study the effect of the variables of illumination intensity and pattern on the PPG signal in a carefully controlled bench test (FIG. 20). In the LED spot light (image 2000), the phantom vessel was placed within the dimmed area of the field of view. Overall the position of the phantom vessel could be resolved. The position of the phantom vessel is accurate and well aligns with the experimental setup. However, as the phantom vessel (left end) close to the spot center (top left corner of the FOV), the imaging result gradually fade, while to the other end, the width of the phantom vessel becomes wider as the illumination intensity decreases along the edges of the field of view. The edge of the petri dish creates a rim of dark shadow, which reduces the effective FOV, and adversely increases the difficulties to interpret the image to users.

For the tungsten light illumination (image 2001), the incident beam is directed slightly away from the axis of the camera, which actually creates a small incident angle. The directivity of the tungsten light bulb then induces a slightly shiny (i.e., specular reflection) area on the phantom surface. This effect saturates the pixels, hindering the detection of PPG signal. The position of the phantom vessel is displaced from its true position. In addition, the mostly infrared light emitted from a Tungsten source induces a large amount heat generating within the object, which quickly denatures the gelatinous tissue-like phantom. The temperature of the surface quickly increases from room temperature to 30-40 degree Celsius in 30 min (not shown here).

For the high power LED emitter illumination (image 2002), the color output in the imaging results was continuous and the width keep constant. The position of the PPG signals aligns with the actual position of the phantom vessel. The image contrast was adequate, which demonstrates the image quality is better than the tungsten light and the spot light. Also, there was no thermal effect accumulated within the phantom. The temperature change within 30 min is less than 0.1 C, which becomes negligible.

Following the evaluation of the three illumination methods, the phantom model was subjected to a test of illumination intensity to determine the effect of illumination intensity on the strength of the measured PPG signal. The purpose of this investigation was to demonstrate the necessity of maximizing illumination intensity in addition to illumination uniformity across the field of view. A bench test was conducted using the tissue-like phantom apparatus in conjunction with the DeepView system with high-powered LED emitter illumination under varying incident light intensity conditions, controlled by varying the voltage input to the LED emitter. By varying the voltage input, the illumination intensity could be varied up to a saturation point that represents the maximum absolute irradiance the imager could resolve accurately. This saturation point occurred with an input voltage of 12.95 V to the emitter, corresponding to an absolute irradiance value of approximately 0.004 W/m$^2$. This saturation point was used as a reference to establish intensity thresholds in increments of 20% of the maximum.

FIG. 21 illustrates a relationship between the PPG signal's power spectral density in the pulsatile region of the tissue-like phantom and the percent of the maximum intensity of light from the LED emitter module below the imager's saturation point (irradiance 0.004 W/m$^2$). Data points reflect an average of 5 pixels sampled from 3 tissue-like phantom replicates. Logarithmic Regression ($R^2$=0.9995), error bars represent standard deviation about the mean.

At each of the illumination levels from 0% to 100%, images were recorded and processed with the proprietary DeepView algorithm (FIG. 17). Using the information from the processed image, several pixels were selected manually from high-pulsatility regions along the phantom tubing. These selected pixels were extracted and individually processed to determine the strength of the PPG signal at the indicative points. The metric used for evaluating the strength of the PPG signal was power spectral density (PSD), a measure of the distribution of signal power across frequencies. The power spectral density at the pulsatile frequency was the subject of investigation and comparison across the samples and levels. This process was repeated for several pixels across three phantoms, creating a sampling at each level, and the PSD values were averaged to reflect values at each level (FIG. 21). The results demonstrate a clear logarithmic trend for which the intensity of PPG signal received constantly increases across the intensity values.

These results indicate that maximizing illumination intensity is a critical parameter and also validates the necessity of even illumination across the field of view since darker regions along the fringes cause a loss in signal intensity of the usable PPG signal.

1.1.2.c. Animal Results

Figure 22:
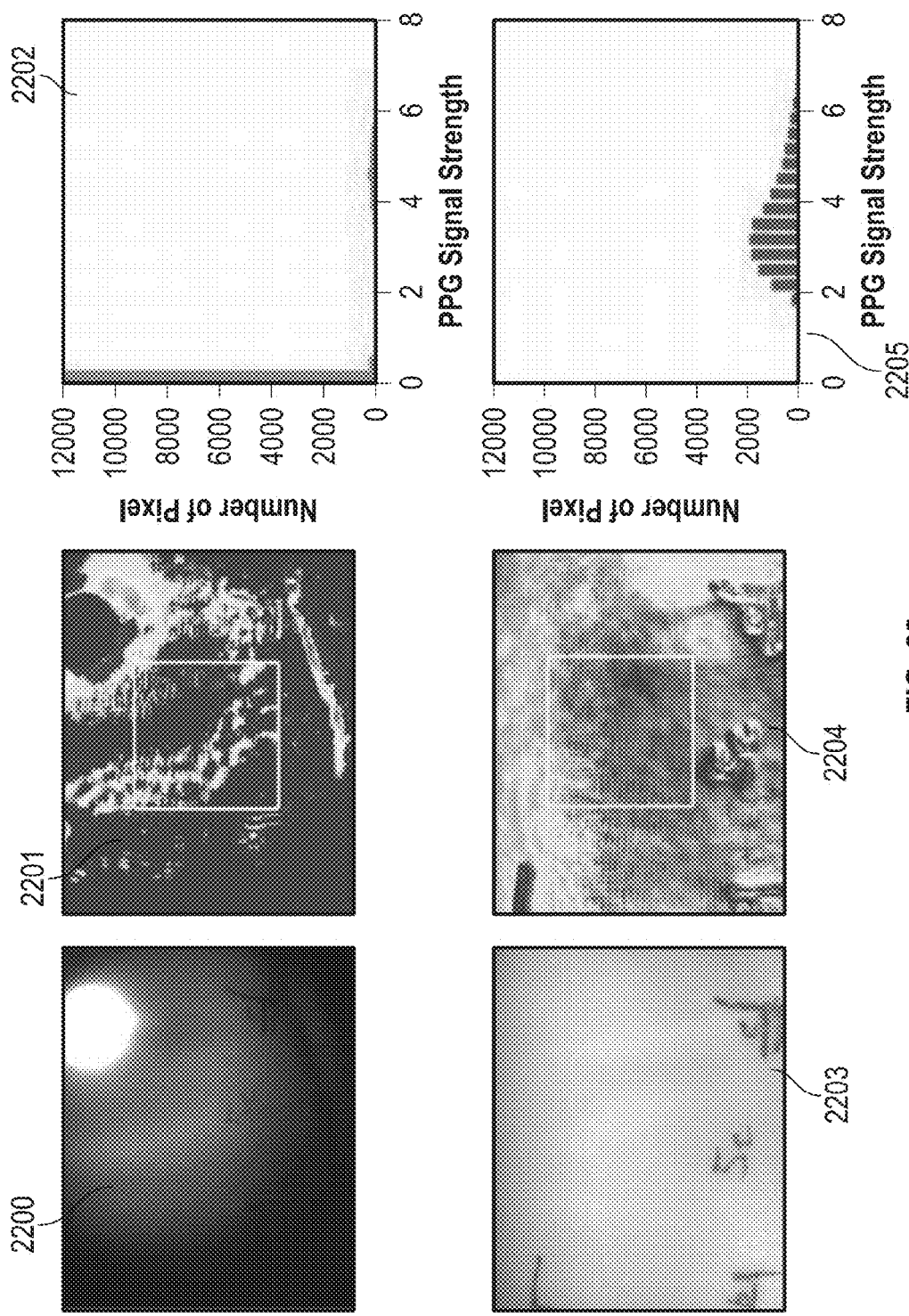
FIG. 22 illustrates the categorization of pixels within region of healthy pig skin based on PPG signal strength where the illumination patterns on the skin are varied.

FIG. 22 illustrates the categorization of pixels within region of healthy pig skin based on PPG signal strength. Image 2201 and graph 2202 are the results of the LED spot illumination (illustrated in image 2200). Image 2204 and graph 2205 reflect the results of LED emitter illumination (image 2203).

From both the LED spot and the LED chip illumination sources we measured the intensity of the light incident on the pig's skin. For the LED spot illumination, the pixels in the region where the light was incident on the tissue were fully saturated (see image 2200). The rest of the pixels in the image were illuminated at 50% or less of the camera's range of sensitivity. On the other hand, the full field illumination demonstrated most of the pig's skin in the imaging area is reflecting a high amount of light in the range of 70-90% of the camera's range (see image 2203). There are very few saturated pixels and none of the pixels are completely dark. The evenness in the LED emitters is expected to result in PPG signals that can be compared from one pixel to the next, because the variable of illumination intensity is better controlled.

To confirm that the blood flow results from the even, LED chip illumination scheme would be more comparable, we studied the PPG signals collected from both LED spots-light and LED emitter illumination types. In order to do this we assessed an area of pig skin that was a uniform tissue type where the blood flow could be assumed to be even throughout. We chose healthy skin as this tissue type, because it is readily available in large areas on the back of the pig, and the blood flow occurring in this tissue is likely to be similar at any point on the pig's back. As expected, we found that the even illumination provided an output image with more uniform PPG signal from the healthy skin. The PPG signal from a region of interest (the box of images 2201 and 2204) was plotted as a histogram to show that the distribution of PGG signal was more Gaussian in shape and there were no pixels lacking PPG signal collected from this region when uniform illumination was used. On the LED spot illumination setup (FIG. 22), many of the pixels collected no PPG signal, and the regions of tissue with PPG signal were sporadic and non-uniform. This data would be difficult to interpret by a physician.

Since blood flow in a wound is a critical factor for healing and assessing tissue viability, an animal burn model was conducted to assess the applicability of these illumination patterns in burn wound assessment. Within a partial-thickness burn, there is damage to the arterial structures that carry blood throughout the tissue. It is expected that little to no blood flows in this damaged area. Therefore, little or no PPG signals would be acquired from burned skin.

FIGS. 23A-23F illustrate various illumination patterns and corresponding images of a burn wound on pig skin. Specifically, FIGS. 23A-23C illustrate illumination patterns using an LED spot light (FIG. 23A), a tungsten light (FIG. 23B), and a LED emitter light (FIG. 23C). The corresponding imaging result (e.g. FIGS. 23D-23F) show performance of detecting the burn wound and healthy tissues, respectively.

For the LED spot illumination (FIG. 23A), the burn wound was 4.0 cm away from the center of the illumination spot, similar to the phantom experiment. Half of the burn circle was under the dimmed rim and another half was in the dark area of the image. The imaging results (FIG. 23D) show the edge of the circular burn area is still readable, but the center does not contrast the surrounding healthy skin tissue. The region of the image where the illumination is directly incident on the tissue is completely saturated and no PPG signal was detected. Similarly, the peripheral regions opposite the light spot are too dark to be assessed by the imager. For these non-burned tissues in the dark area and the spot area, the imaging result does not show any blood flow signal, despite physiologically being healthy tissue.

For the tungsten light illumination module (FIG. 23B), the FOV was approximately evenly illuminated. In the imaging results (FIG. 23E), the edge, shape, and area of the burn wound were resolved. The SNR contrast is adequate, too, indicating the illumination induces sufficient PPG signal from the surrounding healthy tissue. Owing to the directivity of the incident beam the illumination intensity on the right hand half of the FOV is weaker than the left half Correspondingly in the imaging results (FIG. 23E), the right half of the image shows higher SNR contrast than the left half, inducing an interpretation error regarding the blood perfusion on the right half is viable than the left half of the FOV.

For the LED emitter module (FIG. 23C), illumination within the FOV is more even than the Tungsten source, corresponding to a better PPG image. The imaging results (FIG. 23F) show the edge, shape, and area of the burn wound correspond to the actual tissue. The healthy tissue surrounding the burn wound also show homogeneous images comparing to the burn site in the imaging results. The edge of hair unshaven on the image bottom brings in a line in the image results, but the healthy tissue (with blood perfusion) under the hair still shows the same contrast as the homogenous background.

1.1.3. Conclusions

The illumination function plays an important role in an optical PPG system. In this research, we study illumination variables including intensity and uniformity for PPG imaging using an LED spotlight, a tungsten light, and an LED emitter array. The preliminary evaluation based on the tissue-like phantom demonstrates that PPG signal is a function of illumination intensity, and therefore, even illumination appears to be ideal for accurate PPG signal acquisition in an imaging setting. In our animal model, we confirmed the result of our tissue phantom, showing that the variable of illumination intensity also affected the PPG signal received the healthy skin tissue, an area of physiological similarity. In the presence of a burn, where tissue damage attenuates blood flow, a reduced PPG signal is expected. The even illumination provided additional advantage over the other two patterns, by improving accuracy for detection of the burn area. While tungsten and LED lights could both result in even illumination patterns, LED sources have a number of other advantages in a clinical setting. They do not induce significant temperature change on the target surface, they are more reliable, and have lower power requirements. A rapid, non-invasive, and safe device such as an optical PPG imager that could perform blood perfusion evaluations in patients is expected to be of great value to a clinician in the wound care setting. With an illumination module such as the proposed emitter array that is more capable of achieving high-intensity, uniform light across the field of view, the PPG imaging technology would be capable of delivering these clinical applications in an accurate and precise manner.

1.2. Example 2: Experiment Involving Wound Debridement Sequentially Characterized in a Porcine Burn Model with Multispectral Imaging We used a porcine burn model to study partial thickness burns of varying severity. We made eight 4×4 cm burns on the dorsum of one minipig. Four burns were studied intact, and four burns underwent serial tangential excision. We imaged the burn sites with 400-1000 nm wavelengths.

Histology confirmed that we achieved various partial thickness burns. Analysis of spectral images show that MSI detects significant variations in the spectral profiles of healthy tissue, superficial partial thickness burns, and deep partial thickness burns. The absorbance spectra of 515, 542, 629, and 669 nm were the most accurate in distinguishing superficial from deep partial thickness burns, while the absorbance spectra of 972 nm was the most accurate in guiding the debridement process.

The ability of a non-specialist to distinguish between partial thickness burns of varying severity to assess whether a patient requires surgery could be improved with an MSI device in a clinical setting.

1.2.1. Materials and Methods

The methods used in this animal study were modified from Branski et al, Gurfinkel et al, and Singer et al. The burn model and study protocol were approved by the Institutional Animal Care and Use Committee (IACUC).

1.2.1.a. Burn Model and Study Protocol

One adult male (age 7.2 months) Hanford mini-pig weighing 47.5 kg was used. The animal was cared for as outlined in the Public Health Services Policy on Humane Care and Use of Laboratory Animals. The procedure was performed in a fully equipped large animal surgical suite. The male mini-pig was food-fasted overnight prior to anesthesia. Anesthesia was induced with a combination of Telazol (~2.2 mg/kg, IM) and Xylazine (~0.44 mg/kg, IM). The animal was intubated and anesthesia was maintained using isoflurane (0.1 to 5% with 100% oxygen). Vital signs monitored and recorded during the protocol included heart rate, blood pressure, respiratory rate, and PPG waveform. At the end of the experiment, the animal was euthanized with sodium pentobarbital (390 mg/mL) at a minimum dose of 1.0 mL/4.5 kg body weight.

Eight 4×4 cm burns were made on the dorsum of the minipig with a metallic aluminum rod set to a temperature of 100° C. Varying burn depths were generated by applying the heated rod for different durations: healthy skin (0 sec); superficial partial thickness (30 sec); deep partial thickness one (DPT1; 45 sec); and deep partial thickness two (DPT2; 90 sec). Two burns of each type were created and organized into two adjacent blocks of four. FIG. 24 illustrates the location of burn injuries on dorsum of the pig. Numbers represent blocks and letters represent treatments. ("1" is block I, "2" is block II, "a" is control, "b" is SPT, "c" is DPT1, "d" is DPT2). FIG. 25 illustrates the dimensions of tissue in Block I (Left) and Block II (Right).

Block I burns were imaged pre-burn, immediately post-burn, and one hour post-burn. These burns were then excised in 5×4×1 cm blocks of tissue (FIG. 25) that included a small strip of healthy neighboring tissue to ensure collection of the entire burn undisturbed. Block I will be referred to as the "Burn Classification Experiment".

Figure 26:
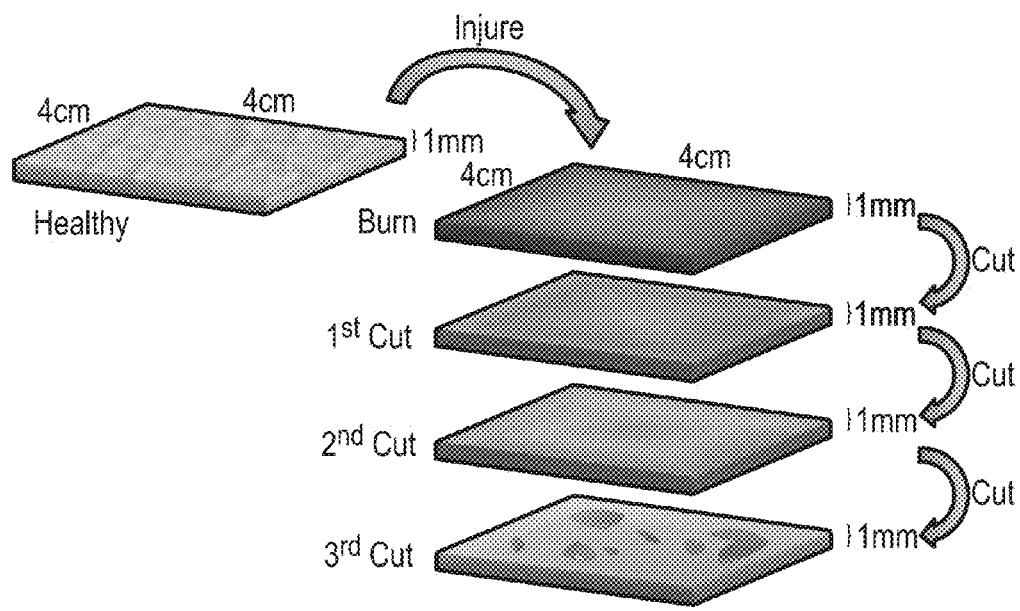
FIG. 26 illustrates a schematic of an example debridement procedure.
Figure 27A:
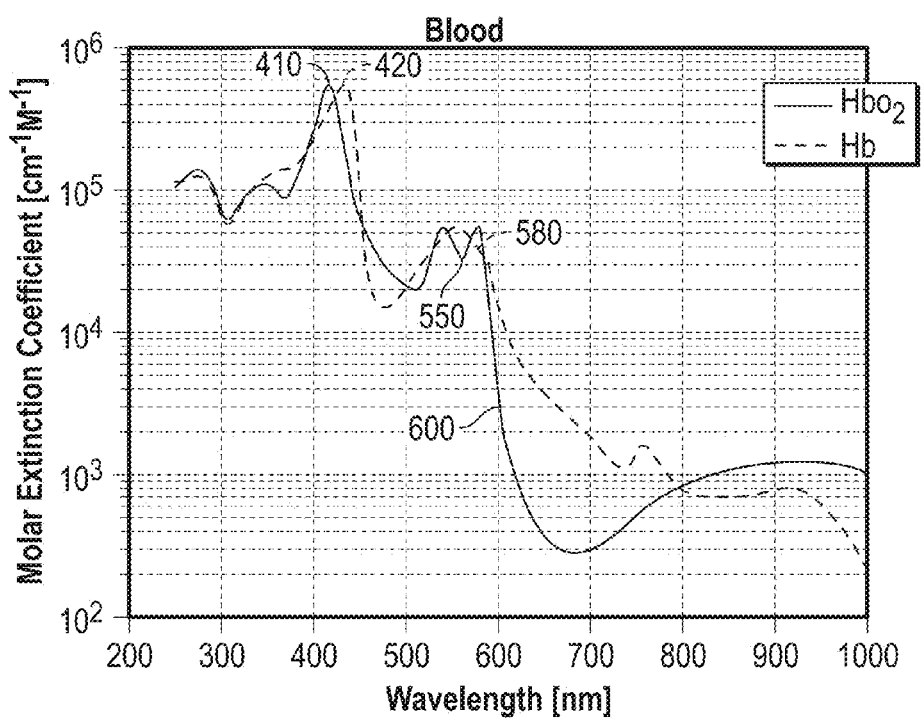
FIGS. 27A-27E illustrate the absorbance spectra of various tissue components.
Figure 27B:
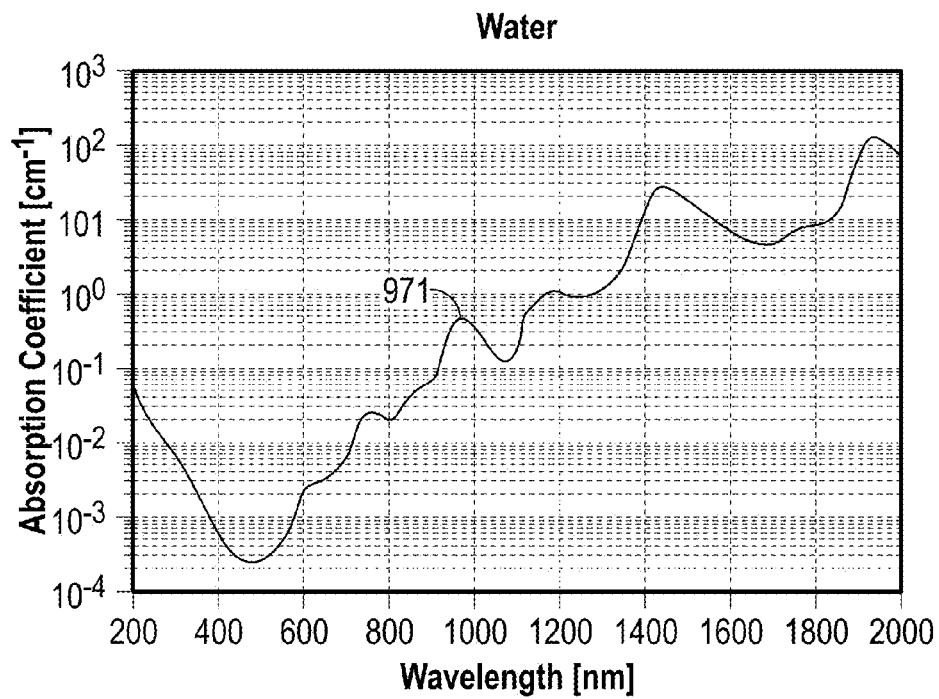
Figure 27C:
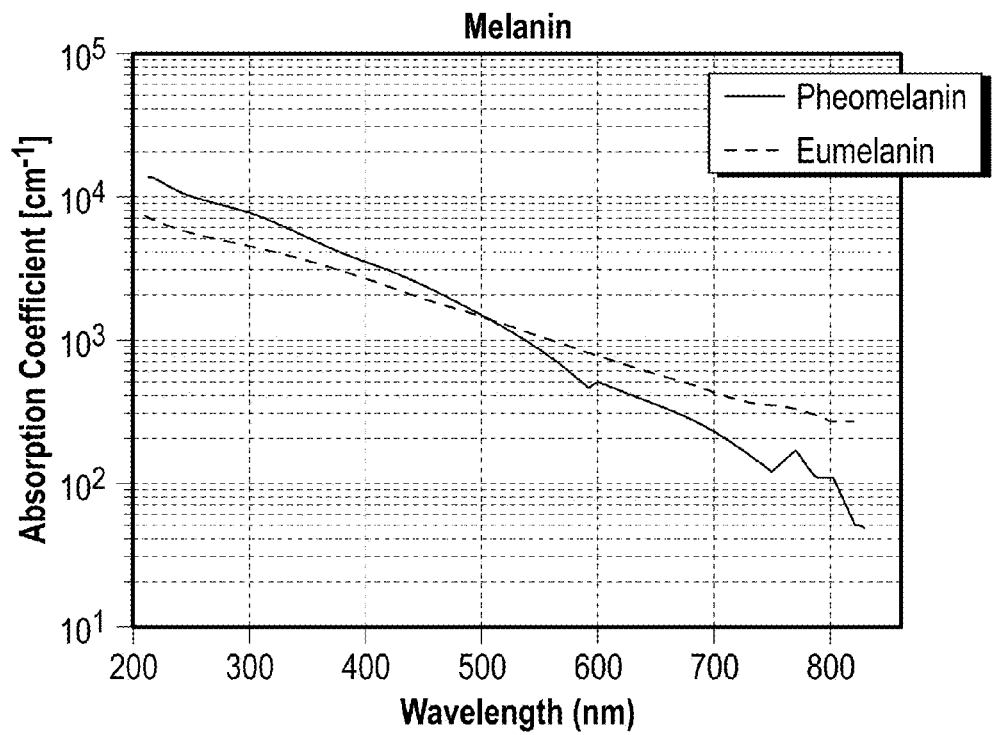
Figure 27D:
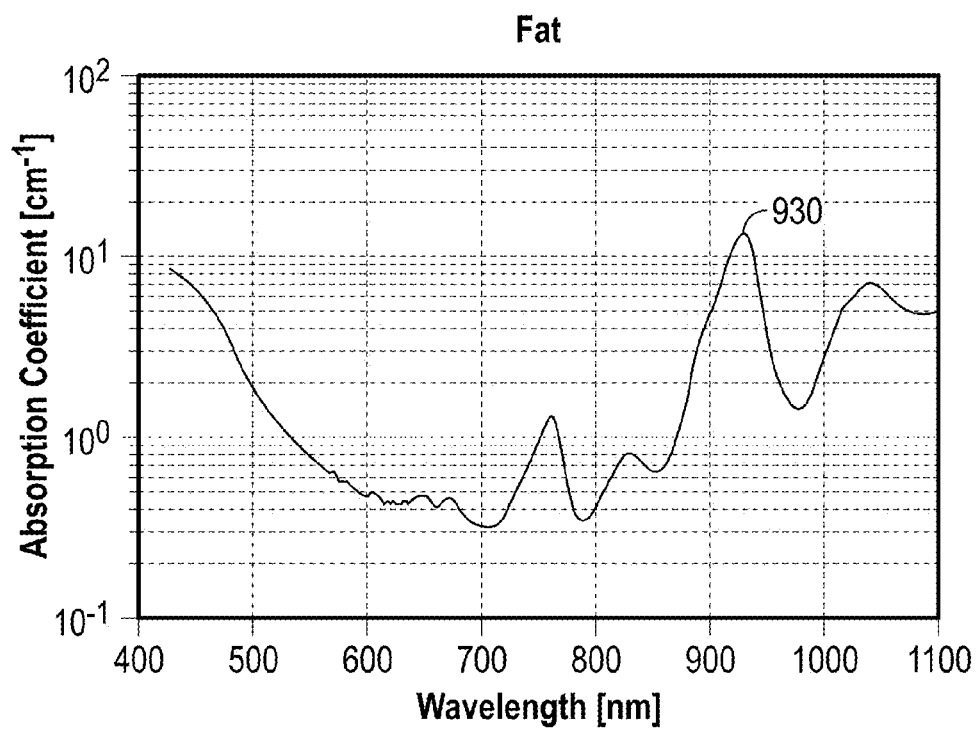
Figure 27E:
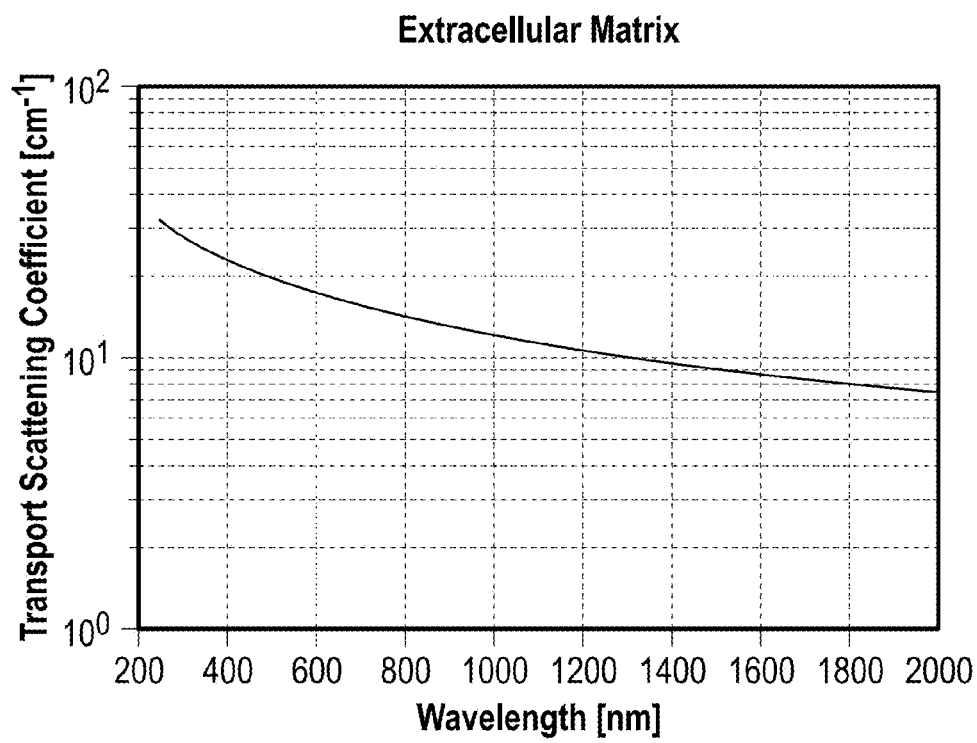

Block II burns underwent serial tangential excision to dissect the burn in a layer-by-layer fashion at a depth of 1 mm with an electric dermatome set (e.g., Zimmer, Warsaw, Ind.). For example, FIG. 26 illustrates a schematic of an example debridement procedure. Tissue was excised in serial 5×5×0.1 cm slices (FIG. 25) until punctate bleeding was observed beneath the wound site (FIG. 26). Block II burns were imaged pre-burn, immediately post-burn, and after each excision. This block will be referred to as the "Burn Debridement Experiment".

Each tissue specimen (tissue block & tangentially excised layers) was stored in 10% Neutral Buffered Formalin and sent for histopathological examination. Each specimen was sectioned and stained with hematoxylin and eosin. For the tangentially excised Block II burns, the precise excision layer at which viable tissue had been reached was determined by two pathologists, each at separate facilities. The overall severity of the burn was determined by the percent dermal damage. Dermal damage less than 20% was classified as a superficial partial thickness burn, and dermal damage greater than 20% but less than 100% was considered a deep partial thickness burn.

1.2.1.b. Instrumentation and Data Analysis

The Spectral MD Wound Assessment Prototype carried out all MSI performance. This camera has a silicon charged coupled device (CCD) specified at 1392 (h)×1040 (v) pixels. A rotary wheel containing eight interchangeable filters spins inside the device allowing for high speed MSI. Its active area is 10.2 mm×8.3 mm. A 250 W tungsten lamp light source was used to illuminate the field (LowePro). The eight filters consisted of the following wavelengths (nm): 450, 515, 542, 620, 669, 750, 860, and 972 (10 nm full-width half-max). All post-acquisition processing was done via MATLAB (v2013b).

1.2.1.c. Statistical Analysis

Histological findings were used to guide the selection of specific regions of each burn image and to sort the signals that made up those regions. Signals from differing burn depths were compared by two-way ANOVA and multiple comparisons (Tukey-Kramer). The tissue debridement analysis was carried out with three-way ANOVA and multiple comparisons (Tukey-Kramer). P-Values were calculated using the Bonferonni method where p-values less than 0.05 divided by the number of comparisons were considered significant.

1.2.2. Theory

Tissue can be simplified by thinking of it as consisting of a unique combination of blood, melanin, water, fat, and ECM. When white light is reflected off of phantoms comprised entirely of one of the above components and measured, we see that each phantom's absorbance spectra has a unique peak or favored wavelength. FIGS. 27A-27E illustrate the absorbance spectra of various tissue components. By focusing on changes that occur at these favored wavelengths, we can better tune into the changes between each burn type. We hypothesized that blood spectra would be key in differentiating between superficial partial thickness and deep partial thickness burns. This was based on the assumption that deep partial thickness burns will have more vessel damage and hemostasis than superficial partial thickness burns. Therefore, the 450-669 nm wavelengths, the range of absorbance peaks for blood, were included in the prototype. ECM wavelengths were included as well since deep partial thickness burns theoretically damage more ECM than superficial partial thickness burns.

The 450, 550, 650, and 800 nm wavelengths have been shown to improve classification of burn depth as compared to traditional clinical judgment alone. After completing a review of the optical properties of skin tissue components, we sought to test eight additional wavelengths, centering on those previously established, with high potential to aid in burn assessment as described above. The complete list of wavelengths tested is as follows: 420, 515, 542, 629, 669, 750, 860, and 972 nm.

1.2.3. Results 1.2.3.a. Histology

Figure 28:
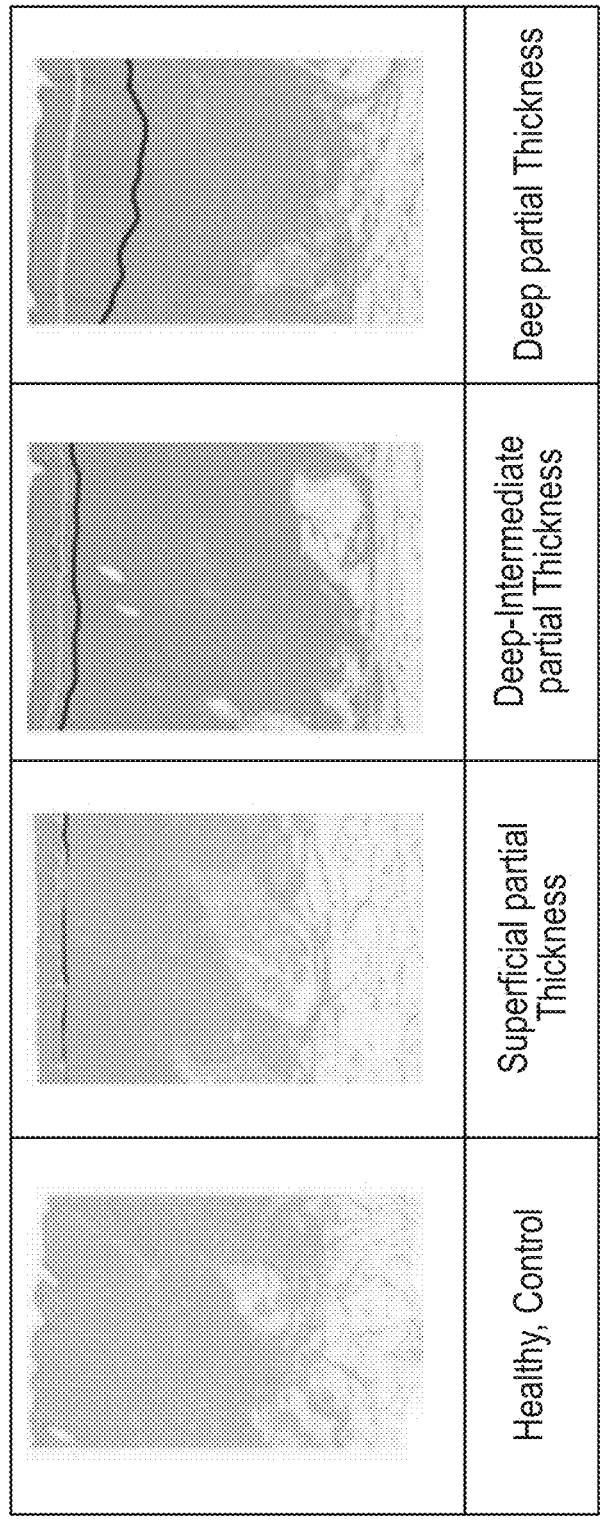
FIG. 28 illustrates the histology of burn tissue at various burn severities in the animal study.

A blinded histopathologist analyzed Block I and Block II pathophysiologic changes layer-by-layer and classified the burn tissue by depth. In total, three superficial partial thickness burns, and three deep partial thickness burns were generated along with two healthy controls. FIG. 28 illustrates the tangentially excised (layer-by-layer excision) burn histology. The black lines indicate the full extent of burn injury whereas yellow lines indicate area of the most severe burn effects.

Figure 29:
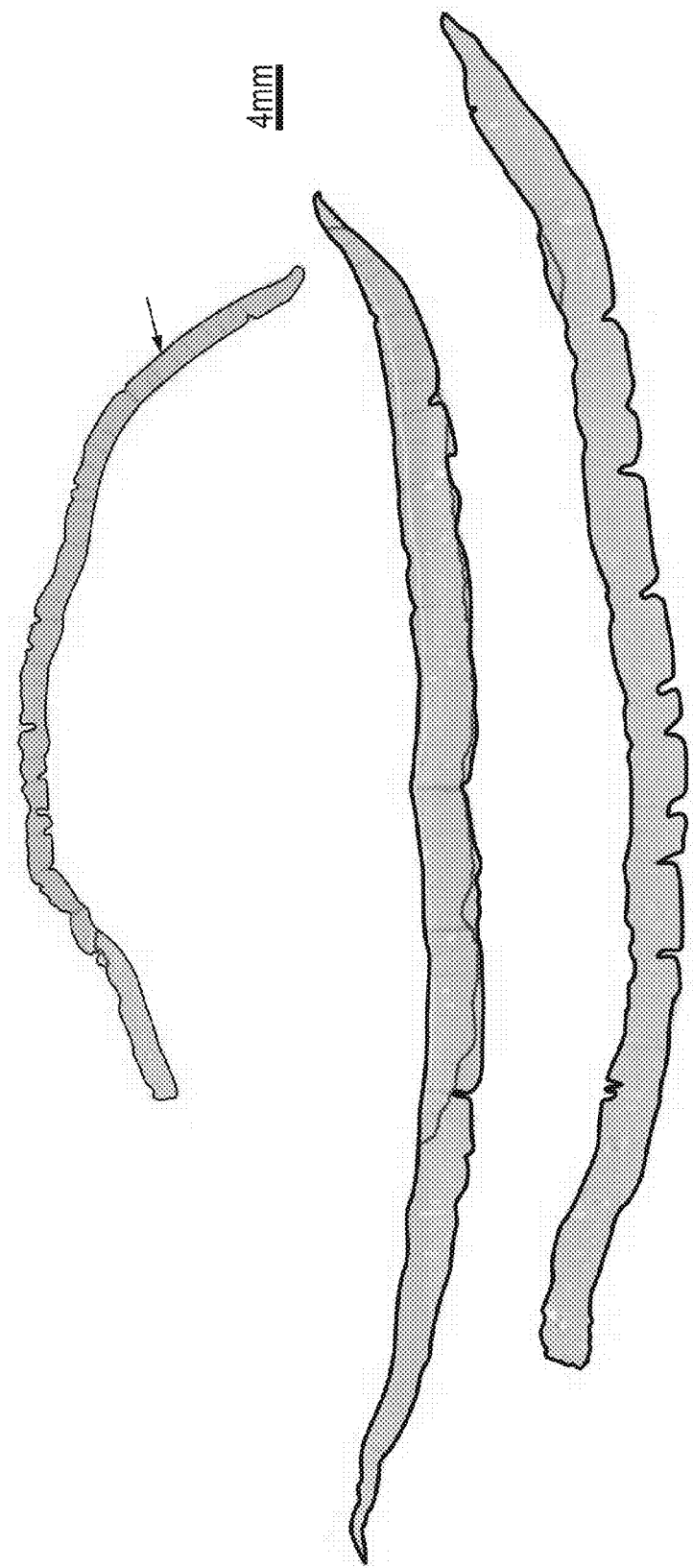
FIG. 29 illustrates histology sections taken from serial tangential excisions of each debridement in the animal study.

The debridement histology was analyzed to see how efficiently sequential excision was able to remove burn tissue with the dermatome alone. Histology showed that at each site, all of the burn tissue had been removed by, at most, four excisions. The final excisions of each procedure removed healthy tissue deep to the burn margins. Occasionally, the last excision contained only healthy wound bed, meaning that debridement could have been halted one step earlier. FIG. 29 illustrates histology sections taken from serial tangential excisions of each debridement in the animal study. The superficial layer of the dermis is the uppermost section and each subsequent layer is deeper into the dermis. The arrow indicates the superficial surface of the tissue section. The black lines indicate the full extent of burn injury whereas yellow lines indicate area of the most severe burn effects.

1.2.3.b. Burn Classification Experiment

Figure 30:
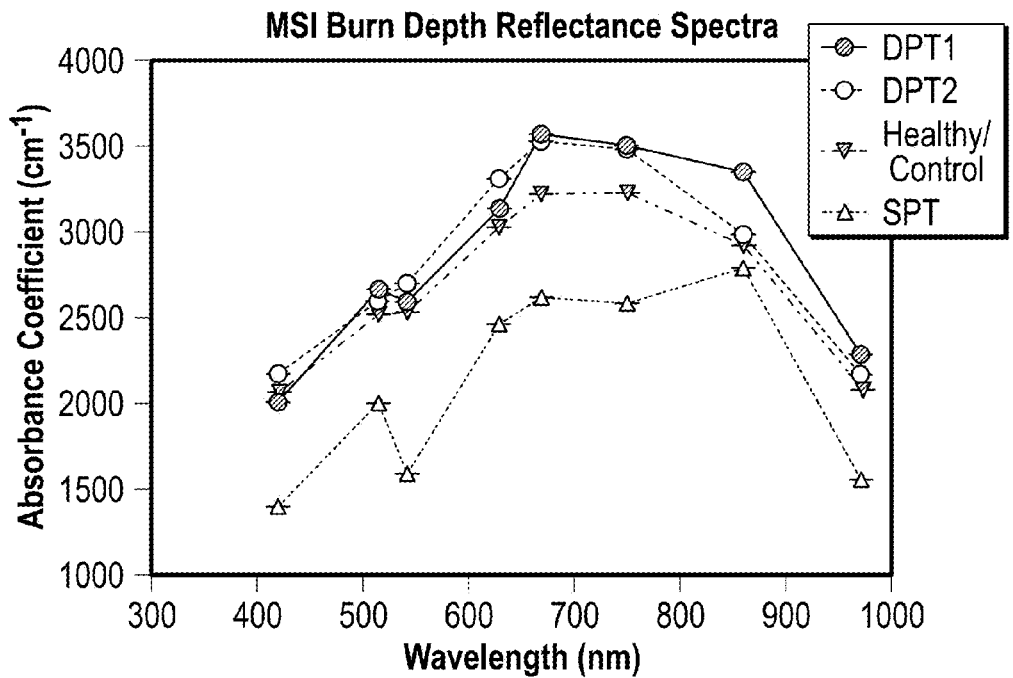
FIG. 30 illustrates a plot of MSI data immediately post-burn suggests that the reflectance spectra for each burn type are initially distinct. It shows four reflectance spectra obtained from all burn sites and the healthy control.

The Spectral MD Wound Assessment Prototype was able to correctly classify each tissue type in Block I as healthy, SPT, DPT1 or DPT2. FIG. 30 illustrates a plot of MSI data immediately post-burn suggests that the reflectance spectra for each burn type are initially distinct. It shows four reflectance spectra obtained from all burn sites and the healthy control. A multiple comparisons statistical analysis confirmed that all wavelengths, except 420 nm, were effective in distinguishing between SPT and DPT1/2 burns. Multiple comparisons also demonstrated that MSI was able to differentiate between DPT1 and DPT2 using the 420, 542, 669, and 860 nm wavelengths. The table below illustrates multiple comparisons between burn classification, where p-value 1 corresponds to SPT vs. DPT1 while p-value 2 corresponds to SPT vs. DPT2 (A significant p-value for this experiment was less than 0.05/6=0.008):

TABLE 3

| SPT vs. DPT | | | DPT1 vs. DPT2 | |
|---|---|---|---|---|
| Wavelength (nm) | p-value 1 | p-value 2 | Wavelength (nm) | p-value |
| 420 | 0.0973 | 0.0043 | 420 | <0.001 |
| 515 | <0.001 | <0.001 | 515 | 0.0191 |
| 542 | <0.001 | <0.001 | 542 | <0.001 |
| 629 | <0.001 | <0.001 | 629 | 0.0421 |
| 669 | <0.001 | <0.001 | 669 | <0.001 |
| 750 | <0.001 | <0.001 | 750 | 0.4 |
| 860 | <0.001 | <0.001 | 860 | <0.001 |
| 972 | <0.001 | <0.001 | 972 | 0.0952 |

Therefore, MSI can differentiate various burn depths by their unique spectral signature at several key wavelengths of light immediately following injury.

Figure 31:
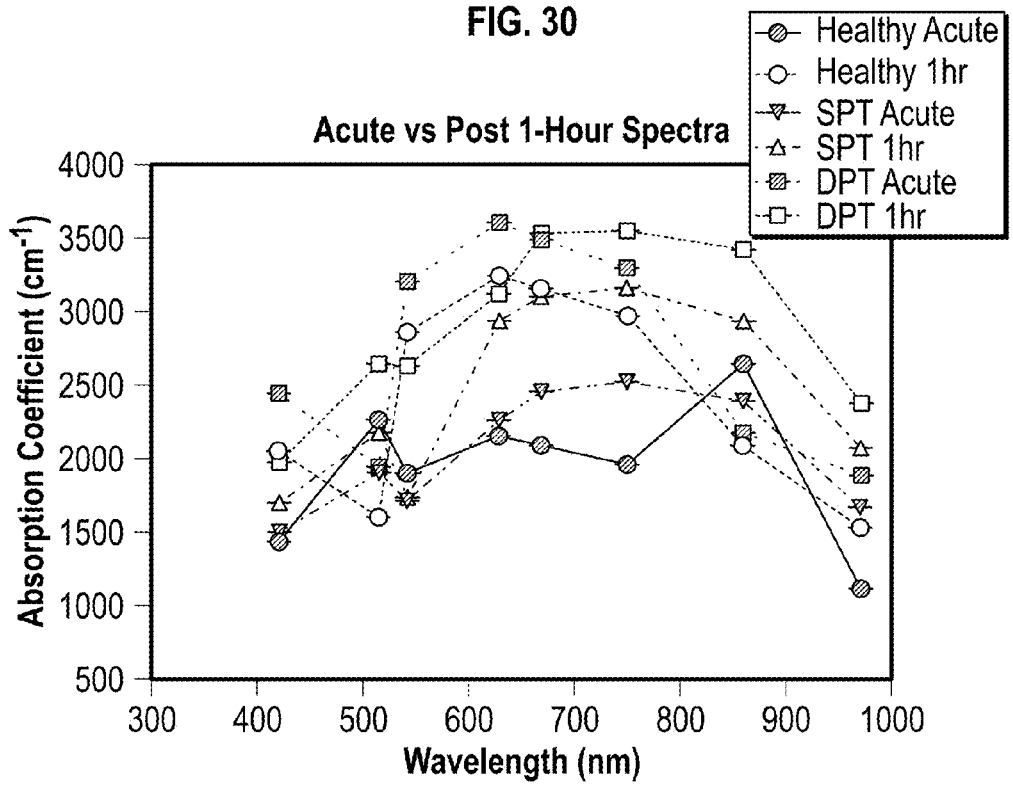
FIG. 31 plots the spectra of each burn type immediately post-burn and 1 hour after injury.

Next, imaging data collected one hour post injury were plotted in the same fashion to test for repeatability in distinguishing severity. FIG. 31 plots the spectra of each burn type immediately post-burn and 1 hour after injury. DPT2 was used in the data analysis to determine whether MSI could differentiate between SPT and DPT. DPT1 versus DPT2 multiple comparisons were not performed on the post-one hour data to focus on clinical relevance. The assessment prototype measured distinct reflectance spectra for each burn type. In this experiment, all wavelengths were effective in distinguishing between SPT and DPT burns.

The results of this multiple comparisons study post 1-hour are as follows (where a significant p-value for this experiment less than 0.05/15=0.003):

TABLE 4

| SPT vs. DPT | |
|---|---|
| Wavelength (nm) | P-Value |
| 420 | <0.001 |
| 515 | <0.001 |
| 542 | <0.001 |
| 629 | <0.001 |
| 669 | <0.001 |
| 750 | <0.001 |
| 860 | <0.001 |
| 972 | <0.001 |

1.2.3.c. Burn Debridement Experiment

The second experiment tested whether the Wound Assessment Prototype was able to identify the optimal layer at which to cease debridement by employing its ability to distinguish between healthy tissue and DPT burn. Here, we considered excision of DPT1 and DPT2 injuries together because the goal was to test whether MSI could identify viable from necrotic tissue, as opposed to depth of burn. SPT data was not included in this debridement analysis because tangential excision is not generally performed on SPT burns. In this mock-debridement procedure, the 972 nm wavelength provided the most useful analysis of debridement. Multiple comparisons found no difference between the initial burn site and the wound bed after the first excision. The burn site after the second excision was not statistically different from the healthy control. The burn site after the third excision was also not different when compared to the healthy control. The table below summarizes these findings, showing the multiple comparisons debridement analysis:

TABLE 5

| Wavelength = 972 nm | P-value | Expected P-Value† | Conclusion |
| --- | --- | --- | --- |
| Healthy Vs. HWB* | 0.2 | >0.001 | Similar |
| Healthy Vs. Burn (no Excision) | <0.001 | <0.001 | Different |
| Healthy Vs. Burnsite Wound Bed (After 1st Excision) | <0.001 | <0.001 | Different |
| Healthy* Vs. Burnsite Wound Bed (After 2nd Excision) | 0.4 | >0.001 | Similar |
| Healthy** Vs. Burnsite Wound Bed (After 3rd Excision) | 0.5 | >0.001 | Similar |
| Initial Burn Vs. Burnsite Wound Bed (After 1st Excision) | 1 | >0.001 | Similar |
| Initial Burn Vs. Burnsite Wound Bed (After 2nd Excision) | <0.001 | <0.001 | Different |
| Initial Burn Vs. Burnsite Wound Bed (After 3rd Excision) | <0.001 | <0.001 | Different |

In the table, *HWB means Healthy Wound Bed, Healthy* means HWB, and Healthy** means Healthy Wound Bed located at depth of excision. A significant p-value for this experiment was less than $0.05/45=0.001$. The "†" indicates that the expected p-values were determined by histopathological examination and classification of tissue samples. All measured p-values matched their expected values.

Figure 32:
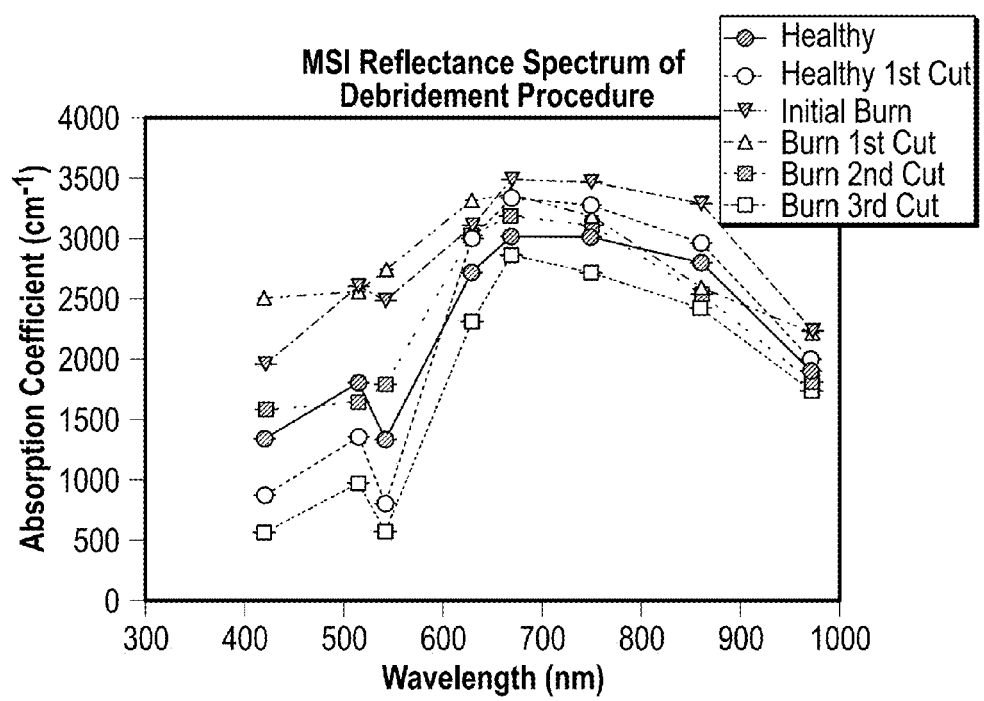
FIG. 32 shows the reflectance spectra of all wavelengths at each excision layer. It plots the absorbance spectra of the healthy control, healthy control debrided once, mean of the burn tissue spectra at each cut, and mean of the wound bed spectra at each cut.

These results corresponded with histological grading that confirmed the second excision of debridement had removed the final margin of burn tissue. The 515, 669, and 750 nm wavelengths found the healthy wound bed and the excess wound beds (wound bed after burn tissue had already been removed) to not be statistically different. FIG. 32 shows the reflectance spectra of all wavelengths at each excision layer. It plots the absorbance spectra of the healthy control, healthy control debrided once, mean of the burn tissue spectra at each cut, and mean of the wound bed spectra at each cut.

1.2.4. Discussion

The Spectral MD Wound Assessment Prototype is able to differentiate between partial thickness burns of varying severity and to determine when a burn wound debridement procedure has been performed to the appropriate depth of excision. Multicomparison statistics pointed toward wavelengths that performed best at resolving the following differentiations: SPT vs. DPT injuries, DPT1 vs. DPT2 injuries, and necrotic burn tissue vs. viable wound bed.

Although differentiating between DPT1 and DPT2 does not change the overall treatment plan of surgical intervention, being able to classify burn severity at this resolution adds functionality to the prototype. With future research, an algorithm can be made that will use MSI to measure depth. This information may then be used to create a total burn contour map containing all depths throughout a large burn to aid the clinician in creating a debridement plan for the entire burn area. Future investigations can be performed to further develop an algorithm that would correlate absorbance spectra with precise burn depth.

As hypothesized in the Theory section, the 515, 542, 629, and 669 nm wavelengths were useful in distinguishing between SPT and DPT injures immediately after injury and one hour post-injury. The 420-669 nm wavelength range correlates with the absorbance spectrum of blood. Since each burn depth will have varying degrees of hemostasis, these wavelengths of light will be handled differently by tissue in each burn classification, allowing for differentiation by MSI. A similar spectra (420, 542, 669 and 860 nm) are capable of distinguishing between DPT1 and DPT2 injuries, further supporting this idea.

The wavelengths correlating with absorbance peaks in ECM (750, 860, 972 nm), water (971 nm), and fat content (930 nm) were also useful in differentiating burn types. Since less dermal damage is done during SPT burns than DPT burns, we hypothesize that SPT has a more intact ECM and more evenly distributed water content as compared to DPT, allowing MSI to distinguish between these tissue types. On the other hand, it is unlikely for the skin-fat content to be different between the DPT1 and DPT2 burn depths because neither are full thickness burns. Our results are consistent with these expectations.

Feasibility for using MSI technology to determine the proper depth of burn wound debridement is also shown in this study. We were able to identify a difference in the reflectance spectra between the partially debrided burn and the viable wound bed using the wavelengths 515, 669, 750, and 972 nm wavelengths. The 515 and 669 nm wavelengths correspond to the blood absorbance peak. The 750 and 972 nm wavelengths correspond to the ECM absorbance spectra with 972 nm also being the absorbance peak of water. These results suggest that the tissue's blood, ECM and water components vary the most when comparing healthy tissue and burn tissue. This is reasonable since burns destroy ECM and vessels. The 972 nm wavelength was shown to be clinically useful for tissue classification in every single experiment. This may be explained by the burn disrupting the water distribution within tissue. This disruption would cause marked differences between healthy tissue and burned tissue detectable with MSI, guiding debridement.

1.2.5. Conclusion

Spectral MD's wound assessment prototype provides data that classifies burns and guides debridement in a porcine burn model. This shows potential for the development of a clinical device that will be able to aid in burn triage and debridement surgery. By implementing this technology for routine use in early burn care, it will be readily available and familiar to the care team during emergency measures.

Future experiments will incorporate the effective wavelengths from this experiment with others to tune the device for automated burn classification. Currently, the Spectral MD Wound Assessment Prototype is simply acquiring data which researchers subsequently analyze and interpret to classify tissues. It is our goal to design an algorithm that will analyze the MSI data, perform an automated classification, and produce output that is easy to view and understand. To do this, the data acquired in this experiment will be added to a spectral reference database and used to train the classification algorithm. Future porcine burn experiments will be required, but with a porcine burn database as a strong foundation, we plan to eventually test the prototype in a clinical setting.

1.3. Example 3: Experiment Using PPG and MSI on Porcine Deep Partial-Thickness Burn Models Burn debridement, a difficult technique owing to the training required to identify the extent and depth of excision, could benefit from a tool that can cue the surgeon as to where and how much to resect. We explored two rapid and non-invasive optical imaging techniques in their ability to identify burn tissue from the viable wound bed during a mock burn debridement procedure.

Figure 34:
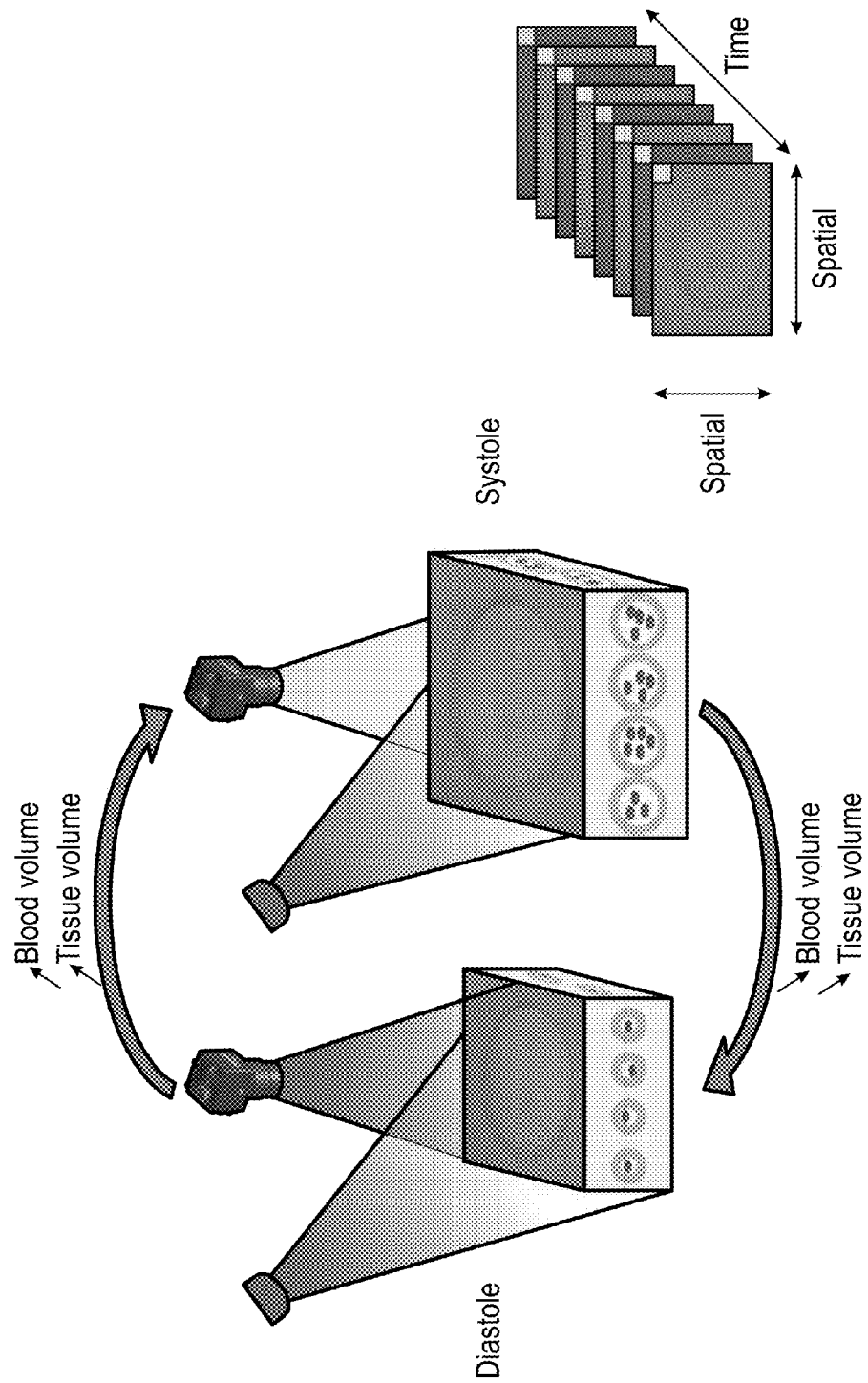
FIG. 34 illustrates components of a reflectance mode and 2-D PPG imaging system (left). Monochromatic light incident on the tissue surface scatters within the tissue as it interacts with molecular structures. A small portion of that light returns to the camera. When measured over time, the intensity changes in the back-scattered light produces a PPG waveform. Each pixel in the raw data cube contains a unique PPG waveform that may be analyzed to generate a single blood flow image of the tissue (right).
Figure 35:
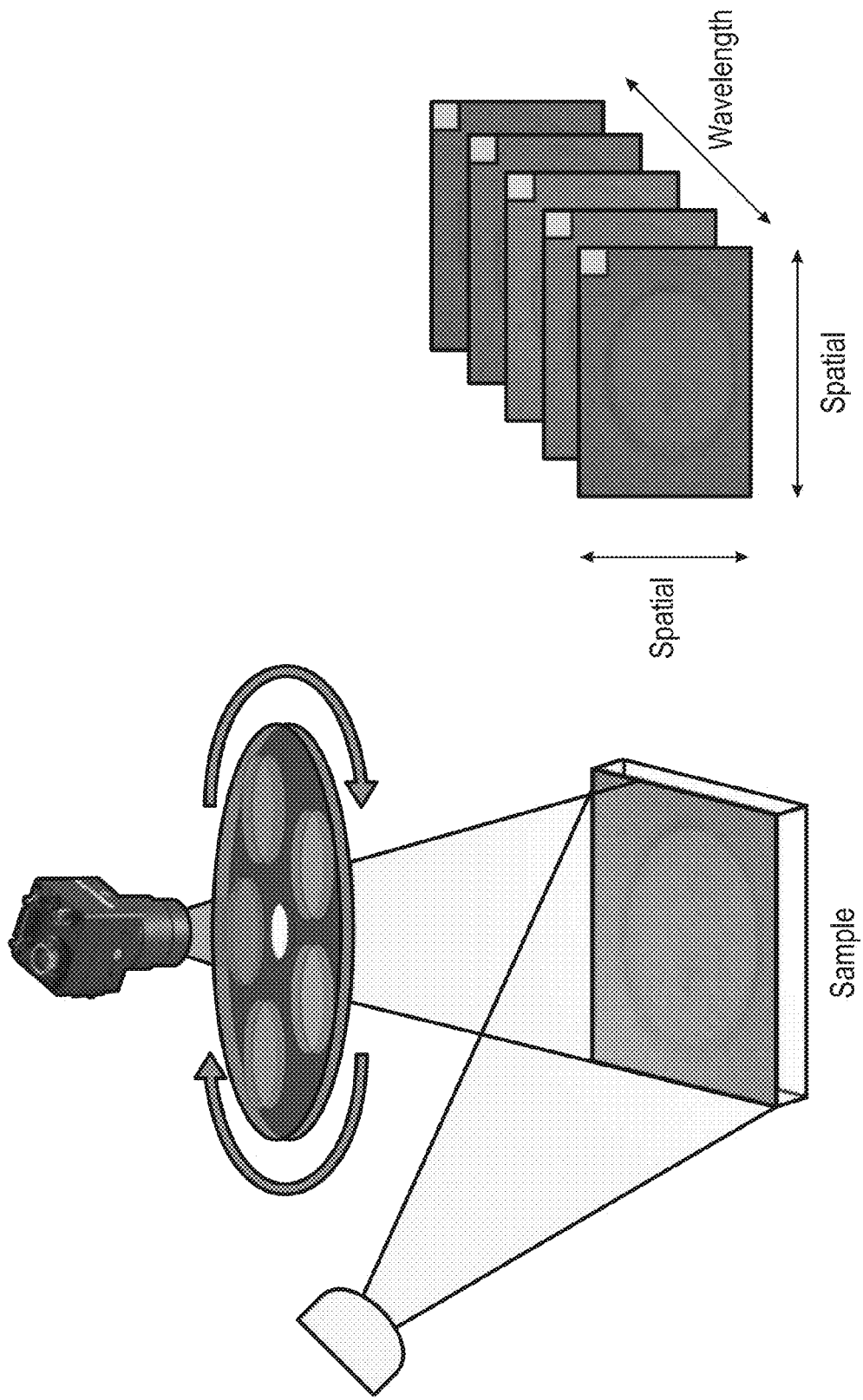
FIG. 35 illustrates components of a multispectral imager including a broad spectrum illumination source, a digital camera, and a rotating filter wheel equipped with various optical filters that isolate predetermined wavelengths of light reflected from the target's surface (left). This system quickly collects an image at each position in the filter wheel to generate a spectral data cube (right). Each pixel in the data cube represents a low spectral-resolution reflectance spectrum of the tissue.

PPG imaging and MSI were used to image the initial, intermediate, and final stages of burn debridement of a deep partial-thickness burn. PPG imaging could map blood flow in the skin's microcirculation and MSI could collect the tissue reflectance spectrum in visible and infrared wavelengths of light to classify tissue based on a reference library. For example, FIG. 33 illustrates a wound debridement procedure and a PPG imaging device that detects the relative blood flow between necrotic and viable wound bed for grafting. Example components of such a PPG imaging system are illustrated in FIG. 34. Components of an MSI system are illustrated in FIG. 35.

In this experiment, a porcine deep partial-thickness burn model was generated and serial tangential debridement accomplished with an electric dermatome set to 1.0 mm depth. Excised eschar was stained with hematoxylin and eosin (H&E) to determine the extent of burn remaining at each stage of debridement.

We confirmed that the PPG imaging device showed significantly less blood-flow where burn tissue was present and, the MSI method could delineate the remaining burn tissue in the wound bed from the viable wound bed. These results were confirmed independently by a histological analysis.

We found these devices can identify the proper depth of excision, and their images could queue a surgeon as to the preparedness of the wound bed for grafting. These image outputs are expected to facilitate clinical judgment in the operating room.

In order to apply PPG imaging and MSI technologies to burn care, scientists and engineers must demonstrate their ability to improve the current standard of care. The experiments involved developing and training a supervised machine-learning algorithm from an animal image database comprising images taken from known time points during wound debridement procedures. We demonstrate that the accuracy of the classification algorithm outperforms the current standard of clinical care. This algorithm will ultimately be applied to translate the imaging data collected by PPG imaging and MSI into essential information for healthcare providers performing excision and grafting surgery.

1.3.1. Methods

1.3.1.a. Photoplethysmography Imager

The PPG imager system consisted of a 10-bit monochromatic CMOS camera (Nocturn XL, Photonis USA), that provides low dark noise and high dynamic range. The 10-bit ADC resolution offers a signal-to-noise ratio of 60 dB. The resolution of this imager was set to 1280×1040 (aspect ratio 5:4). The camera was mounted vertically and facing down to the object surface. A common field of view (FOV) of 20×16 cm was controlled for inter-system comparison. The exposure time of the camera was calibrated with a 95% reflectance reference standard (Spectralon SG3151; LabSphere Inc.; North Sutton, N.H.). To illuminate the tissue, four monochromatic and high-power LED emitters (SFH 4740, OSRAM) were positioned in a 2×2 array mounted in the same plane as the sensor. The LED emitter array was placed with camera at 15 cm to the target surface. LED emitters were chosen, because they provide an even illumination of the tissue in the camera's FOV (i.e., the spatial intensity variation was less than 15%). The FOV of the camera was controlled by the optical lens and was slightly narrower than the illumination area.

The introduction of noise into the PPG signal by the motion of the animal during respiration made initial analysis of PPI imaging difficult. We were able to reduce the influence of respiratory motion using a signal processing method called envelope extraction. To each pixel in the image, the signal was smoothed with a low pass filter to extract the envelope of the noisy signal. The noisy signal was then divided by its envelope to remove the dramatic motion spikes in the signal. The remaining clear signal demonstrated information that was then processed into the PPG image.

1.3.1.b. Multispectral Imager

Multispectral images were collected by the Staring method using a filter-wheel camera (SpectroCam, Pixelteq; Largo, Fla.) equipped with eight unique optical band-pass filters between 400 and 1,100 nm wavelengths. To select the most relevant filters for our system we tested 22 unique filters identified in previous studies and performed wavelength selection data analysis using a technique called feature selection. Wavelength filters with the following peak transmission were used in this study: 581, 420, 620, 860, 601, 680, 669, and 972 nm (filter widths were ±10 nm; Ocean Thin Films; Largo, Fla.). The system was calibrated using a 95% square reflectance standard (Spectralon SG3151; LabSphere Inc.; North Sutton, N.H.) in order to compensate for the different spectral response of the imaging sensor. The light source used was a 250 W Tungsten-Halogen lamp (LowePro) equipped with a frosted glass diffuser to create a more even illumination profile within the imager's field of view. The System utilized a telescopic lens (Distagon T*2.8/25 ZF-IR; Zeiss Inc.; USA).

1.3.1.c. Swine Model

The methods used in this animal study were modified from Branski et al., 2008, and Gurfinkel et al., 2010. Adult Hanford swine weighing approximately 40 kg were acclimated prior to surgery. Under appropriate anesthesia and analgesia, deep partial-thickness burns were created proximal to the midline of the dorsal side of the pig. Injuries were generated using a hot brass rod heated to 100° C. and pressed to the skin (pressure 0.24 kg/m2) for 60 seconds. The brass rod was 3.6 cm in diameter, and resulting wounds were of identical dimensions. A total of six injuries were generated on each pig in order to maintain spacing between wounds that would allow the use of healthy tissue adjacent to each circular burn as uninjured control tissue.

In order to calibrate the imaging devices to the proper excision depth, a standard model for sharp tangential excision was developed. Tangential excision is the partial excision of a burn in a uniform, serial, and repeatable fashion. This was accomplished by passing an electric dermatome set to 1.0 mm in depth (6.0 cm width) over the burn multiple times until the entire burn was excised to the depth of the viable wound bed.

Figure 36:
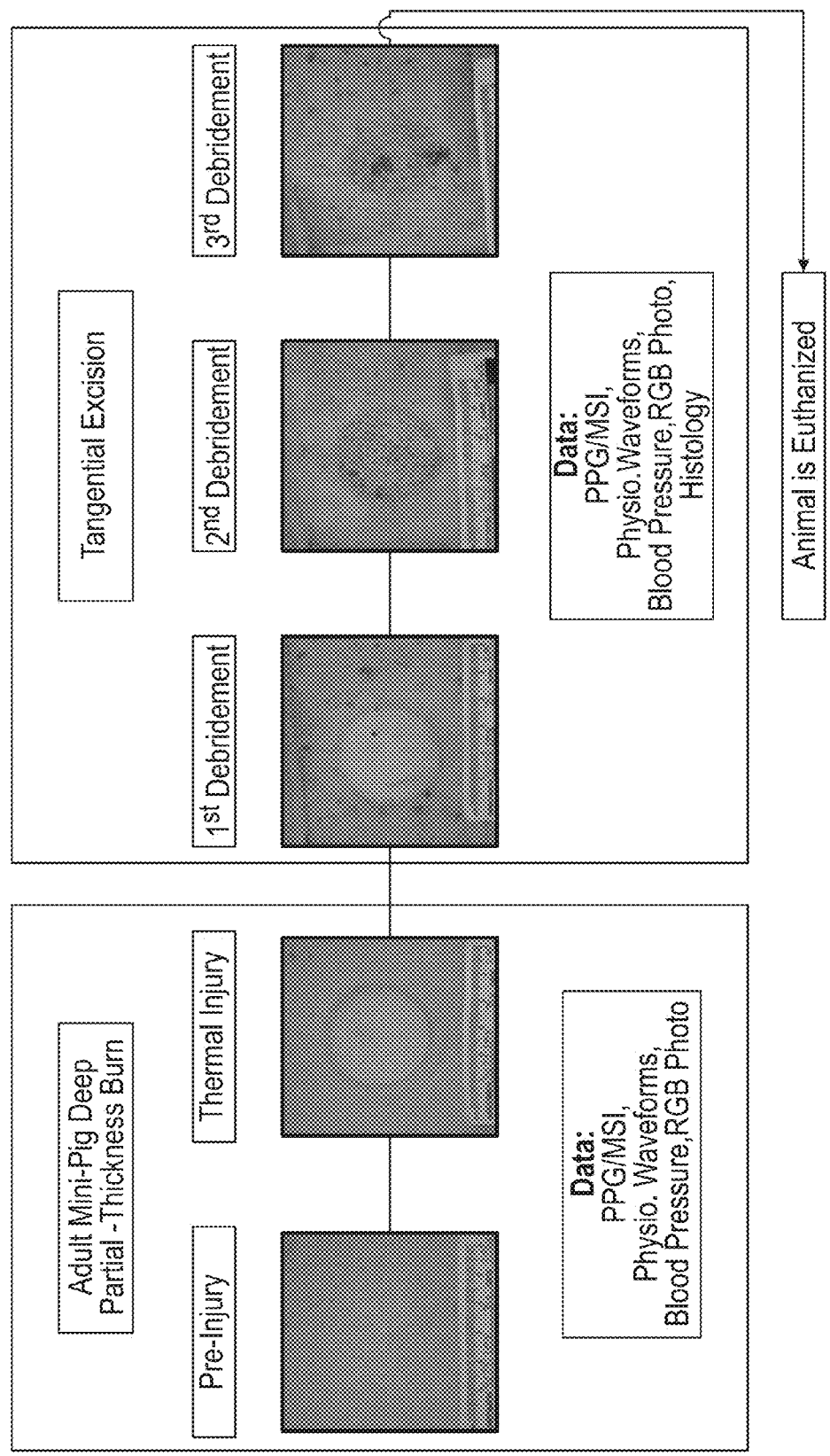
FIG. 36 illustrates the steps involved in the deep partial-thickness porcine burn debridement model. The five time points, color photographs, and data collection from each time point are depicted.

We excised the deep partial-thickness burns in three passes of the dermatome to expose the viable wound bed below. During the experiment, a debridement was deemed successful if we had removed the tissue to a point where punctate bleeding was present. The healthy tissue adjacent to each circular burn was used as uninjured control tissue. Data collection time points were: 0) pre-injury; 1) immediately post injury; 2) at each of the three debridement layers (FIG. 36). At each time point we collected PPG images, MSI images, and physiologic data including: heart rate; respiratory rate; and blood pressure. After each tangential excision, we saved the excised tissue for histology.

1.3.1.d. Identification of Variable Wound Bed

A histopathologist, who was blinded to the details of the study, determined the depth at which the viable wound bed tissue was exposed using histology and color photography. Histology was performed according to Gurfinkel et al., 2010. Briefly, each tangentially excised tissue sample was fixed in 10% Neutral Buffered Formalin (NBF) and sent for processing and examination by a board certified histopathologist (Alizee Pathology, Thurmont, Md.). One representative biopsy was taken from each sample and stained using hematoxylin and eosin (H&E). To determine at which tangential excision the viable wound bed was reached, the histopathologist identified the margins of the most severely burned areas of the thin slice of tissue, and morphometric analysis was used to find the depth of this burn. At each time point in the study, we also took digital photographs of the burns. A color reference strip was placed beside the wounds for standardization of color.

1.3.1.e. Classification Algorithm for Multispectral Imaging

In order to automate the classification of pixels in the raw MSI data cube, a classification algorithm and a burn tissue spectral reference database were generated. For database generation, three things occurred: first, we wrote a program that our technicians could use to select specific pixels out of the images from our animal study data; second, tangentially excised tissue specimens from the animal experiment were processed and read by a certified histopathologist to identify the location and severity of the burn in each section; third, an experienced surgeon viewed color photographs to identify the location of punctate bleeding and viable versus non-viable tissue in the debrided tissue. Following the completion of these steps, two technicians hand-selected the pixels from approximately 120 MSI images.

We built a machine learning algorithm to sort pixels into six different physiologic classes based on the reference data generated in the previous step. We used quadratic discriminant analysis (QDA) as our classifier algorithm. The algorithm's accuracy was determined as follows: Once the pixels from each MSI image were sorted into their appropriate classes according to the histology we trained our classification algorithm with 2,000 pixels per each of the six classes across all 24 burn sites. Then, without replacement of the training pixels, we randomly selected a new set of 2,000 per class as data to test the classification algorithm's efficiency. Classification accuracy was calculated according to Sokolova & Lapalme.

These are the six physiologic classes used in the experiment and their descriptions:

Healthy Skin—Healthy skin was a common tissue present in almost all of our images.

Hyperemia—Hyperemia is one of the three zones of burn injury described by Jackson in 1947. Vasculature is vasodilated, and complete recovery is expected.

Wound Bed (Graftable)—Graftable wound bed tissue is the ideal surface for applying skin grafts. It has white or pink in color with punctate bleeding.

Blood—Large accumulations of blood on the surface of the tissue should queue the surgeon to suction blood away and re-image this area.

Less Severe Burn—Tissue with minor burn injury that may heal spontaneously within two weeks.

Severe Burn (Ungraftable)—Zone of coagulation where necrosis and irreversible burn injury has occurred; will not heal spontaneously or accept skin graft.

1.3.1.f Statistics & Image Processing

All image processing and statistics were performed on MATLAB (v2013b).

1.3.2. Results 1.3.2.a. Burn Generation and Depth

Figure 37:
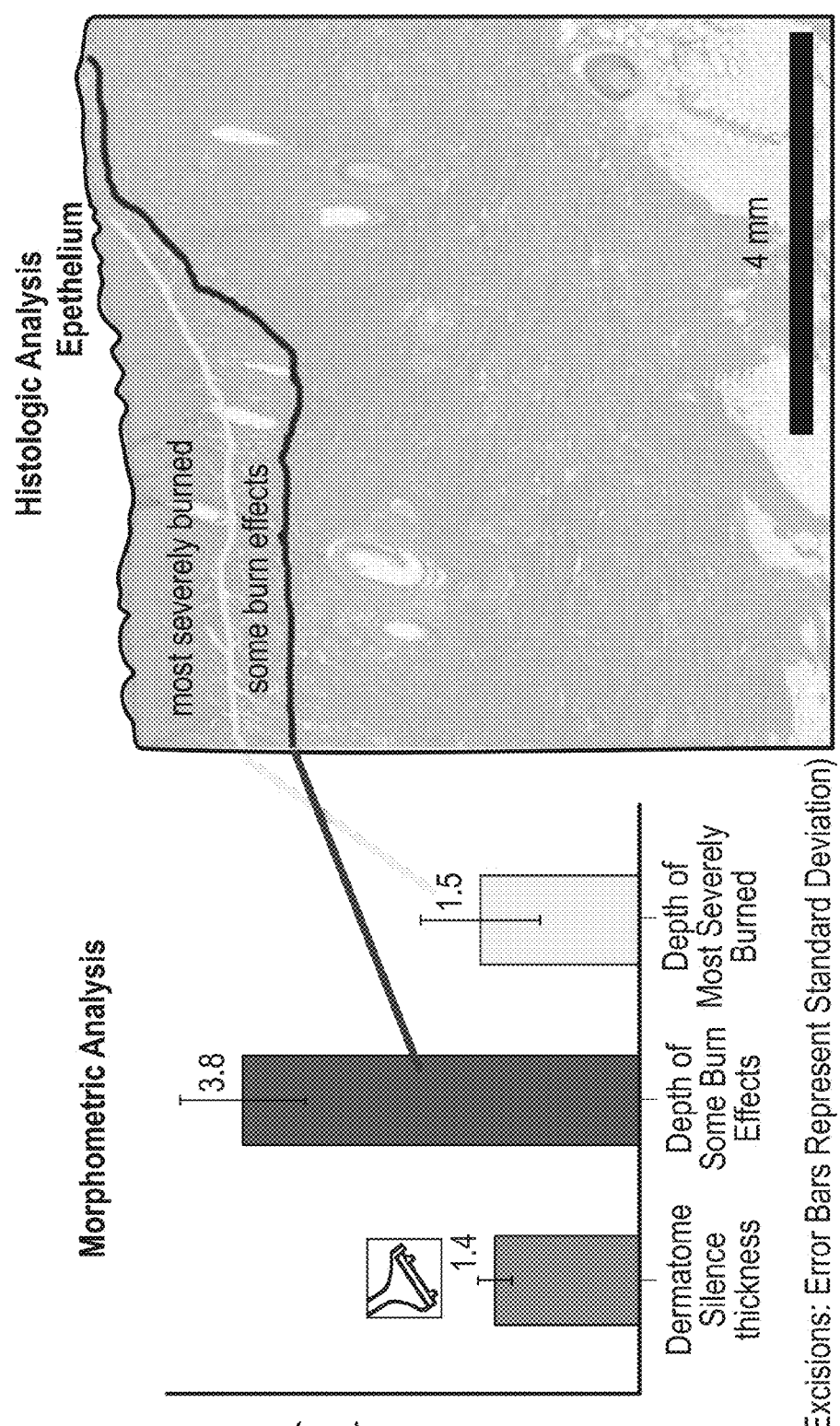
FIG. 37 illustrates (Left) the average thicknesses of each dermatome excision performed to excise the pig burns. Also, the average depth of the burn injury segmented by severe burn and some minor burn effects. Error bars represent standard deviation. (Right) H&E stain of a partial thickness burn showing the histologists markings on the tissue.

Twenty four (24) deep partial-thickness burns were generated on four minipigs. We found that 16 of 24 (67%) wounds had homogeneous wound areas with the pressure controlled burn rod. From each burn three tangential excisions were taken, and the extent of the burn in each section was determined by a histopathologist. From each of these 72 sections, morphometric analysis was performed to quantify the consistency of the burn depth and the consistency of each tangential excision generated by the dermatome. The average dermatome excision thickness was 1.36±0.16 mm (12% standard deviation; FIG. 37).

The burn tissue was differentiated into regions with any burn effects and regions with severe burn effects. We found that the average total depth of the burned tissue was 3.73±0.58 mm (16% standard deviation) and the depth of the severely burned portions was approximately 1.49±0.59 mm (±39% standard deviation). These results are summarized in FIG. 37. The latter metric had the highest variance which was likely related to the more subjective tissue changes used by the histopathologist to delineate this region from the region of some burn involvement.

Figure 38:
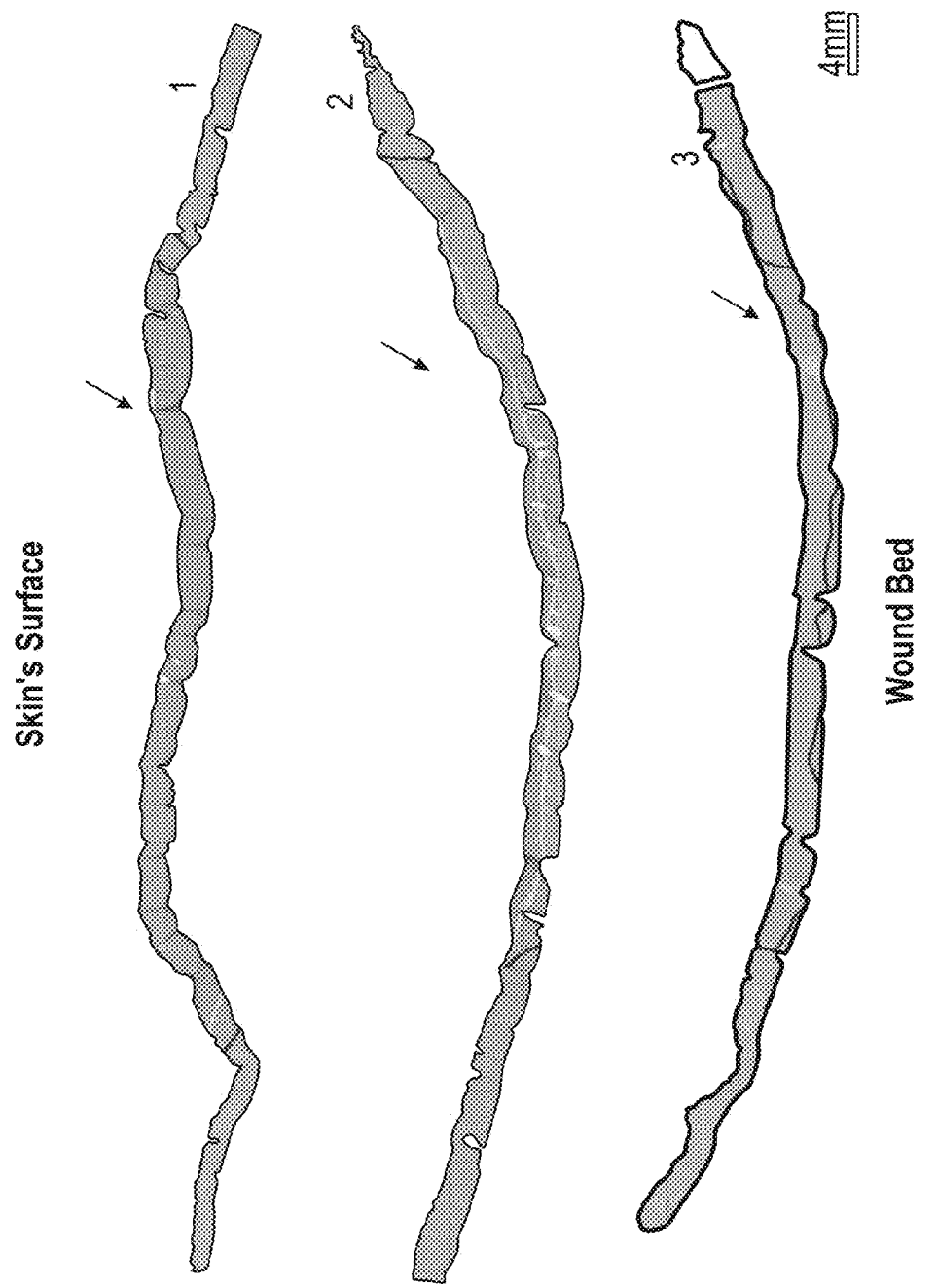
FIG. 38 illustrates the histology of tangentially excised tissue specimens from a deep partial-thickness burn. Numbers indicate the order of excision from epidermis into the dermal layer, and arrows indicate the most superficial aspect of each dermatome specimen. The most severely burned tissue may lie superficial to the yellow lines. Tissue with minor burn effects lies between the black and yellow lines. Tissue deep to the black lines was deemed to be without burn effects.

With the tangentially excised burn tissue, histology was performed to verify that we had reached the viable wound bed after three passes with the dermatome. A debridement was deemed successful if we had removed the tissue to a point where punctate bleeding was present. In 24 out of 24 injuries (100%) we removed the tissue to reveal even and punctate bleeding across the wound bed. This was confirmed by histology which showed that all of the severely burned tissue was removed in three or fewer passes of the dermatome (FIG. 38). Despite evidence of punctate bleeding, the histology demonstrated that in 8 out of 24 injuries (33%) we had not completely removed all tissue with any burn effects. However, a board certified surgeon blinded to the imaging data, reviewed our color photographs of the wound beds after debridement and confirmed that grafting on the tissue with these minor burn effects would be acceptable and that this tissue would not likely convert to severe injury.

1.3.2.b. Photoplethysmography Imaging

We looked at the differences in the PPG signal from three tissues present in the images: healthy skin; burn injury; and wound bed tissue. We found a significant difference between the signal-to-noise ratio of the PPG signal from the burned tissues compared to the other two tissue types (healthy skin: 6.5±3.4 dB; viable wound bed: 6.2±4.1 dB; and burned tissue: 4.5*±2.5 dB; *p<0.05). These results were repeatable. PPG images collected from 20 out of 24 burn sites were able to identify the proper point of excision.

Figure 39:
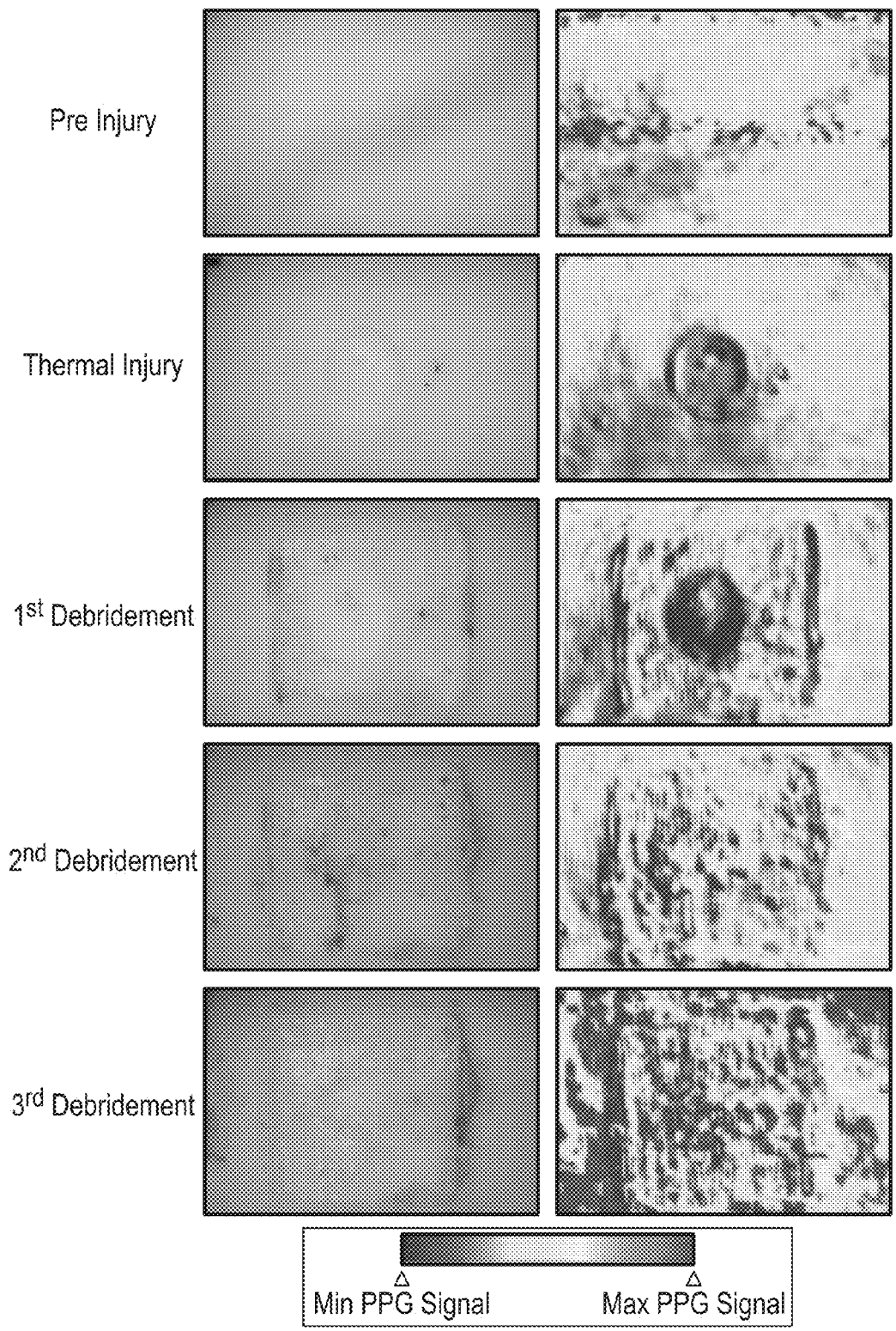
FIG. 39 illustrates PPG imaging results from the serial tangential excision of a deep partial-thickness burn. As the first 1.0 mm layer of skin is removed, the burn tissue is still evident in the wound bed as indicated by the lower relative PPG signal. At the depth of approximately 2 to 3 mm (after the second cut), the PPG signal has returned in the area of the wound bed.

We present one series of images from an injury to highlight the PPG signal changes throughout the depth of the burn (FIG. 39). Initially, the PPG signal is relatively uniform across the uninjured skin. The signal dramatically decreases in the center of the image where the burn injury was created. As the first 1.0 mm layer of skin is removed, the burn tissue is still evident in the wound bed, and the lower relative PPG signal correlates to the presence of this tissue. At a depth of approximately 2 to 3 mm (after the second cut), the PPG signal has returned in the burn wound bed.

1.3.2.c. Multispectral Imaging

From the labeled database of pixels selected under surgeon and histologist supervision, 2,000 pixels randomly selected from all 24 burns were combined into a test data set. The test set was classified by the previously trained QDA algorithm and compared to their actual class labels to generate a confusion matrix (FIG. 42). This matrix shows the number of correct classifications across the diagonal in the center of the matrix. Incorrect classifications are in the off-diagonal elements. We found overall classification accuracy to be 86%. Blood expressed from the wound bed could be classified by our algorithm with 92% success rate, the highest accuracy of the six classes. The other five classes were classified with similar rates of accuracy with 'Severe Burn' having the lowest classification accuracy at 81%. The confusion matrix demonstrates that a common inaccuracy was the misclassification of severely burned tissue as healthy skin, and healthy skin as severe burn. Also, we find that hyperemic tissue is often misclassified as blood and vice versa.

Figure 40:
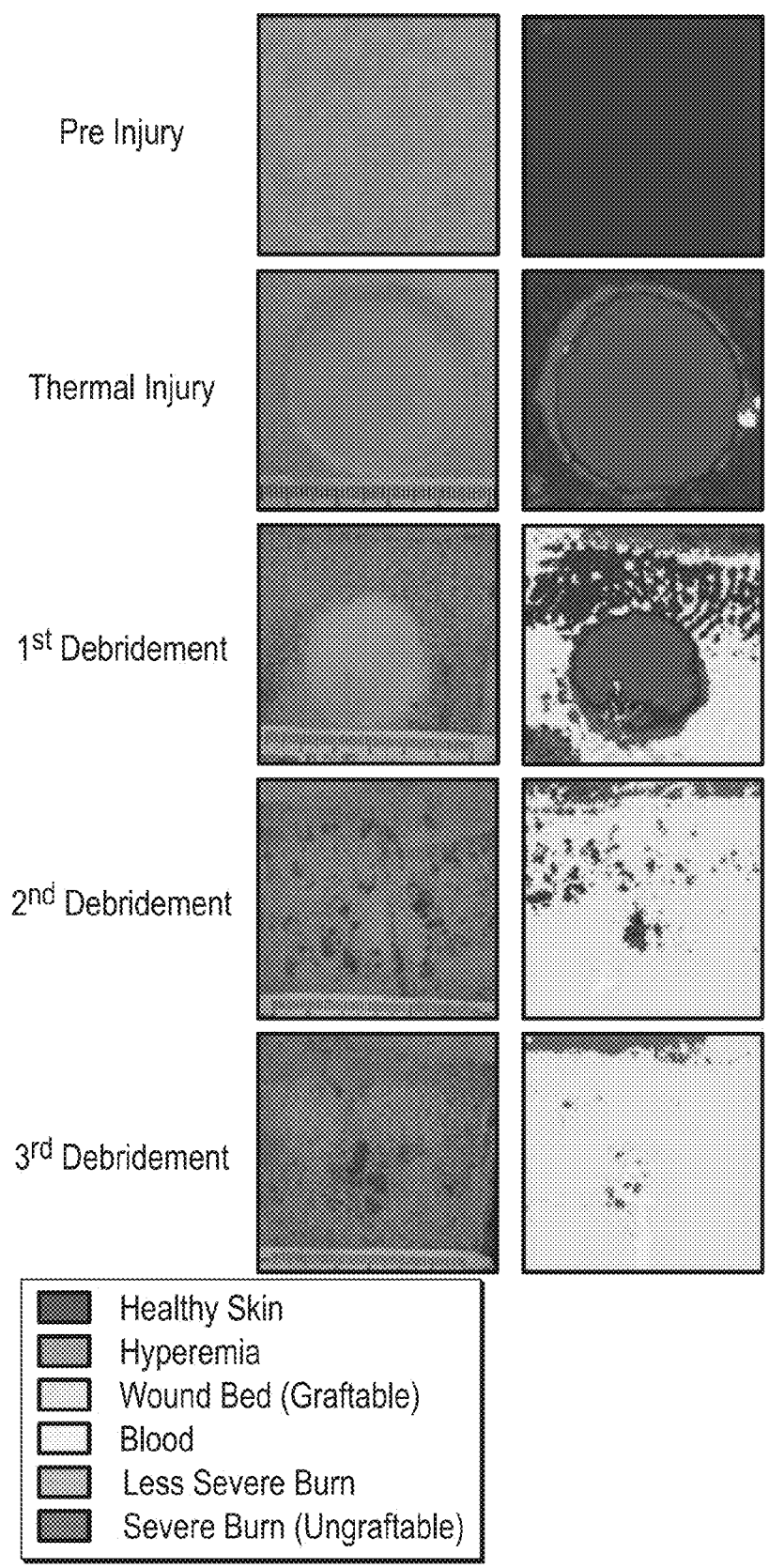
FIG. 40 illustrates multispectral images from a serial tangential excision of a deep partial-thickness burn. The presence of severe burn decreases as more layers of skin are removed. At the second debridement, the burn is nearly completely excised and is completely removed at the third debridement. Some error is present, notably in the first debridement where healthy wound bed is classified as healthy skin. Error can be decreased through algorithm and hardware improvements, or selecting more effective wavelengths.

The classified MSI image outputs demonstrate the location of the burn and its margins well (FIG. 40). MSI could clearly identify the viable wound bed as we cut deeper into the burn area with the dermatome. Again, the misclassification of pixels mentioned previously by our confusion matrix analysis, is seen in these images. The spatial representation shows that errors are not typically random, but rather they occur in certain areas of the image with higher frequency, such as much of the wound bed being classified as healthy skin in error only in the top portion of the 1st Debridement image from FIG. 40.

Figure 41:
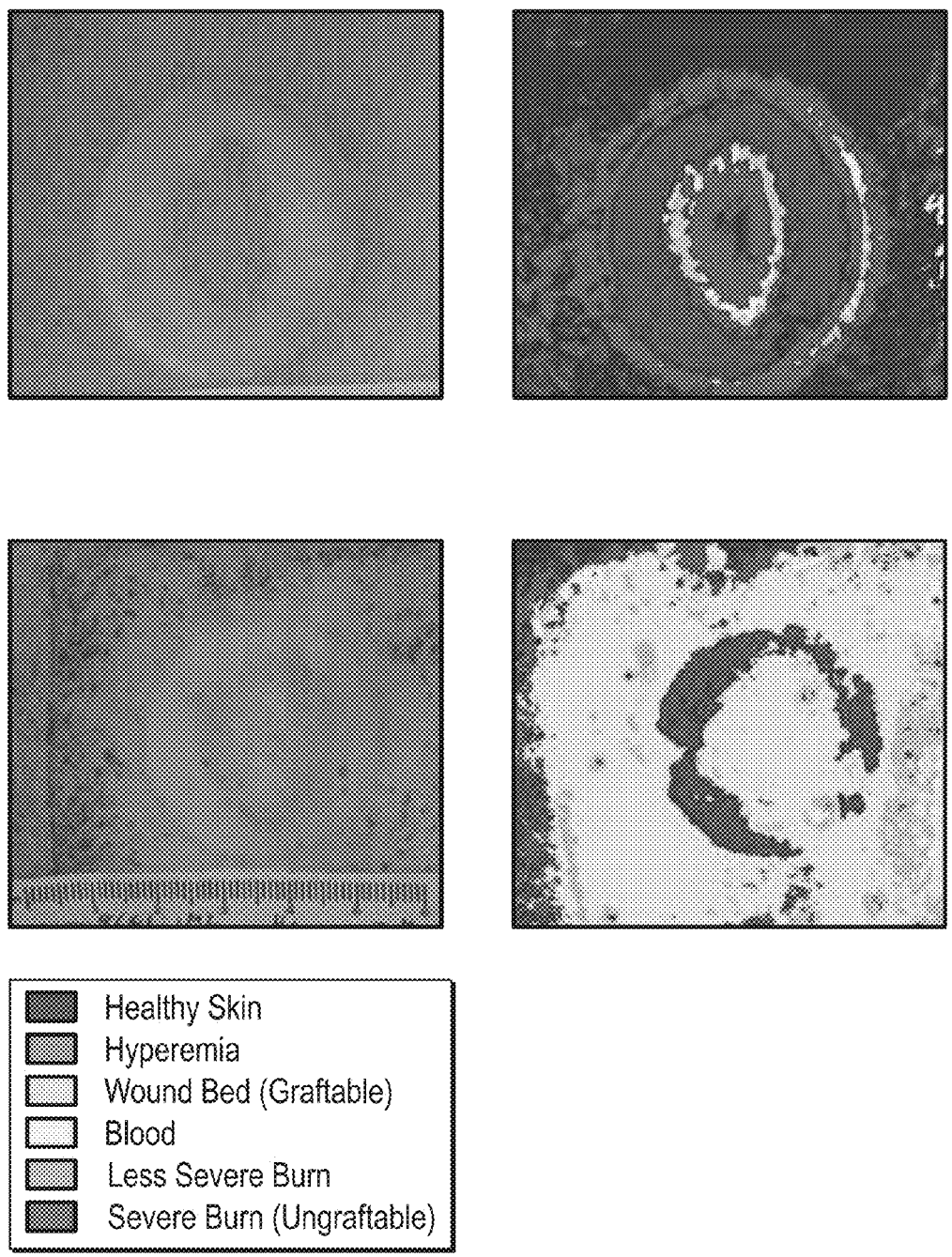
FIG. 41 illustrates the effectiveness of the MSI technique in a heterogeneous burn. Upon presentation, the surgeon must determine the tissue that needs surgery (top). During surgery, the surgeon encounters burns of non-uniform depth. These images can queue the surgeon as to where more burn injury must be removed, and where viable wound bed is already reached (bottom).

For a burn that contained different burn depths within the same injury, a common clinical scenario, the MSI image results could identify the more severely burned areas (FIG. 41). This was the case for the time points that occurred immediately after injury and during the excision process. These images are provided to show just how effective this tool can be in surgical planning, especially for the inexperienced burn surgeon.

1.3.3. Conclusions

Results from our PPG imaging data demonstrate that burned tissue has significantly less PPG signal compared to healthy tissue. From a clinical standpoint, this means that a suspected burn injury can be identified with the assistance of PPG imaging technology. As a surgeon excised tissue, they could expect a corresponding increase in PPG imaging signal as they removed necrotic tissue to expose a viable wound bed. When the signal reached an intensity characteristic of viable tissue, a PPG imaging device would indicate to a surgeon that there is adequate blood flow in the wound bed and the tissue would support a graft.

Results from MSI imaging are also promising. With the eight wavelengths used in this study, we arrived at an average of 86% accuracy in classification of various tissue classes. The current standard of care for burn tissue classification is the clinical judgment of experienced burn surgeons. Although no studies have reported the accuracy of surgeon classification during excision and grafting procedures, a clinical study of the of initial burn depth assessment by experienced surgeons demonstrated 60-80% accuracy. Although surgeon accuracy during initial assessment does not necessarily inform how accurate experienced surgeons are intraoperatively, we expect that the challenge to correctly determine the optimal excision depth during burn surgery is similarly difficult as initial assessment. Therefore, we believe that the demonstrated accuracy of MSI imaging in this study is on par with the most skilled experts, and MSI undoubtedly has the potential to improve the clinical decision making of inexperienced surgeons.

Features calculated from the PPG data can be combined with the reflectance spectrum data using the same machine learning techniques already established for MSI data analysis. Since both PPG and MSI raw data cubes can be collected with the same optical hardware, it is a matter of statistical analysis to determine the salient features from each system to include in the classifier equation. While MSI alone can effectively identify the margins of the burn, we believe the dynamic blood-flow information from the PPG signal will combine with the reflectance data to include critical tissue viability information.

The proper classification of burn wounds during excision and grafting is essential to optimizing care for burn patients. PPG imaging and MSI are two technologies that can aid burn surgeons and non-specialist surgeons alike to guide debridement. PPG imaging detects blood flow to identify healthy tissue by its characteristically higher blood content. MSI gathers reflected light of key wavelengths to generate and categorize unique reflectance spectra for each tissue class. Using a porcine burn model, we have applied these technologies to demonstrate their feasibility and practicality for clinical application. PPG imaging and MSI, individually or together, can increase the diagnostic accuracy of healthcare providers and help to optimize the debridement process during skin grafting procedures.

1.3.3.a. Applicability to Practice

A physician undergoes years of training to properly perform surgical debridement. An inexperienced surgeon tasked with performing multiple surgeries during a mass casualty situation faces innumerable obstacles. Under- and over-excision of the tissue both have severe complications. Under-excised burns result in placement of grafts on devitalized tissue causing poor graft uptake and increased risk for infection. Conversely, over-excision risks excessive blood loss, which also compromises graft take. In addition to performing the technical aspects of the procedure, the surgeon must be able to dictate the proper fluid and blood management perioperatively. Furthermore, timing is critical, as patients who undergo excision for wounds even after only 48 hours lose twice the amount of blood as compared to similar patients who receive surgery 24 hours earlier. Finally, multi-region burns that vary in depth over the total burn area further complicate provision of burn care. Excision and grafting of these burns is challenging to plan in order to ensure maximal removal of unviable tissue with minimal excision of still viable skin.

To decrease the gap between a burn surgeon and a non-burn surgeon, an assistive tool is needed. The ideal solution would: identify regions that must be excised; determine the proper depth of excision; and monitor vitals to guide therapeutic management of the patient. Further requirements for clinical adaption would be an increase in diagnostic accuracy, accommodation of realistic patient conditions, and provision of useful data immediately to the treatment team. Furthermore, an optimal solution could be easily employed to aid non-specialists in a situation where burn-specialists were overwhelmed with patients, such as in a mass casualty event.

As previously discussed, several imaging modalities have been proposed as potential solutions to this problem. To date, most technologies have proven impractical in clinical practice for a variety of reasons. Some technologies are less accurate than the unaided clinical judgment of surgeons. Other solutions require patients to lie immobilized for prolonged periods, have data acquisition times on the order of days, or require invasive procedures for accurate diagnosis. Clinical tools with these limitations have not been readily adopted by healthcare providers.

MSI and PPG imaging, including the experiments outlined in this disclosure, have shown promise that these technologies may in fact meet these requirements to improve burn care. By working to translate these technologies into clinical tools that can be utilized at the bedside, outcomes in quality-of-life metrics can be improved for burn victims in the United States.

This solution would have global impact as well. Impoverished people in developing nations rely on open fires for cooking and lighting. These living conditions expose women and children to increased risk for severe burns. In South Asia, for example, more women and children die from severe burns than from HIV/AIDS or malaria infections. A lack of access to medical care means that relatively minor burns result in permanent disability that could be prevented by reducing the skills necessary to administer treatment through burn care assistive devices.

1.4. Example 4: Experiment to Improve Burn Injury Diagnostic Imaging Device's Accuracy by Outlier Detection and Removal The methods, systems, algorithms, techniques, and/or disclosures described in this Example 4, and substantially similar versions and/or variations, may be used in computations in any of the methods or devices described in this disclosure.

In this experiment, we utilized multi-spectral imaging (MSI) to develop a burn diagnostic device that would assist burn surgeons in planning and performing burn debridement surgery. In order to build a model, training data that accurately represents the burn tissue is needed. Acquiring accurate training data is difficult, in part because the labeling of raw MSI data to the appropriate tissue classes is prone to errors. We hypothesized that these difficulties could be surmounted by removing the outliers from the training dataset which would lead to an improvement in the classification accuracy. We developed a pig burn model to build an initial MSI training database and study our algorithm's ability to classify clinically important tissues present in a burn injury. Once the ground-truth database was generated from the pig images, we then developed a multi-stage method based on Z-test and univariate analysis to calculate outliers in our training dataset. Using 10-fold cross validation, we compared the algorithm's accuracy when trained with and without the presence of outliers. We demonstrated that our outlier removal method reduced the variance of the training data from wavelength space. Once outliers were removed from the training dataset, the test accuracy was improved from 63% to 76% and get better outputs. Establishing this simple method of conditioning for our training data improved the accuracy of our algorithm to be as good as the current standard of care in burn injury assessment. Given that there are few burn surgeons and burn care facilities in the country; this technology is expected to improve the standard of burn care for burn patients with less access to specialized facilities.

1.4.1 Multispectral Imaging Application

The technology of multispectral imaging (MSI) and hyperspectral imaging (HSI) which originate from the technology of widely in different application with the development of camera technology, such as, astronomy by NASA, agriculture, defense, geology, medical imaging application.

We introduce an application of MSI technology for burn wound analysis. For burn treatment, it is important to determine the depth of the initial injury. Shallower burns, known as superficial partial thickness burns, do not require surgical therapy and typically heal with supportive therapy. More severe burns, categorized as deep partial thickness or full thickness burns depending on their depth, require surgical excision of all necrotic tissue in order to expose a viable wound bed as a base for grafting surgery. Currently, the gold standard of burn wound classification is the clinical judgment of expert burn surgeons. However, the accuracy of such experts has been estimated to be only 60% to 80%, and the accuracy of nonexperts is no higher than 50%. A technological solution to improve the accuracy of burn classification, particularly in medical centers where burn experts are not available, is needed to improve clinical decision making regarding burn treatment. MSI can classify burn tissue into different clinical categories with a potentially high degree of accuracy, allowing burn surgeons to more frequently and quickly select appropriate treatment solutions. During the debridement of necrotic tissue from severe burns, surgeons aim to minimize the removal of any excess healthy tissue. MSI has the further potential to aid surgical excision by categorizing burn tissue intraoperatively to differentiate burn injury from healthy wound bed, preventing unnecessary excision of healthy tissue.

Human skin is a multilayer tissue consisting of multiple chromophore components, of which there are four significant constituents: blood, water, melanin, and fat. Blood, water, melanin, and fat in the various skin layers have well-established spectral responses to optical illumination with certain wavelengths of light, especially in the visible and near-infrared bands. By capturing and analyzing different tissues' responses to multiple incident characteristic wavelengths with MSI, one can, e.g., identify the presence of blood among other tissues by its unique spectral response. Tissue response to incident light is quantified by its absorbance. The collection of absorbance data over a range of wavelengths by MSI allows the classification of different tissue types based on the relative amounts of tissue constituents present within each tissue class.

Although MSI is capable of capturing unique spectral data from various tissue types, a classification model must be developed to interpret new spectral images and correctly identify tissues. A difficulty arises when developing the model, because it must be built from the same type of data that it will later be used to classify, through a process called machine learning. Therefore, during initial model construction, a "training" dataset must first be collected and manually classified as the "ground truth." Establishing the ground truth is a key step in any machine learning application and is, therefore, one of the most scrutinized stages in the development of these applications. A highly accurate ground truth is necessary to build an accurate classification model. The manner by which the ground truth is established varies depending on what the classification model is being constructed to assess. In every instance, however, it must be established by clinical experts using the current gold standard to gather the necessary information. For burn wounds, the gold standard for tissue classification is histopathological assessment. We present the details of our technique for establishing the ground truth.

The training set is then used to develop the classification model, which is subsequently tested on additional collected data to determine its accuracy against the ground truth. Various algorithms have been developed to build classification models from ground truth training datasets. For example, the support vector machine (SVM) algorithm has been used previously in kernel-based machine learning for hyperspectral imaging data analysis.

Ultimately, manual demarcation of training data establishes the ground truth, so there is a potential bias in the resulting model due to classification errors. For example, if healthy skin is inappropriately classified as blood in the training data, the resulting model would subsequently have difficulty in accurately classifying healthy skin versus blood. As the training data is the sample space used to build the classification model, reducing any such bias is the key to improving the model's accuracy.

The inevitable bias in any training set ultimately reduces the model accuracy when it is tested after development. To reduce variance and improve model accuracy, the identification and removal of "outliers" from the training dataset are helpful. An outlier is defined as an observed variable that is statistically different from other observed variables. Outlier detection (also known as anomaly detection or novelty detection) is a key element of statistical pattern recognition research, with applications in fields such as credit card fraud, sensor events, medical diagnosis, and network security. There are several established methods of outlier detection. One commonly implemented outlier detection technique is the model-based algorithm.

In model-based algorithms, a statistical test estimates the parameters of the sample distribution. For example, a Gaussian distribution is described by two parameters: mean and standard deviation. These parameters are determined by the maximum likelihood or maximum a posteriori estimation. In a univariate Gaussian distribution, outliers are the points that have significantly extreme probabilities (high or low) of being included within the model parameters as quantified by a Z-score (standard score). Traditionally, samples with probabilities greater than 0.95 or less than 0.05 are considered outliers in univariate analysis.

The model-based algorithm correctly identifies outliers in many cases. However, it is important to note that the parameters that define these models are sensitive to any potential outliers when they are initially calculated. That is, the parameters are generated using the entire sample set, before outliers can be identified and removed. Therefore, by identifying and removing outliers before these algorithms are used to generate classification models, the accuracy of these models can be increased. In this research, we present a machine learning algorithm in the medical space to which we apply the concept of outlier removal. MSI imaging data was first captured from an established porcine burn model. Then we assessed the multispectral images and provided a statistical solution to quantitatively improve the classification accuracy of a model designed to classify the different tissues present in the burn injury images.

1.4.2 Outliers Detection and Removal

Outlier detection and removal is an important area in statistic and pattern recognition area, which has been used widely in different areas, such as, credit card fraud, interesting sensor events, medical diagnosis, network security etc. Outlier detection may have other names, like anomaly detection, novelty detection, etc. Most outlier detection is model-based and proximity-based direction. For model-based algorithms, we can use statistical tests to estimate the parameters of the sample distribution, for example it may be considered as Gaussian distribution based on the central limit theorem (CLT). For Gaussian distribution, two parameters can be considered: the mean; and standard deviation. We can get these parameters from the maximum likelihood or maximum a posteriori estimation. In the model-based approach, outliers will be the points that have low probability of occurrence, which can be estimated by calculating the Z-score (standard score). As a rule-of-thumb, if the value of probability is greater than 0.95, or less than 0.05, these samples may be considered as outliers. This is based on the univariate analysis. If it is multivariate normal distribution:

$$N(x) = \frac{1}{(2\pi)^d |\Sigma|} e^{-\frac{(x-\mu)^T \Sigma^{-1}(x-\mu)}{2}}$$

$\mu$ is the mean value of all points, $\Sigma$ is the covariance matrix from the mean. We can calculate the Mahalanobis distance of point x to $\mu$. The Mahalanobis distance follows a $\chi^2$ distribution with d degrees of freedom. (d is the dimension of the data). Finally, for all of points x, if the Mahalanobis distance is greater than $\chi^2$ (0.975). Then the point will be consider to outliers. The thinking of statistical test can work in most of cases, however, the parameters are sensitive to the potential outliers when estimating the parameters process. At the same time, if the dimensional is high, the mahalanobis distance will be similar with the larger of degree of freedom. Depth-based approaches search for outliers at the border of the data space and deviation-based approaches minimize the variance when removing the outliers.

In proximity-based outlier detection, the nearest neighbor idea can be used to generate an approximation of inclusion or exclusion At first, the concept of distance is important. If there are N samples and M variables, the size of matrix is N*M, and for example by using Euclidean distance, we can calculate the distance among sample space by defined distance by: $d(q, p) = \sqrt{(q_1-p_1)^2 + (q_2-p_2)^2 + ... + (q_m-p_m)^2}$. Clustering methods are a common method that employs this concept of distance. In clustering algorithms, we can define a radius $\omega$, for any group of points from which a center has be identified (centroid), I If the points is less or equal this radius, it could be considered a good point, from which the centroid is updated based on the inclusion of this new data point. For the K nearest neighbors algorithms, the sum of the distance to the k-nearest neighbors of the points. However, if the dataset has high dimension, this method may not work because of the "curse of dimensionality".

There are other methods still based on other definitions of central tendency. For instance, the local outlier factor (LOF) is based on density. Density can be estimated from clusters of points. If a certain cluster or grouping of points has a lower density than its neighbors, the points within this cluster may be potential outliers. Again, if the datasets are high order dimensional data, these algorithms may not work. Angle based outlier degree (ABOD) and Grid-based subspace outliers detection have been proposed to handle high dimensional dataset.

2. METHODOLOGY 2.1 Hardware and Imaging and Animal Model

The multispectral image data were acquired using a home-made bench top imaging setup. FIG. 1 illustrates the schematics of this image acquisition system. The lighting source and the image capture module were both placed in a reflective mode at a distance of 60 cm away from the target surface. A tungsten light (ViP Pro-light, Lowel Inc.) provided a broad spectral projection on the target surface in DC-mode. One piece of frosted glass (iP-50, Lowel Inc.) was mounted in front of the tungsten light to diffuse the light and increased the uniformity of spatial illumination. Some incident light penetrated through the target surface, while any back-scattered optical signal was collected by the image capture module. The image capture module consisted of a high-performance IR-enhanced optical lens (model: Distagon T*F-2.8/25 mm, Zeiss), an eight-slot filter wheel, and a 12-bit monochromatic camera (BM-141GE, JAI Inc.). The optical bandpass filters were designed and selected to isolate a single wavelength of light for the camera. The following eight bandpass filters were installed in the filterwheel. The center wavelength (CWL) and the full width at half maximum (FWHM) of the eight filters were (CWL-FWHM, both in nm): 420-20, 542-10, 581-20, 601-13, 726-41, 800-10, 860-20, and 972-10. Wavelength intensity was normalized by using a Reflectance Zenith Lite Panel (SphereOptics GmbH), and the maximum value of a pixel was 4098 (12 bits). The eight implemented wavelengths were selected based on known skin tissue absorption behavior at these wavelengths that would allow for accurate tissue differentiation for useful classification. The camera sequentially captured single wavelength images through each of the eight filters as the filter wheel rotated. Images were saved on the computer in an uncompressed format. All calculations and statistics were performed using MATLAB® software (version 2014 b).

Figure 43C:
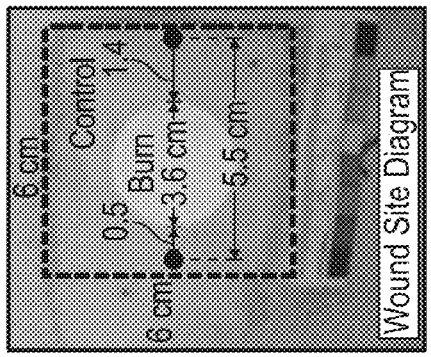
FIGS. 43A-43C illustrates an example hardware system set (FIG. 43A), animal burn (FIG. 43B), and first cut in burn tissue (FIG. 43C)
Figure 43B:
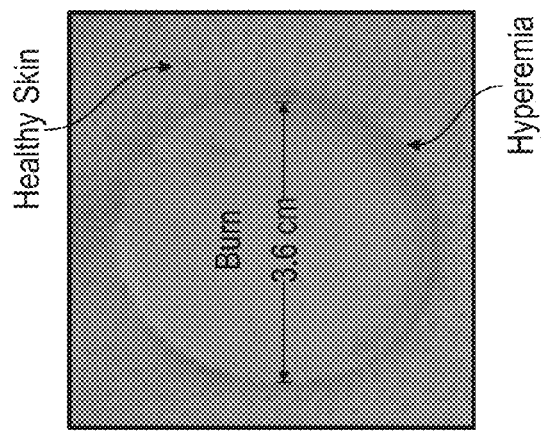
Figure 43A:
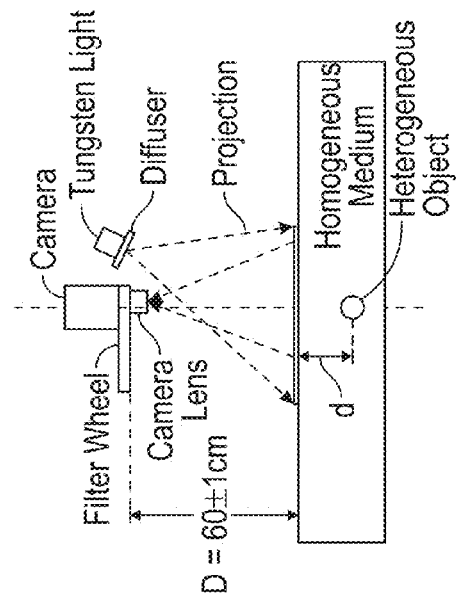

FIGS. 43A-43C illustrate an example hardware system set-up (FIG. 43A. (B). The multispectral image data were acquired using a home-made bench top imaging setup. FIG. 43A shows the schematics of the image acquisition system. Though a tungsten light was used in the example of FIGS. 43A-43C, in other embodiments the light source can be any broad spectrum illumination source, or any illumination source that matches the desired wavelengths of light necessary for data analysis.

We use the system above to collect the animal data by following a scientific burn model study protocol that was designed under the Institutional Animal Care and Use Committer (IACUC). In order to approximate human skin (epidermis thickness: 50 to 120 µm), male Hanford swine (epidermis thickness: 30 to 40 µm) were selected as the animal model.

Circular burns (diameter=3.6 cm) were made on the backs of swine (FIGS. 43 (b), (c)). At this stage, three skin tissues were visualized: healthy, burned, and hyperemia (reddening of the skin due to increased blood perfusion following an injury). Debridement was carried out in serial 1-mm depth tangential excision layers, and the area of each debridement for each burn was 6 cm×6 cm (FIG. 43 (b)). During debridement, six different skin tissues were appreciable: healthy, partial burn or full burn (depending on burn severity), blood, wound bed, and hyperemia. Each tangentially excised layer was stored in 10% neutral buffered formalin and sent for histopathological examination. Each specimen was sectioned and stained with hematoxylin and eosin (H&E). The purpose of the histological examination was to obtain the "gold-standard" identification of the tissue types previously mentioned, and their location in the multispectral images. The depth of burn damage and the precise excision layer at which viable tissue had been reached were determined by two pathologists.

Three pigs with six burn locations on each pig were used. For each burn location, we performed image acquisition using all eight wavelengths during at least five different time points baseline images taken prior to injury, burn images taken directly after thermal injury, an image following the first 1-mm tangential excision with the dermatome, and two more images following the next two tangential excisions.

2.2 Training Data Collection & Classification Algorithm

Figure 44:
FIG. 44 illustrates example burn injured skin.
Figure 46A:
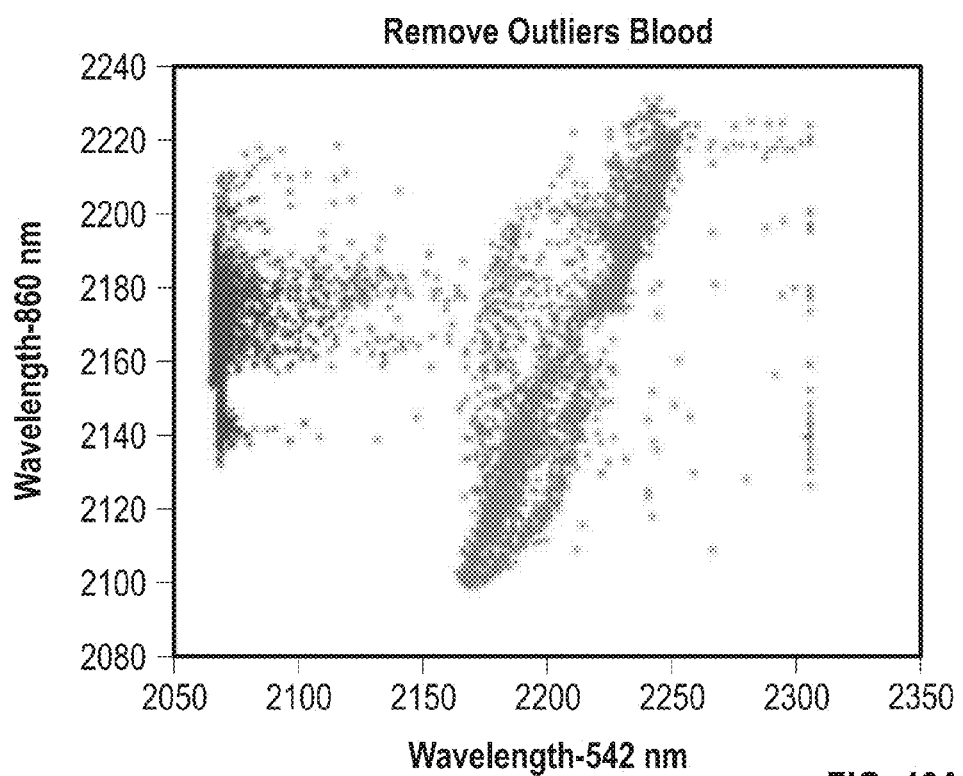
FIGS. 46A-46F illustrate example training sets.
Figure 46B:
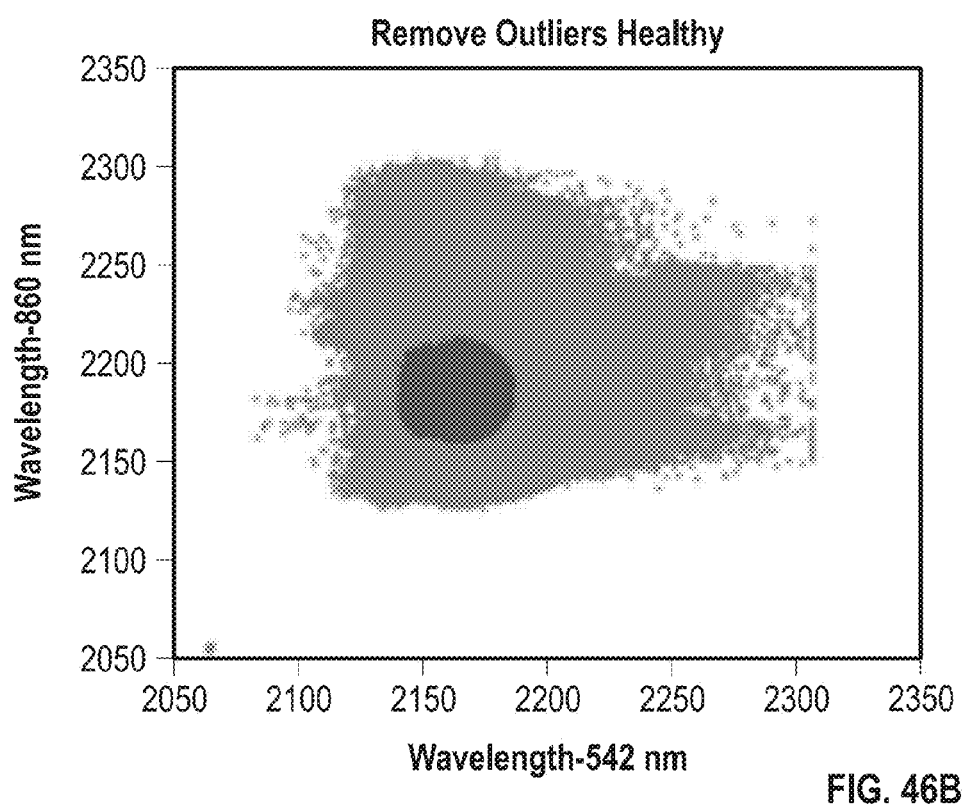
Figure 46C:
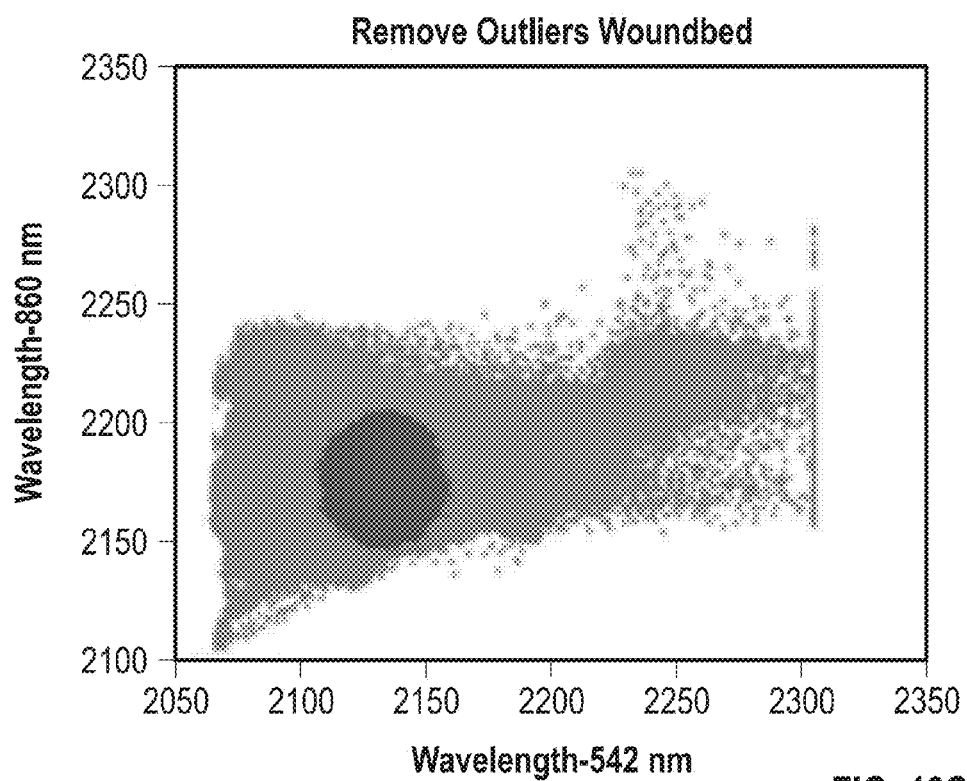
Figure 46D:
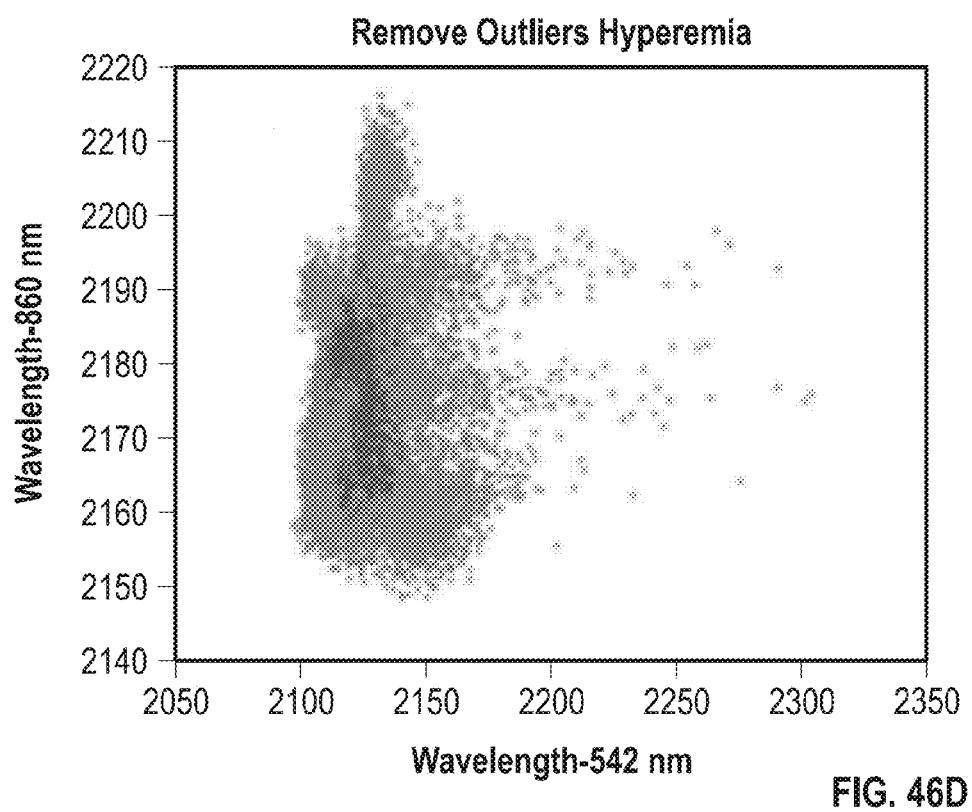
Figure 46E:
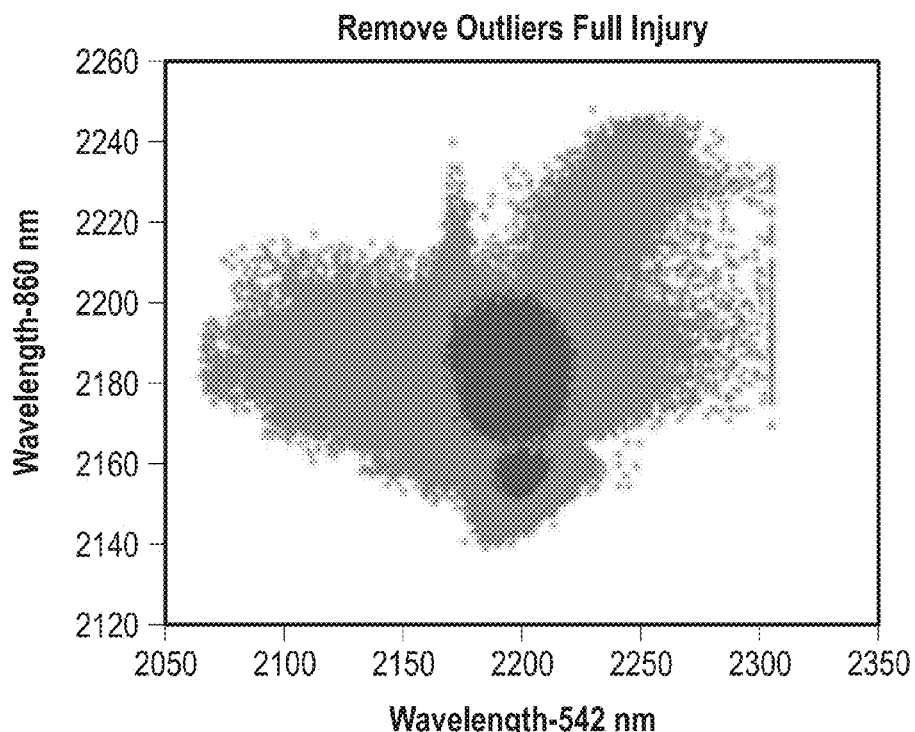
Figure 46F:
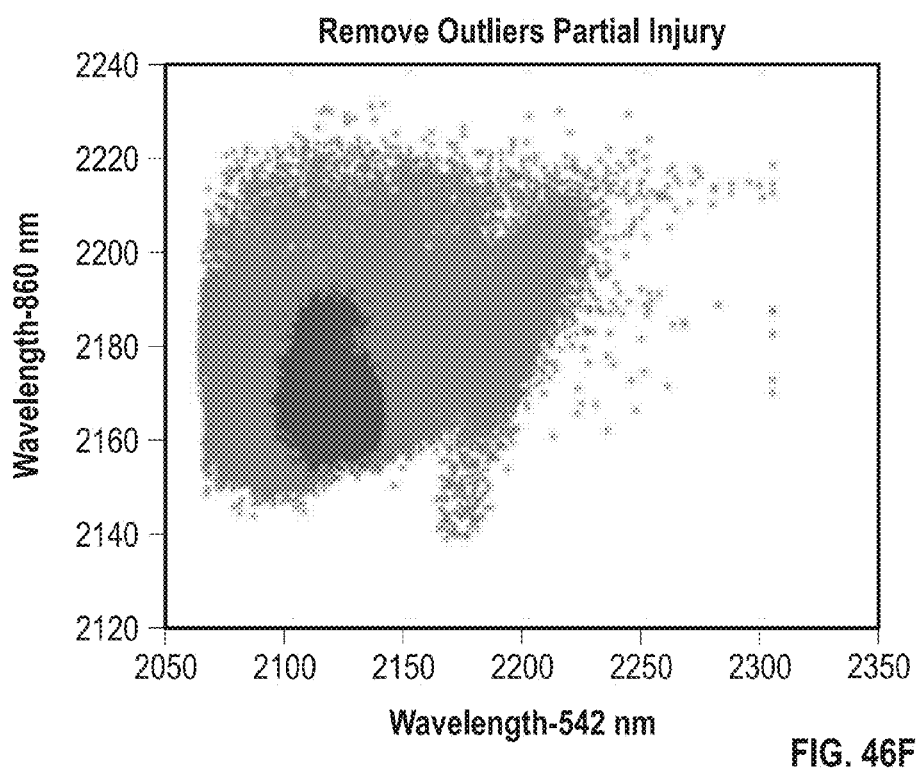

A supervised learning method was implemented to generate the classification model. To build a training database consisting of the six skin tissue classifications, we extracted the pixel intensity and the location of each of the six tissue types in every acquired image using the histology data as a reference. Each slice of tangentially excised skin was sectioned to show the burn depth as determined by board-certified pathologists according to well-established protocols (FIG. 44). We developed a drawing tool to mark the regions of healthy, partial burn injury, full burn injury, blood, wound bed, and hyperemia. The pathologists used the following parameters to determine these regions from the H&E-stained burned eschar: full burn injury is the zone of maximum damage. There is irreversible tissue loss due to coagulation of collagen and other tissue components. Histologically, this region is characterized by the loss of cellular detail. Partial burn injury has decreased tissue perfusion, with evidence of vascular occlusion. Collagen generally retains its structural integrity. However, there is some evidence of cellular necrosis with pyknotic nuclei. This tissue zone is considered to have the potential of being salvaged. Healthy wound bed was demarcated where essentially normal histological findings were present deep to burn tissue. These regions were then correlated with the previously acquired spectral imaging data, thereby establishing a ground truth by which our classification algorithms could be judged.

Figure 49:
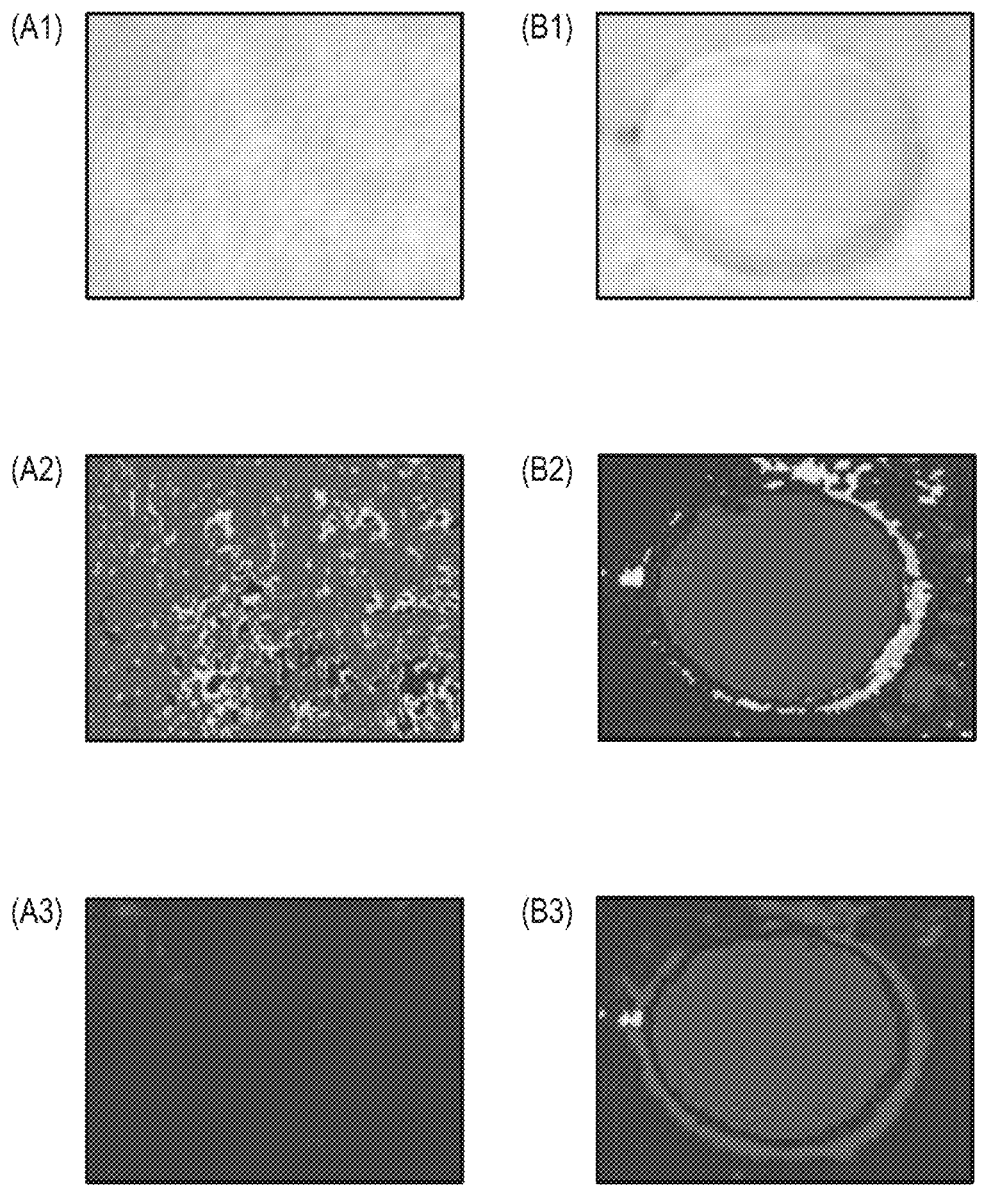
FIG. 49 illustrates example: (A1). Healthy case, (A2). Result—Before outliers removal, (A3). Result—After outliers removal, (B1). Burn case, (B2). Result—Before outliers removal, (B3). Result—After outliers removal.

Using Support Vector Machine (SVM) and k nearest neighbor (KNN) classification algorithms (Please see the FIG. 49) A2, FIG. 49) B2), we did not get a good result. For the output of health case A1, there should be a health skin tissue, however, we observed that there are other tissues, like wound bed present in the output. For the burn case, from the physiology, we knew that hyperermia should be around the burn, furthermore, the healthy skin should not be classified as full injury in the output, FIG. 49) B2. Using 10-folder cross validation. We show the model accuracy is 63% which is much lower than the required accuracy. we expected. From these two result, we can justify the detection and remove the outliers in our small database.

2.3 Outlier Detection

To reduce the influence of outliers on the model, an outlier detection algorithm utilizing two novel concepts was developed from the well-established foundation of maximum likelihood estimation as previously described. First, a subset of samples located around the median of the sample space was taken as a subspace to calculate the mean and the standard deviation parameters for the model using the maximum likelihood estimation. We called this subspace the "first window," and its size was adjusted by novel coefficients $\alpha_1$ and $\alpha_2$ (from 0 to 0.5, unitless), defined as distances to the left and right, respectively, of the median of the sample space (thus, the width of the first window equals $\alpha_1+\alpha_2$). As the width of the entire sample space was normalized to 1, setting $\alpha_1=\alpha_2=0.5$ would result in the entire sample being selected as the "first window." By properly adjusting these coefficients, outliers may be excluded before calculating the distribution parameters [mean ($\mu$) and standard deviation ($\sigma$) in Gaussian distribution] for the classification models. Second, the probabilities (from Z-score or other distribution function) were weighted ($W_i$) by a novel feature importance ($w_i$) to generate a threshold for detecting outliers within the first window. The technical details of these steps are as follows.

We began with a large sample space consisting of spectral data collected from the animal model. The foundation of the algorithm consisted of the well-established maximum likelihood estimation technique. For an independent and identically distributed sample, the joint density function is $$f(x_1, x_2, x_3, \ldots, x_n | \theta) = f(x_1|\theta) \times f(x_2|\theta) \times f(x_3|\theta) \ldots \times f(x_n|\theta)$$

Where $x_1; x_2, x_3, :::, x_n$ are the samples and $\theta$ denotes the parameters of the model. The likelihood of the function is $$L(\theta, x_1, x_2, x_3, \ldots, x_n) = f(x_1, x_2, x_3, \ldots, x_n | \theta) = \prod_{i=1}^{n} f(x_i|\theta)$$

In practice, the logarithm of the likelihood function, known as log-likelihood, can be applied as follows:

$$\ln L(\theta; x_1, x_2, x_3, \ldots, x_n) = \sum_{i=0}^{n} \ln f(x_i|\theta),$$

To estimate $\theta_0$, the value of $\theta$ that maximizes the following equation is calculated $$\theta \subseteq \arg\max L(\theta; x_1; x_2; x_3; \ldots; x_n).$$

We can calculate the parameter $\theta 0$ from the method of maximum likelihood. If the sample distribution is Gaussian, the mathematical equations that describe the maximum likelihood parameters are as follows:

$$\mu = \frac{1}{n} \sum_{i=0}^{n} x_i;$$

$$\sigma = \frac{(\mu - x_i)^2}{n - 1};$$

where xi is the value of the sample around the median. Our first novel outlier detection and removal method calls for these parameters to be controlled by the coefficients $\alpha i$ as follows:

$$n = (\alpha_1 \times N) + (\alpha_2 \times N).$$

At this juncture, we apply the second of our novel outlier detection and removal methods. We designate weights to replace probabilities when detecting outliers. First, the probabilities ($p_i$) and feature importance ($w_i$) are determined. The probabilities, pi, can be calculated with the distribution parameters of the sample distribution function. For example, for Gaussian distribution, $p_i$ is generated from a standard Z-score, which is calculated as follows:

$$z = \frac{x - u}{\sigma}$$

$$W_i = p_1 \times w_1 + p_2 \times w_2 + \ldots + p_{n-1} \times w_{n-1} + p_n \times w_n$$

$$= \sum_{i=1}^{n} p_i \times w_i w$$

where $\mu$ is the mean of the samples and $\sigma$ is the standard deviation of the samples. The Z-score determines pi as follows:

$$\Phi(z) = P(Z \leq z) = \int_{-\infty}^{z} \frac{1}{\sqrt{2\pi}} e^{\frac{-x^2}{2}} dx$$

For our outlier detection algorithm, we adjusted the probability pi values according to the following:

$p_i = 2 \times p_i$ if $0.05 \leq p_i \leq 0.5$, $p_i = 2 \times (p_i - 0.5)$ if $0.5 < 2 \times p_i < 0.95$, $p_i = 0$ if $0.95 > p_i$ or $p_i < 0.05$.

The feature importance, wi, can vary depending on the desired application 20,21 and can be adjusted to improve the accuracy of any model. In our case, the feature importance was determined by the relative utility of each of the eight wavelengths implemented in the MSI machine toward distinguishing different tissue classes from one another. In the area of machine learning, the wavelength with more discriminant information was given higher weight values.

After calculating the probabilities, pi, and feature importance, $w_i$, in the steps above, the sample weights ($W_i$) are calculated as follows:

$$W_i = p_1 \times w_1 + p_2 \times w_2 + \ldots + p_{n-1} \times w_{n-1} + p_n \times w_n$$

$$= \sum_{i=1}^{n} p_i \times w_i.$$

Finally, a threshold weight ($W_{threshold}$) is assigned to generate a "second window" of data. If $W_i$ is greater than $W_{threshold}$ for a given sample, this sample is assigned to the training set (the second window). Otherwise, this sample point is considered an outlier and is removed from the training set.

Empiric testing was repeated to find effective values for the algorithm coefficients ($\alpha_1$, $\alpha_2$, $w_i$, and $W_{threshold}$).

3. RESULTS 3.1 Outlier Detection

Prior to implementing the data classification and outlier removal algorithm, unfiltered spectral imaging data was analyzed by SVM and k-nearest neighbors (KNN) classification algorithms to train multiple burn classification models. When these models were given test data to classify after training, the average accuracy of classification was 63% overall as compared to the ground truth. After establishing this baseline accuracy for the burn model, the data classification and outlier removal algorithm was applied to the spectral imaging datasets before they were used to train these same classification algorithms.

Figure 48A:
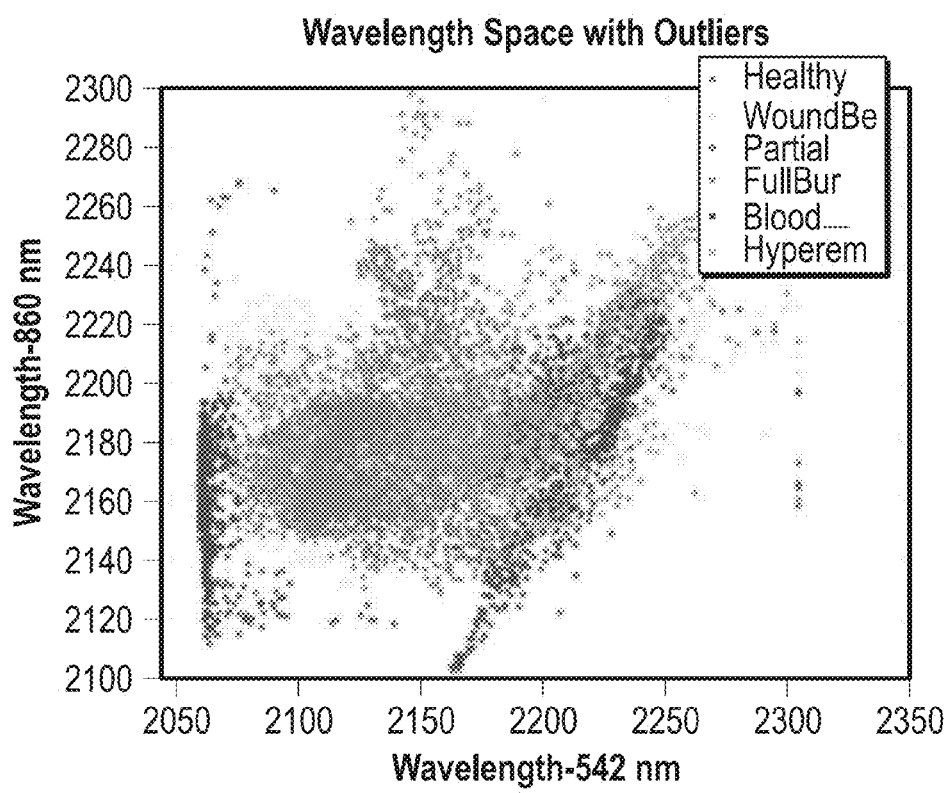
FIGS. 48A-48B illustrates example Six Classes in 2-D feature spaces with outliers (FIG. 48A) and without outliers (FIG. 48B).
Figure 48B:
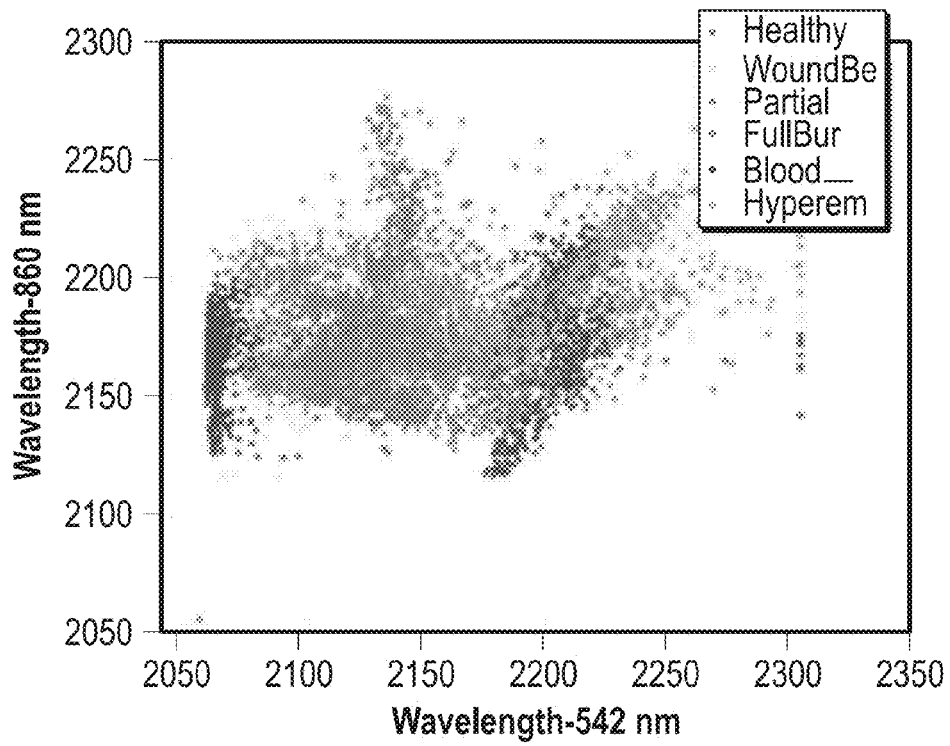

Through empiric testing, effective values of the algorithm coefficients were found to be: $\alpha 1 = \alpha 2 = 0.2$, $w1 = w2 = \ldots = w8 = 1$, and Wthreshold=7. With these parameters assigned, the mean and the standard deviation parameters of the "first window" were calculated for each of the eight wavelengths implemented by MSI The results of the data classification algorithm after outlier detection and removal are presented in FIGS. 48A-48B. FIGS. 48A-48B illustrates example Six Classes in 2-D feature spaces with outliers (FIG. 48A) and without outliers (FIG. 48B). For purposes of presentation, the sample space (red) is shown in two-dimensions with only two of the eight implemented wavelengths represented. After outlier detection and removal, the second window subspace (blue) used to train the burn classification model became more homogenous and tightly clustered, theoretically allowing for greater accuracy in the resulting model.

To visualize the results of the data classification and outlier detection algorithm across all eight MSI wavelengths, boxplots representing the samples collected for all wavelengths in each tissue classification were plotted before and after outlier detection and removal. In the initial sample space [FIGS. 46A-46F and FIGS. 47A-47B], all tissue classifications, especially blood, included a significant number of outliers. After outlier and detection removal, the number of outliers remaining in the subspace was drastically reduced as illustrated by FIG. 47B.

Representative two-dimensional sample spaces with spectral data for all six tissue classifications plotted together are represented in FIGS. 48A-48B. Before outlier detection and removal, data from FIGS. 47A-47B boxplots depicting sample spaces (a) before and (b) after outlier detection and removal for all eight wavelengths with each tissue classification. Boxes represent the interquartile range. Red plus signs demarcate data outlier. The number of outlier remaining in the sample space after outlier detection was significantly reduced in all tissue classes, most notably in the blood class the various tissue classes were generally plotted in clusters, with the notable exception of blood, but a significant amount of overlap between the various clusters was appreciable. After applying the outlier detection and removal algorithm, a better separation between tissue classes was clear. After removal of outliers, new burn classification models were generated using the same classification algorithms (SVM, KNN, and so on). The overall average model accuracy improved from 63% to 76%.

After showing the process of outliers detection process and the effect in statistical side by boxplot in each band in FIGS. 46A-F and FIGS. 47A-47B. Furthermore, we used the two most importance wavelength to construct the 2-D feature space to show the effect of the algorithm we proposed. Because of the blood property in the visible and near-infrared band, color blue spreads in whole sample space. By using the algorithm, it is obvious to see the convergence of the blood class. The same explanation applies to color red—health class.

3.2 Animal Model Results

The improvement in model classification accuracy is demonstrated in FIG. 49 Prior to outlier removal, the classification models could not accurately detect healthy skin or the hyperemic zone that physiologically surrounds a burn. The model also predicted several different classes of tissue where, in reality, healthy skin was present. In place of the hyperemic zone around the burn, the models predicted the presence of blood. Furthermore, healthy skin beyond the hyperemic zone was incorrectly classified as full burn injury. However, after outlier removal, the models accurately classified both healthy skin in the control image and burn image, as well as a hyperemic zone around a burn.

4. CONCLUSIONS

Several points from this experiment are worth highlighting. First, the assigned values for the algorithm coefficients ($\alpha_1$, approach in a recursive process. The values were selected because they effectively increased the accuracy in the particular MSI application presented in this manuscript. However, with other applications, these values would likely need to be adjusted to achieve the desired result.

Interestingly, the optimal feature importance ($w_i$) for all wavelengths was set to a value of 1 after empiric testing to identify the best value for each wavelength. That all of the feature importances ($w_i$) were ultimately assigned a value of 1, reflects the fact that each of the eight wavelengths employed in our MSI device were selected to provide unique spectral information independently from one another. This result was not surprising given that the wavelengths were selected according to previously described optical characteristics of skin tissue and burn tissue.

The most challenging tissue to accurately classify was blood. This was evident given the heterogeneous sample space collected for blood as represented in both FIGS. 47A-47B and FIGS. 48A-48B. The bimodal distribution of spectral data characterizing blood is a result of blood's unique absorbance spectrum in the visible and near-infrared light bands, which is also bimodal. Each of the other tissue classes has a single absorbance peak, resulting in somewhat more homogenous distributions of spectral data in these other cases.

Ultimately, the outlier detection and removal algorithm significantly improved the accuracy of the MSI application for skin tissue classification. The algorithm successfully reduced the variance in the sample space for each of the tissue classes. By restricting the variance in this fashion, the overlap in spectral characteristics was reduced in a corresponding manner. With reduced overlap, the training of classification models was improved with a discernable increase in classification accuracy. By achieving a final accuracy of 76%, we improved our model to, at a minimum, meet the current clinical standard in burn tissue classification, clinical judgment by burn experts. This model has the potential to aid decision-making for physicians treating burn victims in settings where burn experts may not be readily available.

Overview of Example Embodiments Relating to Amputation

The above-described lack of a sufficiently accurate metric/test to determine healing potential and the multiple factors that are known to affect the body's wound healing capacity means that a multivariate approach to diagnosis is required for improved assessment. Spectral MD is uniquely positioned to address this problem, because our device is designed to handle information in the form of multiple independent variables to classify tissue pathological processes. The Spectral MD imaging device uses a Machine Learning Algorithm to combine two optical imaging techniques, photoplethysmography imaging (PPG Imaging) and multispectral imaging (MSI), with patient health metrics, such as diabetic control or smoking, to generate prognostic information (FIG. 50).

Figure 50:
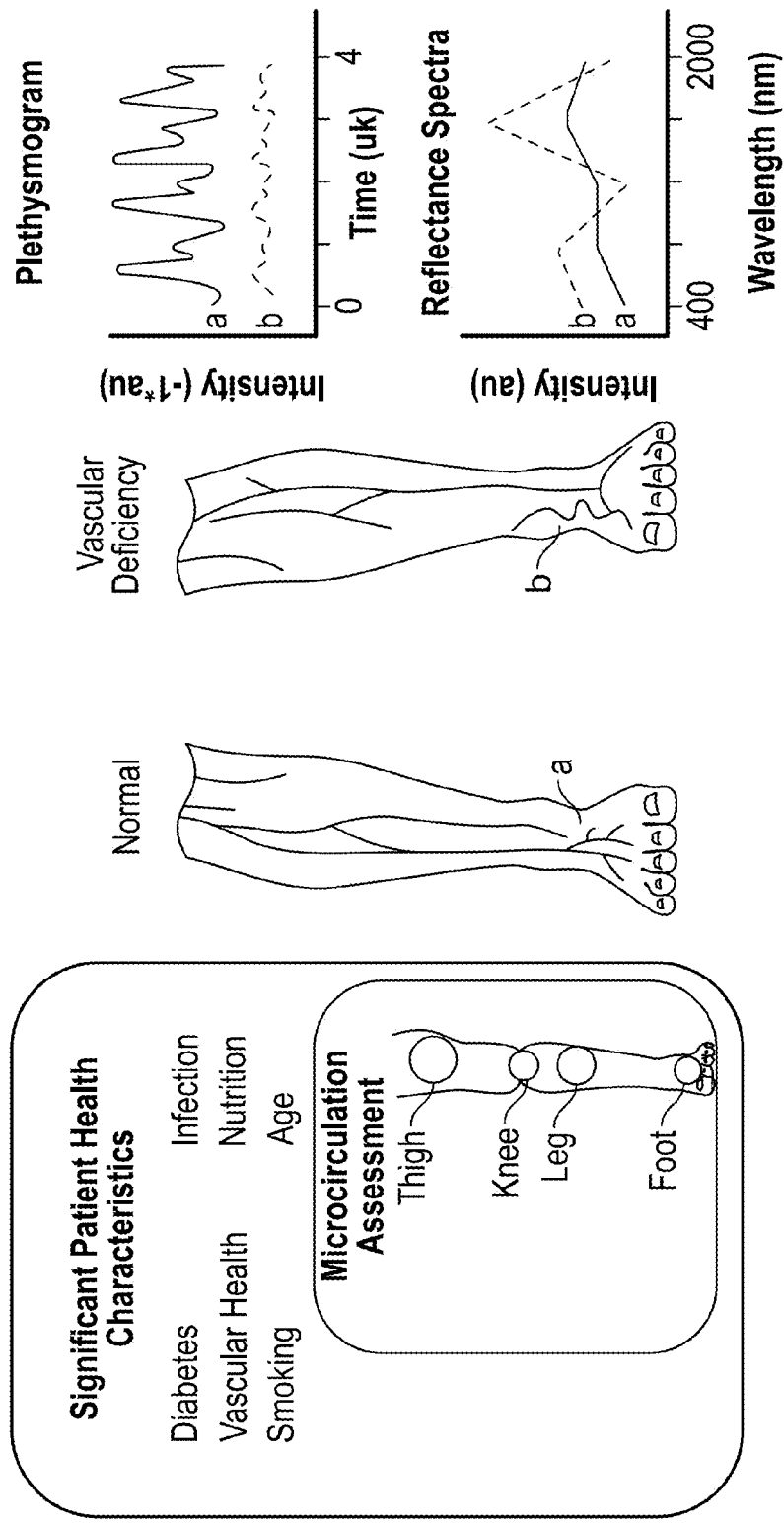
FIG. 50 illustrates a high-level graphical overview of two optical imaging techniques, photoplethysmography imaging (PPG Imaging) and multispectral imaging (MSI) that can be combined with patient health metrics to generate prognostic information according to the present disclosure.

FIG. 50 illustrates a high-level graphical overview of two optical imaging techniques, photoplethysmography imaging (PPG Imaging) and multispectral imaging (MSI) that can be combined with patient health metrics to generate prognostic information according to the present disclosure. We call this device DeepView (Gen 2). DeepView (Gen 2) is expected to maintain the high sensitivity and specificity necessary to select appropriate LOA in patients with dysvascular disease. The two optical imaging methods are designed to infer important tissue characteristics, including arterial perfusion and tissue oxygenation. These two measures are one key to selecting LOA because wound healing in patients with dysvascular disease is hampered by a critical lack of arterial perfusion, resulting in low tissue oxygenation (Norgren, Hiatt, Dormandy, Nehler, Harris, & Fowkes, TASC II Working Group. Inter-Society Consensus for the Management of Peripheral Arterial Disease (TASC II), 2007) (Mohler III, Screening for Peripheral Artery Disease, 2012). Using our method, we can assess perfusion at the tissue level over large areas of the leg simultaneously to identify under-perfused regions of the limb. This is in contrast to the guess work that is involved when using clinical judgment alone, during which the observer must assess for the proper LOA based on patient history and physical exam combined with vascular studies that rarely include a thorough evaluation of the patient's microcirculation. Meanwhile, DeepView (Gen 2) also assesses patient health metrics that have systemic effects on wound healing potential. By combining a local assessment of tissue microcirculation with a global assessment of systemic factors affecting wound healing, DeepView (Gen 2) accounts for the plurality of factors affecting wound healing rather than a single variable.

Our DeepView (Gen 2) system utilizes a statistical discipline called Machine Learning to study multi-variate systems for predictive analysis in an applicable manner. We believe this approach will provide key information to the patient's overall likelihood of primary wound healing by incorporating data from local microcirculatory assessment with systemic factors affecting wound healing (such as diabetes mellitus, smoking status, age, and nutritional status) that cannot be readily observed in the microcirculation with current technology. Because both local and systemic factors affect the ultimate likelihood of healing, the DeepView (Gen 2) system accuracy will be improved by considering all of these factors together.

Our device will have at least 95% sensitivity and 95% specificity for predicting likelihood of primary wound healing after amputation at the investigated level (see Test of Feasibility for Phase I and Success Criteria for Phase II). If used for routine assessment of patients prior to amputation at this sensitivity and specificity, we expect DeepView (Gen 2) to reduce the rate of re-amputation by 67%, which would result in 10,000 fewer re-amputations per year while improving quality of life for amputees and reducing health costs associated with their care. Currently, an ABI exam prior to amputation costs Medicare approximately $150 per patient, and most of the cost incurred is from the technician's time in performing the exam and the practitioner's time in interpreting the results (Criqui, et al., 2008). The proposed device will have no impact on the current cost of LOA assessment, because it is expected to cost the same as current vascular assessments. Unlike some current LOA tests, our imaging system does not require disposables. Its routine cleaning and servicing costs are similar to those of systems currently on the market. Costs are further detailed in the Commercialization Plan.

Figure 51:
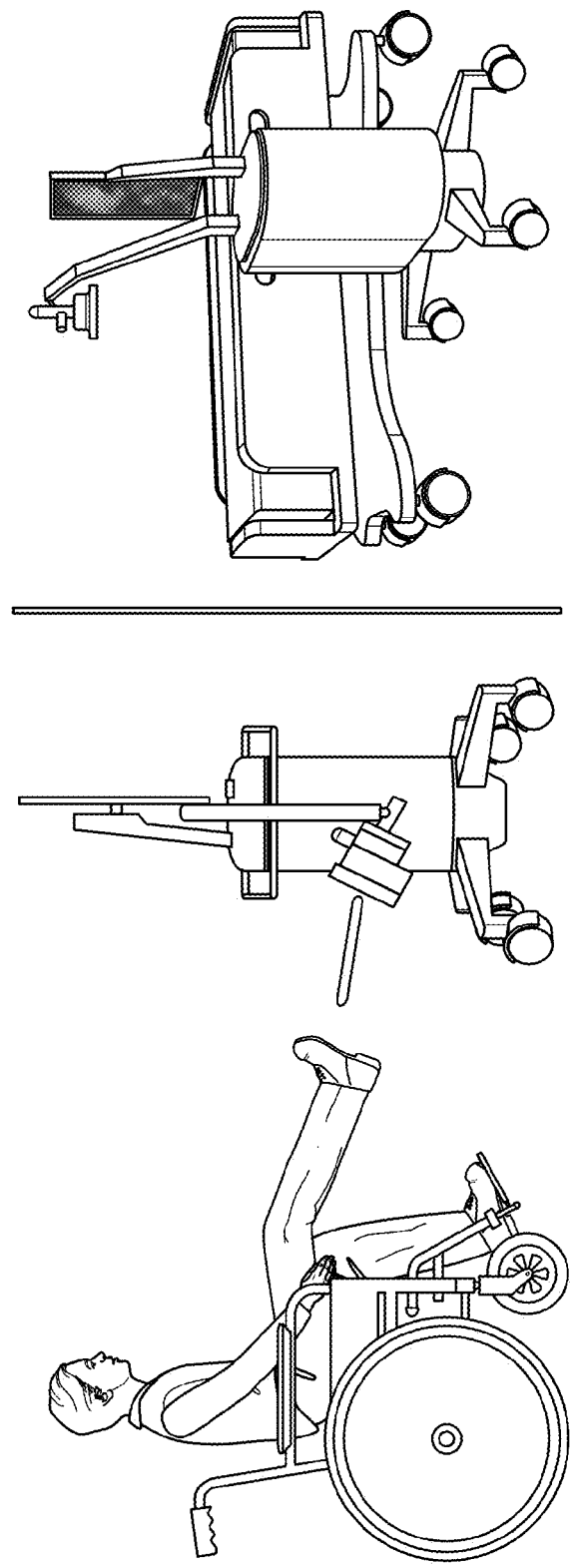
FIG. 51 illustrates example views of an apparatus designed to fuse the optical imaging techniques of photoplethysmography imaging (PPG imaging) and multispectral imaging (MSI).

Spectral MD's DeepView (Gen 2) imaging technology is, to our knowledge, the first system designed to fuse the optical imaging techniques of photoplethysmography imaging (PPG imaging) and multispectral imaging (MSI). FIG. 51 illustrates example views of an apparatus (DeepView) designed to fuse the optical imaging techniques of photoplethysmography imaging (PPG imaging) and multispectral imaging (MSI). Moreover, it is the first imaging technology, to our knowledge, capable of incorporating key patient health metrics into its assessment algorithm. Prior to the development of this system, Spectral MD was the first company to provide a 2D image of the plethysmography waveform cleared by the FDA for sale in the US (Gen 1 technology). Our Gen 2 technology is now capable of combining blood flow assessment (i.e. arterial pulse amplitude) with tissue characterization (i.e., spectral analysis). When these measurements are taken from the tissue together, they provide a more accurate assessment of the tissue than does either measurement alone (see Preliminary Studies below).

Studies to determine likelihood of healing at a certain LOA have demonstrated marked differences in tissue oxygen levels between sites resulting in successful vs. unsuccessful amputations. These studies investigated tissue oxygenation using transcutaneous oxygenation measurement (TCOM). However, the use of TCOM have not surpassed clinical assessment despite the availability of this technology for decades, and no clear cutoff for tissue oxygenation at a given LOA that is prognostic for successful amputation has been determined in a large clinical trial. According to the assessment of experts, TCOM has not been adopted into clinical practice for several reasons. First of all, TCOM collects data from a very small area of interest. The TCOM procedure also requires heating of the patient's skin, which can occasionally lead to skin burns, particularly in patients with dysvascular disease. Finally, results of TCOM are subject to variations in ambient temperature and localized tissue edema, limiting the intra-temporal consistency of the device.

DeepView (Gen 2) has been designed to overcome the various limitations of TCOM and other available devices to prognosticate likelihood of healing at a selected LOA. The device captures data across a large tissue surface area, allowing the characterization and mapping of tissue oxygenation and perfusion variability across the entire surface rather than in an isolated area. DeepView (Gen 2) is non-invasive and non-contact and does not emit harmful radiation, so no major risk of patient harm is inherent to the device. The device is also not affected by minor variations in ambient temperature. Most importantly, however, DeepView (Gen 2) analyzes clinically significant patient health metrics such as diabetes mellitus history, presence of infection, smoking status, and nutritional status to provide the end-user with a comprehensive assessment of wound healing potential, whereas previous technologies have only been able to assess local tissue oxygenation.

Approach

Aspects of the proposed imaging device encompass non-invasive optical imaging for a variety of tissue classification applications, including optimal selection of LOA. Spectral MD's DeepView (Gen 2) imaging system is a point of care perfusion imaging system that provides diagnostic images derived from measurements of tissue perfusion and patient health metrics. Nursing staff can be easily trained to perform the imaging test. The imaging of a limb takes approximately 10 minutes, with results stored electronically for physician review. From the patient's perspective, the test is highly acceptable because it has no harmful side effects, does not contact their skin, and causes no discomfort.

A major innovation to be studied in this proposal is the addition of patient health metrics to microcirculation assessment in order to improve the accuracy of diagnosing wound healing potential during amputation planning. We will present the individual value of each of the DeepView components in the following section, then conclude with a brief discussion about how these multiple variables can be combined into a single prognostication of wound healing potential.

As stated previously, the DeepView (Gen 2) device simultaneously performs two optical imaging methods of blood-flow assessment. The first of these, PPG imaging, is the same technology used in pulse oximetry to capture vital signs including heart rate, respiratory rate, and SpO2, though DeepView (Gen 2) is more advanced because it captures over 1 million unique PPG signals across a large area of tissue (Severinghaus & Honda, 1987). The PPG signal is generated by measuring light's interaction with dynamic changes in the vascularized tissues. Vascularized tissue expands and contracts in volume by approximately 1-2% with each incoming systolic blood pressure wave at the frequency of the cardiac cycle (Webster, 1997). This influx of blood increases the volume of the tissue and brings additional hemoglobin proteins that strongly absorb light. Therefore, the total absorbance of light within the tissue oscillates with each heartbeat. This information can be translated into the vital signs reported by pulse oximeters.

In order to generate images from the plethysmogram, we take advantage of light's pathway through the tissues (Thatcher, Plant, King, Block, Fan, & DiMaio, 2014). A small portion of light incident on the tissue surface scatters into the tissue. A fraction of this scattered light exits the tissue from the same surface it initially entered (Hu, Peris, Echiadis, Zheng, & Shi, 2009). Using a sensitive digital camera, this back-scattered light is collected across an area of tissue so that each pixel in the imager contains a unique PPG waveform determined by changes in intensity of the scattered light. To generate a 2-D visual map of relative tissue blood flow, the amplitude of each unique waveform is measured. To improve accuracy, we measure the average amplitude over many heart beat samples.

The second optical measurement captured by DeepView (Gen 2) is MSI. This technique measures the reflectance of select wavelengths of visible and near-infrared (NIR) light (400-1,100 nm) from a tissue's surface. Spectral characterization of substances is primarily used in remote sensing (e.g., satellite or in-flight imaging) for geological exploration or the detection of military targets, but this technology is gaining ground in medical applications (Li, He, Wang, Liu, Xu, & Guo, 2013). This method is effective for quantifying key skin properties relevant to a number of pathologies, including PAD. Relevant to selecting LOA, MSI can quantify the volume fraction of hemoglobin and the presence of oxygenated hemoglobin (Jolivot, Benezeth, & Marzani, 2013) (Zonios, Bykowski, & Kollias, 2001). Other uses of this technology are described below in our Preliminary Study work.

The wavelengths of light employed by MSI in DeepView (Gen 2) are selected based on well-established characterizations of light-tissue interaction. Melanin within the stratum corneum and the epidermis mainly absorbs UV and visible wavelengths. Near infrared wavelengths (700-5000 nm) are the least absorbed by melanin and have been found to be the best at penetrating through the dermis to determine its depth. Hemoglobin is largely contained by vessels coursing through the dermis, and its concentration determines the degree of dermal absorption of wavelengths greater than 320 nm. Hemoglobin absorption of light also changes depending on whether the molecule is oxygenated for deoxygenated. As tissue melanin and hemoglobin concentration, as well as the oxygenated hemoglobin fraction, are altered during disease states, MSI is able to detect changes in the resulting reflectance spectrum. Therefore, abnormal skin tissue can be identified by changes in its reflectance spectrum as compared to healthy tissue. Although MSI uses a lower number of unique wavelengths to describe the tissue as compared to newer hyperspectral imagers, MSI remains superior when the combination of spatial resolution, spectral range, image acquisition speed, and cost are considered together (Lu & Fei, 2014).

The third component of data utilized by DeepView (Gen2) is the relevant patient health metrics collected during routine patient assessment. A variety of factors that affect wound healing have been identified and described in great detail. Many or all of these factors (including patient age, diagnosis of diabetes mellitus, history of smoking, infections, obesity, medications, nutritional status) commonly affect patients with dysvascular disease subjected to lower limb amputations. Although clinicians currently consider a gestalt of these variables when assessing potential LOA, DeepView (Gen 2) is capable of assessing these metrics quantitatively to predict likelihood of primary wound healing at a given LOA. The integration of patient health metrics with optical imaging data is performed by the DeepView device with its Machine Learning Algorithm. A practitioner simply inputs relevant patient health metrics into the device at the time of imaging. This data is treated as additional variable(s) by our Machine Learning Algorithm, no different than the optical data collected by PPG imaging and MSI. The Machine Learning Algorithm is trained to generate a quantitative output after assessing all data collected by DeepView (Gen 2). The quantitative output is translated into an image identifying areas of the scanned tissue surface that are likely or unlikely to heal following amputation.

Figure 52:
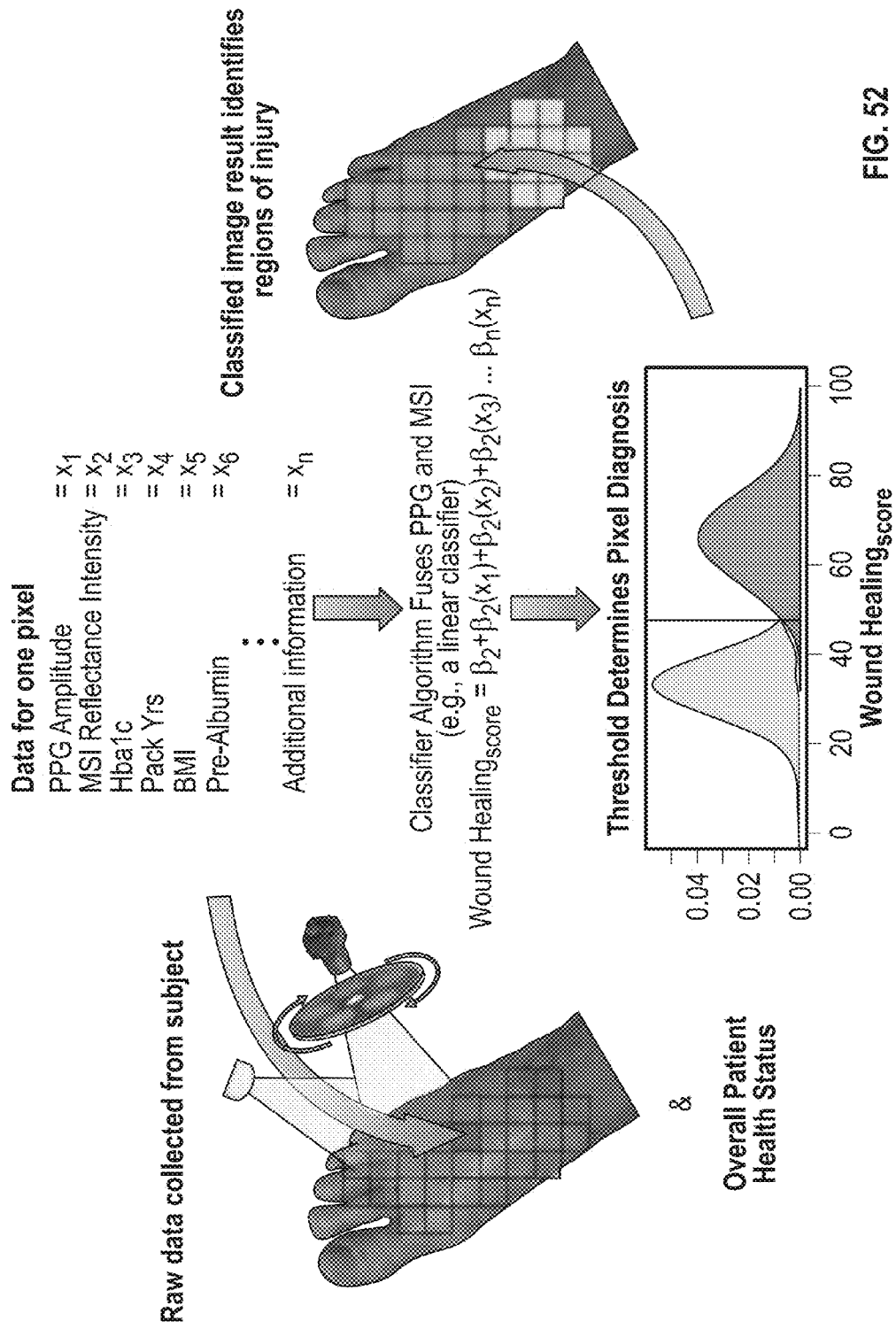
FIG. 52 illustrates an example of a combination of the DeepView Gen 1 PPG imager, the MSI camera, and objective patient health metric inputs

The DeepView (Gen 2) device is a combination of the DeepView Gen 1 PPG imager, the MSI camera, and objective patient health metric inputs (FIG. 52). FIG. 52 illustrates an example of a combination of the DeepView Gen 1 PPG imager, the MSI camera, and objective patient health metric inputs.

Preliminary Studies

By adjusting system settings and algorithms, DeepView (Gen 2) can be tuned to assess tissue characteristics under different pathological conditions. For our LOA studies in Phase I of this proposal, we will develop specific algorithms and use specific optics and filters that are tailored to measures of pulse amplitude and tissue oxygenation for prediction of wound healing following primary amputation (see Experimental Design and Methods section). The proposed technology has successfully undergone a series of benchtop, pre-clinical, and pilot clinical testing for other potential applications. We present the results of those tests to support the use of our instrument during selection of LOA Pre-Clinical Burn Model For use in guiding surgeons during burn debridement surgery, we used optics, filters, and algorithms specific to the detection of a combination of blood flow (i.e. arterial pulse amplitude) and tissue structural integrity, including blood volume, inflammation, and necrosis (e.g., spectral analysis). Our PPG and MSI algorithms to assess the status of epidermal microvasculature were subsequently proven to accurately identify necrotic tissue following burn, both individually and together. Using the DeepView Gen 1 PPG imaging system, we identified a significant difference between blood flow in the necrotic burn tissue compared to surrounding healthy tissue. With a MSI camera, we demonstrated that the presence of the burn tissue that needed to be surgically removed could be accurately identified according to a histopathological gold-standard, in an IACUC-approved porcine burn model experiment (96% sensitivity and 82% specificity).

Briefly, twenty-four (24) deep partial-thickness burns were applied on four minipigs using a pressure controlled burn rod. Beginning ten minutes after injury, we obtained PPG signal and MSI signals immediately following serial 1.0 mm debridements until healthy tissue was reached. Following each debridement, the excised tissue specimens were processed and given to a histopathologist for evaluation in a blinded manner. During gold-standard histopathology assessment, a board certified histopathologist identified healthy wound-bed tissue and non-viable burn tissue in each excision. In addition, a board certified surgeon reviewed color photographs of the burn injuries in a blinded manner to delineate healthy wound-bed tissue and non-viable burn tissue. We worked independently and blind to the results of the histopathologist and surgeon's analyses to determine the results of our PPG and MSI assessments.

By identifying differences in PPG signal strength between different tissue classes, our PPG imager was able to identify the proper point of debridement as judged by histological assessment. The progression of data collection began with a measurement of PPG signals in the region of interest before a burn wound was introduced, and, as expected, the PPG signal across the uninjured skin uniformly indicated healthy tissue. However, the PPG signal dramatically decreased in the center of the image, where the burn was generated, while the surrounding tissue still exhibited a signal consistent with healthy, uninjured tissue.

Figure 53:
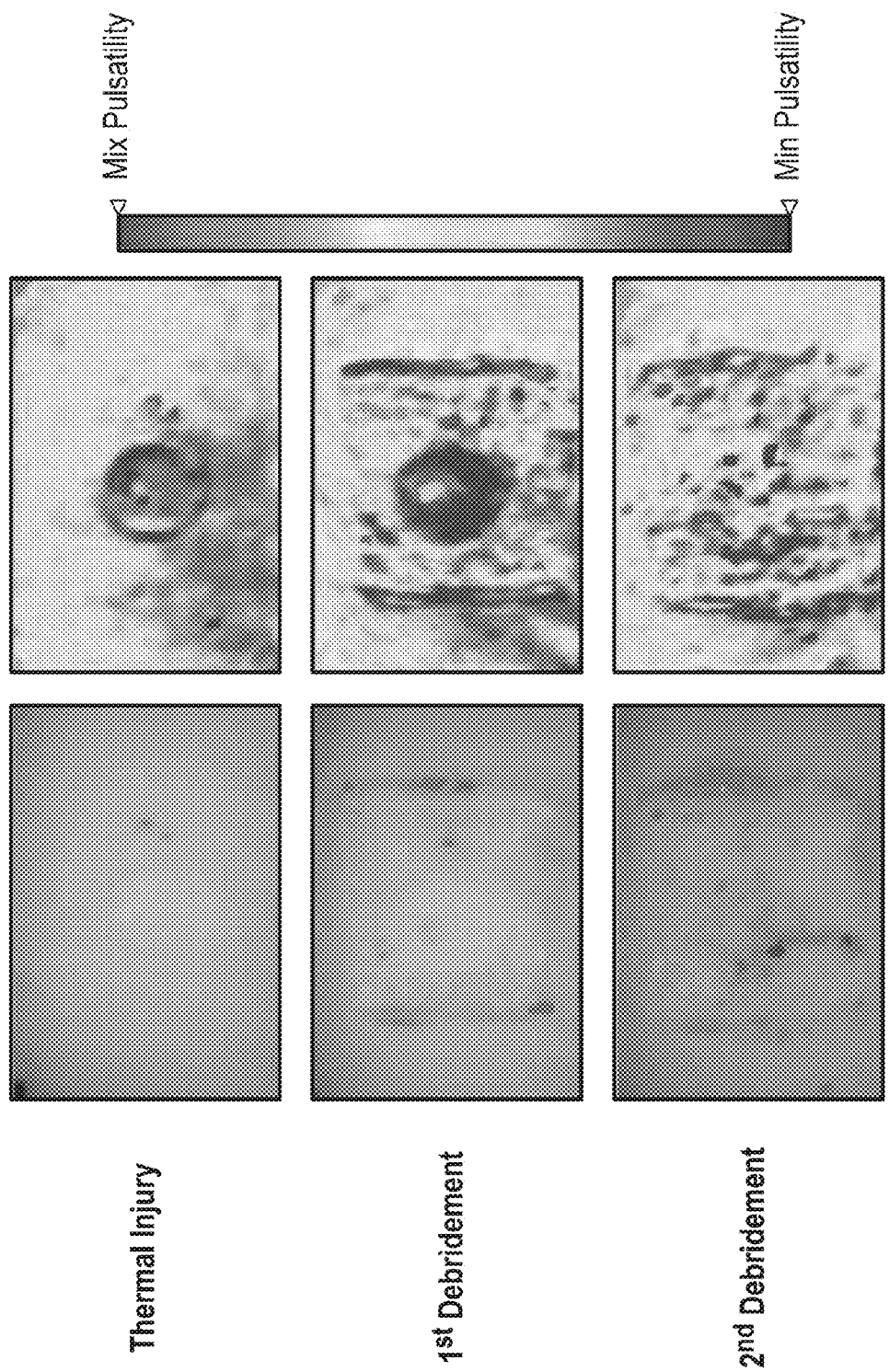
FIG. 53 illustrates differences between the signals of burned tissue and a healthy wound bed uncovered by debridement.

FIG. 53 illustrates differences between the signals of burned tissue and a healthy wound bed uncovered by debridement. Following serial debridements, subsequently processed images revealed significant differences between the signals of burned tissue that would require further excision and the healthy wound bed that was eventually uncovered by debridement. The average signal strength for burn tissue was 2.8±1.8 dB while both healthy skin and healthy wound bed tissue had significantly greater signal strengths, 4.4±2.2 dB and 4.2±2.6 dB, respectively ($p<0.05$). Not surprisingly, there was complete agreement between the PPG findings and those of the histopathologist and surgeon.

Throughout the same experiment, MSI assessment was able to accurately classify key physiological tissue classes present during a burn debridement procedure with 82% accuracy; specifically, for necrotic burn tissue, we achieved 96% sensitivity and 82% specificity as determined by histopathology. Six possible physiological classes were implemented in the MSI assessment: healthy skin, hyperemia, wound bed, blood, minor burn, and severe necrotic burn. FIG. 54 illustrates these six example physiological classes. Similarly to the PPG signal progression through the burn site phases, the MSI results initially detected uniformity of the healthy skin before burn generation, followed by accurate discernment of the various viable and non-viable tissue types during serial debridement until a healthy wound bed had been reached.

Figure 55:
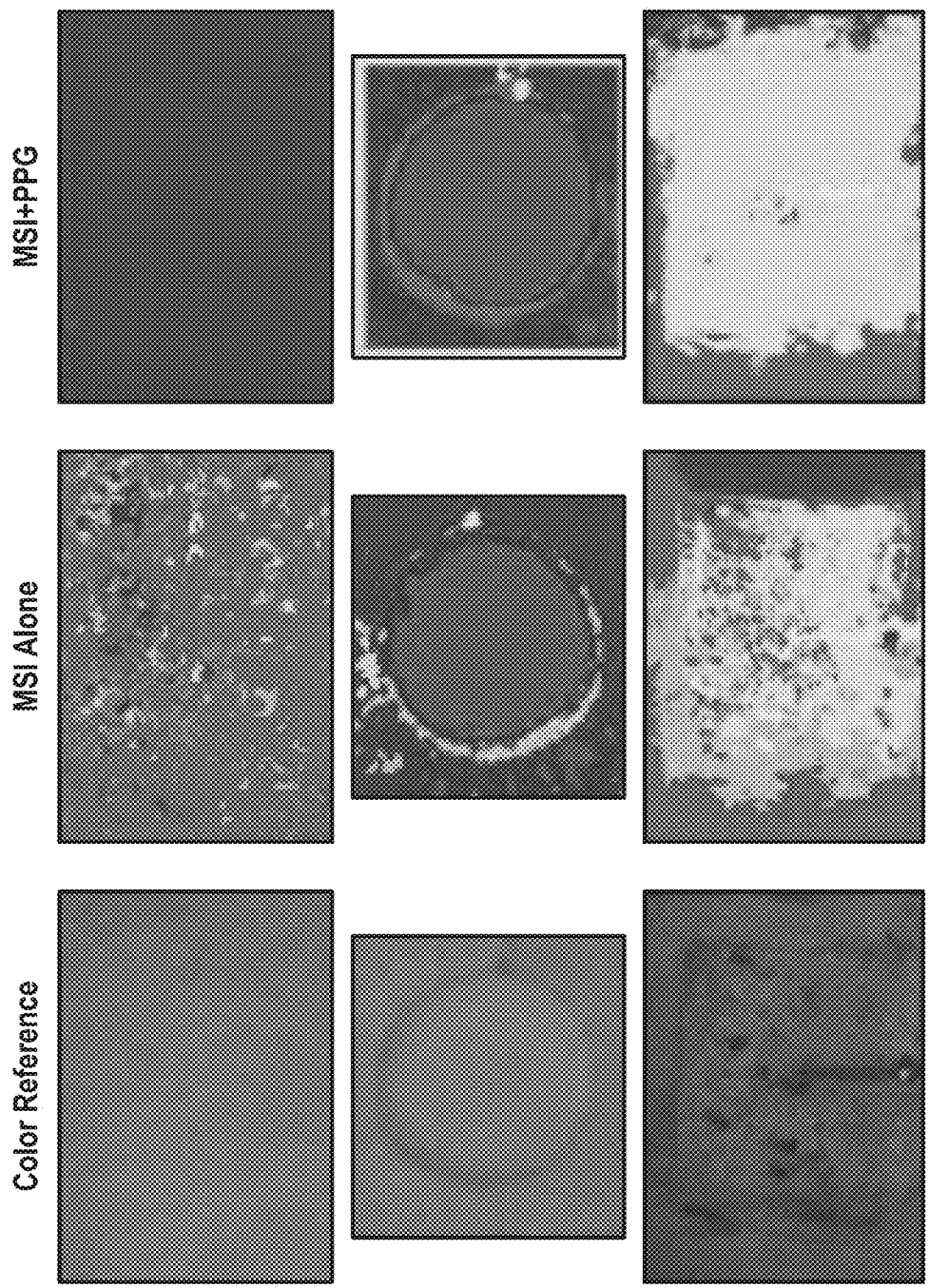
FIG. 55 graphically illustrates example results of PPG data, MSI data, and a combination of PPG and MSI data.

The final step assessed the efficacy of combined PPG and MSI data. We collected the PPG signal and the MSI signal simultaneously with one imaging system on the same burn injuries as previously described. Using combined data, we tested the efficacy of fusing both measurements using a Machine Learning Algorithm. From this dataset, we found the accuracy of MSI alone was 82%. Including the PPG data in the classifier with the MSI data increased the overall accuracy to 88%. FIG. 55 graphically illustrates these results of PPG data, MSI data, and a combination of PPG and MSI data.

Pilot Clinical Feasibility Testing

Figure 56:
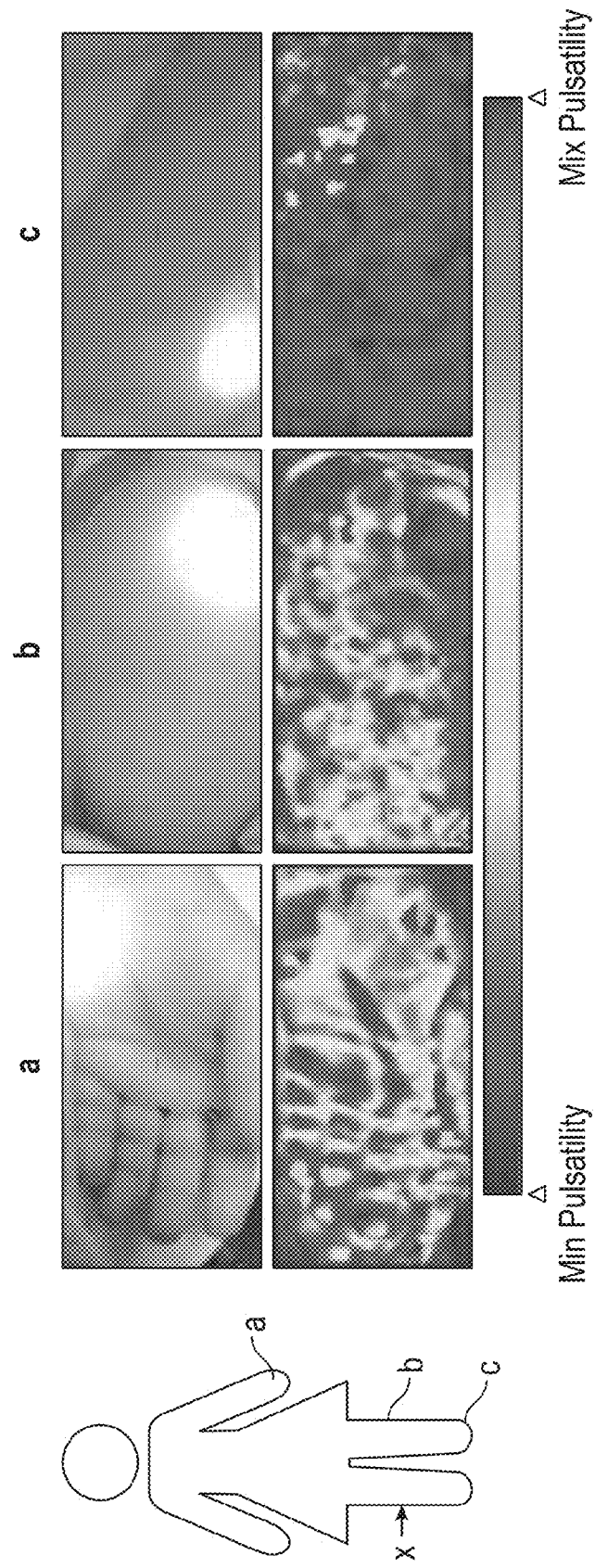
FIG. 56 illustrates example PPG signals present in hand, thigh, and foot regions.

FIG. 56 illustrates example PPG signals present in hand, thigh, and foot regions. The DeepView (Gen 1) PPG imaging device also underwent a pilot clinical study to ascertain the ability of PPG imaging to provide useful blood flow data in a variety of clinical applications. Data included PPG images of cutaneous blood flow collected from patients in a cardiovascular ICU to determine tissue viability in decubitus ulcers, skin grafts, and lower extremity ischemia. As an example of our pilot clinical assessments, we present a case study of a woman with an aortic dissection that resulted in bilateral clotting of her popliteal arteries and differential blood flow to her extremities. Based on clinical assessment of vascular surgeons, we knew to expect diminished blood flow in her legs distal to the knee. We measured the presence of pulsatile blood flow in the hand, thigh (proximal to the knee), and foot. The resulting images demonstrated PPG signals (regions of pulsatility) present in the hands and thigh, but the foot showed no pulsatile flow, results that correlated with the patient's known clinical status. The proven ability of DeepView technology to detect blood flow as demonstrated in these preliminary studies is an essential feature of the device's ability to guide selection of LOA.

Summary and Discussion

We have demonstrated the feasibility of identifying tissue lacking in blood flow and oxygen content in a burn model and patient case study using our instrument with PPG and MSI capabilities. While the direct implementation of our technology differs between classifying burn wounds and identifying the LOA in PAD, the fundamental principles of the process remain the same. Whether the clinical user is investigating a burn wound or assessing potential primary wound sites at various LOAs, the same physical tissue components are measured in both situations. Only a different algorithm and filter set would be used for burn assessment vs. LOA assessment (or other potential assessments). As shown above, using both PPG and MSI in our technology allows for a more accurate investigation of the epidermal microvasculature and pathologies caused by reduced blood perfusion. Our technology should be able to predict healing potential at a given LOA based on the same principles that informed the burn study; the addition of important patient health metrics that affect wound healing outcomes should further increase the accuracy of DeepView (Gen 2). Our Phase I study will test this hypothesis.

Experimental Design and Methods—Phase I, Pilot Clinical Study

In Phase I, our Specific Aim is to test the feasibility of using our device to diagnose amputation site healing capacity in a pilot clinical study. As part of this assessment, we gather data from numerous amputation patients with the purpose of training a diagnostic machine learning algorithm for diagnosing the healing potential in various amputation scenarios. Humans are an appropriate model for this stage of testing because the device is rapid, non-invasive and imaging studies can be performed in routine care settings such as the bedside or pre-operatively.

Figure 57:
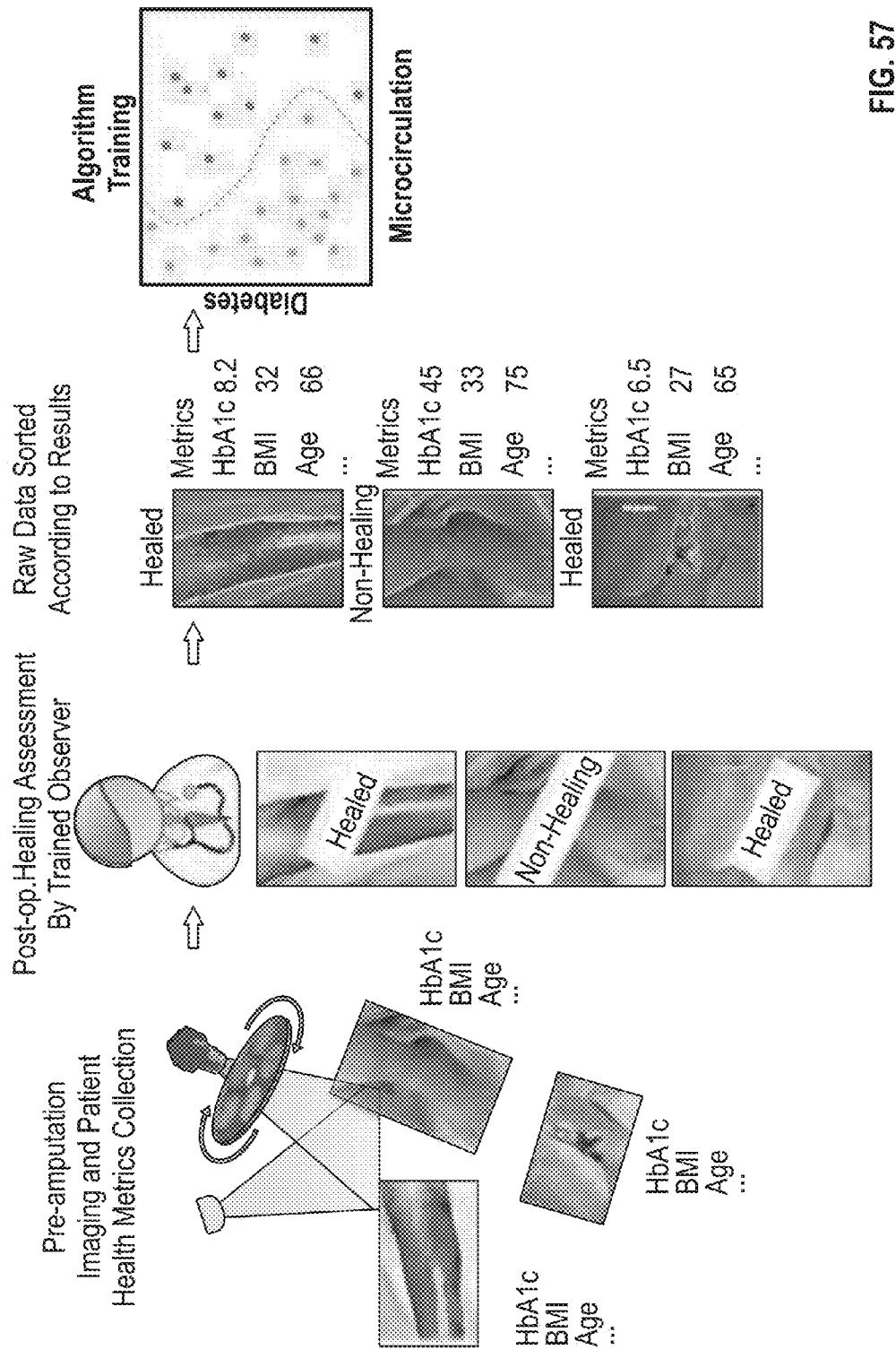
FIG. 57 illustrates an example process for training a machine learning diagnostic algorithm.

FIG. 57 illustrates an example process for training a machine learning diagnostic algorithm. Training a diagnostic machine learning algorithm requires data from the population on which it will eventually be used (FIG. 57). Importantly, the accuracy of the algorithm can only be as accurate as the methods used to identify the true status of the training data, in this case the non-healing vs. healing amputation groups. To address this, we have generated a standardized amputation healing assessment system to track and classify outcomes. As outcomes are being established for study subjects, we can start to develop the algorithm and work on analysis. The machine learning algorithm development will iterate from an initial determination of accuracy, conducting research to improve accuracy, and then assessing the new accuracy. This feasibility pilot study will provide the evidence to show that combining the microcirculation imaging with patient health metrics will have a high chance of success in a larger pivotal study.

This is a pilot clinical study design consisting of a 60-patient study investigating the DeepView Gen2 system's accuracy of predicting primary healing in amputations on patients with PAD compared to the current standard of care.

The DeepView Gen2 imager collects spectral and PPG signals from a large area (up to 15×20 cm of tissue) of the cutaneous blood supply using optical methods. This instrument is well suited to study large regions of the lower extremity skin microcirculation. A unique aspect of the device is that it is capable of integrating important patient health characteristic into its diagnostic algorithm to increase accuracy. The pilot study will identify the promising patient health metrics to be confirmed in the pivotal study. As a major task in this study we will confirm patient health metrics included in the device's machine learning diagnostic algorithm improve accuracy over the microcirculation measurements alone. In this study we will determine the microcirculation at each traditional LOA combined with patient health characteristics affecting wound healing and determine how this correlates to the patient's primary wound healing potential after amputation.

The lower limb to be amputated of every patient will be examined and included in the study. Clinically relevant patient health information will be gathered by the facility's care providers. Measurements taken with our experimental imaging device will be carried out by hospital staff previously trained by Spectral MD to perform the imaging tests.

The region of skin used for covering the stump of an amputation will be graded for positive or negative healing capability with the DeepView Gen2 LOA algorithm. The technician performing the DeepView Gen2 analysis will be blinded to the results of the clinical decision as to where the amputation will be performed.

To obtain our true positive (+) and true negative (−) events, or non-healing and healing subjects, we will use a standardized primary wound healing after amputation assessment (table 2). This assessment consists of three categories including: successful amputation; successful amputation with prolonged healing; and failure to heal. Successful amputation is considered healing within 30 days with completed granulation and no need for additional amputation. Successful amputation with prolonged healing is considered delayed healing with granulation incomplete at 30 days, but with eventual healing within six months and no need for re-amputation to a more proximal level. Lastly, failure to heal will be characterized by development of necrosis and/or gangrene, and/or the need for re-amputation to a more proximal level. Additionally, we will consider a wound requiring revascularization to heal as a failed amputation.

TABLE 5

Standardized Wound Healing Assessment

| Event | Category | Characteristics |
|---|---|---|
| Negative (−) | Healing | Healing within 30 days with completed granulation and no need for additional amputation |
| | Delayed Healing | Incomplete healing with granulation at 30 days, but with eventual healing within six months and no need for re-amputation to a more proximal level |
| Positive (+) | Non-healing | Development of necrosis and/or gangrene, and/or the need for re-amputation to a more proximal level |

These healing assessments will take place 30 days post operatively. For the subjects with delayed healing, we will make a second healing assessment at six months following surgery. Subjects that are not healed at six months and have not had a more proximal re-amputation will be categorized to the non-healing group.

Figure 58:
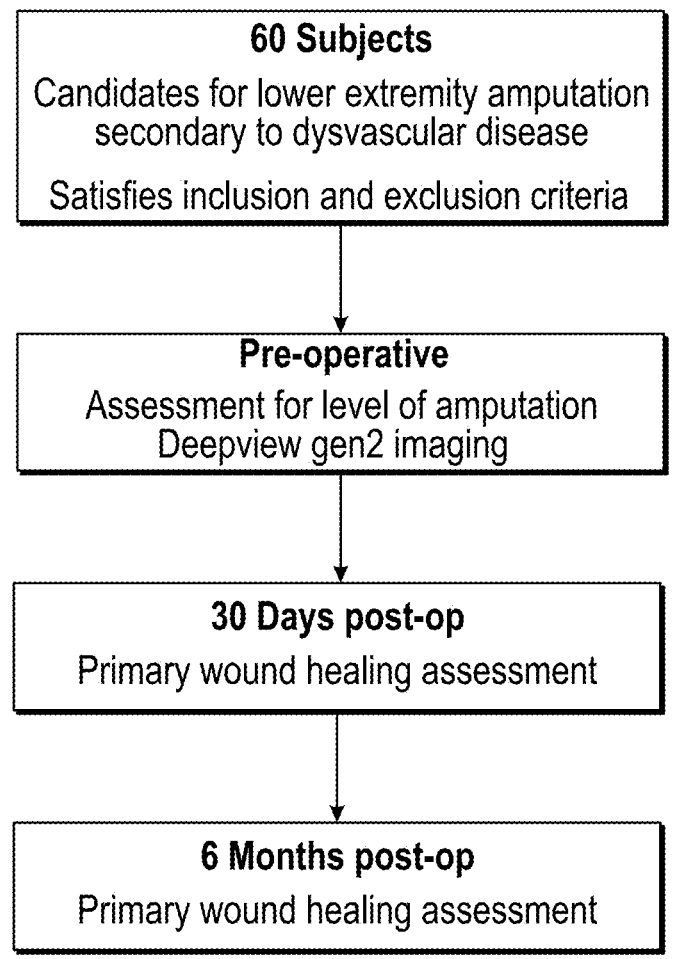
FIG. 58 illustrates an example clinical study flow diagram.

FIG. 58 illustrates an example clinical study flow diagram. DeepView Imaging Evaluation (FIG. 58): Microcirculation data for each subject will be collected by imaging the skin using the Spectral MD Gen2 device. Scans of approximately 30 sec each will be obtained from each leg awaiting amputation. We will image regions of the ankle and foot according to the traditional surgical methods of amputation in PAD patients including: above the knee (AKA), below the knee (BKA), above the ankle (i.e., foot), trans-metatarsal, or toe. The regions of skin that are used as a flap to cover the stump will be selected for analysis (FIG. 59).

Figure 59:
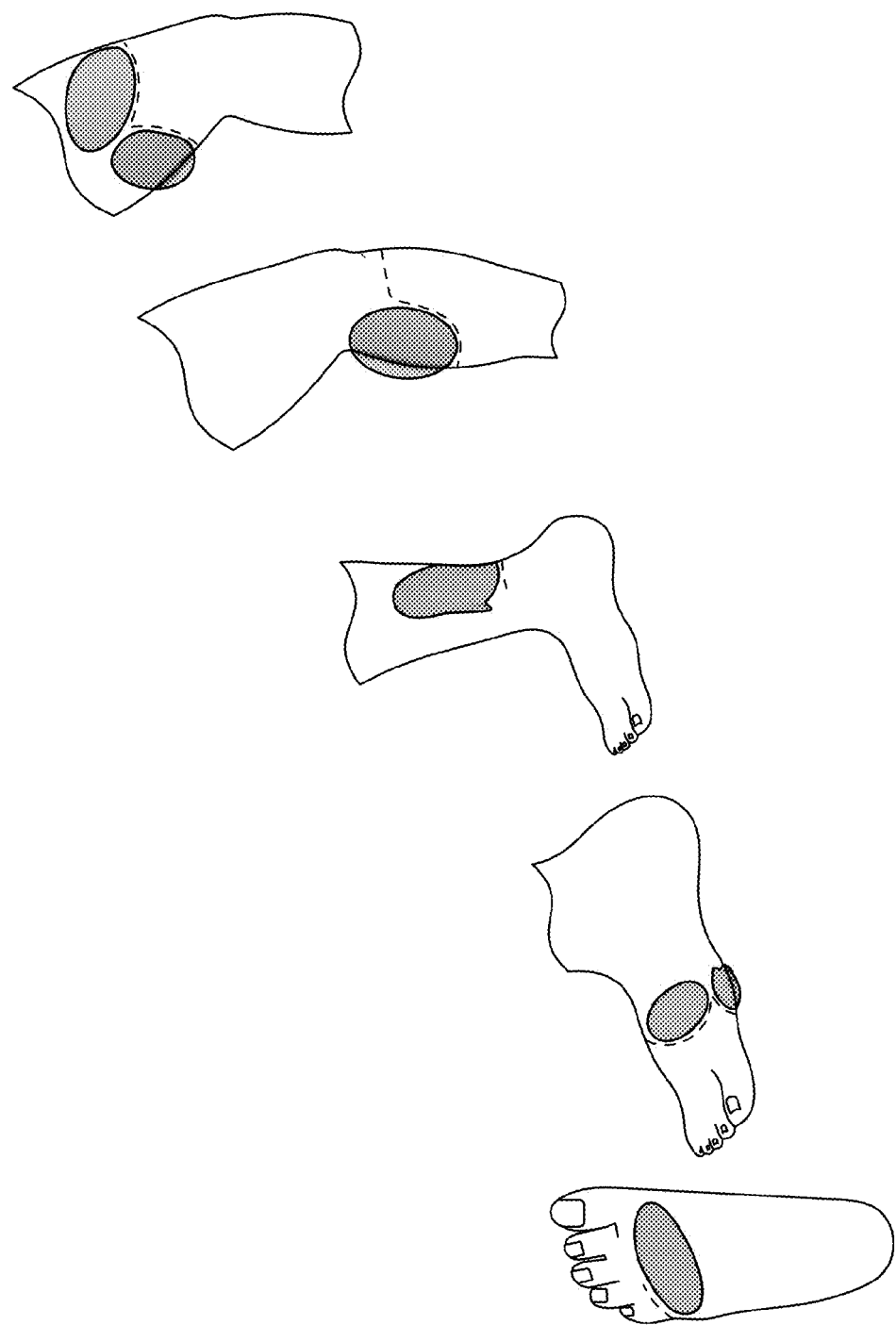
FIG. 59 illustrates a graphical example diagram of tissue involved in traditional amputation procedures.

FIG. 59 illustrates a graphical example diagram of tissue involved in traditional amputation procedures. Dotted lines indicate location of skin incisions and red ovals indicate location of skin that must be viable for successful primary healing of the amputation.

Significant patient health information that will be used in the diagnostic model will be collected by the clinical staff at the individual clinical sites. We will not collect any data that is beyond standard of care. These metrics will be include, but are not limited to: metrics of diabetic control (e.g., HbA1c, glucose, and insulin), smoking history, obesity (e.g., BMI or waste circumference), nutrition (e.g., albumin, pre-albumin, transferrin), infection (e.g., WBC, granulocyte status, temperature, antibiotic use), age, mechanism of injury, and important medication (e.g., glucocorticoids or chemotherapy). This information will be added to the diagnostic algorithm by inputting the information into the software on the DeepView imaging device.

A machine learning algorithm to sort subjects into the non-healing (+event) and healing (−event) classes will be developed based on the clinical features collected for each patient. We will initially include all of the features in the algorithm. The algorithm's accuracy will then be determined by 10-fold cross-validation as follows: first generating the algorithm coefficients with 60% of the subjects included at random, and then the remaining 40% of the subjects will then be sorted by the trained classifier. The algorithm's accuracy in sorting the subjects in the 40% hold-out group will be calculated using standard sensitivity and specificity methods. This will be repeated 10 times to generate a robust quantification of accuracy.

Figure 60:
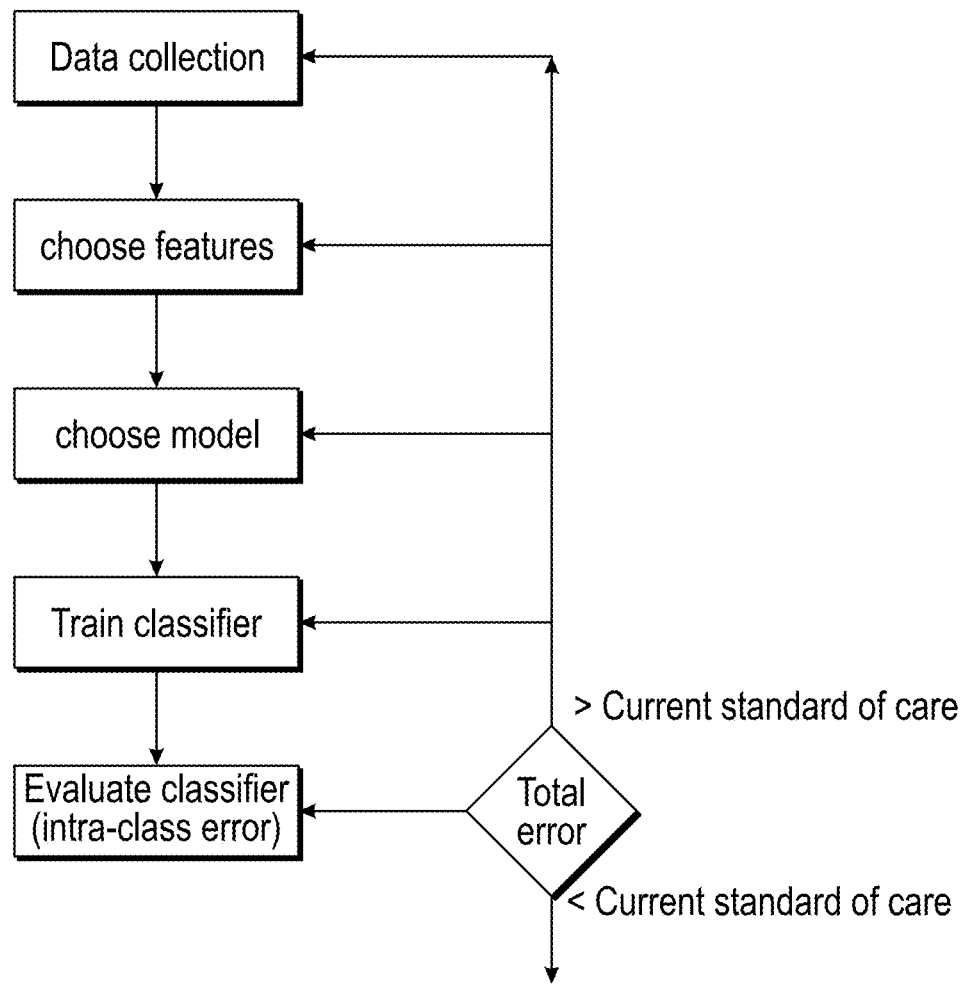
FIG. 60 illustrates example steps in generating a classifier model for a level of amputation.

FIG. 60 illustrates example steps in generating a classifier model for a level of amputation. After the initial accuracy is established, we will begin developing upon the algorithm with a standard set of methodologies for improving accuracy (FIG. 60). One critical issue in this process is to address the bias-variance trade-off that comes with large models such as the model we will have at this stage. In other words, the algorithm may fits very well to the data in the current study cohort, but not transfer to the general population. In order to address this we will conduct feature selection (Toward Integrating Feature Selection Algorithms for Classification and Clustering, Huan Liu and Lei Yu) to establish a combination of microcirculatory measurements and patient health data with a high accuracy but a minimum redundancy between variables (i.e., eliminate information from the model with co-variance). At this stage we will also study a range of classifier models for sorting the data. These will include: linear and quadratic discriminant analyses, decision trees, clustering, and neural networks.

Criteria for Success: We must demonstrate that the device can predict primary healing of an amputation at a rate comparable to the current standard of care (70-90%), and justify that a reasonable chance of increasing this accuracy can be achieved in a larger clinical study.

Possible Problems and Solutions: Revascularization procedures are sometimes performed with amputation surgery, and this additional procedure may influence the results of the diagnosis. We will record these cases and consider them in the statistical analysis to identify if there is any interaction between these procedures and the outcome of the diagnostic decision.

Another potential issue is in combining the delayed healing group with the healing group in our dichotomous device output. We may in fact find that there are significant differences in the delayed healing population and the healing population that can be included as a separate category in the diagnostic output. Conversely, the delayed healing group may have data that more closely agrees with the non-healing group, and they cannot be separated easily. In this case we could include the data from more proximal images into the algorithm. The clinical utility of the device may still be valuable in this case as a tool to identify complications in amputation rather than simply success or failure.

Skin pigmentation differences will introduce variability to the measurements collected from the subjects in this study. In order to overcome these differences our method will include the identification of a healthy region of the patient's tissue to which the DeepView measurement can be normalized.

Another issue is that normal blood-flow to the skin can be seen in patients with PAD. This could be the result of compensation by collateral vessels. However, it is shown that patients with PAD have poor response to exercise and short-term ischemia. One alteration to the study that can be easily performed would be to test the patient's DeepView signal after inflation of a pressure cuff in the measured limb to create ischemia for 3 min. PAD is known to lengthen the time to reach 50% of peak reactive hyperemia response, and this can be measured by the same optical properties of the tissue that DeepView assesses.

Experimental Design and Methods—Phase II

Phase II is a Diagnostic Clinical Performance Study to evaluate the sensitivity and specificity of our device for predicting the likelihood of primary wound healing following initial amputation in patients with PAD. We chose this population because it includes a revision rate of approximately 20% making it easier to obtain subjects that will have negative wound healing if LOA is selected using the current clinical standard of care. Diagnostic clinical performance of the DeepView Gen2 device will be characterized by measures that quantify how closely the DeepView Gen2 diagnosis correctly predicts wound healing outcomes as the primary endpoint. We will standardize the wound healing assessment using the gold standard methods used in previous studies to classify wound healing following amputation in PAD.

DeepView Gen2 images will be collected from the region of skin that would be used for the skin flap over the most distal portion of the stump at each traditional level of amputation. This region of tissue is selected because it is critical to the primary healing of the surgical site. While traditional studies of diagnosing healing potential of the amputation only measure microvascular flow, the purpose of this study is to assess the accuracy of our DeepView Gen2 algorithm that includes both microcirculation measurements and patient health metrics.

The sensitivity and specificity of DeepView Gen2 imaging to evaluate likelihood of successful amputation as determined by our standardized wound healing assessment.

This is a pivotal clinical study design consisting of a 354-patient study investigating the DeepView Gen2 system's accuracy of predicting primary healing in amputations on patients with PAD compared to the current standard of care.

The DeepView Gen2 imager collects spectral and PPG signals from a large area (up to 15×20 cm of tissue) of the cutaneous blood supply using optical methods. This instrument is well suited to study large regions of the lower extremity skin microcirculation. A unique aspect of the device is that it is capable of integrating important patient health metrics into its diagnostic algorithm to increase accuracy. The pilot study will have taken place to identify the most promising patient health metrics to be confirmed in this pivotal study. As a major task in this study we will confirm patient health metrics that was identified in the pilot study as important information to include in the device's machine learning diagnostic algorithm. In this study we will determine the microcirculation at each traditional LOA combined with patient health characteristics affecting wound healing and determine how this correlates to the patient's primary wound healing potential after amputation.

Data Collection: The lower limb to be amputated of every patient will be examined and included in the study. Clinically relevant patient health metrics will be gathered by the facility's care providers. Measurements taken with our experimental imaging device will be carried out by hospital staff previously trained by Spectral MD to perform the imaging tests.

The region of skin used for covering the stump of an amputation will be graded for positive or negative healing capability with the DeepView Gen2 LOA algorithm. The technician performing the DeepView Gen2 analysis will be blinded to the results of the clinical decision as to where the amputation will be performed.

To obtain our true positive (+) and true negative (−) events, or non-healing and healing subjects, we will use a standardized primary wound healing after amputation assessment (table 2). This assessment consists of three categories including: successful amputation; successful amputation with prolonged healing; and failure to heal. Successful amputation is considered healing within 30 days with completed granulation and no need for additional amputation. Successful amputation with prolonged healing is considered delayed healing with granulation incomplete at 30 days, but with eventual healing within six months and no need for re-amputation to a more proximal level. Lastly, failure to heal will be characterized by development of necrosis and/or gangrene, and/or the need for re-amputation to a more proximal level. Additionally, we will consider a wound requiring revascularization to heal as a failed amputation.

These healing assessments will take place 30 days post operatively. For the subjects with delayed healing, we will make a second healing assessment at six months following surgery. Subjects that are not healed at six months and have not had a more proximal re-amputation will be categorized to the non-healing group.

Figure 61:
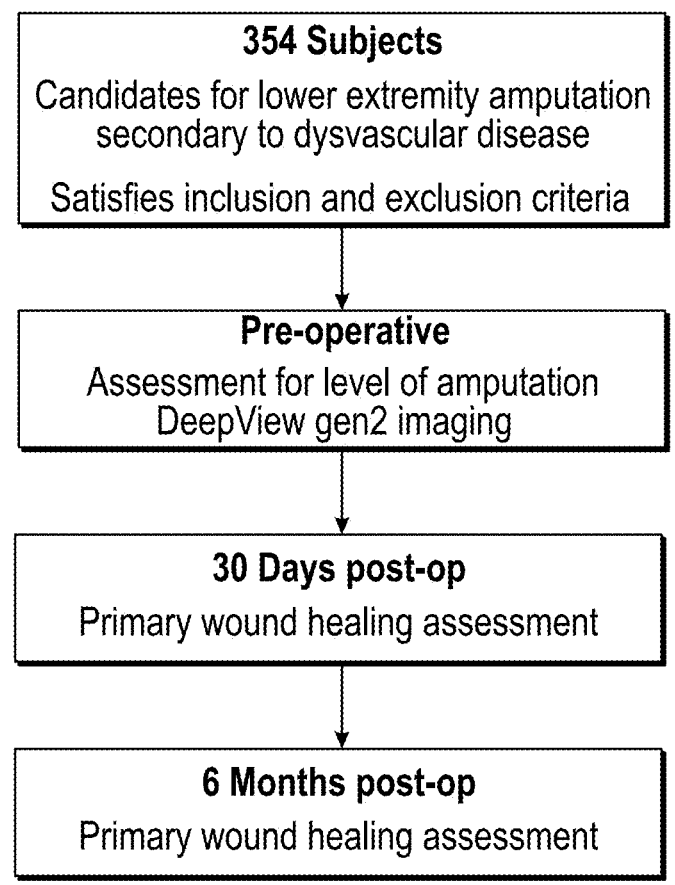
FIG. 61 illustrates an example clinical study flow diagram.

FIG. 61 illustrates an example clinical study flow diagram for DeepView imaging evaluation. Diagnosis of amputation site healing will be made during imaging using the Spectral MD Gen2 imaging device. Scans of approximately 30 sec each will be obtained from each leg awaiting amputation. We will image regions of the ankle and foot according to the traditional surgical methods of amputation in PAD patients including: above the knee (AKA), below the knee (BKA), above the ankle (AAA), transmetatarsal, or toe. The regions of skin that are used as a flap to cover the stump will be selected for analysis (FIG. 59).

Collection of patient health metrics: Significant patient health information that will be used in the diagnostic model will be collected by the clinical staff at the individual clinical sites. We will not collect any data that is beyond standard of care. These metrics will be identified in the pilot study, but are expected to include: measured of diabetic control (e.g., HbA1c, glucose, and insulin), smoking history, obesity (e.g., BMI or waste circumference), nutrition (e.g., albumin, pre-albumin, transferrin), infection (e.g., WBC, granulocyte status, temperature, antibiotic use), age, and important medication (e.g., glucocorticoids or chemotherapy). This information will be added to the diagnostic algorithm by inputting the information into the software on the DeepView imaging device.

Data Analysis and Statistics: DeepView Gen2 imaging measurements from the five amputation sites of the affected limb will be evaluated to determine the wound healing potential. From each limb, we will determine an overall healing score and compare these measurements to the actual amputation success in the limb to get an overall accuracy of the assessment. This will result in receiver operating characteristics (ROC), our primary outcome measure of sensitivity and specificity.

For our primary outcome measure of grading wound healing, we will compare the DeepView Gen2 diagnosis from the location of amputation determined by the clinician to the success of that amputation determined by the standardized wound healing assessment. This analysis will result in a receiver operator characteristic (ROC) curve for the DeepView diagnostic algorithm.

Power Analysis: The clinical trial is deigned to establish the device's sensitivity and specificity and to test that these numbers outperform clinical judgment to select LOA. We have established the goal of our study is for the DeepView Gen2 system to achieve 95% sensitivity and 95% specificity in diagnosing LOA to overcome the poor 70-90% accuracy of current clinical judgment. In order to establish a sample size we need to first put this in terms of positive predictive value (PPV) and negative predictive value (NPV), which requires that the prevalence of the disease be known. We identified the prevalence of re-amputation to a more proximal level in the population to be screened by the DeepView Gen2 (patients >18 years of age requiring initial amputation on the affected limb due dysvascular disease) to be approximately 20% (reference). Therefore, the desired positive predictive value (PPVDeepView) is 97% and the desired negative predictive value (NPVDeepView) is 93%.

An analysis of sample size to test the following hypotheses was performed using the methods outlined by Steinberg et al., 2008, "Sample size for positive and negative predictive value in diagnostic research using case-control designs," Biostatistics, vol. 10, no. 1, pp. 94-105, 2009. Where the significance level ($\alpha$) is 0.05 and the desired power ($\beta$) is 0.80.

For PPV $$H_0: PPV_{DeepView} = PPV_{clinical\ Judgment}\ H_1:$$
$$PPV_{DeepView} > PPV_{clinical\ Judgment}$$

for NPV $$H_1: NPV_{DeepView} > NPV_{clinical\ Judgment}\ H_1:$$
$$NPV_{DeepView} > NPV_{clinical\ Judgment}$$

Figure 62:
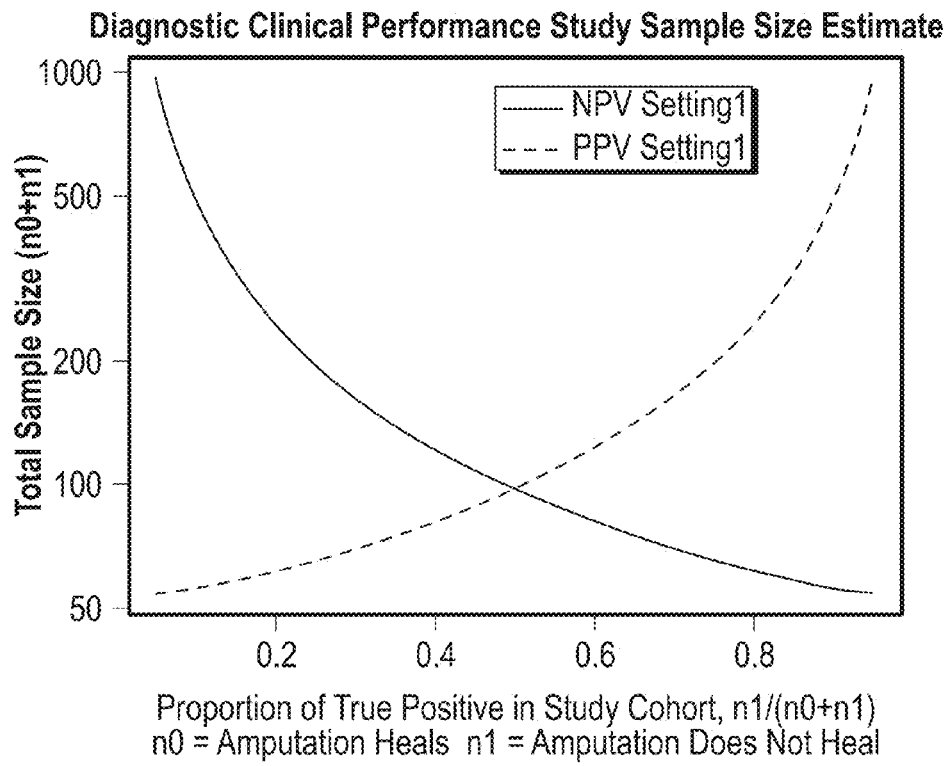
FIG. 62 illustrates example statistical sample size analysis results.

The results show to reject these null hypotheses ($H_0$) we must enroll a total number of 236 lower limbs with ⅕ of the limbs being non-healing (+event) according to our healing assessment (FIG. 62). However, we cannot pre-select this ratio to be ⅕, because we do not know the disease state of the subjects prior to enrollment. Therefore, this ratio may differ. If the ratio is much lower, 1/10 of the limbs being non-healing (+), the study will require approx. 450 total limbs and if much higher, ⅗ non-healing (+) limbs, we will require only 124 total limbs.

FIG. 62 illustrates example statistical sample size analysis results. Total sample size according to the ratio of non-healing (+) to healing (-) amputations in the study cohort. Significance level ($\alpha$) is 0.05 and the desired power ($\beta$) is 0.80.

To account for the possible variations in the ratio of positive to negative subjects, we will include approx. 50% more subjects to the original estimate of 236. Therefore, our total sample size will be established at 354 total subjects. We are confident that this number can be achieved because this is a minimal risk study and busy clinics perform about 100 amputations per year. We will monitor the study data as it is taken and calculate the total number of limbs studied and the ratio unsuccessful (+event) to successfully amputated (-event) limbs, and stop the study once an appropriate ratio and total sample size is obtained.

Expected Results: To determine how well the DeepView output correlates to primary wound healing, we will compare the DeepView results to the standardized healing assessment that sorts subjects into healing or non-healing groups. From this comparison, we expect a correlation to exist that supports a high sensitivity and specificity for predicting primary healing after amputation.

Criteria for Success: The ROC will need to contain a decision threshold value that results in a sensitivity and specificity greater than the required values established by the current standard of care (70-90% accuracy).

Possible Problems and Solutions: We may have trouble getting a sample size large enough to powering the importance of all non-imaging data (patient health metrics) used in the diagnostic algorithm. For instance, diabetes is an important clinical feature, but we may find that all the patients in our cohort have diabetes or that it does not occur at a ratio that allows for sufficient power to study its effects. Therefore, the presence of this comorbidity in our diagnostic algorithm could not be interpreted. We anticipate this patient cohort to have many similarities in their overall health status, but some of these variables can be measured at various levels and not simply dealt with as dichotomous. For instance, diabetic subjects may have a range of control as measured by the HbA1c and blood-glucose testing. For the case where this is not possible, we will consider the continued collection of this data in post-market analysis where we can look at a much larger amputation population.

Overview of Performance Examples

Experimental data indicates example benefits of fusing PPG and MSI features into one algorithm, as illustrated by the Figures discussed below.

In the following discussion, feature sets include photoplethysmography (PPG), multispectral imaging (MSI), real image (RI). Example methodology includes drawing ground truth, training a classification algorithm with all three feature sets both separately and also together, classifying images, and reporting error in order to compare classifiers with different feature set compositions. Currently, features have been developed and can be used for classification. These features are broken into three categories of feature sets: PPG, MSI, and RI. For the following examples a classifier, QDA (Quadratic Discriminant Analysis), was trained with a variety of feature sets. The feature sets were combined until all 33 features were included in the model. Each classifier developed (i.e., each classifier with distinct feature sets) were compared based on their classification error.

Figure 63A:
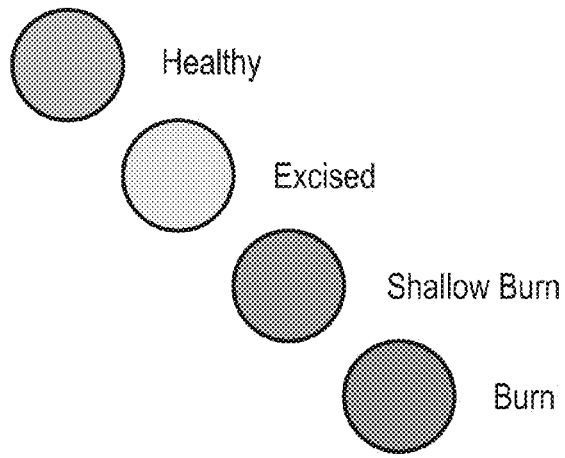
FIG. 63A illustrates a color key for the example results of FIGS. 63B-63F.

FIGS. 63B-63F illustrate example reference images, ground truth images, classification results, and error images for a variety of different classifiers as described in more detail below. FIG. 63A illustrates a color key for the example results of FIGS. 63B-63F, where blue represents healthy tissue, green represents excised tissue, orange represents a shallow burn, and red represents a burn.

Figure 63B:
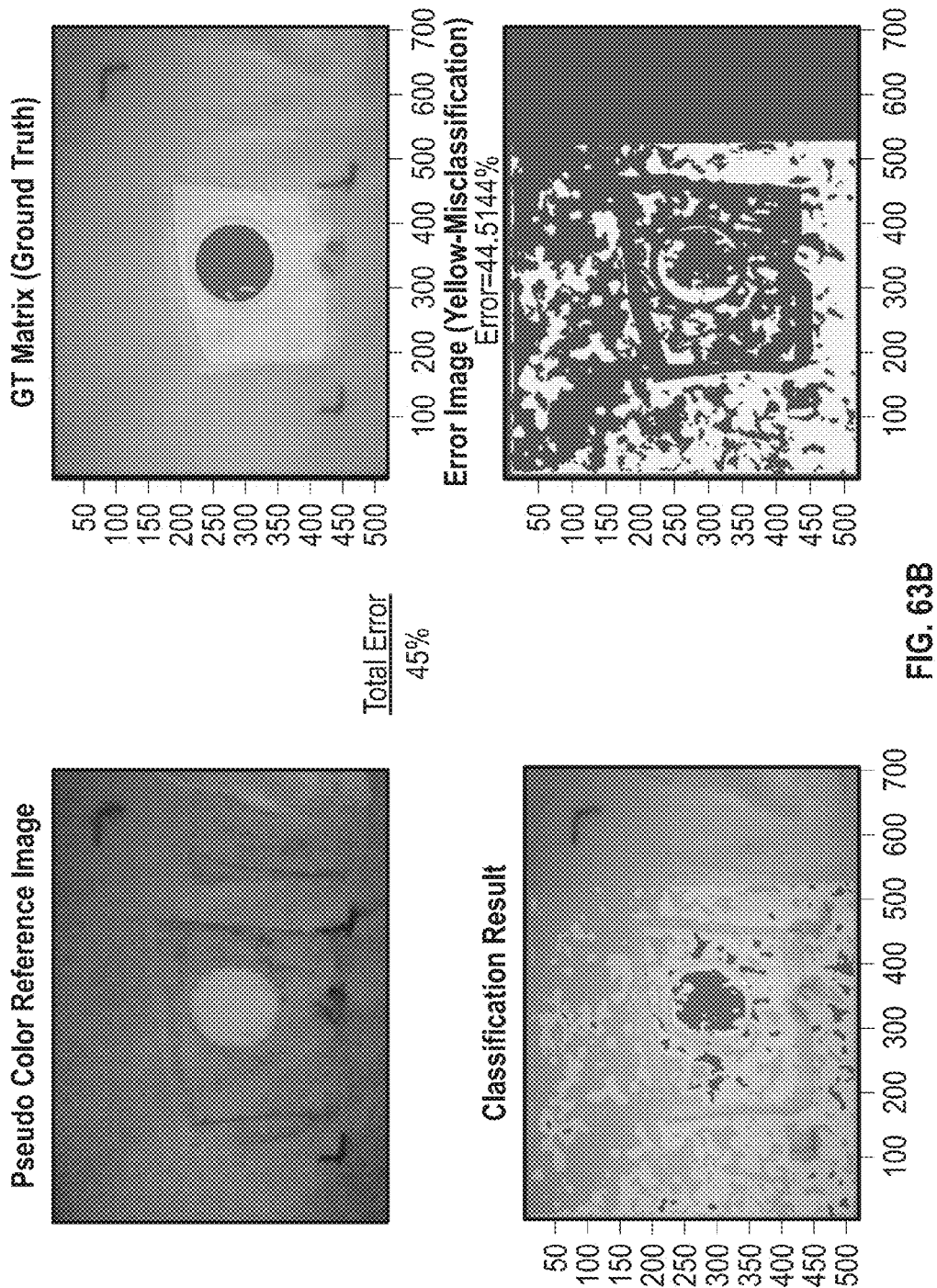
FIGS. 63B-63F illustrate example reference images, ground truth images, classification results, and error images for a variety of different classification techniques.

The DeepView classifier features include the following 14 features:
1. Deep View Output
2. Maximum over mean
3. Standard deviations away from mean
4. Number of crossings
5. SNR a small neighborhood
6. Improved SNR
7. Lighting normalized
8. DeepView image Normalized
9. Standard deviation
10. Skewness
11. Kurtosis
12. X-gradient
13. Y-gradient
14. Standard deviation of the gradients FIG. 63B illustrates example reference images, ground truth images, classification results, and error images for the DeepView classifier. As illustrated by the percentage of yellow in the error image (or white/the lighter color in grayscale reproductions of FIG. 63B), the total error rate for the DeepView classifier was 45%.

Figure 63C:
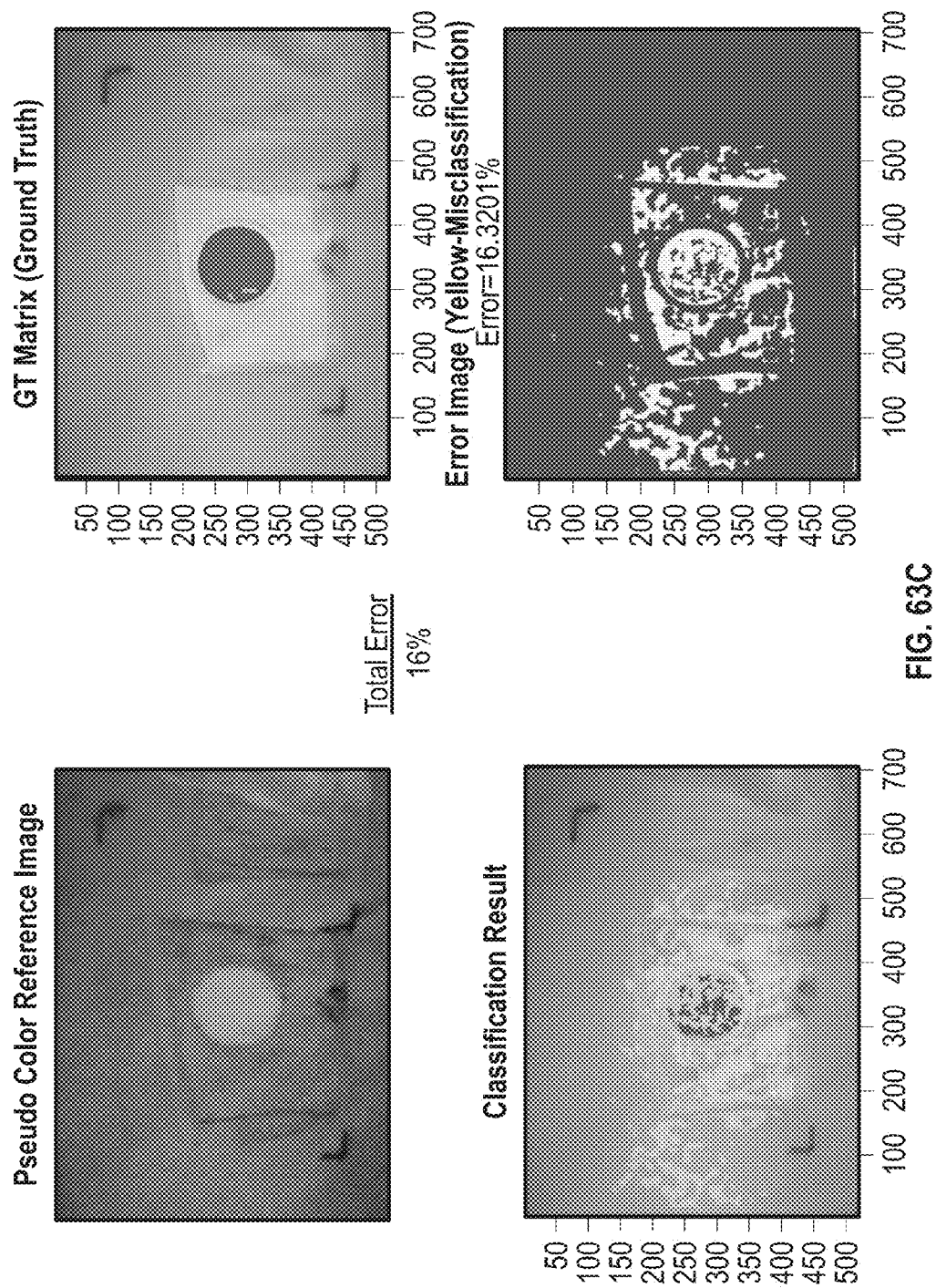

The Real Image classifier features include the following 11 features:
1. Real image
2. Real image normalized
3. Skewness
4. Kurtosis
5. X-gradient
6. Y-gradient
7. Standard deviation within X-gradient
8. Range within a small neighborhood
9. Range within a small neighborhood normalized
10. Range within a big neighborhood
11. Range within a big neighborhood normalized FIG. 63C illustrates example reference images, ground truth images, classification results, and error images for the Real Image classifier. As illustrated by the percentage of yellow (or white/the lighter color in grayscale reproductions of FIG. 63C) in the error image, the total error rate for the Real Image classifier was 16%.

Figure 63D:
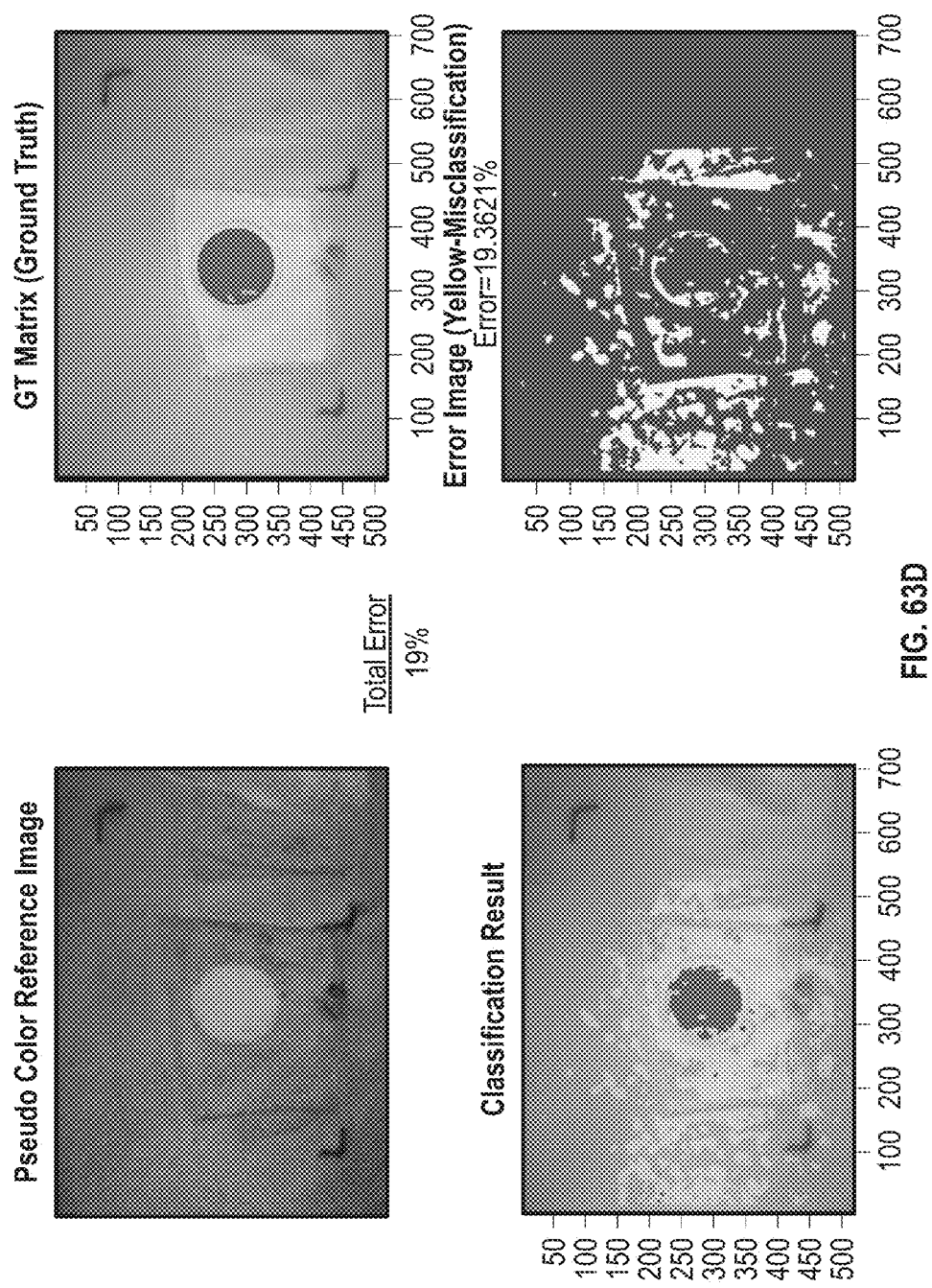

FIG. 63D illustrates example reference images, ground truth images, classification results, and error images for a combination of the DeepView classifier and the Real Image classifier. This DeepView/Real Image combination classifier used 25 features including the 14 DeepView features and the 11 Real Image features described above. As illustrated by the percentage of yellow (or white/the lighter color in grayscale reproductions of FIG. 63D) in the error image, the total error rate for the DeepView/Real Image combination classifier was 19%.

Figure 63E:
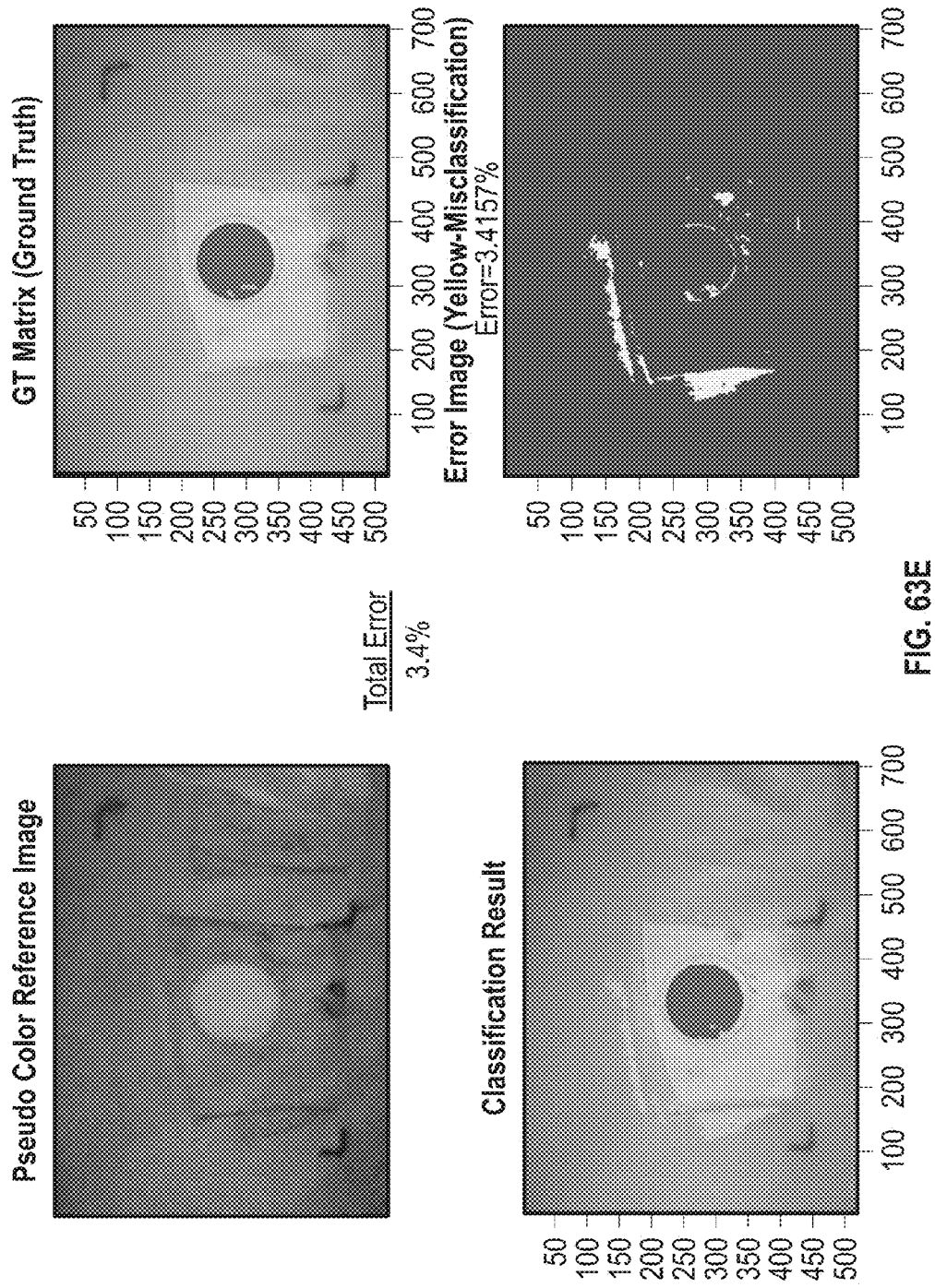

The MSI classifier features include the following 8 features:
1. MSI $\lambda_1$
2. MSI $\lambda_2$
3. MSI $\lambda_3$
4. MSI $\lambda_4$
5. MSI $\lambda_5$
6. MSI $\lambda_6$
7. MSI $\lambda_7$
8. MSI $\lambda_8$ FIG. 63E illustrates example reference images, ground truth images, classification results, and error images for the MSI classifier. As illustrated by the percentage of yellow (or white/the lighter color in grayscale reproductions of FIG. 63E) in the error image, the total error rate for the Real Image classifier was 3.4%.

Figure 63F:
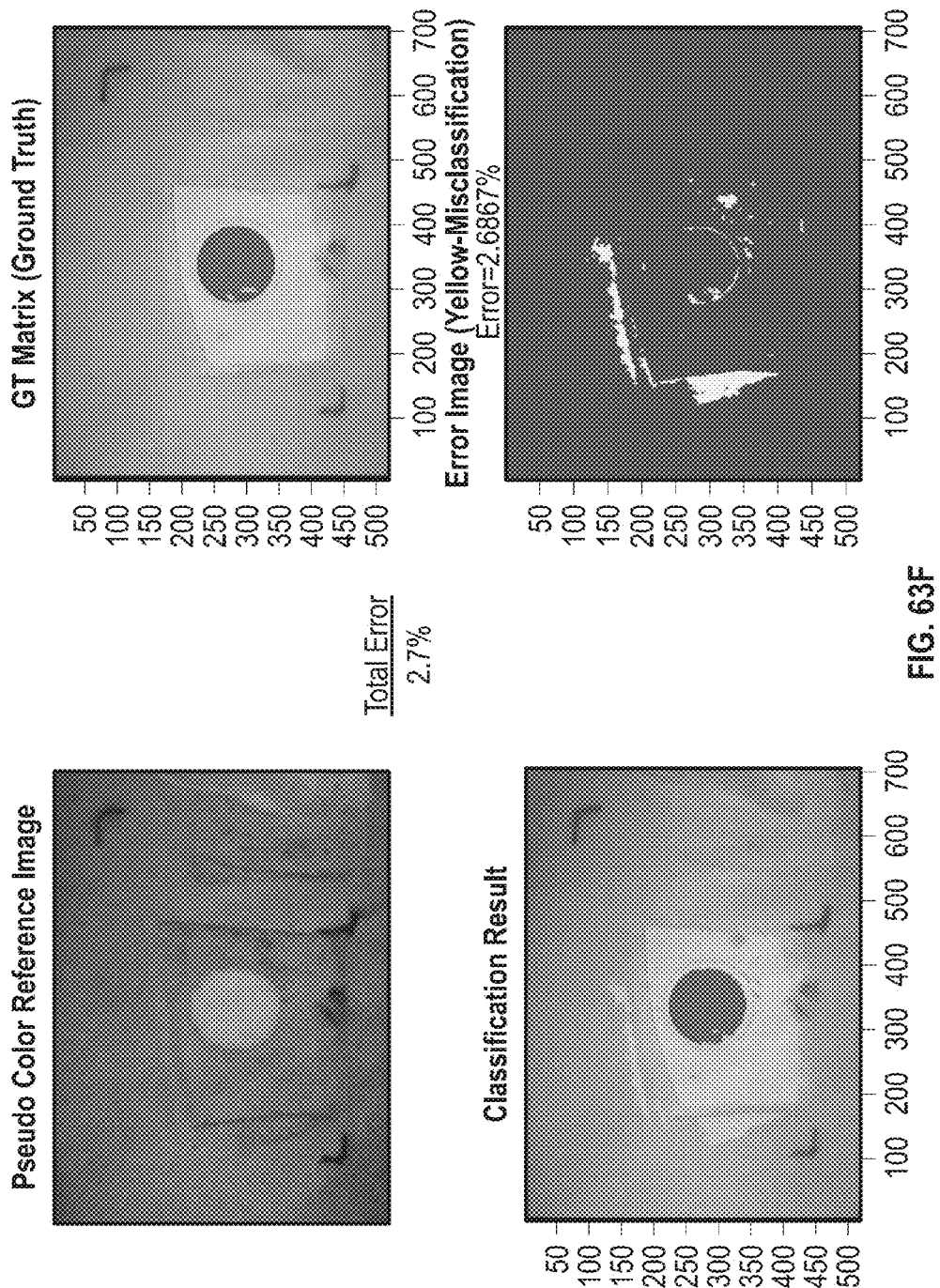

FIG. 63F illustrates reference images, ground truth images, classification results, and error images for a combination of the DeepView classifier, the Real Image classifier, and the MSI. This DeepView/Real Image/MSI combination classifier used 33 features including the 14 DeepView features, the 11 Real Image features, and the 8 MSI features described above. As illustrated by the percentage of yellow (or white/the lighter color in grayscale reproductions of FIG. 63F) in the error image, the total error rate for the DeepView/Real Image/MSI combination classifier was 2.7%.

Figure 64A:
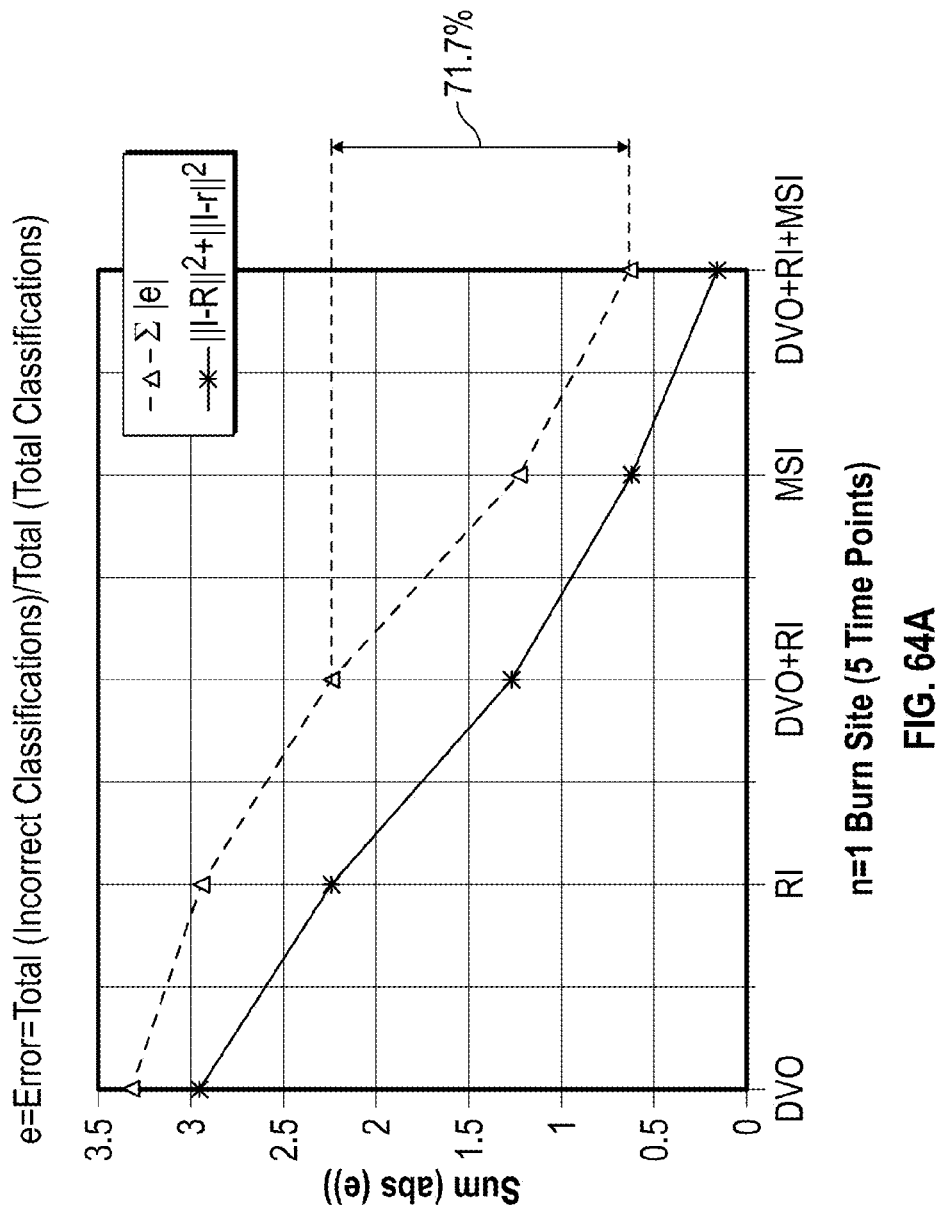
FIGS. 64A and 64B illustrate comparisons of feature composition in different classification techniques.
Figure 64B:
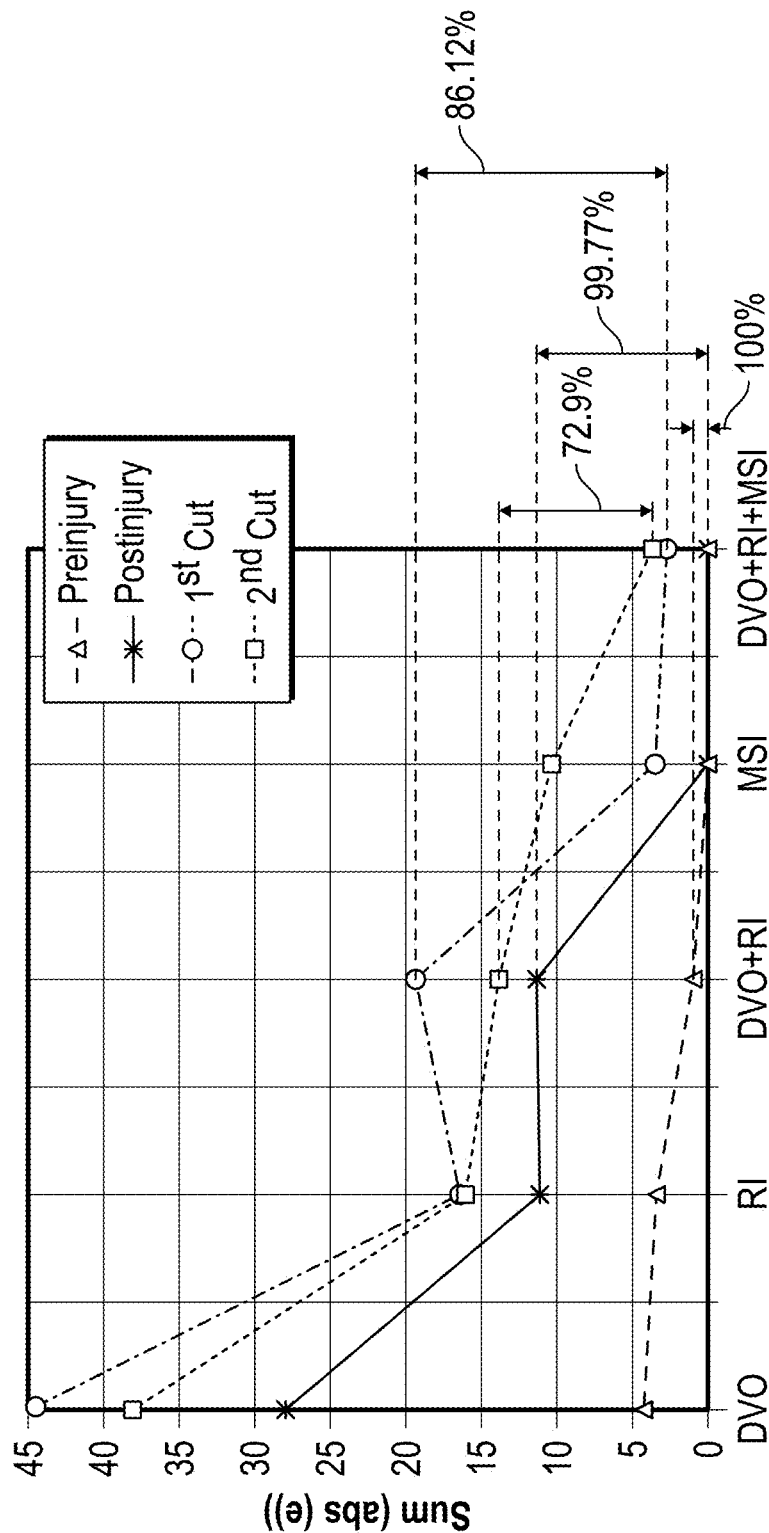

FIGS. 64A and 64B illustrate comparisons of feature composition in different classification techniques. FIG. 64A illustrates a comparison of the error (e) of DVO (DeepView), RI, DVO+RI, MSI, and DVO+RI+MSI classifiers, where e=error=total(incorrect classifications)/total(total classifications). As illustrated, the DVO+RI+MSI classifier is 71.7% less than the error between the DVO+RI classifier.

FIG. 64B illustrates a comparison of the error (e) of DVO (DeepView), RI, DVO+RI, MSI, and DVO+RI+MSI classifiers by study time point.

As illustrated by the data represented by FIGS. 63B-64B, error reduction increases as more features are added. Groups of features can be ranked in order of importance, and in one example can be ranked as: (1) MSI, (2) RI, (3) PPG. Some embodiments of the classification algorithms can be transferable, meaning that the algorithm can be trained on a first subject and then used to classify injuries on a second subject.

Overview of Example Intraoperative Burn Surgery Imaging and Signal Processing

Burn debridement is a challenging technique that requires significant skill to identify regions requiring excision and appropriate excision depth. A machine learning tool is being developed in order to assist surgeons by providing a quantitative assessment of burn-injured tissue. Three noninvasive optical imaging techniques capable of distinguishing between four kinds of tissue—healthy skin, viable wound bed, deep burn, and shallow burn-during serial burn debridement in a porcine model are presented in this paper. The combination of all three techniques significantly improves the accuracy of tissue classification.

I. Introduction

This disclosure presents a signal processing technique to develop an intraoperative burn surgery assist device (DeepView Wound Imaging System, Spectral MD, Dallas, Tex.).

The viable wound bed, which must be exposed to allow for skin grafting, is distinguished from three other types of tissues: healthy skin, viable, deep burn, and shallow burn. The input metrics are based on three main sets of features: photoplethysmography (PPG) features, which identify pulsatile blood flow in the skin's microcirculation; real image (RI) features, taken from a black-and-white photograph of the injury; and multispectral imaging (MSI), which collects the tissue reflectance spectrum at key visible and infrared wavelengths of light. Tissue classification is performed using quadratic discriminant analysis (QDA), a popular machine learning technique. The system has been tested on sample wounds from pigs, using different combinations of input features from the three available imaging techniques. The results of this testing are reported to demonstrate that increasing the number of features improved the performance of the classifier.

II. Description of the Experiment

The experimental setup of the porcine burn model has been previously described. Briefly, an imager (Nocturn XL, Photonis USA) equipped with a filter wheel containing eight unique optical band pass filters (400-1100 nm) was mounted vertically above the field. An accessory LED array (SFH 4740, OSRAM) illuminated the field. PPG imaging, RI, and MSI were performed concurrently on four adult Hanford swine anesthetized and prepped for dorsolateral burns. A spring-loaded brass rod (diameter 3.6 cm) was heated to 100 C and pressed to the skin for 45 seconds per injury to create a total of six burns on each animal. An electric dermatome (Zimmer; Model No.: 8821-06) set to 1 mm depth (width 6 cm) was passed over each burn sequentially until the viable wound bed was exposed. Punctate bleeding, visible after three layers of excision for all burns, was the visual queue for sufficient exposure of the viable wound bed.

Imaging with all three techniques was performed pre-injury (healthy skin), immediately post injury (acute burn), and after each layer was excised. The initial excision layer was taken 20 minutes after injury, and a maximum of 80 minutes elapsed from the time of initial injury to final excision.

III. Technical Approach

A. PPG Output Preprocessing

Figure 65:
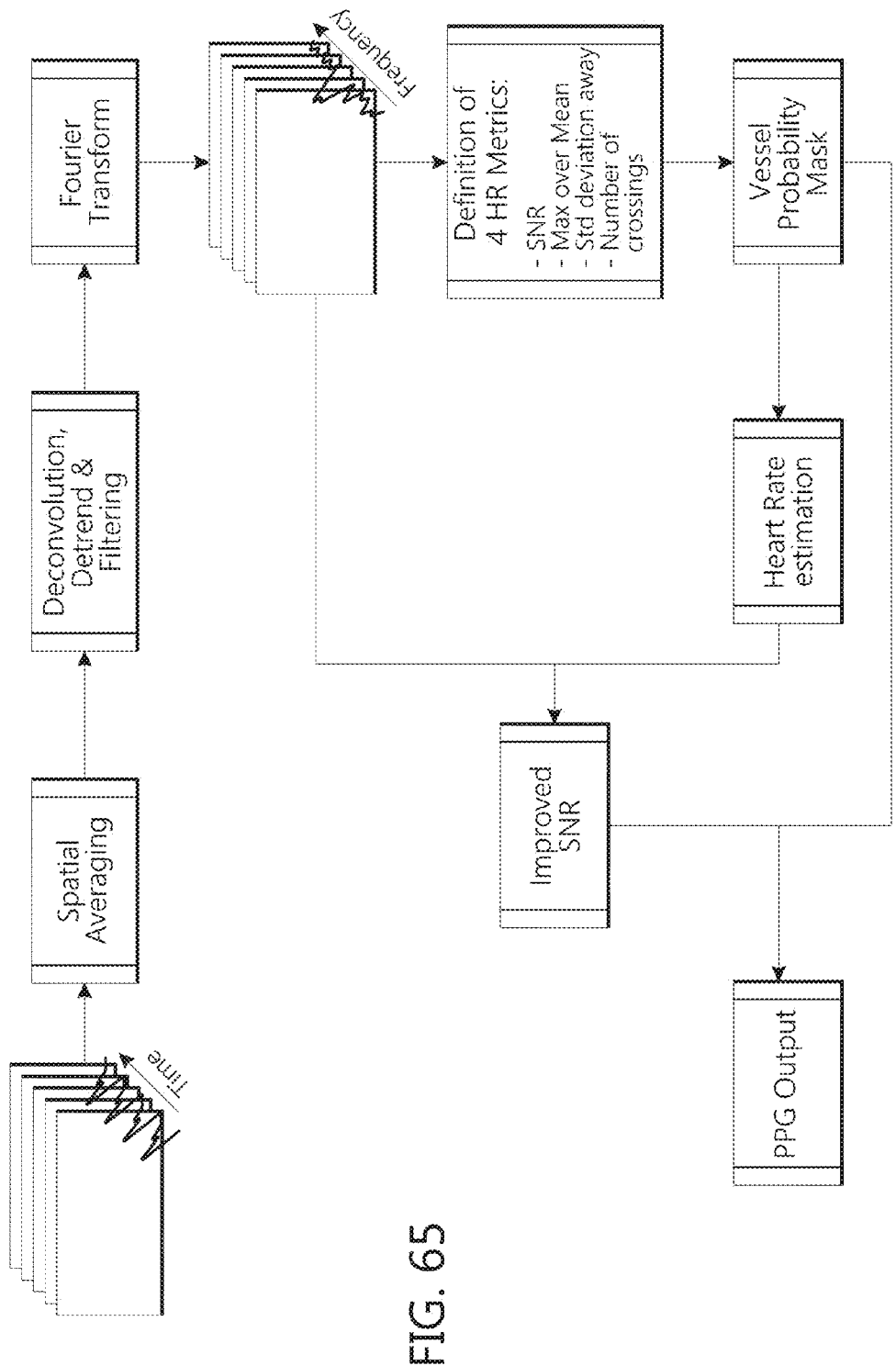
FIG. 65 illustrates an example block diagram of PPG output preprocessing.

FIG. 65 illustrates an example block diagram of PPG output preprocessing. PPG images are created according to 800 frames from a 27 second video of the burn wound are collected for each image. A PPG signal in time is defined for each pixel. The purpose of this pre-processing is to obtain some physiological information related to the heart rate of the subject, as well as some initial features for the classification step. From this time domain signal (one for each pixel), a pre-processing algorithm is carried out, which is schematized in FIG. 65 and summarized as follows.

An initial spatial averaging is computed; then, a deconvolution is performed in which the high amplitude component at low frequency—corresponding to the artificial ventilation of the sedated pig—is removed. A linear detrend of the signal, as well as a band pass filtering over the range of frequencies where the heart rate is expected, is performed. A fast Fourier transform algorithm is applied to the time domain signal of each pixel in order to compute the frequency domain version.

For each pixel, four metrics are obtained from these sets of frequency signals: (1) Signal to Noise Ratio (SNR), (2) Max over Mean, (3) Number of Standard Deviations Away from Mean, and (4) Number of crossings of the signal over the zero level. These four metrics are used for establishing a vessel probability in each pixel of the image. The vessel probability indicates how useful a pixel is for providing information about heart rate. For those pixels whose vessel probability is >0:9, the values of the heart rate corresponding to the maximum of the frequency signal are stored. The most repeated value is selected as the true heart rate of the pig for the current step. From this value, an improved SNR metric is calculated. Finally, a mask is defined setting to 1 those pixels whose heart rate corresponds with the calculated rate, and setting a value between 0-1 to the rest of pixels, depending on their degree of difference from the true heart rate. The PPG Output metric is the result of the product between the improved SNR and that mask.

All these 6 metrics give physiological information about the blood flow approximately 1 cm below the surface of the body of the subject under study for each pixel of the image.

B. Definition of Features

Three main sets of features have been used for determining the properties of each pixel of the image under analysis. There are a total of 33 features distributed as follows: 14 features from the PPG Output process; 11 features from RI; and 8 features from MSI, one per each wavelength of light. The table below indicates the description of each feature.

| PPG Output | Real Image | Multispectral Images |
|---|---|---|
| PPG Output image | Real image | MSI $\lambda_1$ |
| Maximum over mean | Real image normalized | MSI $\lambda_2$ |
| Standard deviations away from mean | Skewness | MSI $\lambda_3$ |
| Number of crossings | Kurtosis | MSI $\lambda_4$ |
| SNR | X-gradient | MSI $\lambda_5$ |
| Improved SNR | Y-gradient | MSI $\lambda_6$ |
| Lighting normalized | Standard deviation within X-gradient | MSI $\lambda_7$ |
| PPG image normalized | Range within a small neighborhood | MSI $\lambda_8$ |
| Standard deviation | Range within a small neighborhood normalized | |
| Skewness | Range within a big neighborhood | |
| Kurtosis | Range within a big neighborhood normalized | |
| X-gradient | | |
| Y-gradient | | |
| Standard deviation of the gradients | | |

C. Definition of Ground Truth Images

In one embodiment, control data may be provided to train the classification algorithm. In one example, a database of Ground Truth (GT) images for all the cases under study was generated. For the purpose of this work, a total of 60 cases are available for one pig: six lesion locations (three at each side of the back of the pig) for the following stages: pre-injury, post-injury, first excision, second excision, and third excision, with two imaging captures taken at each stage. In order to generate the training data, each injury site is analyzed and the status of each area of tissue is decided. This data is used to separate the image data into classes corresponding with each tissue type. The GT matrices define the different kinds of tissue in each capture. Some sets of indeterminant pixels were discarded. This prior definition of the tissues is used in the classification algorithms since they represent the ideal output of the classifier.

D. Classifiers

The classifier employed for this experiment is Quadratic Discriminant Analysis (QDA), a popular supervised classification algorithm for machine learning applications. QDA is trained by assuming that the data follows a Gaussian distribution in n-dimensional space, where n is the number of features being used. This algorithm tries to find the type of class k which maximize the conditioned probability $\hat{G}$ that a given pixel x belongs to a class. Mathematically, the decision is given by:

$$\hat{G}(x) = \underset{k}{\mathrm{argmax}} P(G = k | X = x) =$$
$$= \underset{k}{\mathrm{argmax}} f_k(x) \pi_k$$
$$= \underset{k}{\mathrm{argmax}} [\delta_k(x)],$$

where $\delta_k(x)$ is called Quadratic Discriminant Function and is defined as follows:

$$\delta_k(x) = -\frac{1}{2} \log|\Sigma_k| - \frac{1}{2}(x - \mu_k)^T \sum_k^{-1} (x - \mu_k) + \log \pi_k.$$

The subscript k indicates the class of tissue, $f_k(x)$ is the probability density function of a n-dimensional Gaussian distribution, $\mu_k$ and $\Sigma_k$ represent the mean and the covariance matrix, respectively, for each class, and $\pi_k$ is the a priori probability for that class k. The values of $\mu_k$ and $\Sigma_k$ are calculated in the training phase with a set of N known pixels (x, k) where the n-dimension vector x represents the values of each feature and k is the class that pixel belongs to. For each tissue k, a value of $\delta_k$ is obtained, representing the likelihood that the unknown pixel x belongs to each class k. The decision boundary between classes k and l is defined as the set of pixels that satisfy $\{x : \delta_k(x) = \delta_l(x)\}$ and, due to the definition of $\delta_k(x)$, this boundary is going to be a quadratic function in x.

IV. Results

Figure 66:
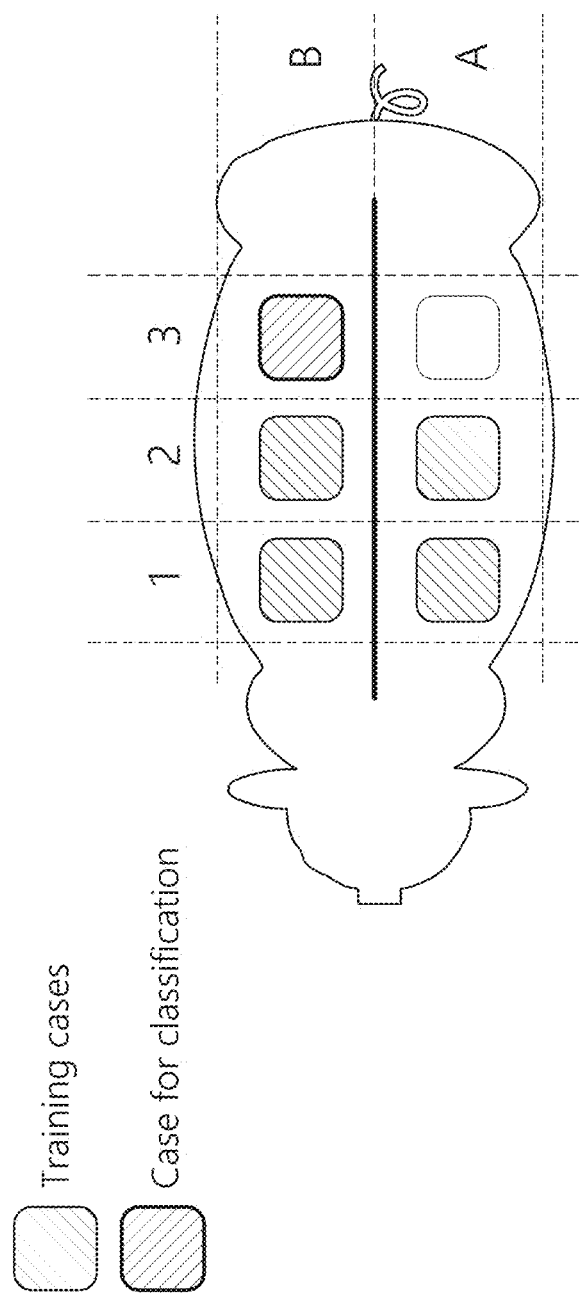
FIG. 66 illustrates an example of locations usable for training cases, classification cases, and cross-validation.

FIG. 66 illustrates an example of locations 1A, 1B, 2A, 2B, 3A, and 3B usable for training cases, classification cases, and cross-validation. From all the available data, ⅔ of the data, corresponding to both captures of all stages in locations 1A, 1B, 2A, and 2B, was used for training the classifier. The cross-validation was performed by classifying pixels from the second imaging capture at location 3B, as FIG. 2 shows. The study was repeated five different times, varying the set of features used in each iteration: (i) using the 14 features from the PPG Output only, (ii) using the 11 features from RI only, (iii) combining the 25 features from the PPG Output plus RI, (iv) using the 8 MSI features only, and (v) combining all 33 features from PPG, RI, and MSI together.

Figure 67F:
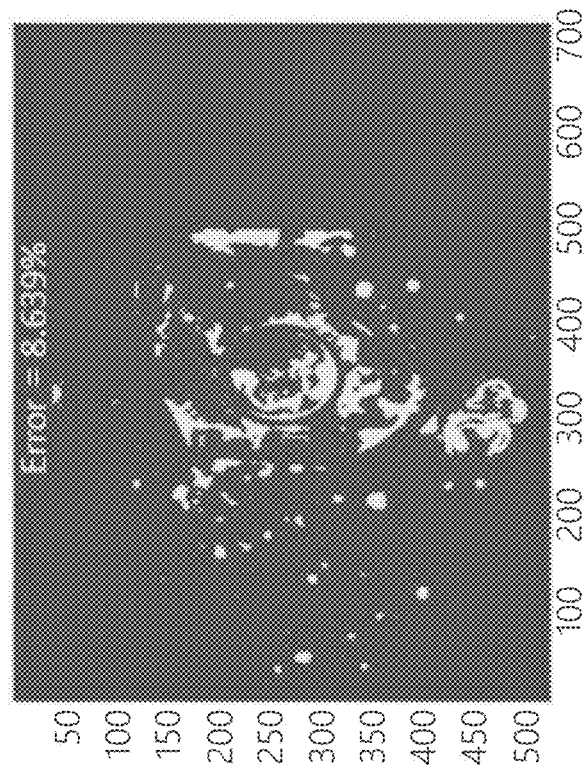
Figure 67E:
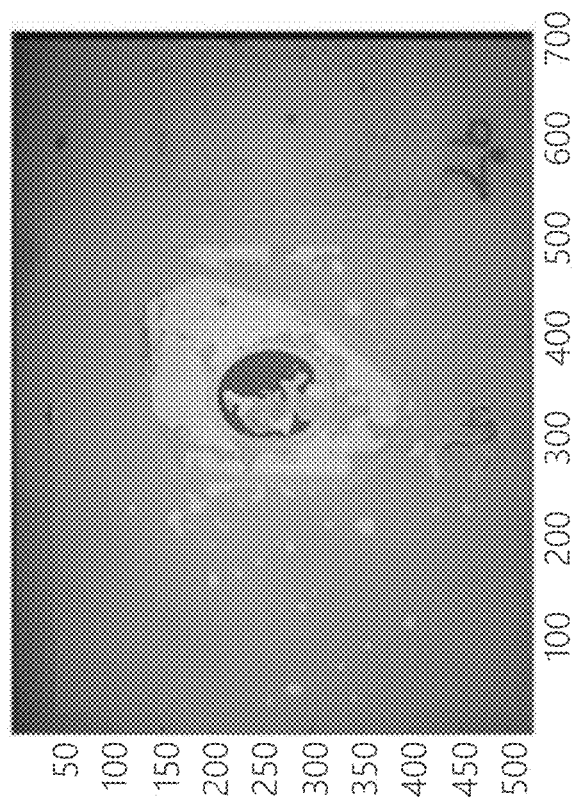
Figure 67J:
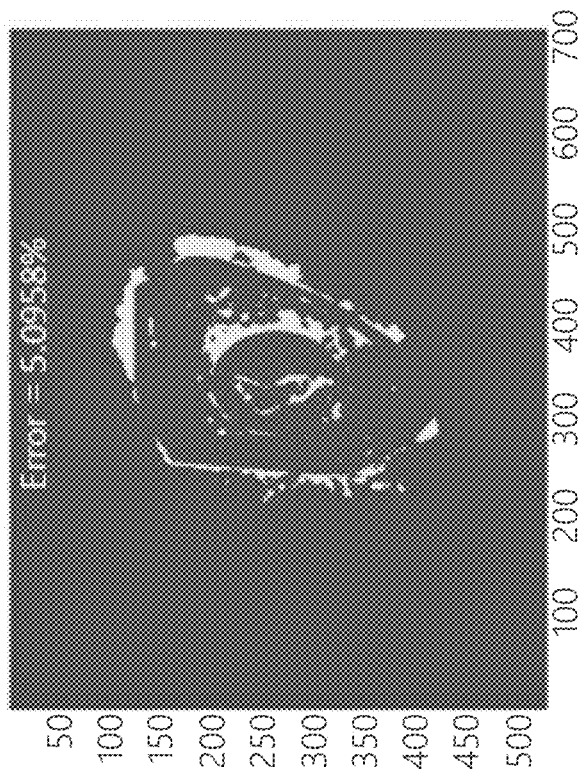
Figure 67I:
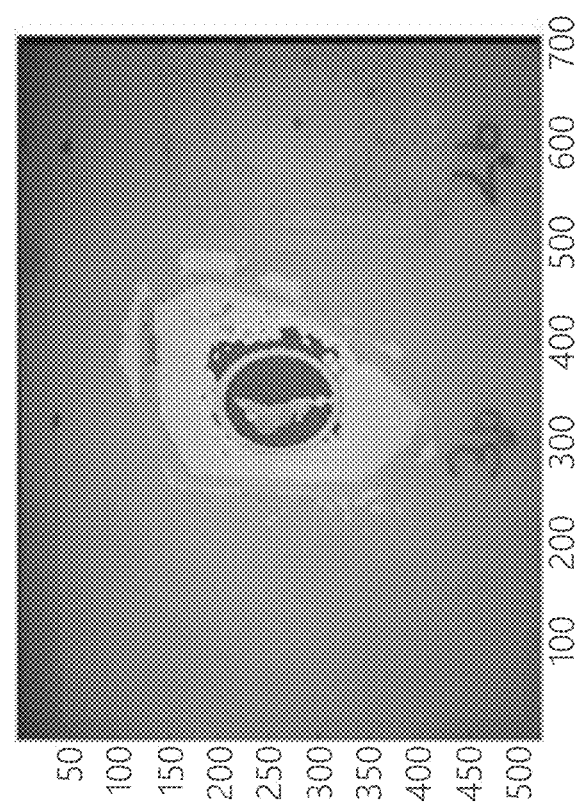
Figures 67K, 67L:
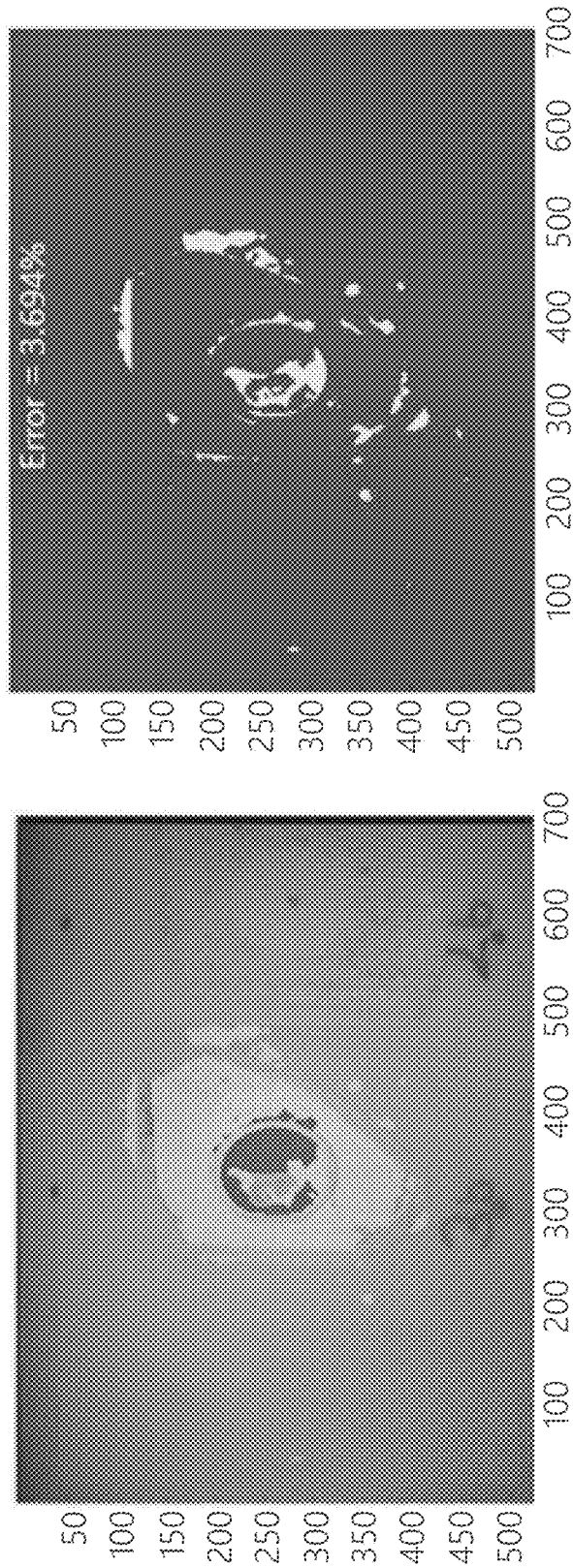

FIGS. 67A-67L illustrate example ground truth images, real images, and classification results of the 1st excision step for the five different classification methods. FIG. 67A illustrates Ground Truth (GT), FIG. 67B illustrates an RGB real image, FIG. 67C illustrates classification with the PPG features, FIG. 67D illustrates classification error (17.6329%) with the PPG features, FIG. 67E illustrates classification with the RI features, FIG. 67F illustrates classification error (8.639%) with the RI features, FIG. 67G illustrates classification with the PPG+RI features, FIG. 67H illustrates classification error (9.5821%) with the PPG+RI features, FIG. 67I illustrates classification with the MSI features, FIG. 67J illustrates classification error (5.0958%) with the MSI features, FIG. 67K illustrates classification with the PPG+RI+MSI features, and FIG. 67L illustrates classification error (3.694%) with the PPG+RI+MSI features. The color code for FIGS. 67A-67L is as follows:

Healthy skin: Blue
Viable wound bed: Green
Shallow burn: Orange
Deep burn: Brown From the results of the classifier, a confusion matrix was constructed for each iteration. The matrix constructed based on the classification with all 33 features is shown in FIG. 68. The parameters included in confusion matrices are defined as follows:

R: reconstruction rate, defined as the probability of a pixel is classified as the decided class, belonging to the actual class, P(decided class/actual class). It is also known as Sensitivity r: recognition rate, defined as the probability of a pixel belongs to the actual class, being classified as the decided class, P(actual class/decided class). It is also known as Precision C: combination rate, defined as the probability of a pixel classified as the decided class and belonging to the actual class, P(actual class \ decided class)

e: estimation index, defined as the difference between the reconstruction and the recognition rates.

The reconstruction and recognition rates are values between 0 and 1, indicating weak or strong performance, respectively. The optimal result would be values of 1 in the diagonal of the matrix and values of 0 out of the diagonal. The total summation of all the combination rate values is equal to 1. Finally, the estimation index should be close to 0 in all entries of the confusion matrix.

The accuracy per class $A_i$ can be defined, from these confusion matrices, as the geometric mean of the reconstruction and recognition rates, as follows:

$$A_i = \sqrt{R_i \cdot r_i},$$

where the subindex i indicates the class. This method of quantitating accuracy rewards high sensitivity and precision combined per each tissue independently, penalizing the cases in which the difference between these two parameters are high. The global accuracy A of the classifier is computed as the arithmetic mean of the accuracy of the N classes:

$$A = \frac{1}{N} \sum_{i=1}^{N} A_i,$$

The table below shows the accuracy values per class and the global accuracy of the experiment for each of the five different classification iterations, depending on the set of features selected for training.

| Set of features | Healthy Skin | Viable Wound Bed | Shallow Burn | Deep Burn | Global |
|---|---|---|---|---|---|
| PPG | 0.8977 | 0.5145 | 0.0161 | 0.2550 | 0.4208 |
| RI | 0.9626 | 0.8046 | 0.1513 | 0.5899 | 0.6271 |
| PPG + RI | 0.9652 | 0.8021 | 0.2009 | 0.5156 | 0.6210 |
| MSI | 0.9809 | 0.8708 | 0.2259 | 0.6277 | 0.6764 |
| PPG + RI + MSI | 0.9909 | 0.9315 | 0.4171 | 0.8855 | 0.8063 |

Figure 69:
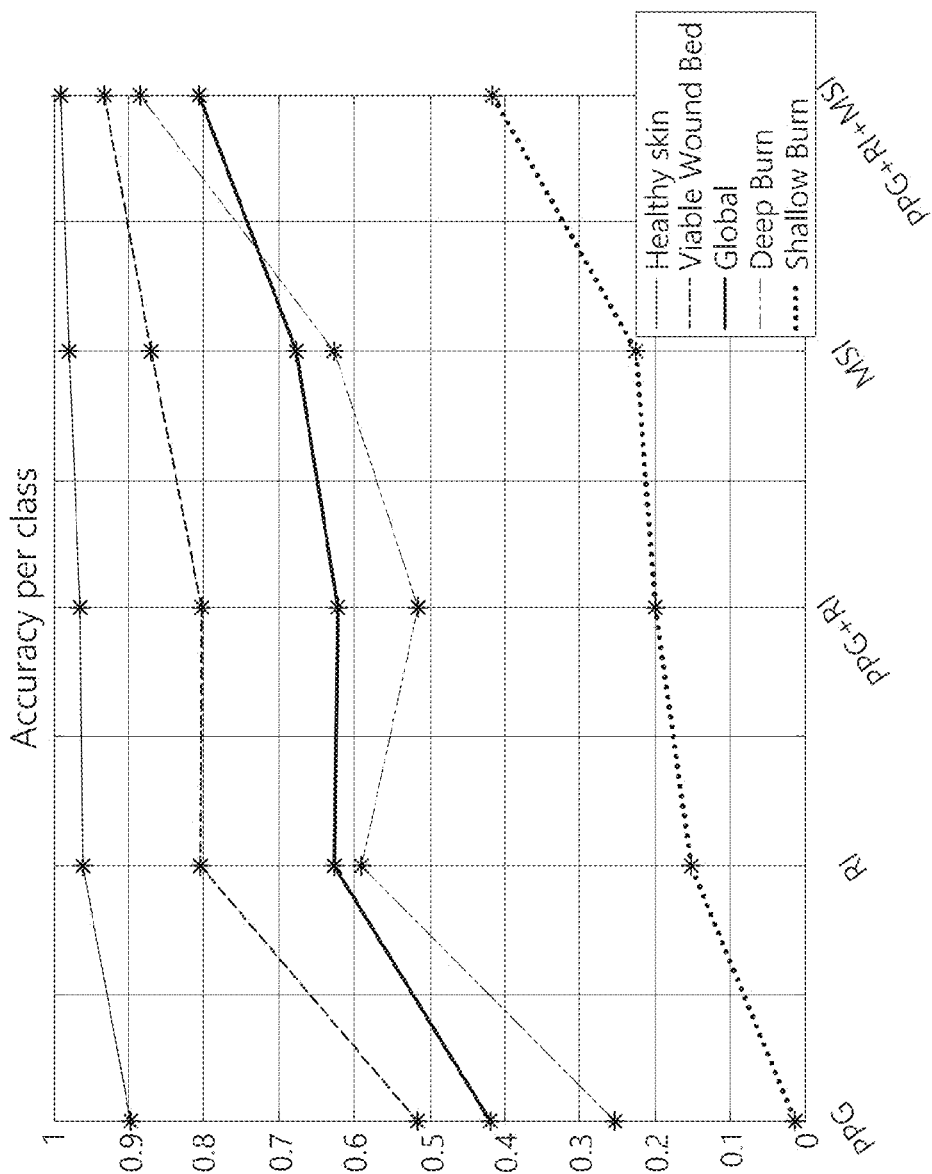
FIG. 69 illustrates accuracy per class results for an example set of features used for classification.

FIG. 69 plots the accuracy comparison of each class of tissue, as well as the global accuracy, performing the classification using the indicated set of features. The addition of MSI features greatly improves the accuracy of the classification model.

V. Conclusions

The imaging system has been shown to provide information capable of distinguishing a viable wound bed among burned tissue. A QDA model has been successfully adapted to complete this task. This disclosure has shown the performance of the cross-validation while increasing the number of features, and how the addition of MSI features significantly improves the accuracy of tissue classification.

Overview of Example Embodiments Wavelength Ranges for MSI

The multispectral images described herein can be captured, in some embodiments, by a fiber optic cable having both light emitters and a light detector at the same end of a probe. The light emitters can be capable of emitting around 1000 different wavelengths of light between 400 nm and 1100 nm to provide for a smooth range of illumination of the subject at different wavelengths, in contrast to previously-used camera systems that use around eight independent wavelength options. In some embodiments the subject can be sequentially illuminated with each wavelength through a determined range of wavelengths, for example between 400 nm and 500 nm (such as, 400 nm, 425 nm, 450 nm, 475 nm, or 500 nm) and between 720 nm and 1000 nm (such as 720 nm, 750 nm, 775 nm, 800 nm, 825 nm, 850 nm, 875 nm, 900 nm, 925 nm, 950 nm, 975 nm, or 1000 nm), or a range defined by any wavelength between any two of the aforementioned wavelengths, with one or more images captured of the subject at each wavelength.

Figure 70B:
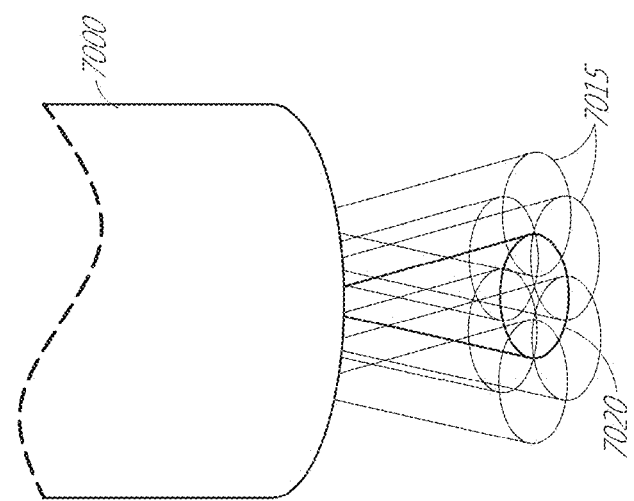
FIGS. 70A, 70B, and 71 illustrate an example fiber optic system that can be used to obtain the image data described herein.
Figure 70A:
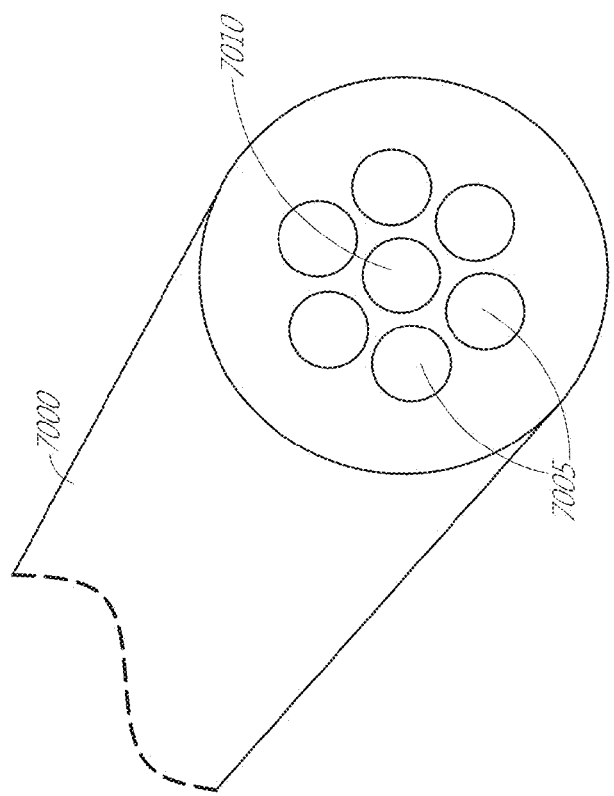
Figure 71:
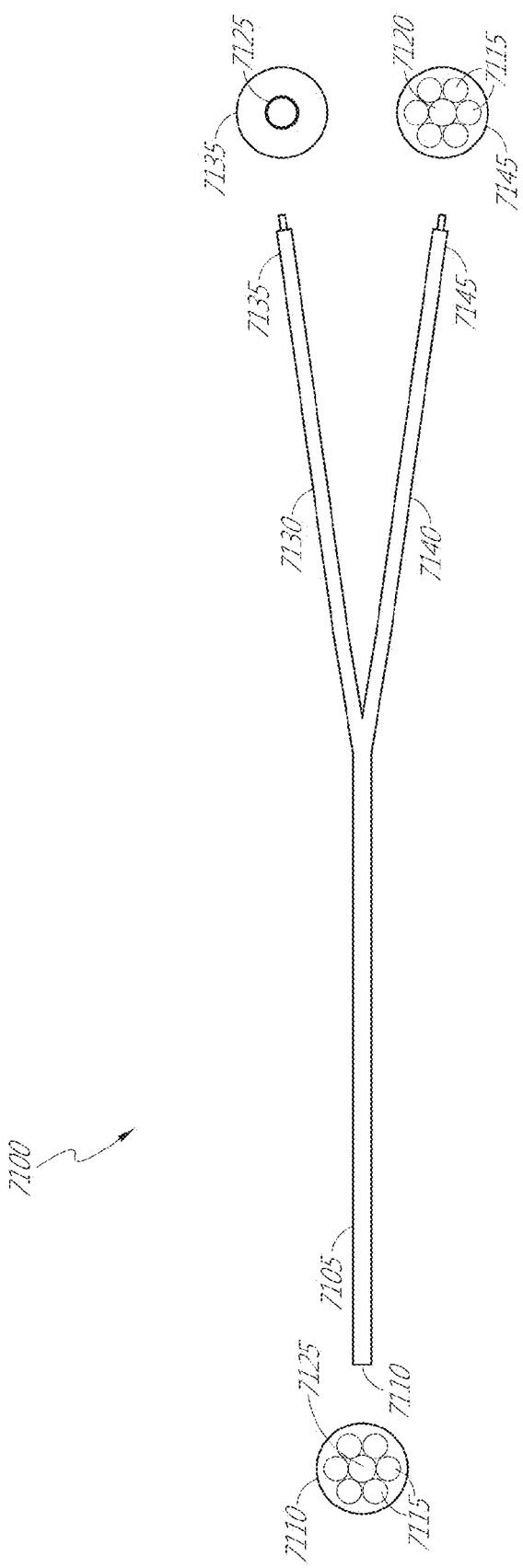

FIGS. 70A, 7B, and 71 illustrate an example fiber optic system that can be used to obtain the image data described herein. As shown in FIG. 70A, a fiber optic probe 7000 can include a number of light emitting fibers 7005 around a light collection fiber 7010. Each of the light emitting fibers 7005 can illuminate one of a plurality of overlapping regions 7015, and the light emitted from the light emitting fibers 7005 can be reflected from the tissue of a subject and collected from an evenly illuminated area 7020 by the light collection fiber 7010. The light emitting fibers can be controlled to sequentially emit one of 1,000 different wavelengths between 400 nm and 1100 nm in some implementation, and signals received the light collection fiber 7010 can be used to generate images of the illuminated tissue at the emitted wavelengths.

In some embodiments the probe 7000 can be a fiber optic spectrophotometer equipped with a co-axial light source for reflection and backscattering measurements. The probe can be configured for blocking ambient light with a sheath (not illustrated) so that the tissue is imaged using only the emitted wavelengths, leading to more accurate classification than tissue illuminated with both ambient light and select emitted wavelengths.

As shown in FIG. 71, a probe 7100 can include a first cable 7105 having a light emitting and detecting end 7110. The light emitting and detecting end 7110 can include a number of light emitting fibers 7115 around a light collection fiber 7125. The light emitting fibers 7115 can pass through the first cable 7105 and split off into a second cable 7140, a cross-section 7145 of which is shown including the light emitting fibers 7115 around a core 7120. This multi-fiber second cable 7140 can be coupled to a light source for providing the desired wavelengths of light through the second cable 7140 to the light emitting and detecting end 7110 of the first cable 7105. The light detecting fiber 7125 can pass through the first cable 7105 and split off into a third cable 7130, a cross-section 7135 of which is shown including only the light detecting fiber 7125. This single-fiber third cable 7130 can provide signals from the light detecting fiber 7125 to an image sensor configured for capture of image data (for example a CMOS or CCD image sensor) or to a spectrometer. The fiber core size can range from 200-600 µm, such as 200 µm, 250 µm, 300 µm, 350 µm, 400 µm, 450 µm, 500 µm, 550 µm, or 600 µm or within a range defined by any two of the aforementioned wavelengths.

Figure 72:
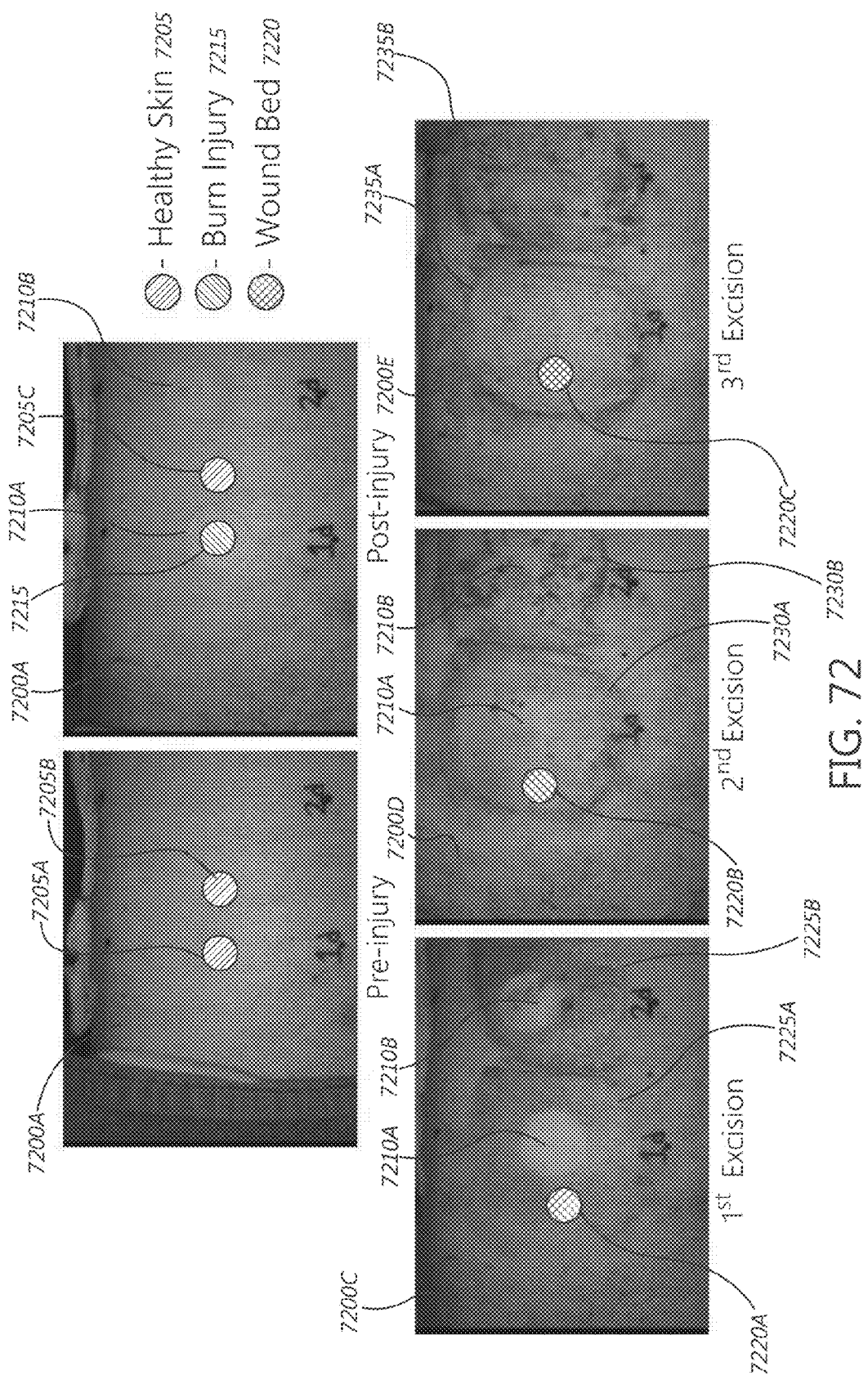
FIG. 72 illustrates five example study time points and a number of probe locations for collecting diffuse reflectance spectrum data in the visible and near-infrared (NIR) range.

FIG. 72 illustrates five example study time points and a number of probe locations for collecting diffuse reflectance spectrum (DRS) data in the visible and near-infrared (NIR) range. A first study time point 7200A corresponds to a pre-injury condition, a second study time point 7200B corresponds to a post-injury condition where the subject has two burns 7210A, 7210B, a third time point 7200C corresponds to the condition of the subject after the first excision, a fourth time point 7200D corresponds to the condition of the subject after the second excision, and a fourth time point 7200E corresponds to the condition of the subject after the third excision. Each excision can remove a layer of skin of around 1.0 mm sequentially to a depth of 3.0 mm. FIG. 72 also illustrates three healthy skin probe locations 7205A, 7205B, 7205C, one burn probe location 7215, and three wound bed (within the excised skin region) probe locations 7220A, 7220B, 7220C.

The experimental setup shown in FIG. 72A used a total of 12 burn regions for data collection. A probe similar to those shown in FIGS. 70A, 70B, and 71 was positioned approx. 1.0 cm from the skin's surface and the area of skin measurement was circular with a radius of approx. 0.5 cm, with ambient light blocked from the measurement site. A total of 76 DRS measurements were taken: one from each deep partial-thickness burn at probe location 7215, three from the adjacent skin surrounding the burn at probe locations 7205A, 7205B, 7205C, and three from the healthy wound bed taken after excising the skin at probe locations 7220A, 7220B, 7220C.

In a patient undergoing treatment implementing the techniques described herein, similar probe locations to those shown in condition 7200B can be used for initial tissue classification, for example to classify burn tissue versus healthy skin and in some embodiments to identify a degree of the burn in the burn tissue. In other implementations more probe locations can be used, for example to classify severity of different regions of a burn. Based on the classification, a physician or automated system may determine a treatment plan including a number of excisions to perform around the area of the burned tissue to facilitate healing.

In a patient undergoing treatment implementing the techniques described herein similar probe locations to those shown in conditions 7200C-7200E can be used for tissue classification during treatment, for example to identify burn tissue versus excised/debrided tissue and in some embodiments to identify a degree of the burn in the burn tissue. In other implementations more probe locations can be used, for example to classify severity of different regions of a burn. As shown in the conditions 7200C-7200E, as the tissue is excised to deeper levels the burn tissue becomes less visible. This can correspond to a reduction in severity of the burned tissue, which can be detected by gathering data from a probe positioned over a portion of the burn tissue and over a portion of the excised tissue. Based on the classification of the burn severity at each excision, a physician or automated system may determine a treatment plan including a number of additional excisions, if any, to perform around the area of the burned tissue to facilitate healing.

The resulting collected data demonstrates that the visible and NIR range is significantly different between burn injury and healthy tissues found during a burn excision surgical procedure, and that the DRS carries adequate information to differentiate these three clinically important tissue types. DRS data was collected per the described test probe locations and at the identified time points from three tissue types in an animal model of burn excision: deep partial-thickness burn injury, healthy intact skin, and the exposed viable underlying wound bed tissue. Significant differences in the DRS between these tissue types was evident from the resulting data, demonstrating regions of the visible and NIR spectrum that can be effective for identifying these tissues in this surgical procedure.

Figure 73:
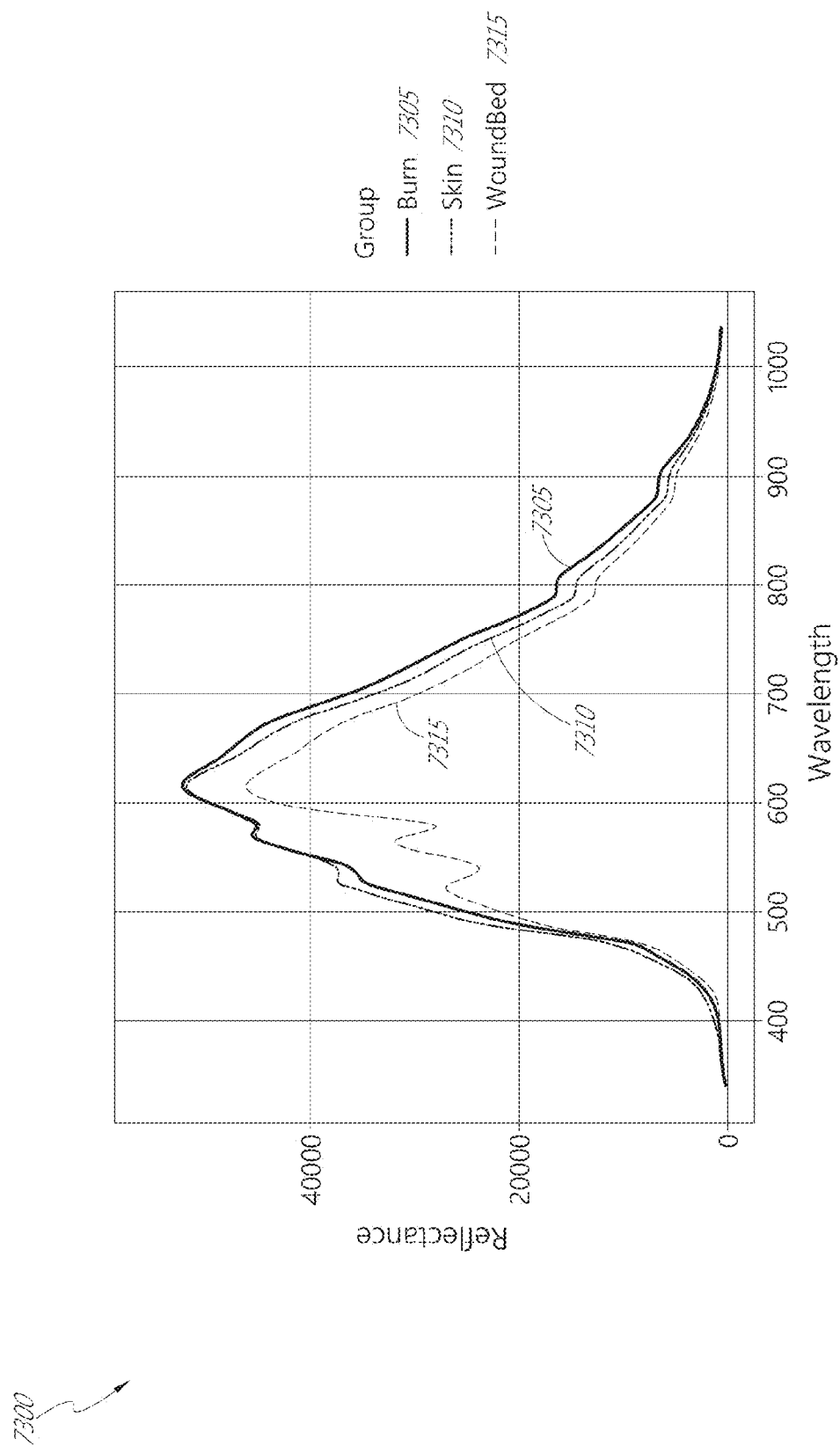
FIG. 73 illustrates average diffuse reflectance spectra from burned tissue, healthy skin, and wound bed tissue.

FIG. 73 illustrates a graph 7300 of the average diffuse reflectance spectra from burned tissue 7305, healthy skin 7310, and wound bed tissue 7315 as a function of wavelength (nm) between 400 nm and 1100 nm and reflectance. High reflectance values are consistent with brighter reflections from the tissue. As indicated by the peak of each of the spectral curves 7305, 7310, 7315 the DRS of burn, healthy skin, and wound bed tissues indicates the highest reflectance values for all three tissue types occurs at approximately 625 nm. There are secondary peaks at 525 nm and 575 nm, again for all three tissue types. Burn injury and healthy skin tissues reflect the most light, while wound bed tissue reflects the least. This is expected because the skin of the swine subjects in the experimental setup did not have dark pigmentation, and the burn injury created a lighter color mark on the surface of the skin. These peak values could shift for subjects having different skin pigmentation. Wound bed tissue reflects less resulting from the blood that is expressed on its surface having arrived there through the patent capillaries that have been broken and exposed owing to the surgical excision.

Figure 74:
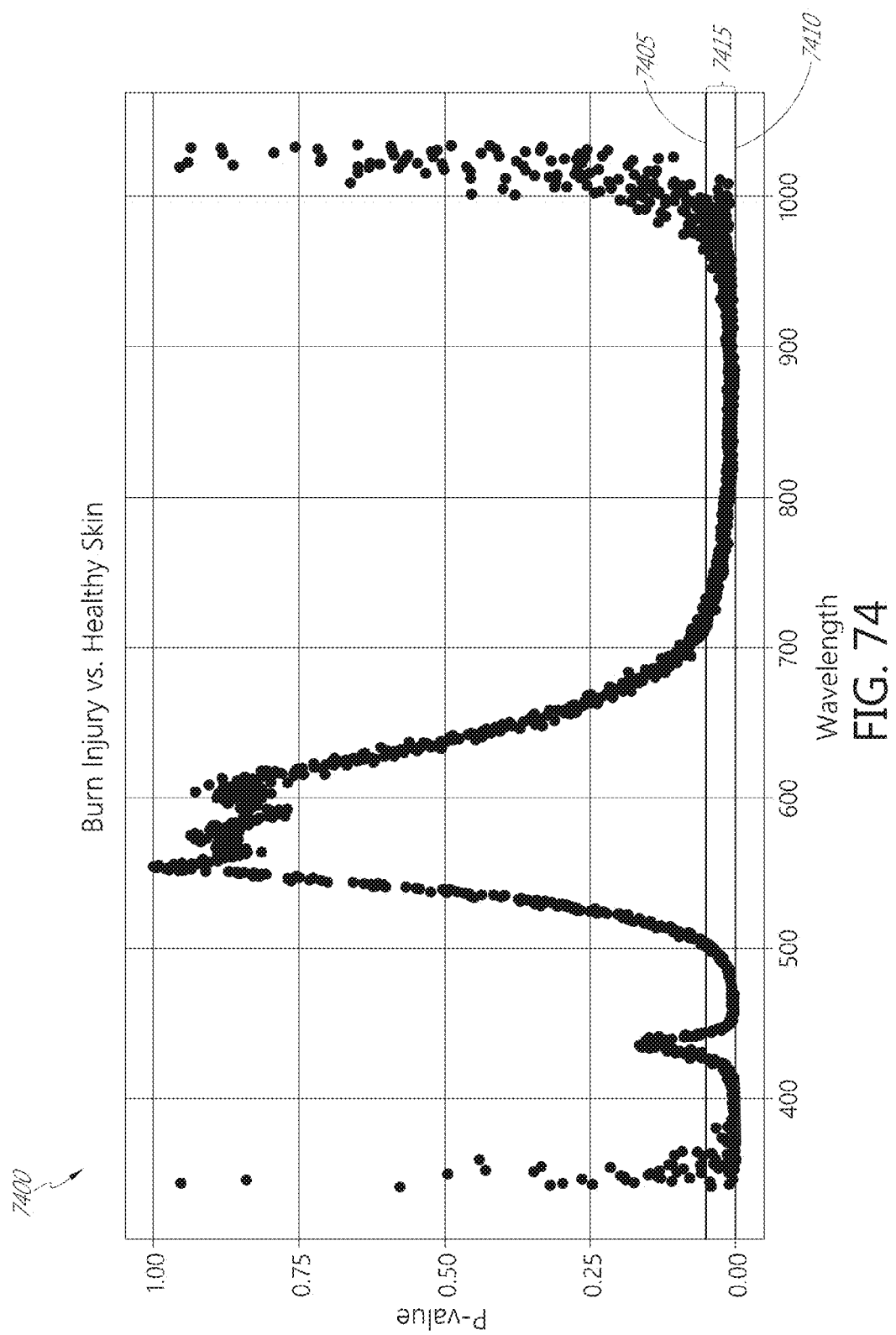
FIG. 74 illustrates P-values versus wavelength for burn injury versus healthy skin.
Figure 75:
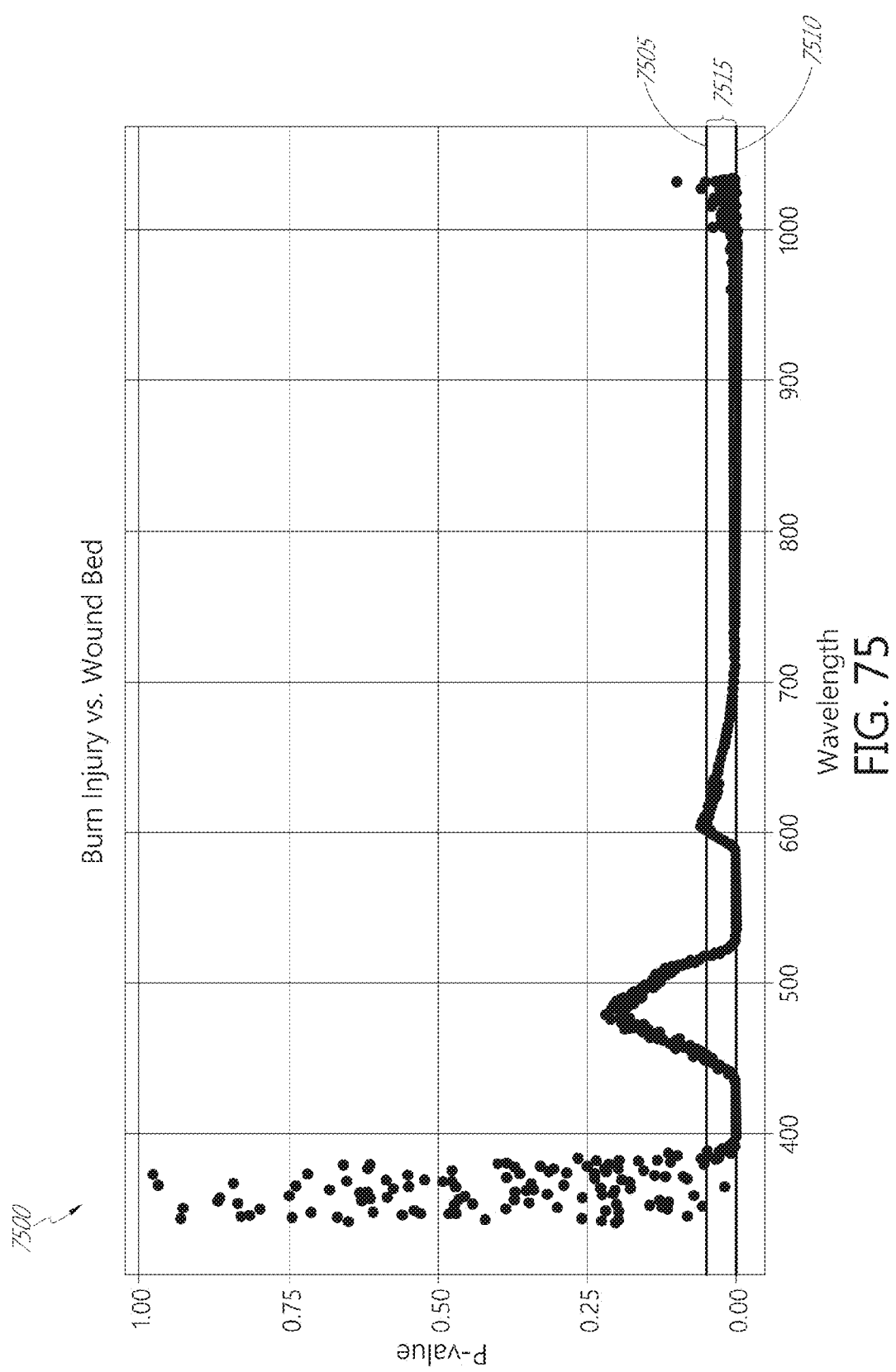
FIG. 75 illustrates P-values versus wavelength for burn injury versus wound bed.

The data from the graph 7300 can be processed using statistical methods to identify wavelengths where there were significant differences in the reflection of light from the tissue types, as shown in FIGS. 74 and 75. Prior to performing tests of significance, the data obtained from the experimental setup shown in FIG. 72 that is used to generate graph 7300 can be split into two separate data sets. Dataset one, including the data used to generate the spectral curves 7305 and 7310 for the burn tissue and healthy skin, respectively, represents the tissue that would be present when a surgeon is making a decision to excise or not excise the burn. Dataset one contains the burn injury and healthy skin data that could be obtained by a physician from a patient in a condition similar to that shown in condition 7200B. Dataset two, including the data used to generate the spectral curves 7305 and 7315 for the burn tissue and wound bed tissue, respectively, represents data that a surgeon wound encounter when performing surgery were they would need to identify the burn tissue remaining in the wound bed from the exposed wound bed tissue. Dataset two contains the burn injury and wound bed tissue data that could be obtained by a physician from a patient in a condition similar to that shown in conditions 7200C-7200E.

FIG. 74 illustrates a graph 7400 of P-values versus wavelength for burn injury versus healthy skin. This graph 7400 represents the difference between the data used to generate spectral curves 7305 and 7310 for the burn tissue and healthy skin, respectively, at the tested wavelengths. The P-values are between 0 and 1 and decrease as the difference between the data used to generate spectral curves 7305 and 7310 increases, with high values indicating little difference and values below 0.05 considered significant. To obtain the P-values for the graph 7400, multiple comparisons were performed by calculating the t-statistic at each wavelength of the collected data used to generate spectral curves 7305 and 7310.

Line 7405 represents the significance level 0.05, which does not control for any errors that could come from multiple comparisons. The line 7410 represents the alpha at 0.05/number of comparisons, which is conservative Bonferroni correction for the family-wise error rate. P-values on the graph 7400 above line 7405 are considered not significant and P-values on the graph 7400 below line 7410 are considered significant. P-values falling in the intermediate range 7415 between lines 7405 and 7410 can undergo additional processing to identify which are significant. For example, these vales can be ordered from lowest to highest and then processed to determine a level of significance according to a metric that is easier to pass as the P-value gets larger, as discussed in more detail with respect to FIGS. 76A and 76B.

For dataset one represented by graph 7400, the most different wavelengths between the burn injury and the healthy skin as indicated by P-values below line 7405 occur between 475 nm and 525 nm; 450 nm and 500 nm; and 700 nm and 925 nm. Accordingly, for classifying burn tissue compared to healthy skin, a multispectral imaging system as described herein may use wavelengths in a low end range and a high end rage that are discontinuous, for example between 450 nm and 525 nm and between 700 nm and 925 nm, or a range defined by any wavelength between any two of the aforementioned wavelengths.

FIG. 75 illustrates a graph 7500 of P-values versus wavelength for burn injury versus wound bed. This represents the difference between the data used to generate spectral curves 7305 and 7315 for the burn tissue and wound bed tissue, respectively, at the tested wavelengths. The P-values are between 0 and 1 and decrease as the difference between the data used to generate spectral curves 7305 and 7315 increases, with high values not significant due to indicating not much difference and values below 0.05 considered significant. To obtain the P-values for the graph 7500, multiple comparisons were performed by calculating the t-statistic at each wavelength of the collected data used to generate spectral curves 7305 and 7315.

Line 7505 represents the significance level 0.05, which does not control for any errors that could come from multiple comparisons. The line 7510 represents the alpha at 0.05/number of comparisons, which is conservative Bonferroni correction for the family-wise error rate. P-values on the graph 7500 above line 7505 are considered not significant and P-values on the graph 7500 below line 7510 are considered significant. P-values falling in the intermediate range 7515 between lines 7505 and 7510 can undergo additional processing to identify which are significant. For example, these vales can be ordered from lowest to highest and then processed to determine a level of significance according to a metric that is easier to pass as the P-value gets larger, as discussed in more detail with respect to FIGS. 77A and 77B.

For dataset two represented by graph 7500, the most different wavelengths between the burn injury and the healthy skin as indicated by P-values below line 7505 occur between: 400 nm and 450 nm; 525 nm and 580 nm; and 610 nm and 1,050 nm. Accordingly, for classifying burn tissue compared to healthy skin, a multispectral imaging system as described herein may use wavelengths in a low end range and a high end rage that are discontinuous, for example between 400 nm and 450 nm or 525 nm and 580 nm and between 610 nm and 1,050 nm, or a range defined by any wavelength between any two of the aforementioned wavelengths.

Results from analyzing graphs 7400 and 7500 to identify P-values below lines 7405, 7505 may be considered conservative since this does not consider the high probability of type II errors occurring from performing multiple t-tests. Accordingly, processing can be applied to P-values in the intermediate ranges 7415 and 7515 to identify their significance. For example, to correct for the probability of type II errors in the intermediate ranges 7415, 7515 the Benjamini-Hochberg method can be used to control for the false discovery rate. The Benjamini-Hochberg method implements a linear stepwise increase in the significance level (alpha). To perform the Benjamini-Hochberg method the P-values in each intermediate range 7415, 7515 were first arranged from smallest to largest. The following modification was then applied to alpha for each individual t-test:

$$alpha_i = alpha_0 * i/m$$

where $alpha_i$ is the significance for the t-test i, $alpha_0$ is the chosen level of significance, here 0.05, i is the index of the particular p-value from the organized list, and m is the total number of p-values, which in the experimental setup was 2048. Results of this calculation for the first and second datasets are shown in FIGS. 76A-76B and 77A-77B, respectively.

FIGS. 76A and 76B illustrate graphs 7600, 7605 of P-values from the first dataset arranged in ascending order 7610 with an indication 7615 of a modified level of significance of the P-values. Graph 7600 is a full graph of all P-values in the range 7415, and graph 7605 is a close-up of a portion of graph 7600 of P-values that are significant in the range of 0-1000.

Figure 77A:
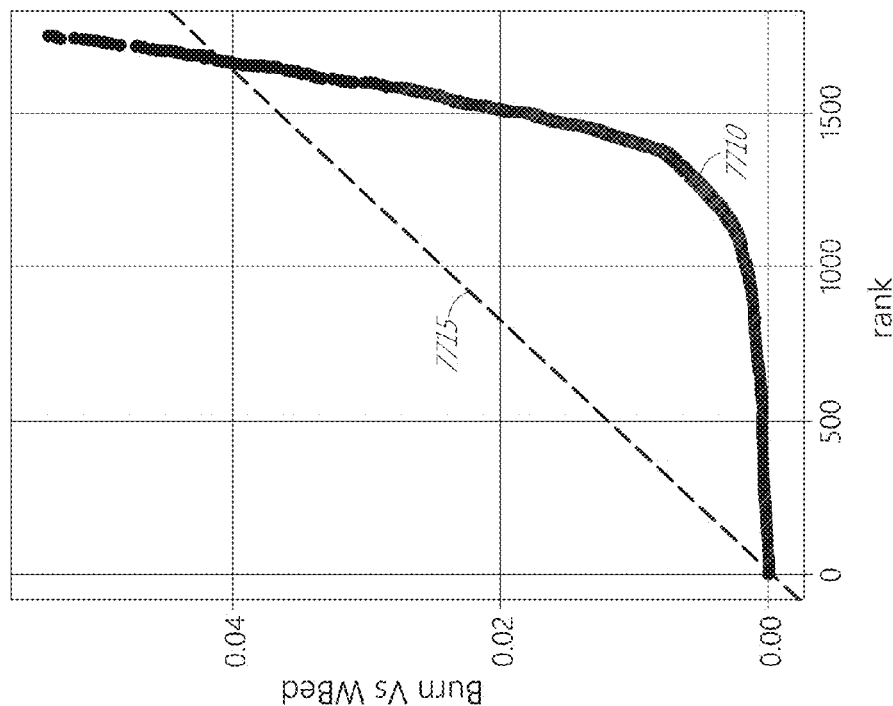
FIGS. 77A and 77B illustrate P-values from a first dataset arranged in ascending order with an indication of a modified level of significance of the P-values.
Figure 77B:
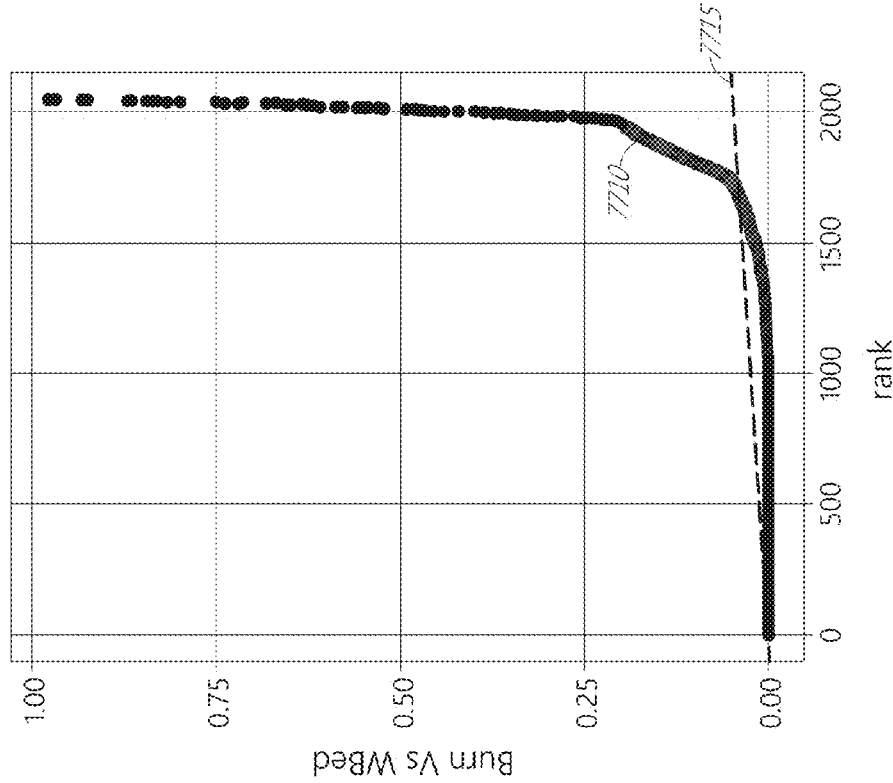

FIGS. 77A and 77B illustrate graphs 7700, 7705 of P-values from the second dataset arranged in ascending order 7710 with an indication 7715 of a modified level of significance of the P-values. Graph 7700 is a full graph of all P-values in the range 7515, and graph 7505 is a close-up of a portion of graph 7500 of P-values that are significant in the range of 0-1000.

Based on the significance values determined from the experimental setup, a multispectral imaging system used for burn tissue classification can use wavelengths in a low end range and a high end rage that are discontinuous, for example between 400 nm and 500 nm and between 720 nm and 1000 nm, or a range defined by any wavelength between any two of the aforementioned wavelengths. For example, a probe as shown in FIGS. 70A, 70B, and 71 can be configured to emit a number of wavelengths between 400 nm and 500 nm and between 720 nm and 1000 nm, or a range defined by any wavelength between any two of the aforementioned wavelengths. In some embodiments, such wavelength ranges may be suitable for tissue classification across a range of skin pigmentation similar to those of the described experimental setup, and a different set of ranges offset from the disclosed ranges can be used for tissue classification of lighter or darker pigmented skin. The different set of ranges can be identified based on separation of the spectrum received from the healthy tissue versus the spectrum received from the tissue of interest (for example, burn tissue or wound bed tissue).

Implementing Systems and Terminology

Implementations disclosed herein provide systems, methods and apparatus for identifying, evaluating, and/or classifying a subject's tissue. One skilled in the art will recognize that these alternatives may be implemented in hardware, software, firmware, or any combination thereof.

In all of the above described experiments, the features, materials, characteristics, or groups described in conjunction with a particular aspect, alternative, or example are to be understood to be applicable to any other aspect, alternative or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing alternatives. The protection extends to any novel one, or any novel combination, of the features disclosed in this specification (including any accompanying claims, abstract and drawings), or to any novel one, or any novel combination, of the steps of any method or process so disclosed.

While certain alternatives have been described, these alternatives have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some alternatives, the actual steps taken in the processes illustrated and/or disclosed may differ from those shown in the figures. Depending on the alternative, certain of the steps described above may be removed, others may be added. Furthermore, the features and attributes of the specific alternatives disclosed above may be combined in different ways to form additional alternatives, all of which fall within the scope of the present disclosure.

It should be understood that any reference to an element herein using a designation such as "first," "second," and so forth does not generally limit the quantity or order of those elements. Rather, these designations may be used herein as a convenient way of distinguishing between two or more elements or instances of an element. Thus, a reference to first and second elements does not mean that only two elements may be employed there or that the first element must precede the second element in some manner. Also, unless stated otherwise a set of elements may include one or more elements.

A person having ordinary skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

A person having ordinary skill in the art would further appreciate that any of the various examples, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various example logic, components, modules, and circuits described in connection with the aspects disclosed herein and in connection with the figures may be implemented within or performed by an integrated circuit (IC), an access terminal, or an access point. The IC may include a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and may execute codes or instructions that reside within the IC, outside of the IC, or both. The logical blocks, modules, and circuits may include antennas and/or transceivers to communicate with various components within the network or within the device. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The functionality of the modules may be implemented in some other manner as taught herein. The functionality described herein (e.g., with regard to one or more of the accompanying figures) may correspond in some aspects to similarly designated "means for" functionality in the appended claims.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

It is understood that any specific order or hierarchy of steps in any disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

Although the present disclosure includes certain alternatives, examples and applications, it will be understood by those skilled in the art that the present disclosure extends beyond the specifically disclosed alternatives to other alternative alternatives and/or uses and obvious modifications and equivalents thereof, including alternatives which do not provide all of the features and advantages set forth herein. Accordingly, the scope of the present disclosure is not intended to be limited by the specific disclosures of preferred alternatives herein, and may be defined by claims as presented herein or as presented in the future. For example, in addition to any claims presented herein, the following alternatives are also intended to be encompassed within the scope of the present disclosure.

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A tissue classification system comprising:
at least one light emitter configured to emit each of a plurality of wavelengths of light to illuminate first and second tissue regions, wherein the first tissue region comprises a tissue region where skin has been debrided and the second tissue region comprises a wound, wherein the at least one light emitter is configured to emit spatially-even light, the plurality of wavelengths of light being within a first range of wavelengths and a second range of wavelengths, the first range of wavelengths being lower than and discontinuous with the second range of wavelengths;
a light detection element configured to collect, from at least a portion of the first tissue region and at least a portion of the second tissue region, light emitted from the at least one light emitter and reflected from the portions of the first and second tissue region;
one or more processors in communication with the at least one light emitter and the light detection element and configured to:
control the at least one light emitter to emit each of the plurality of wavelengths of light;
receive a plurality of signals from the light detection element, a first subset of the plurality of signals representing light emitted at the plurality of wavelengths reflected from the portion of the first tissue region and a second subset of the plurality of signals representing light emitted at the plurality of wavelengths reflected from the portion of the second tissue region;
apply multispectral imaging processing to the plurality of signals;
identify tissue differences between the portion of the first tissue region and the portion of the second tissue region based at least partly on the multispectral image processing;
classify the portion of the first tissue region and the portion of the second tissue region based at least in part on the tissue differences wherein the one or more processors classifies the first tissue region as the tissue region where skin has been debrided and classifies the second tissue region as the wound; and
output a classified image of the first and second tissue regions to a display, the classified image including a first representation of pixels classified as the tissue region where skin has been debrided and a different second representation of pixels classified as the wound.

2. The tissue classification system of claim 1, further comprising a fiber optic probe, the light detection element comprising a first fiber of the fiber optic probe and the at least one light emitter comprising and a plurality of additional fibers of the fiber optic probe.

3. The tissue classification system of claim 2, wherein the first fiber is in data communication with one of an image sensor or spectrometer and wherein the plurality of additional fibers receive light at the plurality of wavelengths from a light source.

4. The tissue classification system of claim 1, further comprising a sheath adapted to be positioned to block ambient light from the illuminated first and second tissue regions.

5. The tissue classification system of claim 1, wherein the first range of wavelengths is between 400 nm and 500 nm and the second range of wavelengths is between 720 nm and 1000 nm.

6. The tissue classification system of claim 1, wherein the first subset of the plurality of signals correspond to different points in a first temporal sequence, and wherein the second subset of the plurality of plurality of signals correspond to different points in a second temporal sequence.

7. The tissue classification system of claim 6, wherein the one or more processors are configured to calculate blood flow perfusion in the portions of the first and second tissue regions by applying photoplethysmography processing to the plurality of signals.

8. The tissue classification system of claim 7, wherein the one or more processors are configured to classify the portion of the first tissue region and the portion of the second tissue region further based at least in part on the blood flow perfusion.

9. The tissue classification system of claim 1, wherein the first range of wavelengths is between 450 nm and 525 nm and the second range of wavelengths is between 700 nm and 925 nm.

10. The tissue classification system of claim 1, wherein the first range of wavelengths is between 400 nm and 450 nm or 525 nm and 580 nm and the second range of wavelengths is between 610 nm and 1,050 nm.

11. A tissue classification method, comprising, by one or more processors:
controlling at least one light source to illuminate first, second, and third tissue regions with light emitted at a plurality of wavelengths, wherein the first tissue region comprises healthy skin, the second tissue region comprises a wound, and the third tissue region comprises a tissue region where skin has been debrided, and wherein the at least one light source is configured to emit spatially-even light, the plurality of wavelengths of light being within a first range of wavelengths and a second range of wavelengths, the first range of wavelengths being lower than and discontinuous with the second range of wavelengths;
receiving, via a light detection element, a plurality of signals from at least a portion of each of the first, second, and third tissue regions, each of the plurality of signals representing light at one of the plurality of wavelengths reflected from the portion of the first tissue region, the portion of the second tissue region, and the portion of the third tissue region;

identifying tissue differences between the portion of the first tissue region, portion of the second tissue region, and the portion of the third tissue region by applying multispectral imaging processing to the plurality of signals;

classifying the portion of the first tissue region as the healthy skin, classifying the portion of the second tissue region as the wound, and classifying the portion of the third tissue region as the tissue region where skin has been debrided based at least in part on the tissue differences; and outputting a classified image of the first, second, and third tissue regions to a display, the classified image including a first representation of pixels classified as the healthy skin, a different second representation of pixels classified as the wound, and a different third representation of pixels classified as the tissue region where skin has been debrided.

12. The tissue classification method of claim 11, wherein the first range of wavelengths is between 400 nm and 500 nm and the second range of wavelengths is between 720 nm and 1000 nm.

13. The tissue classification method of claim 11, wherein a fiber optic probe comprises the at least one light source and the light detection element.

14. The tissue classification method of claim 11, further comprising calculating blood flow perfusion in the portions of the first, second, and third tissue regions by applying photoplethysmography processing to the plurality of signals.

15. The tissue classification method of claim 14, wherein classifying the portion of the first tissue region, the portion of the second tissue region, and the portion of the third tissue region is further based at least in part on the blood flow perfusion.

16. A tissue classification method, comprising, by one or more processors:

controlling at least one light source to illuminate first and second tissue regions with light emitted at a plurality of wavelengths, wherein the first tissue region comprises a tissue region where skin has been debrided and the second tissue region comprises a wound, and wherein the at least one light source is configured to emit spatially-even light, the plurality of wavelengths of light being within a first range of wavelengths and a second range of wavelengths, the first range of wavelengths being lower than and discontinuous with the second range of wavelengths;

receiving, via a light detection element, a plurality of signals from at least a portion of each of the first and second tissue regions, each of the plurality of signals representing light at one of the plurality of wavelengths reflected from the portion of the first tissue region and the portion of the second tissue region;

identifying tissue differences between the portion of the first tissue region and the portion of the second tissue region by applying multispectral imaging processing to the plurality of signals;

classifying the portion of the first tissue region as the tissue region where skin has been debrided and classifying the portion of the second tissue region as the wound based at least in part on the tissue differences; and outputting a classified image of the first and second tissue regions to a display, the classified image including a first representation of pixels classified as the tissue region where skin has been debrided and a different second representation of pixels classified as the wound.

17. The tissue classification method of claim 16, wherein the first range of wavelengths is between 400 nm and 500 nm and the second range of wavelengths is between 720 nm and 1000 nm.

18. The tissue classification method of claim 16, further comprising calculating blood flow perfusion in the portions of the first and second tissue regions by applying photoplethysmography processing to the plurality of signals.

19. The tissue classification method of claim 18, wherein classifying the portion of the first tissue region and the portion of the second tissue region is further based at least in part on the blood flow perfusion.

* * * * *